(12) United States Patent
Ruscetti et al.

(10) Patent No.: US 11,633,401 B2
(45) Date of Patent: Apr. 25, 2023

(54) COMBINATION THERAPY WITH MEK INHIBITOR AND CDK4/6 INHIBITOR TO TREAT PANCREATIC CANCER

(71) Applicant: Memorial Sloan Kettering Cancer Center, New York, NY (US)

(72) Inventors: Marcus Ruscetti, New York, NY (US); John P. Morris, IV, New York, NY (US); Scott Lowe, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 33 days.

(21) Appl. No.: 17/258,054

(22) PCT Filed: Jul. 3, 2019

(86) PCT No.: PCT/US2019/040647
§ 371 (c)(1),
(2) Date: Jan. 5, 2021

(87) PCT Pub. No.: WO2020/010280
PCT Pub. Date: Jan. 9, 2020

(65) Prior Publication Data
US 2021/0205319 A1    Jul. 8, 2021

Related U.S. Application Data

(60) Provisional application No. 62/694,519, filed on Jul. 6, 2018.

(51) Int. Cl.
| | |
|---|---|
| *A61K 31/535* | (2006.01) |
| *A61P 35/00* | (2006.01) |
| *A61K 31/145* | (2006.01) |
| *A61K 31/18* | (2006.01) |
| *A61K 31/185* | (2006.01) |
| *A61K 31/4184* | (2006.01) |
| *A61K 31/44* | (2006.01) |
| *A61K 31/4412* | (2006.01) |
| *A61K 31/4523* | (2006.01) |
| *A61K 31/506* | (2006.01) |
| *A61K 31/519* | (2006.01) |

(52) U.S. Cl.
CPC .......... *A61K 31/535* (2013.01); *A61K 31/145* (2013.01); *A61K 31/18* (2013.01); *A61K 31/185* (2013.01); *A61K 31/4184* (2013.01); *A61K 31/44* (2013.01); *A61K 31/4412* (2013.01); *A61K 31/4523* (2013.01); *A61K 31/506* (2013.01); *A61K 31/519* (2013.01); *A61P 35/00* (2018.01)

(58) Field of Classification Search
CPC .................................................... A61K 31/535
See application file for complete search history.

(56) References Cited

U.S. PATENT DOCUMENTS

| | | | |
|---|---|---|---|
| 9,700,557 B2 | 7/2017 | Caponigro et al. | |
| 2005/0171182 A1 | 8/2005 | Briesewitz | |
| 2005/0222163 A1 | 10/2005 | Eck et al. | |
| 2015/0164897 A1* | 6/2015 | Caponigro | A61K 31/519 514/252.16 |
| 2017/0182043 A1 | 6/2017 | Strum et al. | |

FOREIGN PATENT DOCUMENTS

WO    WO-2018/218633 A1    12/2018

OTHER PUBLICATIONS

Infante et al., "A randomized, double-blind, placebo-controlled trial of trametinib, an oral MEK inhibitor, in combination with gemcitabine for patients with untreated metastatic adenocarcinoma of the pancreas", European Journal of Cancer, pp. 2072-2081, Jun. 7, 2014 (Year: 2014).*
Juttila et al., "Modeling Targeted Inhibition of MEK and PI3 Kinase in Human Pancreatic Cancer", Small Molecule Therapeutics, pp. 40-47, Jan. 13, 2015 (Year: 2015).*
Franco et al., "CDK4/6 inhibitors have potent activity in combination with pathway selective therapeutic agents in models of pancreatic cancer", Impact Journals, vol. 5 No. 15, Jul. 26, 2014 (Year: 2014).*
"Administration Breakthrough Therapy Designation for Potential Treatment of Patients with Breast Cancer", Pfizer, Apr. 9, 2013 (Year: 2013).*
International Search Report and Written Opinion on PCT PCT/US2019/040647 dated Oct. 4, 2019 (9 pages).
Manchado et al. "A combinational strategy for treating KRAS mutant lung cancer," Nature, Jun. 22, 2016 (Jun. 20, 2016), vol. 534, No. 7609, pp. 1-41.

\* cited by examiner

*Primary Examiner* — Daniel R Carcanague
*Assistant Examiner* — Gillian A Hutter
(74) *Attorney, Agent, or Firm* — Foley & Lardner LLP

(57) ABSTRACT

The present technology provides methods for treating pancreatic cancer using a MEK inhibitor and a CDK4/6 inhibitor. Also disclosed herein are methods for increasing patient responsiveness to chemotherapeutic and/or immunotherapeutic regimes for pancreatic cancer. Kits for use in practicing the methods are also provided.

11 Claims, 142 Drawing Sheets

Figure 18

| | 8988 V | 8988 T | 8988 P | 8988 C | Panc V | Panc T | Panc P | Panc C | Mia V | Mia T | Mia P | Mia C |
|---|---|---|---|---|---|---|---|---|---|---|---|---|
| S100A11 | 424.921165 | 514.208765 | 1074.66873 | 1016.10883 | 1028.506 | 1546.95279 | 1819.08525 | 2089.58242 | 941.989975 | 1394.72638 | 1530.99514 | 1411.72189 |
| TNFAIP2 | 17.9774339 | 955.590677 | 725.691164 | 1334.63225 | 342.089625 | 1571.05303 | 614.025154 | 1990.47625 | 57.9605131 | 139.312955 | 139.058529 | 251.697305 |
| CYP1B1 | 24.9533536 | 408.248058 | 107.224985 | 451.814334 | 409.079184 | 600.696748 | 397.131598 | 884.707147 | 10.2813028 | 16.0000155 | 11.5814617 | 16.9733922 |
| MAP1LC3B | 443.984044 | 625.169604 | 599.594809 | 965.68139 | 209.169864 | 233.21061 | 295.463183 | 380.173324 | 469.152078 | 560.423934 | 692.55109 | 1394.14083 |
| SAT1 | 75.3596587 | 444.378784 | 594.335174 | 653.602466 | 243.777657 | 386.42264 | 345.033353 | 472.273062 | 167.707713 | 240.148047 | 227.118102 | 791.524796 |
| OPTN | 61.8954044 | 218.106617 | 155.302769 | 317.957003 | 30.6689585 | 52.2339516 | 50.9410798 | 76.9600667 | 12.8204437 | 44.100692 | 45.7853158 | 49.9688675 |
| TNFAIP3 | 15.5434345 | 238.517571 | 130.093883 | 395.177488 | 59.1193321 | 157.246851 | 81.1463535 | 246.607421 | 20.0587587 | 45.0318725 | 32.7361981 | 86.8041854 |
| CDKN1A | 71.1954005 | 164.929407 | 199.014394 | 264.078333 | 125.519754 | 236.406887 | 154.42956 | 171.890272 | 5.17827901 | 12.2490185 | 15.646478 | 14.6184745 |
| EPS8 | 3.6597954 | 3.00362802 | 3.40770255 | 3.14526201 | 44.7197164 | 38.8840647 | 34.651657 | 33.5145155 | 14.201451 | 23.5217136 | 24.9147672 | 10.0162167 |
| SQSTM1 | 909.451249 | 3009.89967 | 1593.72776 | 3670.86036 | 363.670338 | 585.549447 | 685.177796 | 833.045379 | 177.778583 | 247.517286 | 302.702438 | 515.030956 |
| NPC1 | 232.431195 | 568.844721 | 708.505828 | 847.519052 | 76.0770272 | 99.507127 | 62.9685868 | 142.117193 | 74.3263405 | 86.072293 | 82.2934423 | 129.522239 |
| CCND1 | 55.3162821 | 13.0246463 | 123.248665 | 26.6317172 | 79.4963498 | 26.0399874 | 89.3005117 | 44.5229334 | 56.0978222 | 38.0055162 | 82.6486664 | 68.1641105 |
| RNF149 | 60.2142714 | 104.156865 | 100.49667 | 134.315603 | 63.0194092 | 80.5198484 | 85.2999122 | 116.343113 | 97.708538 | 90.0973496 | 123.647489 | 138.628336 |
| CCNE1 | 20.198686 | 17.1003174 | 20.8117704 | 17.300599 | 9.81828758 | 14.6506456 | 23.4856586 | 12.7993775 | 17.2994566 | 20.8981765 | 24.8635785 | 17.8876956 |
| RAB27B | 4.63703652 | 12.0150087 | 21.6862763 | 15.8944662 | 133.042806 | 284.885036 | 176.81961 | 357.801858 | 836.220139 | 1194.1777 | 1131.63213 | 2476.50043 |
| ORC6 | 143.351839 | 87.6513412 | 86.5628551 | 83.4726353 | 44.36263 | 18.3563972 | 44.5288088 | 26.4520469 | 133.879423 | 121.088712 | 139.351684 | 77.793468 |
| WEE1 | 25.3352169 | 17.7595083 | 16.1689615 | 10.6169773 | 49.9308148 | 44.7871373 | 32.9131494 | 27.1273028 | 22.9631421 | 33.9765483 | 35.0298873 | 21.0302694 |
| IQGAP3 | 10.3483044 | 11.5019584 | 12.3959785 | 6.44780934 | 18.8547382 | 11.2320177 | 7.37186115 | 5.27265384 | 19.743875 | 38.4046686 | 27.5204773 | 10.5265928 |
| NEURL1B | 7.97110411 | 7.69938258 | 3.7058303 | 2.27402199 | 5.41305759 | 9.53894491 | 0 | 1.95653784 | 40.7833456 | 53.7839516 | 39.4131285 | 5.40530065 |
| ID1 | 3.22446644 | 3.01258538 | 34.655079 | 5.43569038 | 114.901541 | 158.176253 | 140.178477 | 136.991111 | 245.117015 | 112.886494 | 154.695238 | 82.1664157 |
| PIR | 80.8650993 | 101.761482 | 33.9267819 | 63.7741345 | 38.0122303 | 40.0150655 | 24.925299 | 24.5265994 | 46.2043713 | 55.7983224 | 42.8288469 | 24.685815 |
| COMMD4 | 43.3056622 | 50.703666 | 31.6087131 | 43.88628 | 62.152504 | 61.3839356 | 73.3883031 | 42.4790588 | 37.0807484 | 47.3812392 | 40.779336 | 21.6072714 |
| IMPA2 | 40.0024533 | 51.8251067 | 49.5932313 | 38.5588198 | 23.7694343 | 17.3091282 | 11.7926146 | 8.33106437 | 60.7759732 | 59.4278096 | 41.1310897 | 21.4748609 |
| RAD51AP1 | 64.2232838 | 31.9075544 | 28.7445209 | 14.8068744 | 58.0171436 | 29.8839527 | 32.5756383 | 19.1779452 | 121.435404 | 115.76362 | 97.1892675 | 46.4859679 |
| NUCKS1 | 121.19112 | 97.3584488 | 75.6373598 | 62.4855454 | 60.4465042 | 46.6456407 | 32.5586718 | 30.2353769 | 95.717809 | 106.559955 | 86.4705162 | 63.6195191 |
| RHNO1 | 108.441952 | 78.9250662 | 70.6685525 | 62.390173 | 119.952727 | 87.6919304 | 113.071977 | 69.070336 | 174.568215 | 169.068897 | 164.452267 | 141.645589 |
| H2AFV | 52.203962 | 39.255054 | 21.6347049 | 17.3107234 | 48.5122519 | 38.8327066 | 36.6291815 | 22.3535992 | 77.3286942 | 66.612893 | 50.7739318 | 26.6929348 |
| NUSA | 135.34 | 59.043 | 50.080 | 28.868 | 66.547 | 43.697 | 37.511 | 19.229 | 140.45 | 129.98 | 111.26 | 40.454 |

| Figure 18 (Contd) | | | | | | | | | | | | |
|---|---|---|---|---|---|---|---|---|---|---|---|---|
| P1 | 2005 | 7657 | 445 | 5563 | 8613 | 9412 | 6728 | 5095 | 4526 | 5372 | 9462 | 8604 |
| DUT | 174.150467 | 80.6956379 | 77.5112135 | 63.8984192 | 150.50726 | 117.893244 | 108.611224 | 76.9342315 | 125.876773 | 84.2451898 | 72.6640039 | 59.4844312 |
| FAM111B | 124.938244 | 44.5176844 | 19.5856544 | 16.4727934 | 126.802524 | 70.8559453 | 99.6404026 | 45.218521 | 107.888631 | 98.0117092 | 66.5429628 | 8.97312867 |
| CENPM | 35.8059864 | 13.6395895 | 11.4886494 | 7.57418814 | 22.7988628 | 10.2067414 | 19.0732723 | 4.81235395 | 14.4080521 | 12.9242361 | 11.8212435 | 4.82406297 |
| RNASEH2A | 47.3431478 | 19.020921 | 23.0113657 | 11.014855 | 69.4334988 | 35.0621278 | 49.0932112 | 22.9443949 | 64.2986682 | 59.9334485 | 51.3759605 | 32.6318928 |
| POLE2 | 64.5431756 | 16.8649541 | 18.6888049 | 9.95163846 | 71.256416 | 33.5529076 | 52.0346222 | 17.5050557 | 50.6942324 | 26.0421994 | 23.9820444 | 12.5282975 |
| HMGB3 | 109.368474 | 54.7793413 | 45.8689164 | 37.8928614 | 564.074863 | 331.711876 | 421.854516 | 176.163125 | 276.934654 | 210.380213 | 188.53047 | 83.2584499 |
| DEPDC1B | 36.6064252 | 11.4236337 | 11.8810915 | 5.85567487 | 20.6728872 | 11.625025 | 11.9809 | 6.74336153 | 29.9125908 | 21.8957128 | 22.5326397 | 10.6978557 |
| NUF2 | 176.177946 | 51.0527843 | 55.9235842 | 22.2348817 | 79.5621611 | 40.9889772 | 33.8491715 | 25.2797112 | 244.091469 | 134.832817 | 112.505628 | 54.0708812 |
| FAM83D | 56.2244894 | 20.9716516 | 22.5949767 | 9.77829455 | 32.815158 | 17.7133357 | 22.6432494 | 11.9740116 | 62.3008685 | 51.3778275 | 54.0140655 | 13.0808276 |
| CCNB1 | 292.583536 | 119.651539 | 111.104615 | 55.4257475 | 114.636593 | 75.7352914 | 109.367937 | 51.2596678 | 319.617514 | 224.555926 | 204.146623 | 79.6066962 |
| AURKA | 141.387459 | 69.2858501 | 64.0124281 | 36.7751993 | 109.706044 | 73.0274946 | 102.141798 | 54.2939252 | 126.691794 | 115.746072 | 99.0017562 | 33.9098158 |
| PLK1 | 48.864833 | 24.0429813 | 23.7022064 | 9.82723964 | 53.7170693 | 34.4042469 | 44.8366044 | 20.1426399 | 69.5502355 | 42.6802509 | 37.8533143 | 12.5746771 |
| SGOL2 | 111.219321 | 50.8442821 | 54.4992804 | 36.0556846 | 203.913685 | 115.543502 | 149.341487 | 93.5194519 | 154.673576 | 105.485102 | 103.672178 | 46.3705118 |
| UBE2C | 281.704879 | 101.930767 | 147.012935 | 50.9849106 | 436.621205 | 281.498924 | 473.263983 | 242.691256 | 331.718116 | 215.424208 | 246.685134 | 146.293667 |
| CDC20 | 185.370726 | 51.3685076 | 82.0037033 | 27.0825837 | 200.844231 | 115.835851 | 170.727138 | 78.2883797 | 285.412518 | 164.807801 | 145.75356 | 44.2210067 |
| CHEK1 | 129.726071 | 97.86998 | 114.142224 | 96.6089705 | 147.136267 | 119.743392 | 126.785175 | 103.775378 | 117.94894 | 87.3890745 | 83.9768925 | 59.6419398 |
| CTDSP1 | 134.905905 | 130.549455 | 142.296609 | 85.926785 | 107.184222 | 81.9850655 | 76.183891 | 51.7511727 | 89.3338775 | 65.4969251 | 50.0979258 | 68.6493814 |
| ASF1B | 54.482364 | 19.6822245 | 19.4600443 | 10.0044819 | 44.0178986 | 21.6341772 | 28.7094896 | 15.3339734 | 63.951117 | 54.9460787 | 49.0538744 | 12.8648256 |
| FBXO5 | 31.1608854 | 13.6148852 | 13.8608094 | 7.41801655 | 28.0750513 | 14.5710032 | 18.8248082 | 11.7257337 | 34.7520058 | 27.9330027 | 25.1952258 | 10.7127467 |
| MCM6 | 59.0522133 | 19.6641619 | 19.790915 | 11.4793677 | 33.1127788 | 23.7519832 | 19.5212593 | 14.0503088 | 71.7039177 | 52.2717136 | 39.8407242 | 28.4261159 |
| HELLS | 128.47526 | 66.5446637 | 65.0714985 | 49.7118477 | 108.242119 | 58.4411308 | 91.2385136 | 43.0438326 | 93.4784966 | 57.0142136 | 52.0595661 | 28.9765168 |
| BUB1B | 226.777333 | 85.6063426 | 103.83317 | 48.0762573 | 195.763738 | 101.774167 | 116.53753 | 66.7806974 | 217.811028 | 163.122399 | 171.556609 | 63.525031 |
| TK1 | 100.488113 | 47.2107411 | 50.3747892 | 21.710764 | 68.8473262 | 42.5024885 | 65.31102 | 24.6285811 | 117.480138 | 91.7416121 | 84.4137741 | 13.2575955 |
| CDK2 | 68.4019436 | 49.647652 | 58.1292178 | 41.2800359 | 70.3190602 | 49.7678663 | 53.163839 | 44.6279806 | 43.2508086 | 38.2648454 | 31.8137103 | 16.0234441 |
| DEK | 177.971275 | 100.661668 | 109.348951 | 65.035569 | 114.721834 | 87.288189 | 77.3971628 | 69.0685834 | 150.771177 | 109.652008 | 86.1191678 | 59.4019198 |
| USP1 | 169.737346 | 88.5275033 | 77.7948693 | 46.639096 | 179.147657 | 127.761428 | 144.427175 | 85.244141 | 214.349438 | 154.306084 | 139.781628 | 101.072464 |
| CDK1 | 432.595102 | 133.641565 | 142.136825 | 70.3720165 | 246.070448 | 127.118399 | 167.23738 | 74.7462404 | 209.37723 | 151.788436 | 148.684823 | 48.1710974 |
| CDCA3 | 30.2415425 | 12.4409589 | 13.0552834 | 5.34271579 | 23.879478 | 14.35323 | 16.9672651 | 6.80747569 | 42.2123548 | 37.9190705 | 27.1073342 | 5.24299475 |
| CCNB2 | 85.6552433 | 38.3615446 | 36.4957258 | 17.4344121 | 45.9875074 | 28.2882854 | 32.316387 | 15.9339637 | 136.283251 | 87.566837 | 88.0667446 | 35.3081464 |

| Figure 18 (Contd) | | | | | | | | | | | | |
|---|---|---|---|---|---|---|---|---|---|---|---|---|
| NCAPD2 | 515.66387 | 229.715825 | 273.699545 | 102.734005 | 374.875093 | 229.127361 | 155.774583 | 108.788865 | 1198.31938 | 763.013523 | 635.493047 | 251.98512 |
| KIF2C | 157.547029 | 54.8815865 | 59.7551006 | 29.5430659 | 208.468936 | 114.505744 | 147.870889 | 59.2810078 | 226.784664 | 147.825529 | 153.619228 | 45.3872131 |
| FOXM1 | 46.6857954 | 25.3049108 | 24.8001712 | 12.3959306 | 37.5200025 | 22.2165663 | 16.4019476 | 10.2764527 | 87.3633733 | 74.259894 | 59.1162708 | 15.6851765 |
| BIRC5 | 54.2363938 | 27.6880784 | 24.7748923 | 12.497894 | 76.617677 | 45.5265467 | 71.0780161 | 21.2202443 | 89.0656349 | 60.6641187 | 53.52421 | 17.6417469 |
| AURKB | 74.8670624 | 27.0636192 | 31.9523376 | 13.3748399 | 64.1791576 | 33.9777048 | 58.7712313 | 13.9017163 | 132.190644 | 98.3307703 | 77.246687 | 20.7321729 |
| H2AFX | 237.554174 | 78.2951155 | 69.2968617 | 37.2423936 | 75.2780571 | 54.325286 | 62.0723338 | 28.3225218 | 135.455309 | 95.1158293 | 64.164455 | 24.4657672 |
| CENPA | 58.8135917 | 33.8782849 | 26.4875272 | 13.6977823 | 34.7009255 | 27.5467951 | 23.8317221 | 18.9207575 | 50.0998494 | 35.8538978 | 35.3675597 | 15.2275776 |
| CCNA2 | 69.6142361 | 29.3348482 | 23.1886478 | 10.141634 | 36.4137952 | 19.3251164 | 21.2716084 | 10.5262715 | 67.2613455 | 47.6673086 | 40.3342933 | 9.20732188 |
| NASP | 229.963056 | 121.059514 | 122.52727 | 84.3586703 | 257.326941 | 192.182196 | 216.080098 | 120.562131 | 428.356245 | 250.42282 | 209.950434 | 132.454604 |
| KIF11 | 50.4509574 | 21.6886311 | 24.4665681 | 10.6542141 | 34.8210801 | 19.6353762 | 18.4816476 | 12.4747404 | 39.7717399 | 25.8474873 | 20.2151316 | 9.28577266 |
| TOP2A | 117.868024 | 43.927799 | 53.5920516 | 17.7897396 | 103.769621 | 57.9752835 | 51.8643613 | 31.0830594 | 213.608955 | 183.230929 | 172.128921 | 44.2994334 |
| TMPO | 127.816928 | 54.73228 | 48.9947981 | 25.1557652 | 59.0207668 | 31.2536339 | 29.0466108 | 17.7167684 | 93.8599081 | 69.4363708 | 54.3962854 | 23.4742574 |
| HMMR | 263.940119 | 83.7353685 | 90.0814553 | 44.4002793 | 127.925775 | 78.9852932 | 71.4386764 | 63.2206291 | 403.557667 | 237.622452 | 245.012256 | 102.875259 |
| MKI67 | 30.669994 | 18.2900197 | 20.6910404 | 8.05508104 | 57.770415 | 31.3825783 | 23.26565 | 16.6603045 | 48.6123245 | 34.6823961 | 27.3848769 | 6.29436774 |
| PRC1 | 84.0278703 | 40.2031538 | 47.1725169 | 21.4072113 | 96.1745471 | 57.3927354 | 67.3065226 | 38.1137957 | 88.8100451 | 67.9223685 | 61.7779749 | 28.131971 |
| LMNB1 | 51.9967252 | 23.0369008 | 21.2773693 | 7.06157446 | 30.5814388 | 20.9252884 | 12.7029366 | 6.80030621 | 89.3301559 | 77.0445637 | 49.9152666 | 18.3508013 |
| SMC4 | 501.36582 | 213.168499 | 257.520996 | 118.287686 | 310.491034 | 174.574201 | 123.612585 | 89.4618639 | 769.329891 | 577.347451 | 484.147629 | 236.258591 |
| DLGAP5 | 75.0917362 | 30.4114069 | 30.2019883 | 14.022879 | 47.0060099 | 28.7880898 | 35.9940218 | 16.7206493 | 63.8453403 | 39.6551952 | 37.4574424 | 8.63494034 |
| TYMS | 112.895936 | 49.608206 | 42.4932978 | 22.147086 | 99.6558721 | 56.7819076 | 77.1394512 | 32.9821425 | 155.537181 | 110.545795 | 88.9654159 | 17.8562741 |
| HMGB2 | 196.042809 | 63.8321496 | 63.5577361 | 23.4781635 | 86.2066673 | 53.686703 | 53.6454715 | 22.7637844 | 186.435588 | 102.891647 | 68.2687008 | 35.8355123 |
| SPC24 | 37.9753512 | 16.0842552 | 21.1755459 | 8.3578391 | 54.0643023 | 25.3112674 | 35.7774513 | 11.6279548 | 60.5277826 | 43.0989358 | 37.9462109 | 9.6866318 |
| CDKN3 | 131.608384 | 53.6027407 | 33.6792204 | 22.5454923 | 46.9370623 | 34.4977488 | 34.5408933 | 17.4299409 | 138.680174 | 83.4423642 | 75.7249418 | 44.4966468 |
| KIF20A | 274.289161 | 165.465257 | 119.004598 | 58.8686991 | 115.218346 | 89.5677948 | 37.715809 | 42.3616799 | 325.159813 | 300.938907 | 221.846478 | 21.3781354 |
| SPC25 | 118.097137 | 39.1439198 | 37.5869288 | 22.7335316 | 57.9528845 | 33.4871176 | 39.890253 | 16.3313365 | 108.242277 | 71.9289584 | 70.2608675 | 14.4273834 |
| STMN1 | 383.937262 | 182.727243 | 133.298324 | 113.195407 | 286.43894 | 179.522441 | 220.880367 | 106.571508 | 348.026817 | 329.01404 | 271.199769 | 136.044642 |
| MYBL2 | 87.4454772 | 38.2776807 | 31.8408418 | 16.2085463 | 74.674914 | 45.3008752 | 41.8903699 | 18.7164827 | 117.213946 | 96.5451483 | 73.7851896 | 15.7995975 |
| H1FX | 83.3891171 | 58.1548255 | 50.2112956 | 26.1429535 | 47.9174131 | 32.1288847 | 26.999375 | 14.5240802 | 69.4233002 | 50.6277862 | 42.0682954 | 23.1106194 |
| HMGN2 | 915.629232 | 482.24086 | 327.44609 | 332.767586 | 702.312505 | 475.929185 | 391.046785 | 242.726862 | 610.875102 | 494.672145 | 369.774356 | 171.685862 |
| EZH2 | 9.46306954 | 6.96333888 | 5.46278092 | 4.39003036 | 27.006006 | 20.1646916 | 20.3468755 | 11.3845676 | 31.5688709 | 24.2566563 | 18.2771433 | 13.4724261 |
| CDK4 | 97.1365339 | 42.0231474 | 42.8364223 | 36.2200439 | 43.8546318 | 25.6975363 | 31.2478724 | 21.5530173 | 56.4217897 | 49.150465 | 47.1347638 | 41.8227327 |

| Figure 18 (Contd) | | | | | | | | | | | | |
|---|---|---|---|---|---|---|---|---|---|---|---|---|
| MCM3 | 90.09959 | 32.5708393 | 37.6337705 | 19.4239685 | 79.6948948 | 47.7429183 | 60.7585492 | 31.602243 | 109.869543 | 69.8425154 | 69.481257 | 38.50422 |
| EXO1 | 63.2227717 | 23.2849252 | 25.9582924 | 12.3569497 | 60.3862321 | 28.9920475 | 35.5538227 | 21.5957479 | 83.6909367 | 61.3361371 | 50.656479 | 12.6208671 |
| DNMT1 | 56.0257124 | 28.4546186 | 29.4875559 | 15.8622956 | 82.5605002 | 49.5079738 | 31.760019 | 25.6050982 | 117.313292 | 80.8528254 | 62.9344264 | 40.1905679 |
| HMGA1 | 713.303324 | 133.539714 | 323.459998 | 152.307529 | 663.107187 | 170.505255 | 604.027297 | 130.333229 | 471.268951 | 84.847309 | 79.286961 | 699.276474 |
| MT-ND2 | 1028.12979 | 1069.05727 | 1167.428 | 1275.15019 | 894.31166 | 1305.2899 | 1344.21037 | 1717.43653 | 1293.69511 | 1698.87049 | 1666.71905 | 1768.40675 |
| L1CAM | 0.23507136 | 4.41201662 | 4.70756207 | 16.6875766 | 19.3912757 | 59.5381601 | 19.9694885 | 82.9265153 | 4.37373669 | 76.4487603 | 59.3388523 | 17.7485315 |
| STXBP1 | 112.422 | 178.218708 | 186.059151 | 174.78133 | 147.965929 | 103.398929 | 80.2594628 | 100.722568 | 67.6716331 | 105.931739 | 119.920771 | 109.700577 |
| GM2A | 118.332476 | 159.562792 | 148.039831 | 233.8809 | 76.2465379 | 134.357999 | 179.083541 | 278.81195 | 65.0421808 | 93.3720011 | 110.013415 | 85.1554779 |
| CSTB | 57.1107966 | 91.372007 | 66.9009939 | 110.898785 | 67.3754244 | 88.8064357 | 98.1363067 | 89.0129741 | 60.9485594 | 82.3042867 | 89.2945152 | 70.7562102 |
| RHOB | 15.3702513 | 41.3238995 | 17.6213302 | 36.682985 | 13.3577808 | 56.1897893 | 35.925216 | 86.0695185 | 15.4933584 | 45.0963899 | 41.3358578 | 32.0540937 |
| KRT8 | 727.785281 | 1119.58423 | 936.169193 | 1325.88424 | 288.286691 | 1044.96916 | 495.429593 | 1517.23436 | 691.811743 | 841.789212 | 1506.64139 | 503.682619 |
| MUC1 | 2.13851624 | 283.08122 | 136.887998 | 223.574283 | 15.9133731 | 32.1799787 | 17.1683147 | 24.2790033 | 7.85805984 | 167.155251 | 127.741412 | 44.2859327 |
| DDR1 | 54.9146752 | 191.45227 | 164.607861 | 232.355652 | 240.696191 | 364.39949 | 173.046953 | 367.019236 | 56.6144356 | 163.187772 | 111.083938 | 159.824661 |
| CLU | 11.316778 | 82.5110619 | 11.3245258 | 45.0987289 | 61.0588063 | 138.852277 | 140.578686 | 170.805754 | 18.2278784 | 89.3273591 | 78.6260921 | 16.0059639 |
| GAS6 | 23.6709674 | 28.8963789 | 24.1306635 | 37.7766102 | 6.99288893 | 16.901299 | 6.5280545 | 21.0094897 | 3.84163329 | 8.50471974 | 6.77117204 | 3.89310345 |
| IL6 | 0 | 45.4961551 | 32.3750509 | 91.039063 | 0.1608497 | 1.15302088 | 0.50274997 | 2.28326813 | 0 | 0 | 0.12893572 | 0 |
| NFKB2 | 143.051752 | 943.8212 | 753.478478 | 966.008182 | 249.259503 | 319.237629 | 337.405169 | 331.215399 | 42.8525623 | 140.420539 | 119.462159 | 295.016885 |
| CX3CL1 | 0 | 0.36067568 | 0.08679936 | 0.98294446 | 53.8420751 | 185.026 | 102.637293 | 289.116908 | 0 | 0.18564707 | 1.06712655 | 2.95411644 |
| CCL2 | 0 | 21.9355897 | 0 | 56.8494035 | 75.0222771 | 197.187143 | 321.164488 | 411.606649 | 0 | 0 | 0.59541789 | 0.24724347 |
| NFE2L2 | 332.252329 | 588.810585 | 382.658103 | 602.156024 | 248.136642 | 264.679871 | 210.906376 | 318.004051 | 248.839637 | 217.819405 | 231.501965 | 309.411883 |
| SERPINE1 | 338.890328 | 85.6110658 | 226.94879 | 342.702955 | 337.884455 | 672.032328 | 587.927639 | 2240.14812 | 45.1503724 | 33.4358526 | 68.199924 | 282.478216 |
| CXCL11 | 0 | 19.3915956 | 17.8592375 | 57.4034797 | 0.61174966 | 2.30223665 | 1.91207773 | 11.0959818 | 0.19474972 | 0.28792058 | 1.47111967 | 4.42882939 |
| ACVRL1 | 0 | 6.09295843 | 2.07009448 | 23.4424313 | 0.88192994 | 14.8565809 | 6.89137531 | 32.6885838 | 0 | 0.55344159 | 1.41389478 | 1.76133226 |
| PVR | 31.3282371 | 38.1856296 | 34.1578042 | 59.1426955 | 26.2730687 | 25.9466109 | 35.2102645 | 40.1958196 | 28.0785755 | 29.3433066 | 38.3703404 | 52.9625989 |
| CD82 | 7.6950673 | 12.9873414 | 13.9308124 | 41.6361591 | 185.810999 | 284.389599 | 346.748899 | 424.477795 | 4.0694728 | 15.7571404 | 8.7826722 | 29.632451 |
| PLAU | 848.649023 | 1470.8077 | 6327.25982 | 3646.06627 | 920.015933 | 1539.45139 | 1443.53698 | 1727.54767 | 432.395149 | 639.258738 | 1107.26693 | 1606.80358 |
| IL15 | 2.58417847 | 8.82969967 | 4.28307127 | 11.2797462 | 2.43297673 | 7.30060629 | 4.24436329 | 14.9924614 | 0 | 0.63911603 | 0.54425667 | 2.20349117 |
| SGMS2 | 67.4617107 | 100.846037 | 101.287465 | 129.19727 | 70.0558471 | 62.0164761 | 45.5079428 | 87.1970423 | 57.5020302 | 80.5095853 | 82.5427887 | 65.3198542 |
| ATP2C1 | 30.3813169 | 33.9802538 | 40.6914593 | 44.5374278 | 47.7533728 | 45.0971753 | 43.7406362 | 58.4895941 | 32.4733606 | 44.3039163 | 49.6642836 | 47.8689246 |
| SAT1 | 75.3596587 | 444.378784 | 594.335174 | 653.602466 | 243.777657 | 386.42264 | 345.033353 | 472.273062 | 167.707713 | 240.148047 | 227.118102 | 791.524796 |

| Figure 18 (Contd) | | | | | | | | | | | | |
|---|---|---|---|---|---|---|---|---|---|---|---|---|
| CD40 | 3.93920141 | 17.0883925 | 14.4213689 | 53.7755564 | 18.0413077 | 52.544942 | 41.0712417 | 137.458948 | 3.25611622 | 5.43790771 | 6.26296511 | 11.6320257 |
| BST2 | 0 | 20.9625486 | 1.98020078 | 31.2616654 | 4.98144726 | 16.0688565 | 12.4308508 | 25.0913018 | 0.15346813 | 2.11763371 | 1.54571029 | 9.86838685 |
| ITGA5 | 11.5743996 | 37.6411568 | 68.5455685 | 57.9943882 | 166.661987 | 426.668245 | 281.202873 | 522.04432 | 8.63930968 | 11.9703345 | 14.3841012 | 12.2730943 |
| HIF1A | 490.228497 | 763.537519 | 908.09842 | 740.224667 | 181.320483 | 174.806422 | 156.561198 | 207.557515 | 519.788051 | 666.165462 | 842.484003 | 496.234883 |
| ATP2A2 | 877.520155 | 1306.48937 | 1246.49575 | 1265.86722 | 697.231748 | 836.398076 | 506.478306 | 771.859727 | 600.112614 | 619.447606 | 648.715106 | 515.10395 |
| CSF1 | 10.1838001 | 334.222592 | 141.632402 | 640.659387 | 256.259494 | 817.167279 | 854.181789 | 1322.98241 | 183.215947 | 680.912039 | 1026.73572 | 290.748031 |
| SQSTM1 | 909.451249 | 3009.89967 | 1593.72776 | 3670.86036 | 363.670338 | 585.549447 | 685.177796 | 833.045379 | 177.778583 | 247.517286 | 302.702438 | 515.030956 |
| IGFBP7 | 2.58560797 | 70.5386319 | 1.9533636 | 44.8948736 | 1.50588328 | 14.4875455 | 4.08745949 | 50.4400381 | 0 | 0 | 0 | 0 |
| KLF6 | 115.367527 | 611.183122 | 674.62049 | 1017.49685 | 379.892668 | 335.770395 | 341.143824 | 433.283501 | 330.780872 | 469.663281 | 440.929288 | 576.88761 |
| IFNAR1 | 269.764237 | 463.949395 | 257.128506 | 488.077887 | 255.442188 | 248.605599 | 250.269942 | 255.680366 | 360.934332 | 365.60462 | 411.095564 | 393.405889 |
| PSEN1 | 150.38616 | 366.403542 | 303.4057 | 473.321149 | 119.869364 | 167.432565 | 137.137162 | 197.089493 | 108.729349 | 145.495529 | 143.784557 | 161.50584 |
| TAPBP | 39.2220015 | 237.818838 | 141.90645 | 274.627628 | 57.739821 | 125.059056 | 64.8429101 | 137.6853 | 19.6780113 | 52.4849315 | 42.6871912 | 52.3937777 |
| IRF1 | 4.328419 | 77.3100619 | 37.4924101 | 107.846398 | 13.3365927 | 45.9966414 | 24.4531182 | 49.1955287 | 2.79647322 | 12.9628886 | 12.2124718 | 26.1781021 |
| IL1R1 | 13.5958825 | 50.8099649 | 25.5600582 | 73.9337198 | 23.1232665 | 31.5126854 | 18.2785526 | 34.3502506 | 268.600478 | 301.433461 | 311.330229 | 374.543401 |
| NAMPT | 15.6222186 | 25.6186789 | 33.8149505 | 42.1562583 | 20.655741 | 23.8238976 | 20.9433438 | 20.9676635 | 49.8640467 | 30.5777686 | 45.8481304 | 90.0341772 |
| CXCL10 | 0 | 44.9855507 | 19.9772479 | 122.518736 | 0.41771682 | 4.94063564 | 4.56963815 | 18.1179397 | 0.39893884 | 3.80091071 | 6.19450629 | 8.13380541 |
| IL15RA | 28.3710641 | 93.3038987 | 61.2389863 | 163.636414 | 4.72102405 | 17.9005179 | 8.73709267 | 28.5108239 | 1.42383028 | 2.57278954 | 2.39010438 | 2.97742661 |
| IFNGR1 | 16.5450504 | 40.6921085 | 25.4030546 | 87.8305112 | 12.8224807 | 22.3066686 | 16.5096604 | 31.7848217 | 19.8130299 | 29.2558176 | 27.3374474 | 37.8389998 |
| TNFRSF9 | 0.20834111 | 4.15255312 | 1.64891691 | 9.42424245 | 2.59709946 | 17.7622777 | 9.58126938 | 54.7952689 | 0.81322946 | 0.80152617 | 0.51192108 | 3.95383829 |
| HLA-C | 179.242986 | 1666.44077 | 663.305358 | 2716.76562 | 237.908009 | 813.314167 | 534.02949 | 1102.58433 | 17.0072813 | 90.9673736 | 110.192846 | 103.115609 |
| HLA-B | 68.9902358 | 1930.85572 | 545.321787 | 3378.26804 | 327.598713 | 1463.24413 | 1043.98936 | 2452.98399 | 24.5063945 | 194.662605 | 254.669114 | 279.791606 |
| HLA-A | 107.523643 | 534.565965 | 245.669682 | 840.795891 | 302.288333 | 678.628092 | 586.254241 | 936.756384 | 62.4531496 | 112.629659 | 142.709896 | 130.116771 |
| TNFAIP2 | 17.9774339 | 955.590677 | 725.691164 | 1334.63225 | 342.089625 | 1571.05303 | 614.025154 | 1990.47625 | 57.9605131 | 139.312955 | 139.058529 | 251.697305 |
| TAP1 | 16.9166097 | 169.005645 | 54.9985911 | 310.636145 | 42.4500196 | 114.145257 | 64.4782774 | 171.142414 | 9.53561134 | 22.859293 | 21.9965763 | 32.5155308 |
| TNFAIP3 | 15.5434345 | 238.517571 | 130.093883 | 395.177488 | 59.1193321 | 157.246851 | 81.1463535 | 246.607421 | 20.0587587 | 45.0318725 | 32.7361981 | 86.8041854 |
| ATF3 | 34.7614079 | 100.991313 | 53.4130041 | 180.102541 | 19.3845174 | 61.8821219 | 36.6915063 | 90.5819477 | 37.2561944 | 35.1333673 | 35.3234581 | 92.6959381 |
| IFIT2 | 1.186571 | 148.995962 | 89.7664671 | 208.771056 | 96.5621442 | 265.386245 | 203.311571 | 438.802819 | 9.23333602 | 23.1045604 | 31.318742 | 38.2414564 |
| GADD45A | 25.9773233 | 93.6785172 | 28.3250779 | 152.894537 | 24.2443287 | 65.4364013 | 70.5605891 | 154.336309 | 77.3557348 | 24.6242662 | 54.6171204 | 147.552784 |
| RCAN1 | 120.191987 | 111.795035 | 116.745566 | 141.080324 | 115.986036 | 295.791364 | 203.440291 | 488.762719 | 494.694802 | 1277.76657 | 2085.01055 | 2066.77076 |
| FOSL2 | 106.701396 | 318.500032 | 270.656953 | 379.223545 | 242.492584 | 464.582038 | 243.202421 | 521.454674 | 234.377077 | 364.351158 | 383.249133 | 312.042643 |

| Figure 18 (Contd) | | | | | | | | | | | | |
|---|---|---|---|---|---|---|---|---|---|---|---|---|
| BIRC2 | 100.772156 | 140.504036 | 155.514388 | 186.548383 | 232.684174 | 359.83082 | 304.264426 | 471.539418 | 261.816416 | 243.917866 | 268.529829 | 292.312217 |
| NINJ1 | 14.2825069 | 21.9737648 | 34.3167449 | 44.8147424 | 18.2791053 | 22.9532164 | 20.076443 | 29.787945 | 16.1145132 | 19.251645 | 15.2159251 | 30.0598643 |
| PNRC1 | 48.6070534 | 221.163147 | 225.027008 | 229.404509 | 28.1938375 | 71.6348134 | 38.1027181 | 113.227435 | 27.5971811 | 63.466728 | 71.6602941 | 85.3620182 |
| KDM6B | 26.561765 | 78.3094661 | 96.7504691 | 102.924622 | 41.1624151 | 66.1464508 | 28.6296667 | 65.2791825 | 29.808005 | 91.9691497 | 70.1606228 | 172.769908 |
| DNAJB4 | 32.3664172 | 81.4102788 | 33.868349 | 93.7045625 | 23.0347276 | 37.8477585 | 27.5045028 | 67.1511002 | 29.3323041 | 32.9705974 | 42.9453779 | 25.0692889 |
| STAT1 | 191.759295 | 626.302717 | 249.347642 | 774.705785 | 289.085239 | 372.580697 | 280.216001 | 366.651651 | 229.504762 | 265.258376 | 305.275451 | 263.022297 |
| ISG15 | 9.39146638 | 605.921452 | 383.536683 | 656.703008 | 315.168807 | 933.077038 | 737.466329 | 889.754159 | 30.7929165 | 100.154246 | 106.05752 | 136.948538 |
| XAF1 | 0 | 17.0835934 | 1.23338912 | 26.1456929 | 3.10274741 | 20.8782762 | 11.2620911 | 32.6775306 | 0 | 0.37685448 | 0 | 0.2998356 |
| MX1 | 22.0825172 | 233.16831 | 111.975268 | 338.726318 | 5.15732259 | 33.5034276 | 8.05983422 | 47.5346261 | 1.84705543 | 3.6409484 | 3.875686 | 3.21870757 |
| IFIT3 | 1.39111096 | 171.080572 | 111.908885 | 220.97918 | 94.7962795 | 275.950048 | 191.463445 | 404.001549 | 7.26784736 | 30.3203285 | 43.3052011 | 39.2071079 |
| B2M | 317.475044 | 1390.10444 | 610.894086 | 1816.38401 | 495.722448 | 1362.02417 | 1123.34762 | 2187.25416 | 178.268671 | 378.548238 | 399.394979 | 480.949233 |
| STAT3 | 24.1849891 | 72.9789407 | 43.8645105 | 79.6223094 | 50.6451224 | 108.632935 | 42.0584172 | 84.9704188 | 24.9743461 | 65.5991124 | 68.697091 | 46.4580611 |

Figure 19 (contd.)
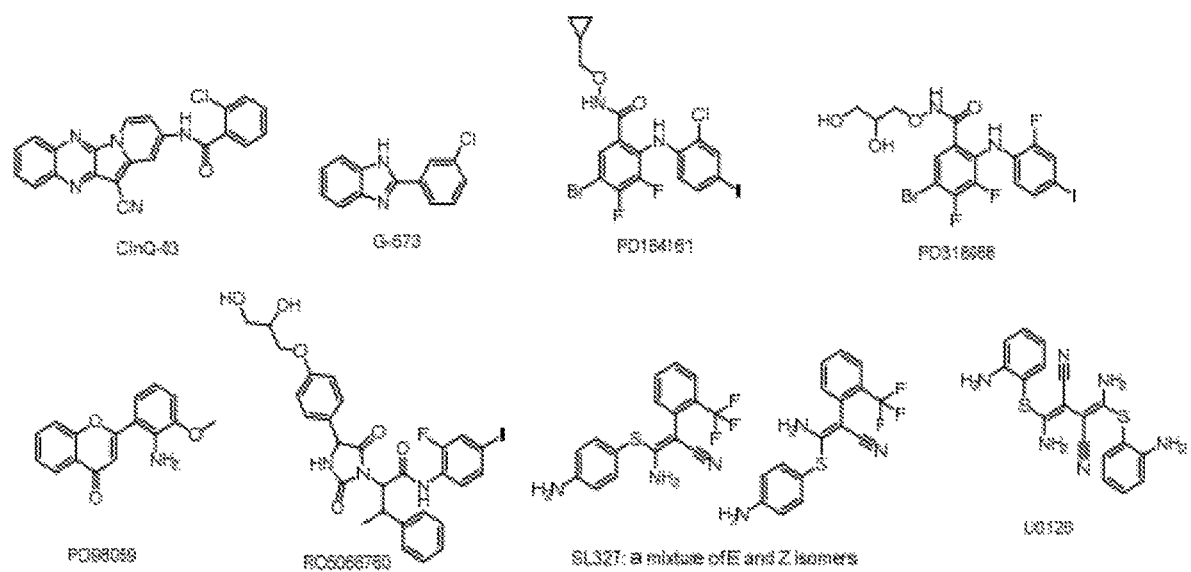

(1) Vehicle
(2) Gem
(3) Combo
(4) Combo + Gem
(5) Combo + Gem + DC101

PR-07 PDX

PR-05 PDX

M1 markers

M2 markers

FIGURE 32(A)

Vessel density

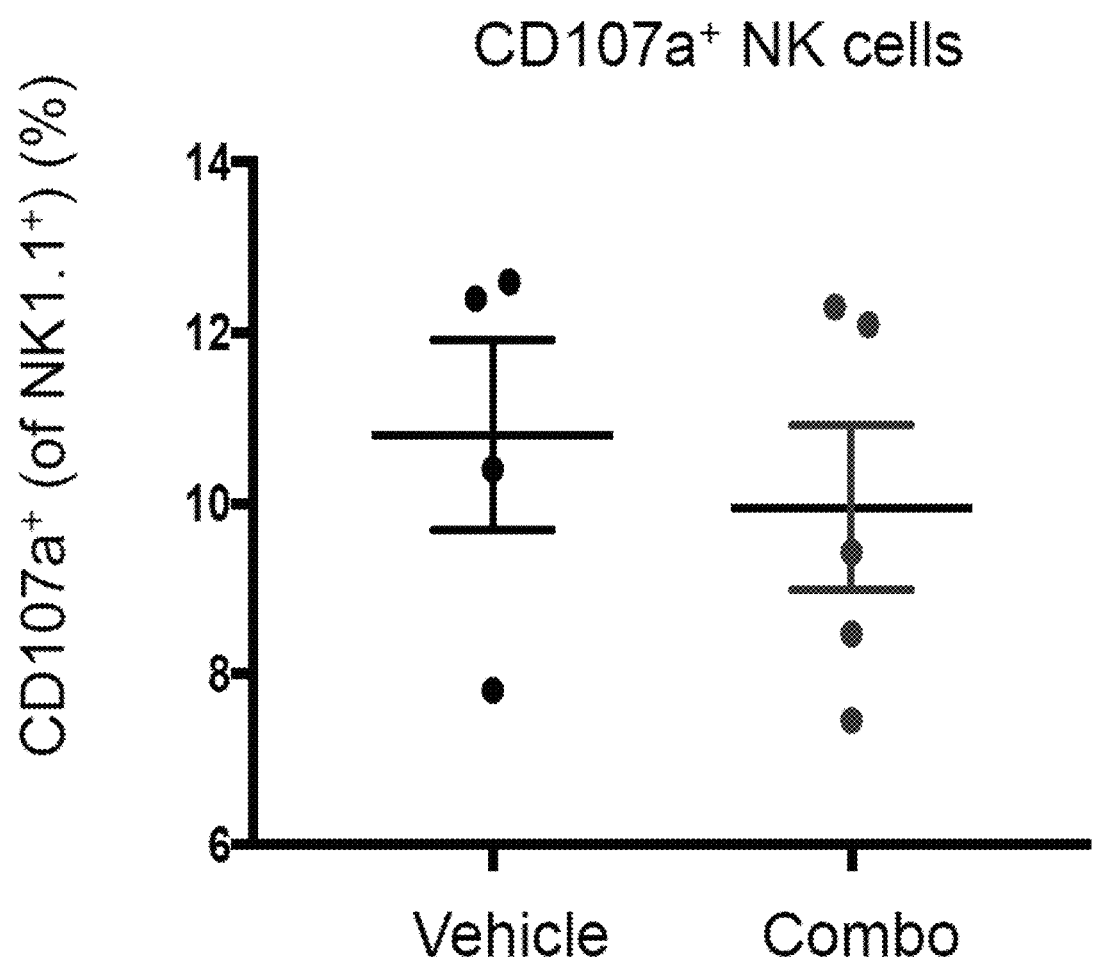

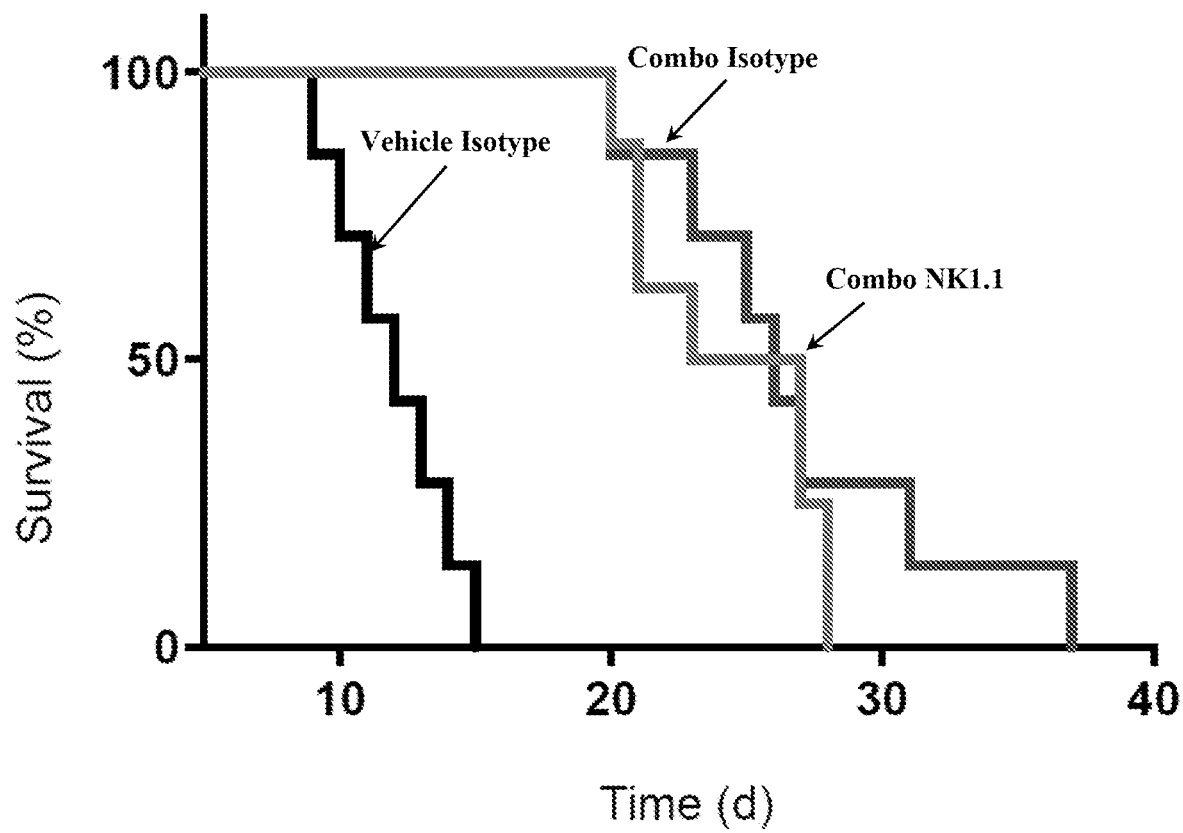

MHCII (tumor cells)

MHCII (endothelial cells)

CDK4/6 inhibitors act synergistically with MEK inhibitor trametinib in KRAS mutant human lung cancer cells

COMBINATION THERAPY WITH MEK INHIBITOR AND CDK4/6 INHIBITOR TO TREAT PANCREATIC CANCER

CROSS-REFERENCE TO RELATED APPLICATIONS

This application is a US National Stage Application under 35 U.S.C. § 371 of International Application No. PCT/US2019/040647, filed on Jul. 3, 2019, which claims the benefit of and priority to U.S. Provisional Appl. No. 62/694,519, filed Jul. 6, 2018, the disclosure of each of which is incorporated by reference herein in its entirety.

STATEMENT OF GOVERNMENT SUPPORT

This invention was made with government support under CA013106, and CA129243, awarded by the National Institutes of Health. The government has certain rights in the invention.

TECHNICAL FIELD

The present technology relates to methods for treating pancreatic cancer using a MEK inhibitor and a CDK4/6 inhibitor. Kits for use in practicing the methods are also provided.

BACKGROUND

The following description of the background of the present technology is provided simply as an aid in understanding the present technology and is not admitted to describe or constitute prior art to the present technology.

Pancreatic cancer was the 12$^{th}$ most common type of cancer in the U.S. in 2014, representing about 2.8% of all new cancer cases. However, pancreatic cancer was the 4$^{th}$ most common cause of cancer-related deaths (Schneider G et al., *Gastroenterology* 128(6):1606-1625 (2005)). In 2014, about 46,420 new cases and 39,590 deaths were attributable to pancreatic cancer in the United States, of which pancreatic ductal adenocarcinoma (PDAC) represents the vast majority. The fact that the annual number of pancreatic cancer-related deaths nearly equals the annual number of new pancreatic cancer cases highlights the lethality of this disease. PDAC, the most common malignancy of the pancreas, is both aggressive and difficult to treat. Complete surgical removal of the tumor remains the only chance for cure, however 80-90% of patients have disease that is surgically incurable at the time of clinical presentation deaths (Schneider G et al., *Gastroenterology* 128(6):1606-1625 (2005)). Accordingly, there is an urgent need for effective therapies for pancreatic cancer.

SUMMARY OF THE PRESENT TECHNOLOGY

In one aspect, the present disclosure provides a method for preventing or treating pancreatic cancer in a subject in need thereof comprising administering an effective amount of a MEK inhibitor and an effective amount of a CDK4/6 inhibitor. The pancreatic cancer may be an exocrine pancreatic cancer or an endocrine pancreatic cancer. Examples of pancreatic cancers include, but are not limited to PDAC, acinar cell carcinoma, solid pseudopapillary neoplasms, pancreatoblastoma, pancreatic neuroendocrine tumors (PNETs), gastrinomas, insulinomas, glucagonomas, somatostatinomas and VIPomas. Additionally or alternatively, in some embodiments, the pancreatic cancer comprises a KRAS mutation such as G12D, G12V, G12C, G12R, G12A, G13D, Q61L, Q61H etc. In certain embodiments, the subject is human. Additionally or alternatively, in some embodiments, the subject is non-responsive to at least one prior line of cancer therapy such as chemotherapy or immunotherapy.

Examples of MEK inhibitors include trametinib, cobimetinib, binimetinib, selumetinib, PD-325901, TAK-733, CI-1040 (PD184352), PD0325901, MEK162, AZD8330, GDC-0623, refametinib, pimasertib, RO4987655, RO5126766, WX-554, HL-085, CInQ-03, G-573, PD184161, PD318088, PD98059, RO5068760, U0126, and SL327. Examples of CDK4/6 inhibitors include palbociclib, ribociclib, and abemaciclib.

Additionally or alternatively, in some embodiments, the subject exhibits an increase in one or more of (a) NK cell immune surveillance, (b) senescent tumor cell clearance, or (c) vascular re-normalization after administration of the MEK inhibitor and the CDK4/6 inhibitor. In any of the above embodiments, the subject exhibits a delay in metastatic onset and/or tumor growth after administration of the MEK inhibitor and the CDK4/6 inhibitor compared to that observed in an untreated control subject diagnosed with pancreatic cancer. Additionally or alternatively, in some embodiments of the combination therapy methods disclosed herein, the time to response and/or duration of response is improved relative to that observed with MEK inhibitor monotherapy or CDK4/6 inhibitor monotherapy.

In one aspect, the present disclosure provides a method for increasing the efficacy of at least one chemotherapeutic agent in a patient with pancreatic cancer comprising administering to the patient an effective amount of a MEK inhibitor and an effective amount of a CDK4/6 inhibitor. Examples of chemotherapeutic agents include abraxane, capecitabine, erlotinib, fluorouracil (5-FU), gemcitabine, irinotecan, leucovorin, nab-paclitaxel, cisplatin, irinotecan, docetaxel, oxaliplatin, tipifarnib, everolimus, sunitinib, dovitinib, ruxolitinib, pegylated-hyaluronidase, pemetrexed, folinic acid, paclitaxel, MK2206, GDC-0449, IPI-926, gamma secretase/RO4929097, M402, and LY293111.

In another aspect, the present disclosure provides a method for increasing the efficacy of at least one immunotherapeutic agent in a patient with pancreatic cancer comprising administering to the patient an effective amount of a MEK inhibitor and an effective amount of a CDK4/6 inhibitor. Examples of immunotherapeutic agents include immune checkpoint inhibitors (e.g., antibodies targeting CTLA-4, PD-1, PD-L1), ipilimumab, 90Y-Clivatuzumab tetraxetan, pembrolizumab, nivolumab, trastuzumab, cixutumumab, ganitumab, demcizumab, cetuximab, nimotuzumab, dalotuzumab, sipuleucel-T, CRS-207, and GVAX.

Examples of MEK inhibitors include trametinib, cobimetinib, binimetinib, selumetinib, PD-325901, TAK-733, CI-1040 (PD184352), PD0325901, MEK162, AZD8330, GDC-0623, refametinib, pimasertib, RO4987655, RO5126766, WX-554, HL-085, CInQ-03, G-573, PD184161, PD318088, PD98059, RO5068760, U0126, and SL327. Examples of CDK4/6 inhibitors include palbociclib, ribociclib, and abemaciclib.

Additionally or alternatively, in some embodiments of the methods disclosed herein, the pancreatic cancer is an exocrine pancreatic cancer or an endocrine pancreatic cancer. Examples of pancreatic cancers include, but are not limited to PDAC, acinar cell carcinoma, solid pseudopapillary neoplasms, pancreatoblastoma, pancreatic neuroendocrine tumors (PNETs), gastrinomas, insulinomas, glucagonomas, somatostatinomas and VIPomas. In certain embodiments, the pancreatic cancer comprises a KRAS mutation such as G12D, G12V, G12C, G12R, G12A, G13D, Q61L, Q61H etc. In some embodiments of the methods disclosed herein, the patient is human.

Additionally or alternatively, in some embodiments of the methods disclosed herein, the MEK inhibitor and the CDK4/6 inhibitor are administered sequentially, simultaneously, or separately. The MEK inhibitor and/or the CDK4/6 inhibitor may be administered orally, parenterally, by inhalation spray, intranasally, buccally, or via an implanted reservoir.

Also disclosed herein are kits comprising a MEK inhibitor, a CDK4/CDK6 inhibitor, and instructions for treating pancreatic cancer.

BRIEF DESCRIPTION OF THE DRAWINGS

FIG. 1(A) shows induction of cell surface (e.g., ICAM-1) and soluble (e.g., TNF-α) SASP factors which leads to NK cell immune surveillance, clearance of senescent tumor cells, and delays in metastatic onset and growth in pancreatic cancer lung metastases. FIG. 1(B) shows induction of pro-angiogenic SASP factors (e.g., VEGF) which leads to increased functional vasculature and enhanced sensitivity to cytotoxic chemotherapies in primary pancreas tumors.

FIG. 7(A) also shows the quantification of relative mean fluorescent intensity (MFI) from three biological replicates (right). One-way ANOVA. Error bars, mean±s.e.m. * $P<0.05$,  $P<0.01$, * $P<0.001$, **** $P<0.0001$.

FIG. 10(A) also shows the quantification of vessel density (number of CD31$^+$ blood vessels) (bottom). One-way ANOVA. Error bars, mean±s.e.m.  P<0.01,* P<0.001.

FIG. 18 shows exemplary RNA-seq data of SASP gene expression in 3 pancreatic cancer cell lines (PANC-1, PU-8988T, and MiaPaca2) following treatment with indicated drugs as described in FIG. 2(B). One biological replicates per cell line are shown. V=vehicle, T=trametinib, P=palbociclib, and C=combination.

FIG. 23(A): Percentage of CD4$^+$ T cells within the CD45$^+$ population. FIG. 23(B): Percentage of CD8$^+$ T cells within the CD45$^+$ population. Data represent the mean±SEM.

FIG. 23(D): Percentage of CD69$^+$ CD8$^+$ T cells. FIG. 23(E): Percentage of CD44$^+$ CD8$^+$ T cells. Data represent the mean±SEM.

FIG. 23(F): Percentage of CD4$^+$ T cells within the CD45$^+$ population. FIG. 23(G): Percentage of CD8$^+$ T cells within the CD45$^+$ population. FIG. 23(H): Percentage of CD69$^+$ CD8$^+$ T cells. FIG. 23(I) Percentage of CD44$^+$ CD8$^+$ T cells. Data represent the mean±SEM.

FIG. 24(A): Percentage of CD4$^+$ T cells within the CD45$^+$ population. FIG. 24(B): Percentage of CD8$^+$ T cells within the CD45$^+$ population. Data represent the mean±SEM.

FIG. 24(E): Percentage of CD44$^+$ CD8$^+$ T cells. Data represent the mean±SEM.

FIG. 25(D): Percentage of PD-1$^+$ CD8$^+$ T cells. FIG. 25(E): Percentage of PD-L1$^+$ CD45$^+$ immune cells. FIG. 25(F): Percentage of PD-L1$^+$ tumor cells. Data represent the mean±SEM. See also FIG. 36.

Figure 26A:
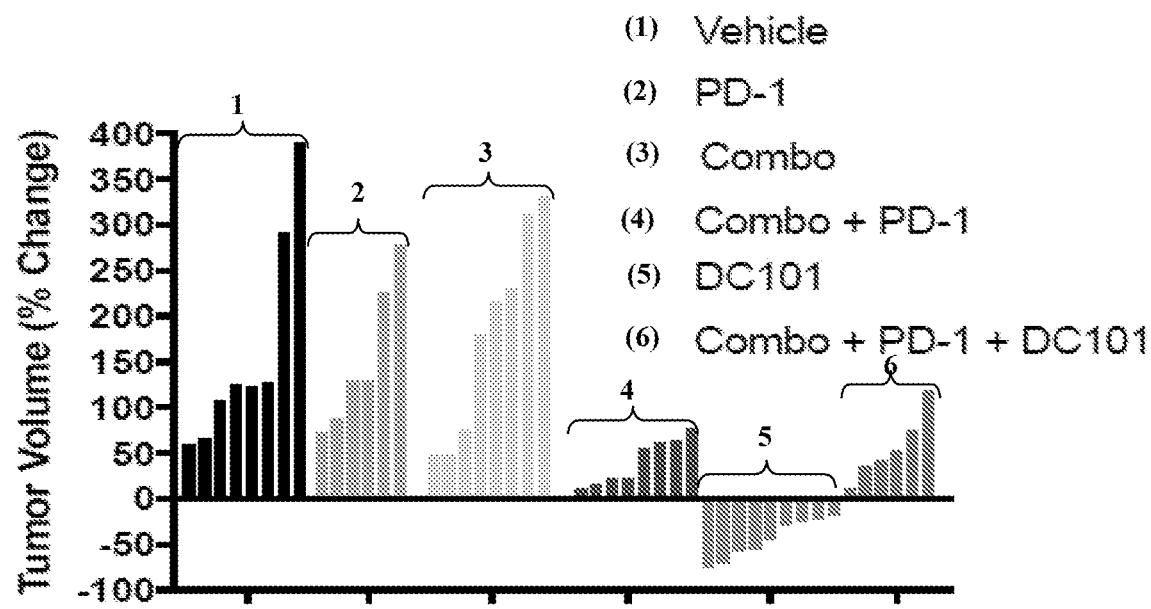
FIG. 26(A): A waterfall representation of the response of KPC$^{mut}$ PDAC organoid transplant tumors after 2 weeks of treatment with vehicle, trametinib (1 mg/kg body weight), palbociclib (100 mg/kg body weight), a PD-1 blocking antibody (RMP1-14; 200 μg per mouse), and/or a VEGFR2 blocking antibody (DC101; 800 μg per mouse) (n≥7 per group).
Figure 26B:
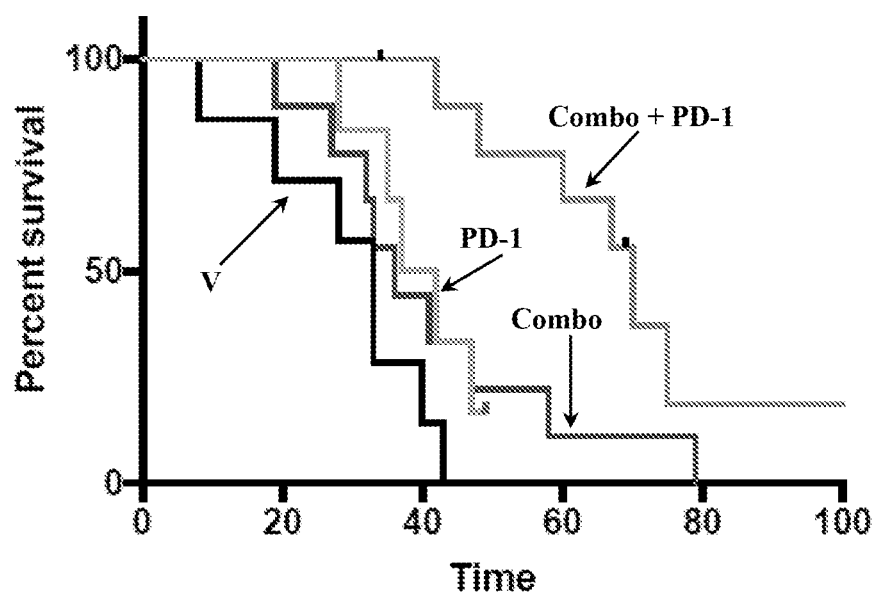
FIG. 26(B): Kaplan-Meier survival curve of KPC$^{mut}$ PDAC organoid transplant mice treated as in FIG. 26(A) (n≥7 per group) (log-rank test).
Figure 26C:
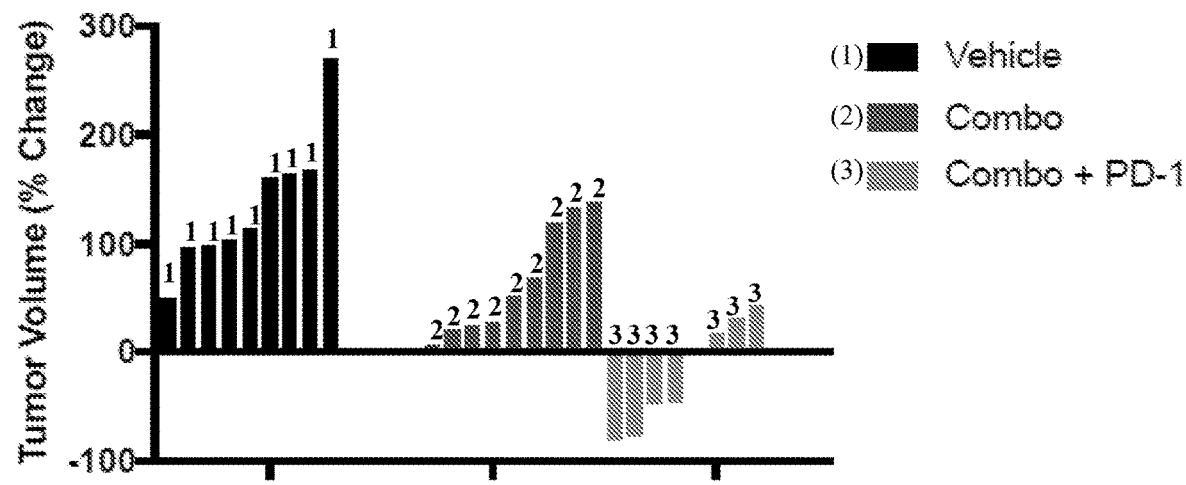
FIG. 26(C): A waterfall representation of the response of KPC GEMM PDAC tumors after 2 weeks of treatment with vehicle, trametinib (1 mg/kg body weight), palbociclib (100 mg/kg body weight), a PD-1 blocking antibody (RMP1-14; 200 µg per mouse), and/or a VEGFR2 blocking antibody (DC101; 800 µg per mouse) (n≥8 per group).
Figure 26D:
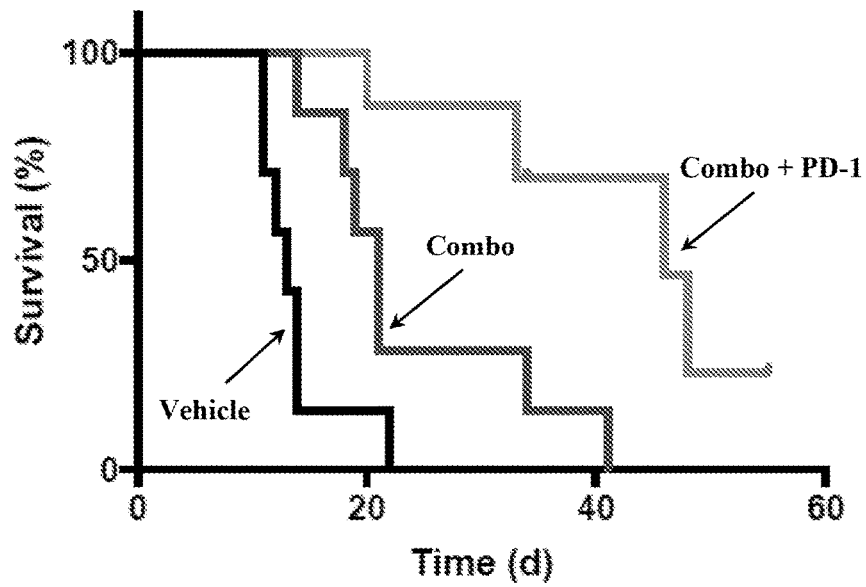

FIG. 26(D): Kaplan-Meier survival curve of KPC GEMM PDAC mice treated as in FIG. 26(C) (n≥5 per group) (log-rank test).

Figure 26E:
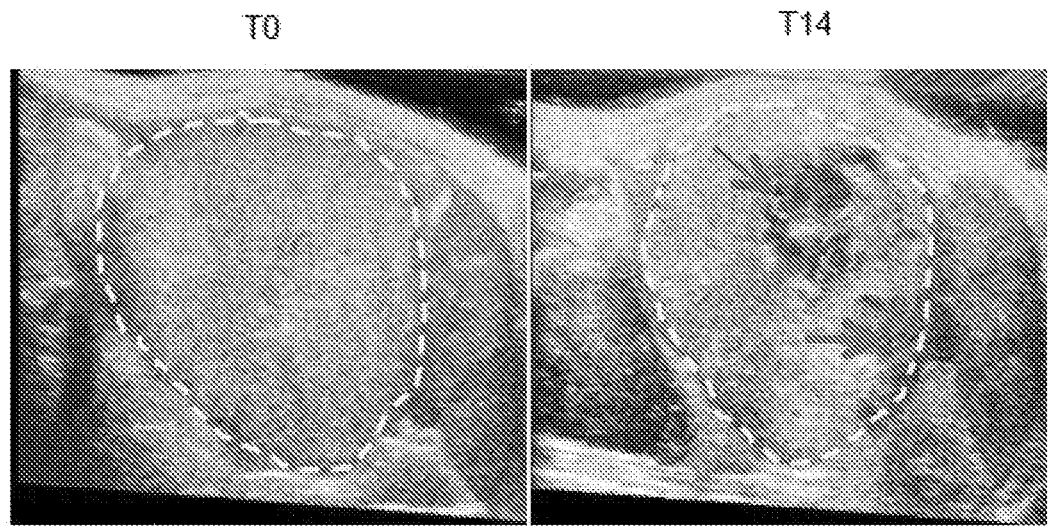

FIG. 26(E): Representative ultrasound images of a KPC$^{mut}$ PDAC organoid transplant tumor (dashed yellow line) at pretreatment (day 0) and after 2 week treatment (day 14) with trametinib (1 mg/kg body weight), palbociclib (100 mg/kg body weight), and a PD-1 blocking antibody (RMP1-14; 200 µg per mouse). Arrows point to areas of tumor necrosis.

Figure 26F:
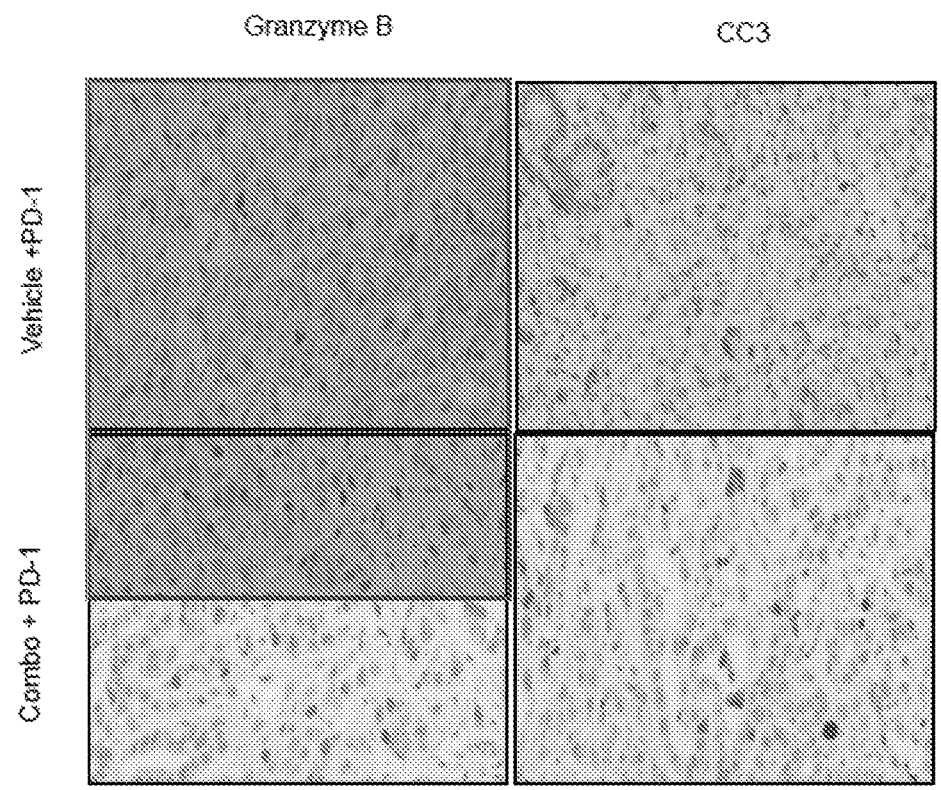

FIG. 26(F): Immunohistochemical staining of KPC$^{mut}$ PDAC organoid transplant tumors treated for 2 weeks with vehicle or combined trametinib (1 mg/kg body weight) and palbociclib (100 mg/kg body weight), followed by 4 day treatment with a PD-1 blocking antibody (RMP1-14; 200 µg per mouse).

Figure 26G:
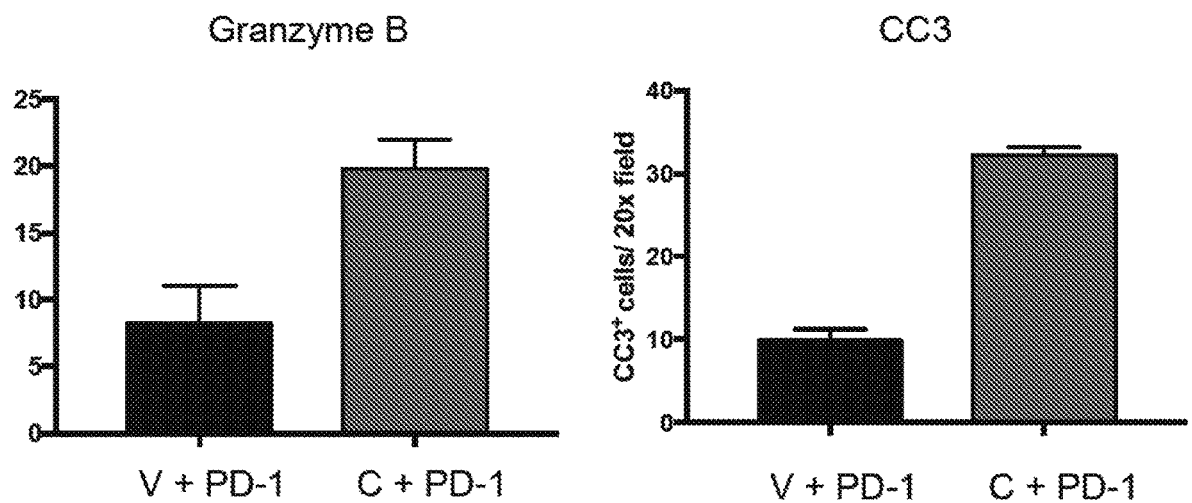

FIG. 26(G): Quantification of Granzyme B- and cleaved caspase-3-positive (CC3) cells per 20× field from samples treated in FIG. 26(F). See also FIG. 37.

Figure 27A:
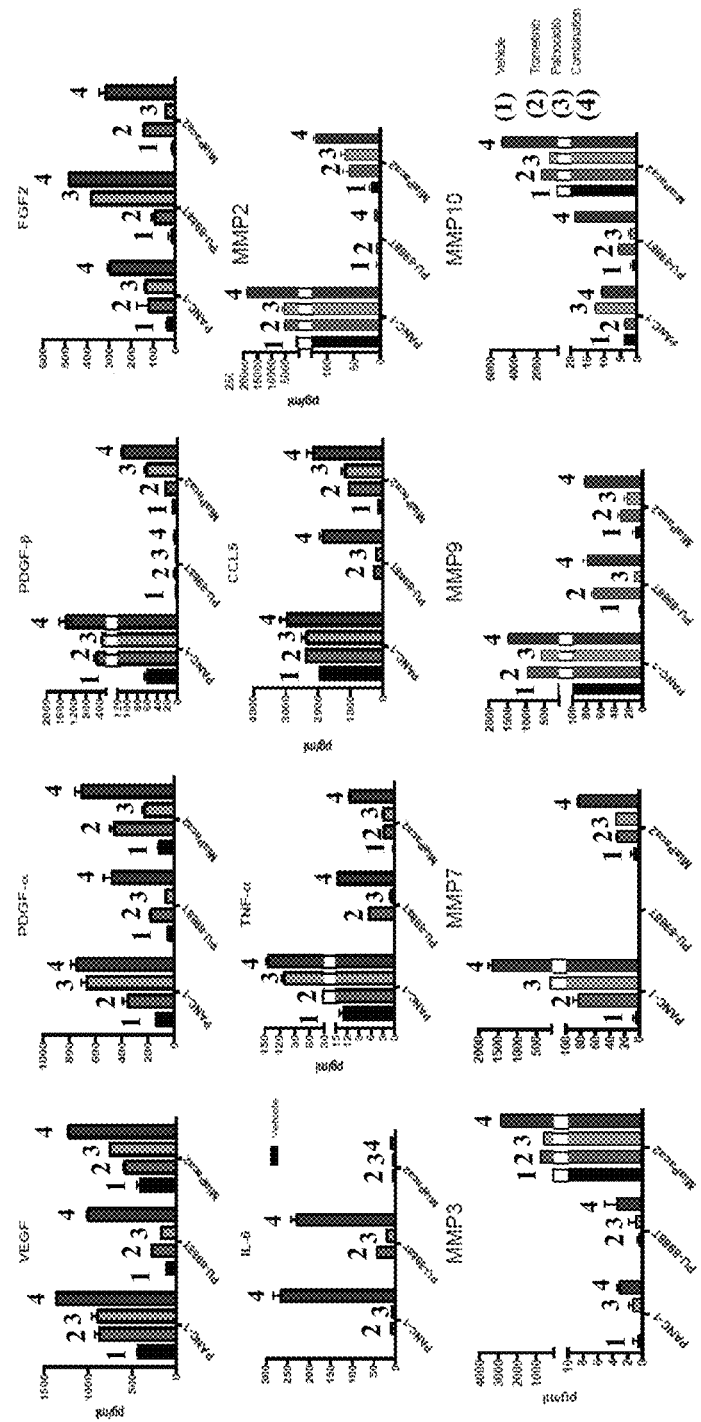

FIG. 27(A): Cytokine array results from conditioned media from human KRAS mutant PDAC cell lines (PANC-1, PU8988T, MiaPaCa2) treated for 8 days with trametinib (25 nM) and/or palbociclib (500 nM). Bars represent the mean±SEM.

Figure 27B:
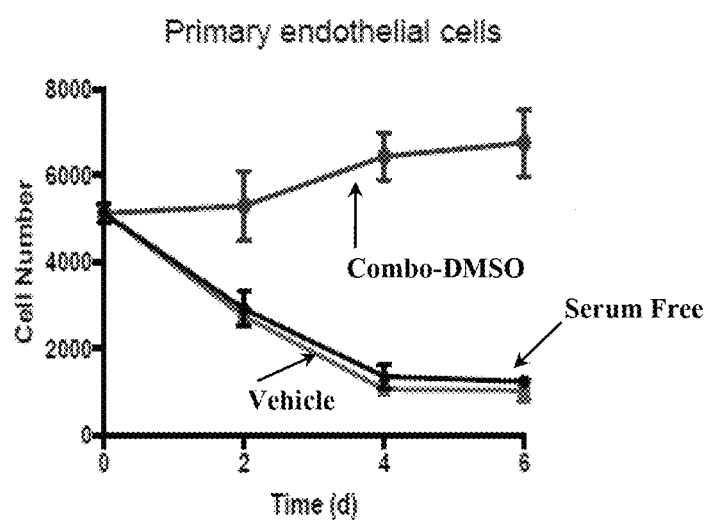
Figure 27:
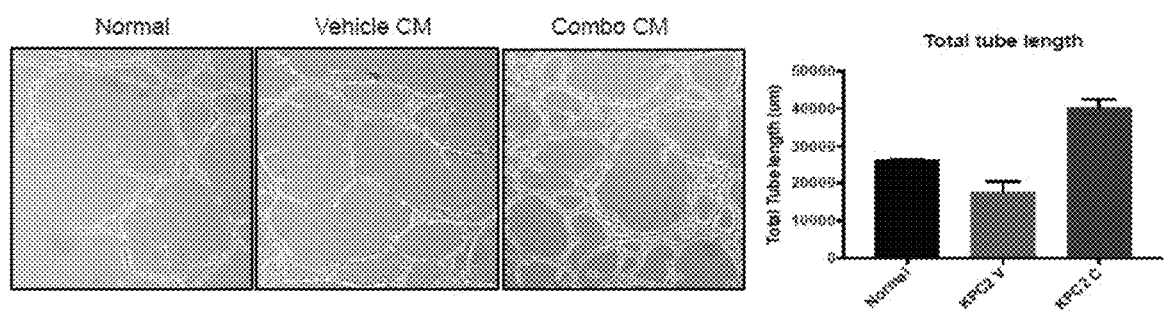

FIG. 27(B): Cell growth analysis of primary murine pancreatic endothelial cells cultured in serum-free media or conditioned media from KPC$^{mut}$ PDAC tumor cells treated for 8 days as in FIG. 27(A). Data represent the mean±SEM.

FIG. 27(C): Endothelial tube formation analysis of 3B-11 cells plated on basement membrane extract and cultured with serum-free media or conditioned media from KPC$^{mut}$ PDAC tumor cells treated for 8 days with vehicle or combined trametinib (25 nM) and/or palbociclib (500 nM). (scale bar, µm). Right, quantification of total tube length. Bars represent the mean±SEM.

Figures 28A, 28B:
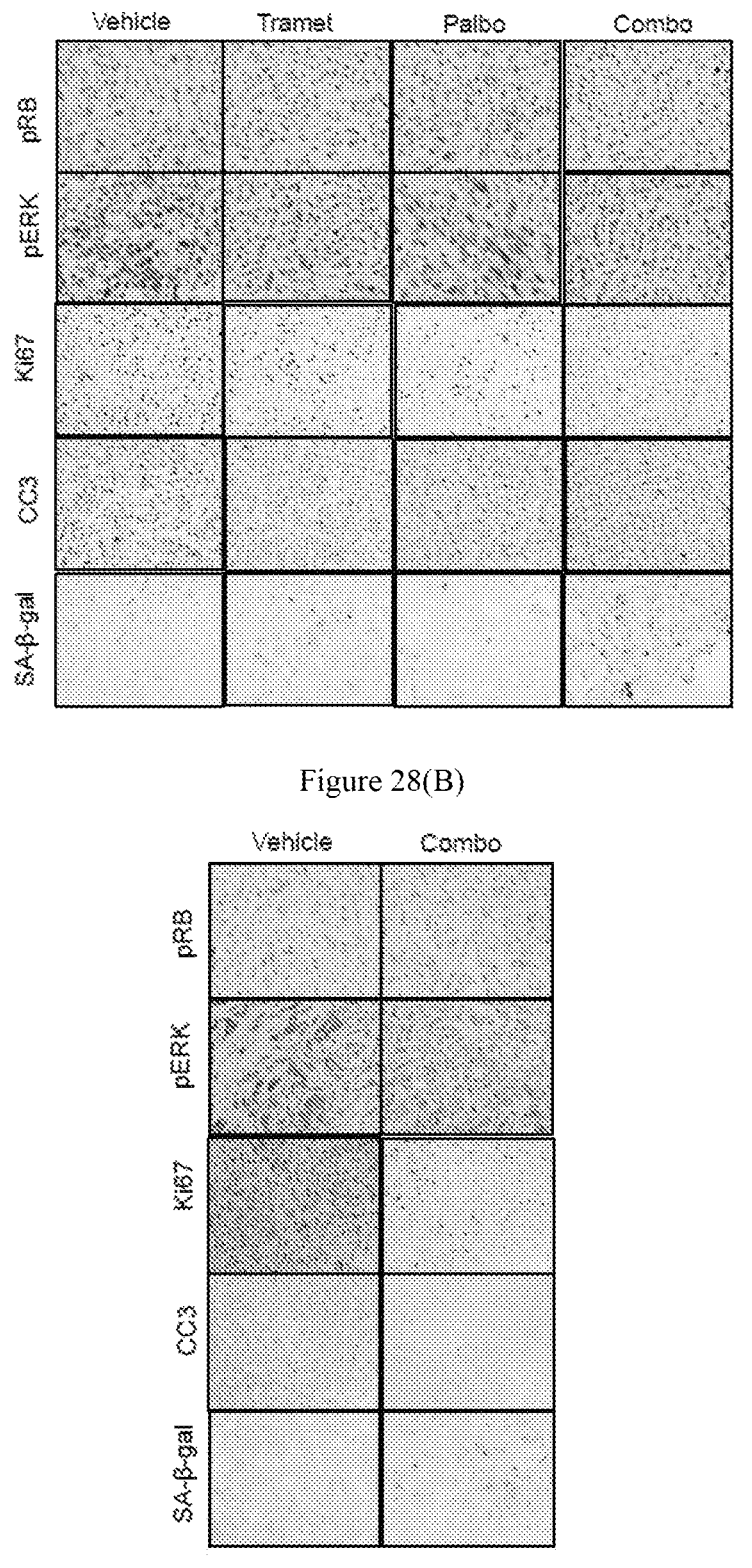

FIG. 28(A): Immunohistochemical staining of KPC$^{mut}$ PDAC organoid transplant tumors treated with vehicle, trametinib (1 mg/kg body weight), palbociclib (100 mg/kg body weight), or both for 2 weeks (scale bar, µm).

FIG. 28(B): Immunohistochemical staining of KPC PDAC GEMM tumors treated with vehicle or combined trametinib (1 mg/kg body weight) and palbociclib (100 mg/kg body weight) for 2 weeks (scale bar, µm).

Figure 28C:
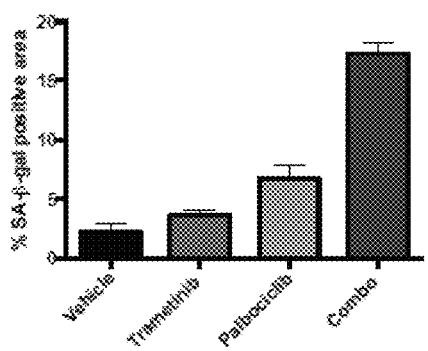
Figure 28C:
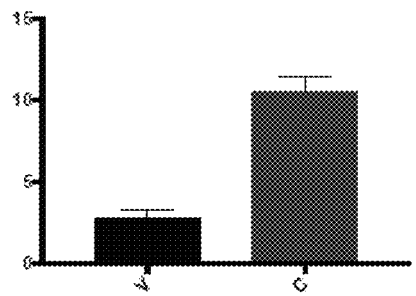

FIG. 28(C): Quantification of SA-β-gal positive staining in KPC$^{mut}$ PDAC organoid transplant (top) and KPC GEMM (bottom) tumors following treatment as in FIG. 28(A). Mean of three biological replicates is plotted.

Figure 28D:
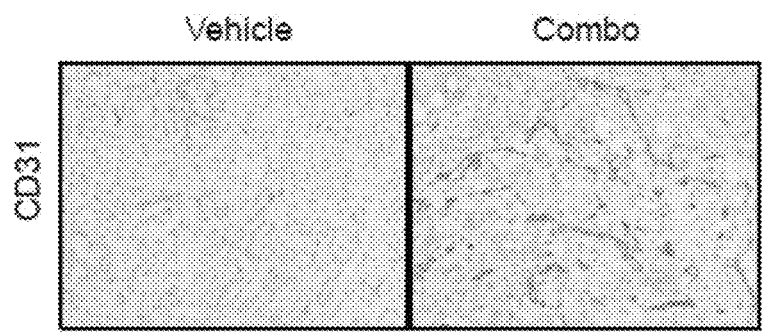

FIG. 28(D): CD31 immunohistochemical staining of KPC GEMM PDAC tumors treated with vehicle or combined trametinib (1 mg/kg body weight) and palbociclib (100 mg/kg body weight) for 2 weeks (scale bar, µm). Arrowhead, collapsed vessel; Arrow, visible vessel lumen.

Figure 28E:
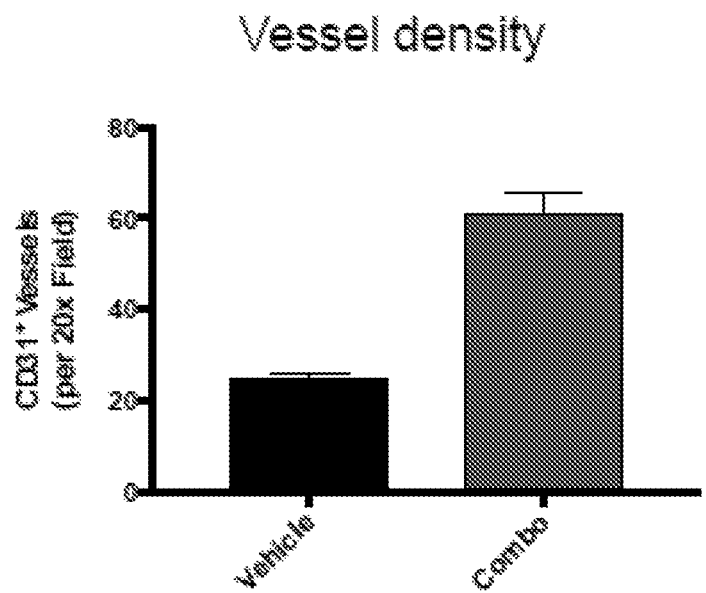

FIG. 28(E): Quantification of number of CD31$^+$ blood vessels per 20× field in KPC GEMM PDAC tumors following treatment as in FIG. 28(D). Bars represent the mean±SEM.

Figure 28F:
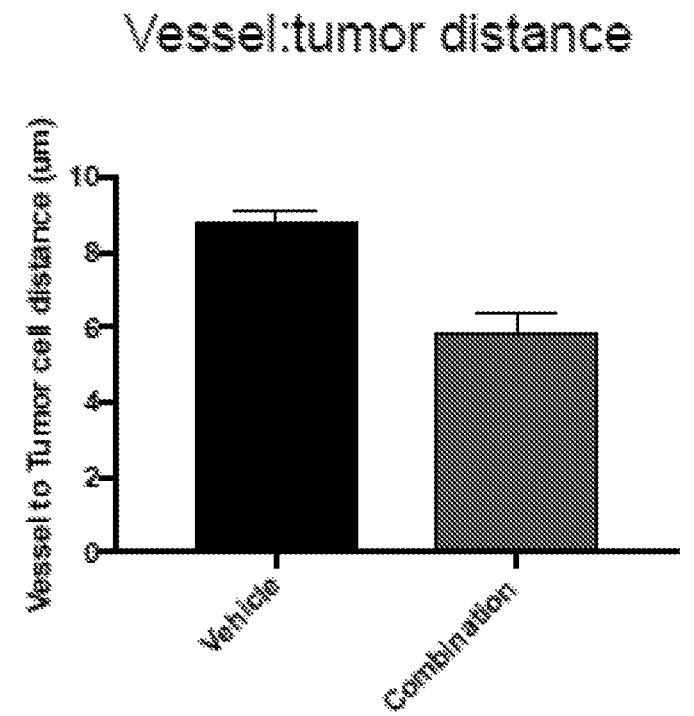

FIG. 28(F): Quantification of the average distance between a CD31$^+$ blood vessel and the 4 nearest tumor cells in KPC GEMM PDAC tumors following treatment as in FIG. 28(D). Bars represent the mean±SEM.

Figure 28G:
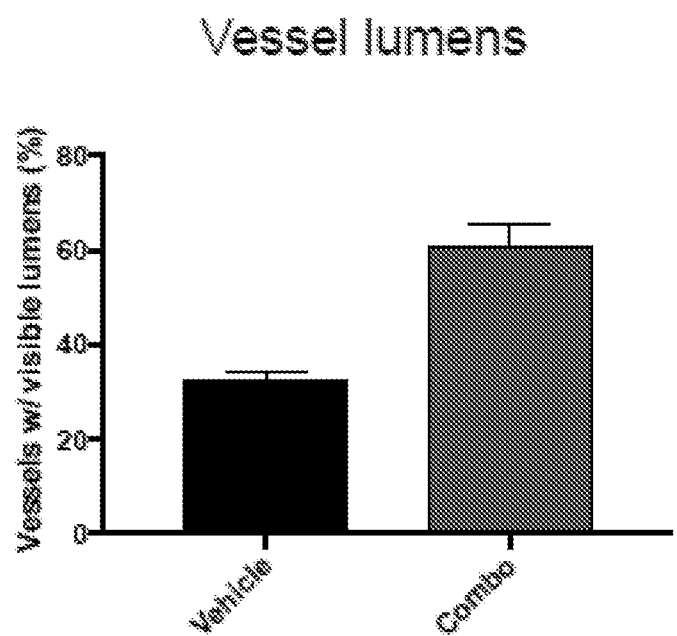

FIG. 28(G): Quantification of the percentage of CD31$^+$ blood vessels with visible/discernible lumens (see arrows in D) in KPC$^{mut}$ PDAC organoid transplant tumors following treatment in FIG. 28(D). Bars represent the mean±SEM.

Figure 28H:
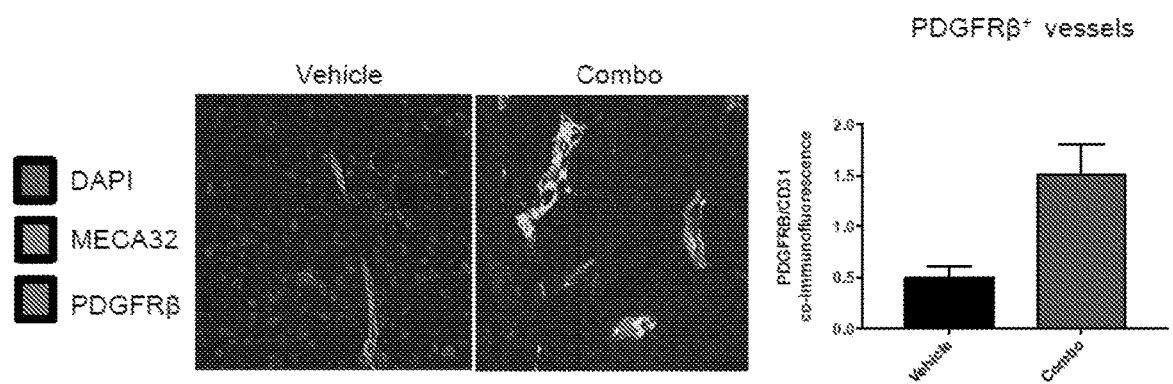

FIG. 28(H): Immunofluorescent images of PDGFRβ (green) co-localization with MECA32$^+$ blood vessels (red) in KPC GEMM PDAC tumors treated with vehicle or combined trametinib (1 mg/kg body weight) and palbociclib (100 mg/kg body weight) for 2 weeks (scale bar, µm) (left). Right, quantification of PDGFRβ/MECA32 co-immunofluorescence. Bars represent the mean±SEM.

Figure 28I:
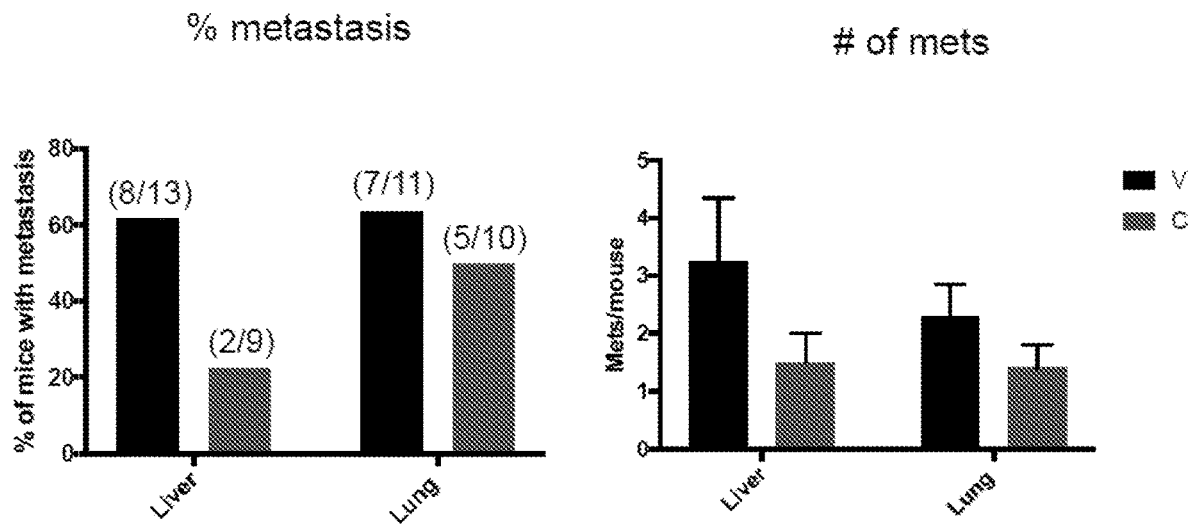

FIG. 28(I): Quantification of metastatic burden in the lungs and liver of KPC GEMM mice at endpoint following treatment with vehicle or combined trametinib (1 mg/kg body weight) and palbociclib (100 mg/kg body weight). Bars represent the mean±SEM.

Figure 29A:
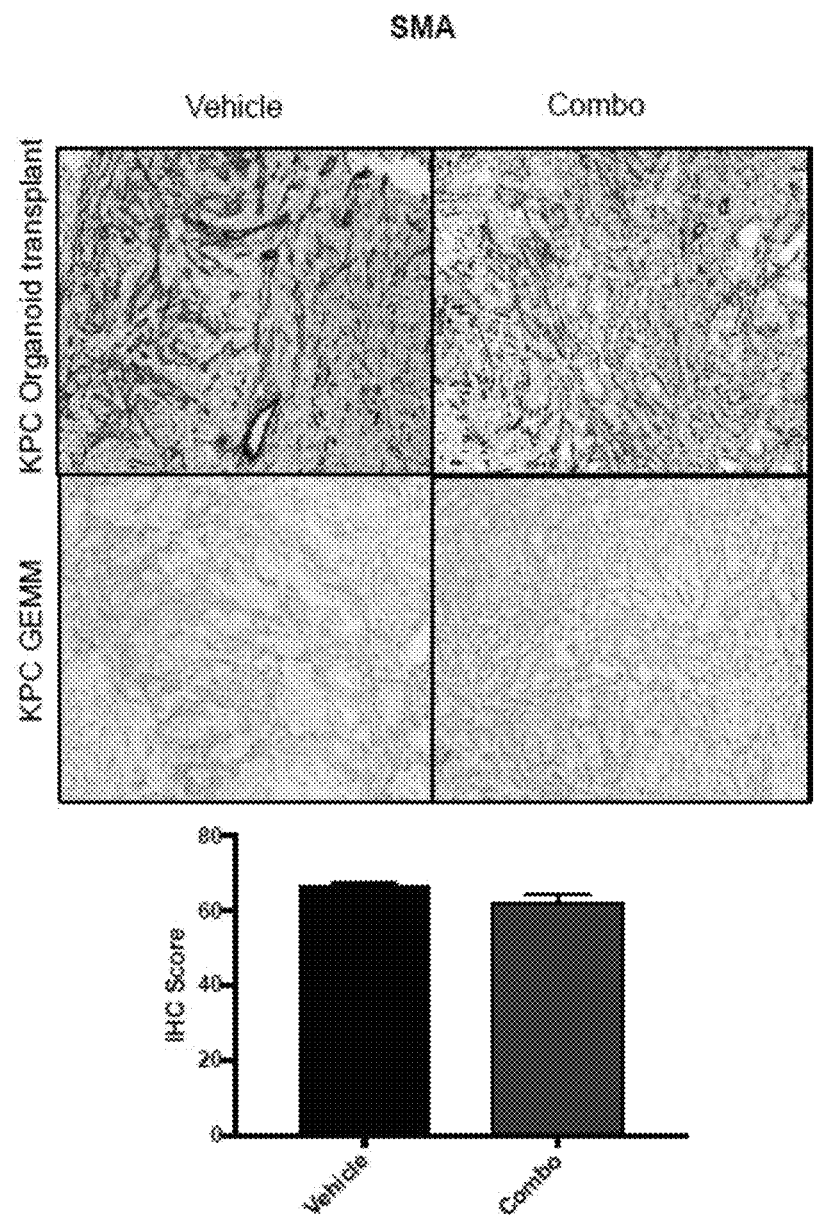
Figure 29B:
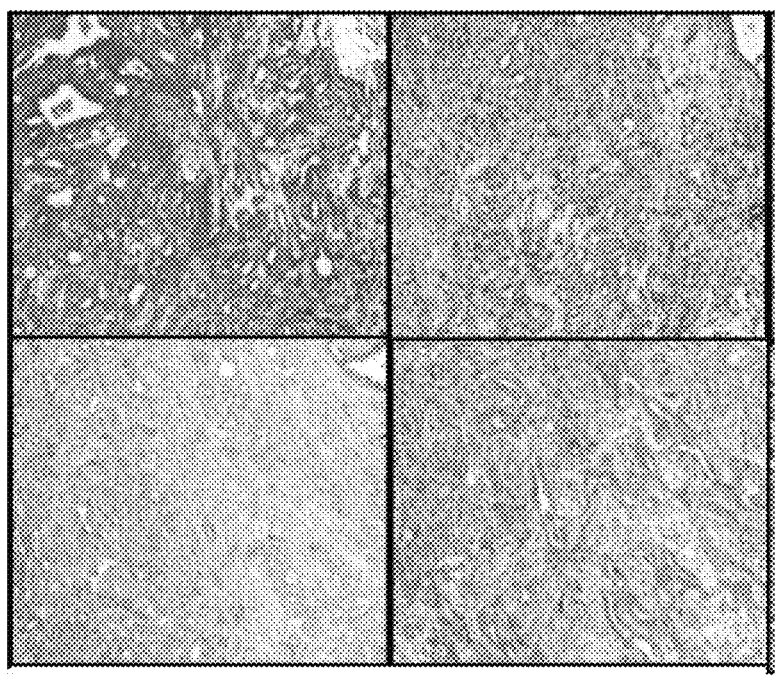
Figure 29B:
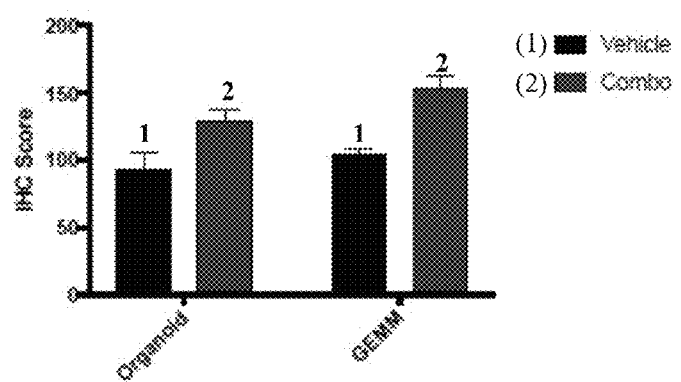
Figure 29C:
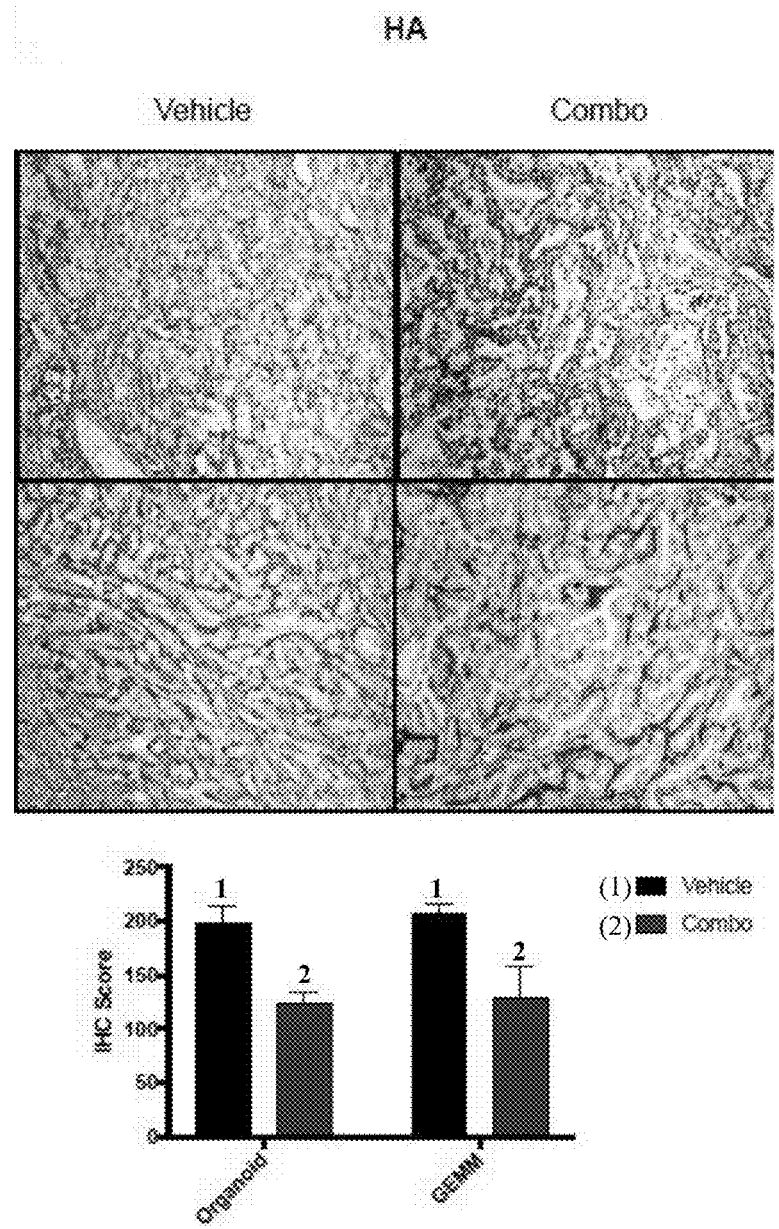

FIGS. 29(A)-29(C): Immunohistochemical staining of KPC$^{mut}$ PDAC organoid transplant (top) and KPC GEMM tumors (bottom) treated with vehicle, trametinib (1 mg/kg body weight), palbociclib (100 mg/kg body weight), or both for 2 weeks (scale bar, µm). Below, quantification of staining intensity of αSMA, collagen, and hyaluronic acid (HA) in the PDAC tumor microenvironment (TME). Bars represent the mean±SEM.

Figure 29D:
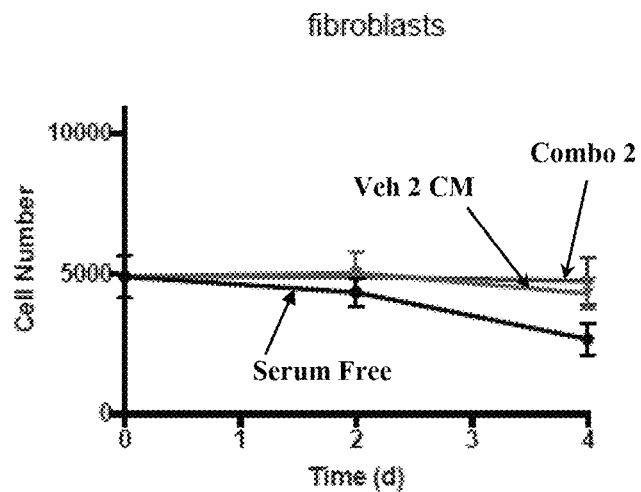

FIG. 29(D): Cell growth analysis of primary murine pancreatic stellate cells cultured in serum-free media or conditioned media from KPC$^{mut}$ PDAC tumor cells treated for 8 days with vehicle or combined trametinib (25 nM) and palbociclib (500 nM). Data represent the mean±SEM.

Figure 29E:
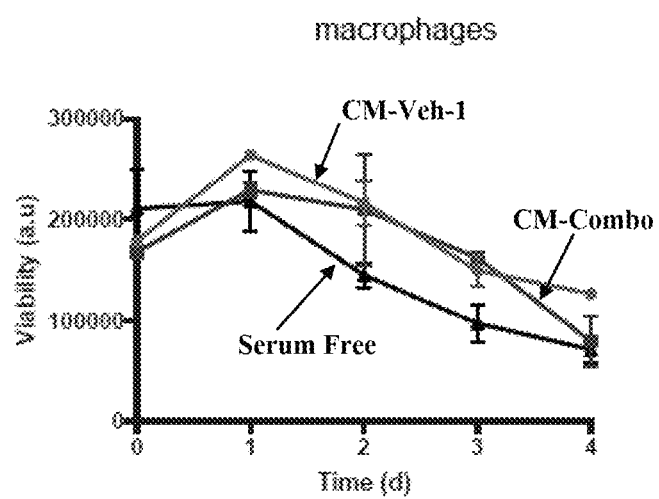

FIG. 29(E): Cell growth analysis of murine bone marrow-derived macrophages cultured in serum-free media or conditioned media from KPC$^{mut}$ PDAC tumor cells treated for 8 days with vehicle or combined trametinib (25 nM) and palbociclib (500 nM). Data represent the mean±SEM.

Figure 29F:
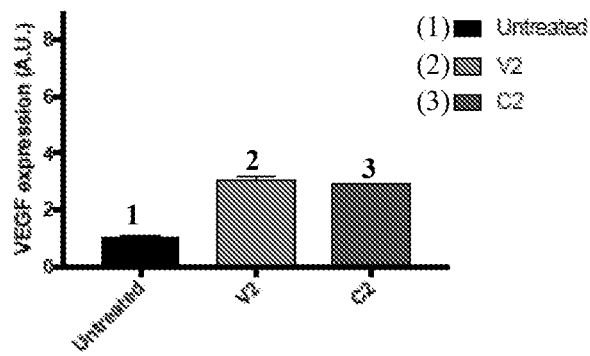

FIG. 29(F): qRT-PCR analysis of Vegfa gene expression in murine bone marrow-derived macrophages cultured in serum-free media or conditioned media from KPC$^{mut}$ PDAC tumor cells treated for 8 days with vehicle or combined trametinib (25 nM) and palbociclib (500 nM). Bars presented as mean of three biological replicates.

Figure 29G:
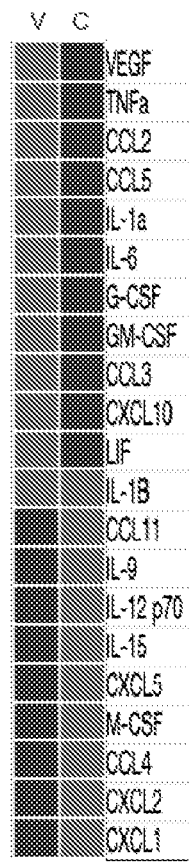

FIG. 29(G): Heat map of cytokine array results from primary murine pancreatic stellate cells cultured in serum-free media or conditioned media from KPC$^{mut}$ PDAC tumor cells treated for 8 days with vehicle or combined trametinib (25 nM) and palbociclib (500 nM). Data presented as mean of three biological replicates.

Figure 29H:
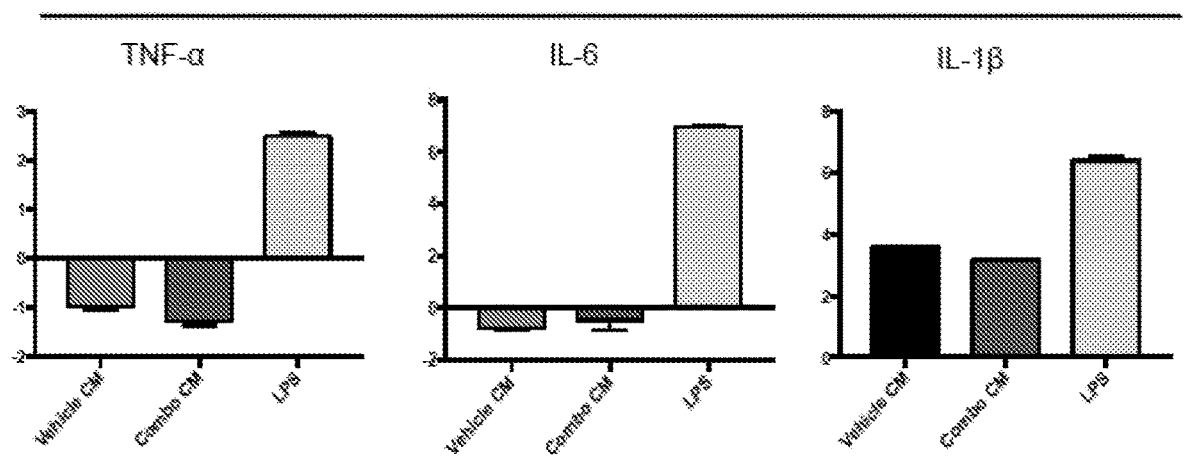
Figure 29H:
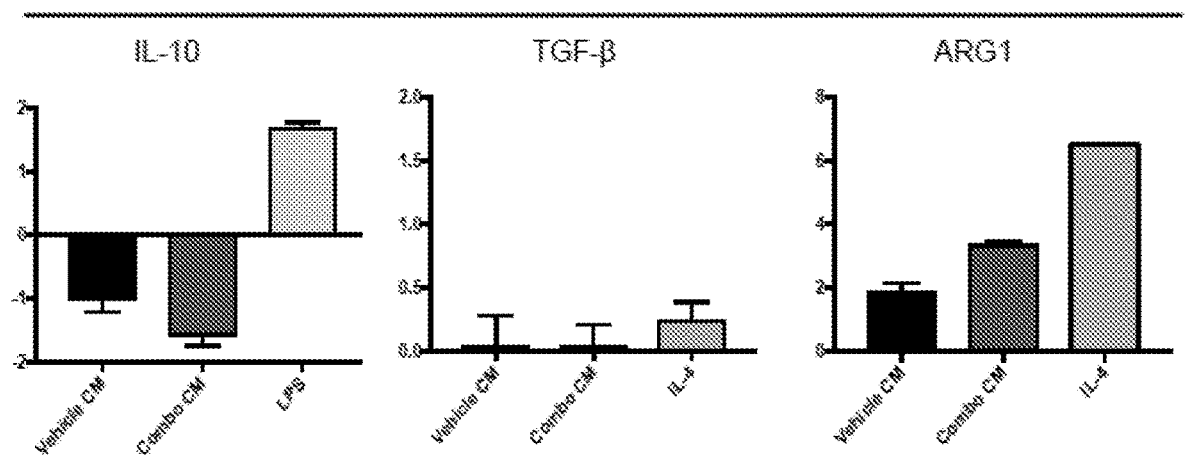

FIG. 29(H): qRT-PCR analysis of M1 and M2 macrophage gene expression in murine bone marrow-derived macrophages cultured in serum-free media or conditioned media from KPC$^{mut}$ PDAC tumor cells treated for 8 days with vehicle or combined trametinib (25 nM) and palbociclib (500 nM). LPS ( ) and IL-4 ( ) were administered as positive controls for M1 or M2 gene expression, respectively. Bars presented as mean of three biological replicates.

Figure 30A:
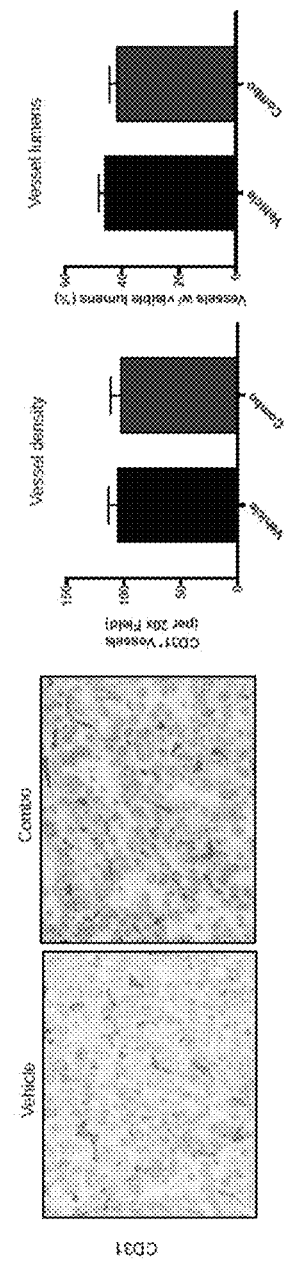

FIG. 30(A): CD31 immunohistochemical staining in KRAS$^{G12D}$; Trp53$^{fl/wt}$ (KP) GEMM lung tumors treated for 2 weeks with vehicle or combined trametinib (1 mg/kg and palbociclib (100 mg/kg body weight) (left). Middle, quantification of CD31$^+$ blood vessel numbers per 20× field. Right, quantification of the percentage of CD31$^+$ blood vessels with visible/discernible lumens. Bars represent the mean±SEM.

Figure 30B:
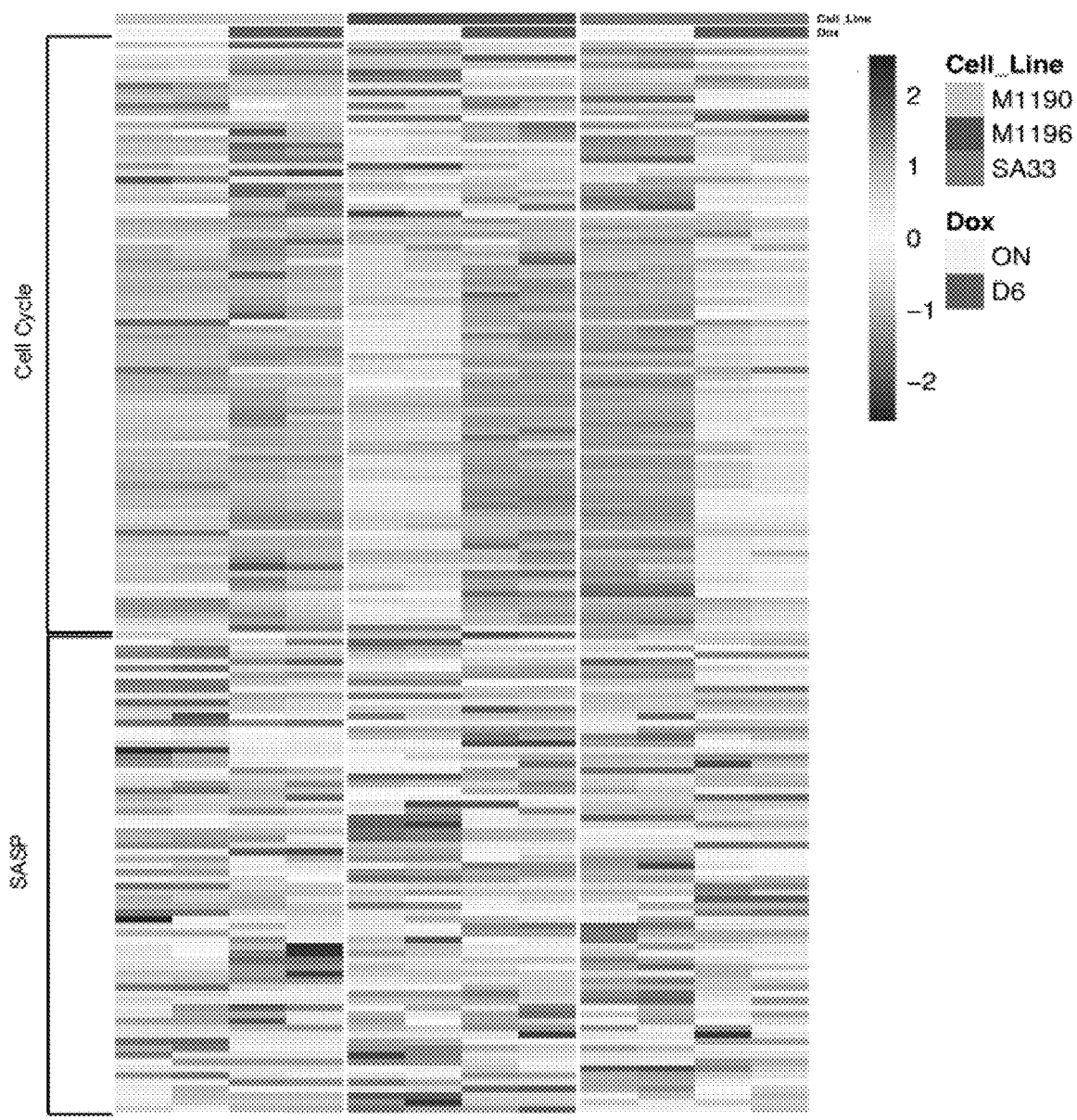

FIG. 30(B): Heat map of senescence-associated cell cycle and SASP gene expression in murine KRAS$^{G12D}$; TRE-shp53 PDAC cell lines cultured in the presence (+) or absence (−) of doxycycline (dox) for 6 days as assessed by RNA-seq. Three biological replicates per cell line are shown.

Figure 30C:
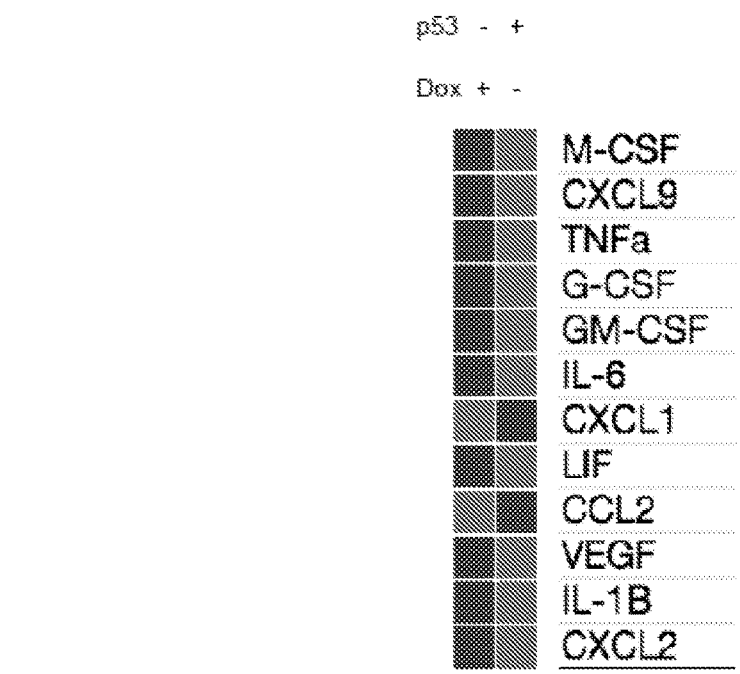

FIG. 30(C): Heat map of cytokine array results from the KRAS$^{G12D}$; TRE-shp53 PDAC cell line M1196 cultured in the presence (+) or absence (−) of doxycycline (dox) for 6 days. Data presented as mean of three biological replicates.

Figure 30D:
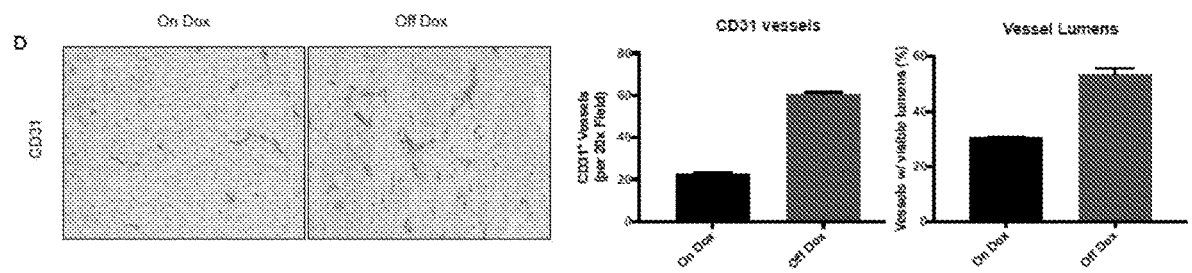

FIG. 30(D): CD31 immunohistochemical staining in $KRAS^{G12D}$; TRE-shp53 cell line transplant PDAC tumors treated with or without doxycycline (dox) for 18 days. Middle, quantification of CD31$^+$ blood vessel numbers per 20× field. Right, quantification of the percentage of CD31$^+$ blood vessels with visible/discernible lumens. Bars represent the mean±SEM.

Figure 31A:
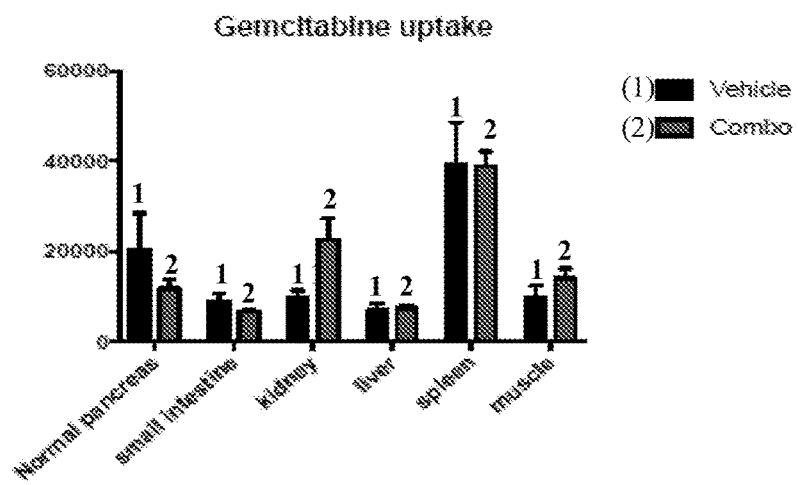

FIG. 31(A): Quantification of $^{14}$C-labeled gemcitabine uptake into the normal pancreas and other indicated organs in KPC$^{mut}$ PDAC organoid transplant mice treated for 2 weeks with vehicle or combined trametinib (1 mg/kg and palbociclib (100 mg/kg body weight). Bars represent the mean±SEM.

Figure 31B:
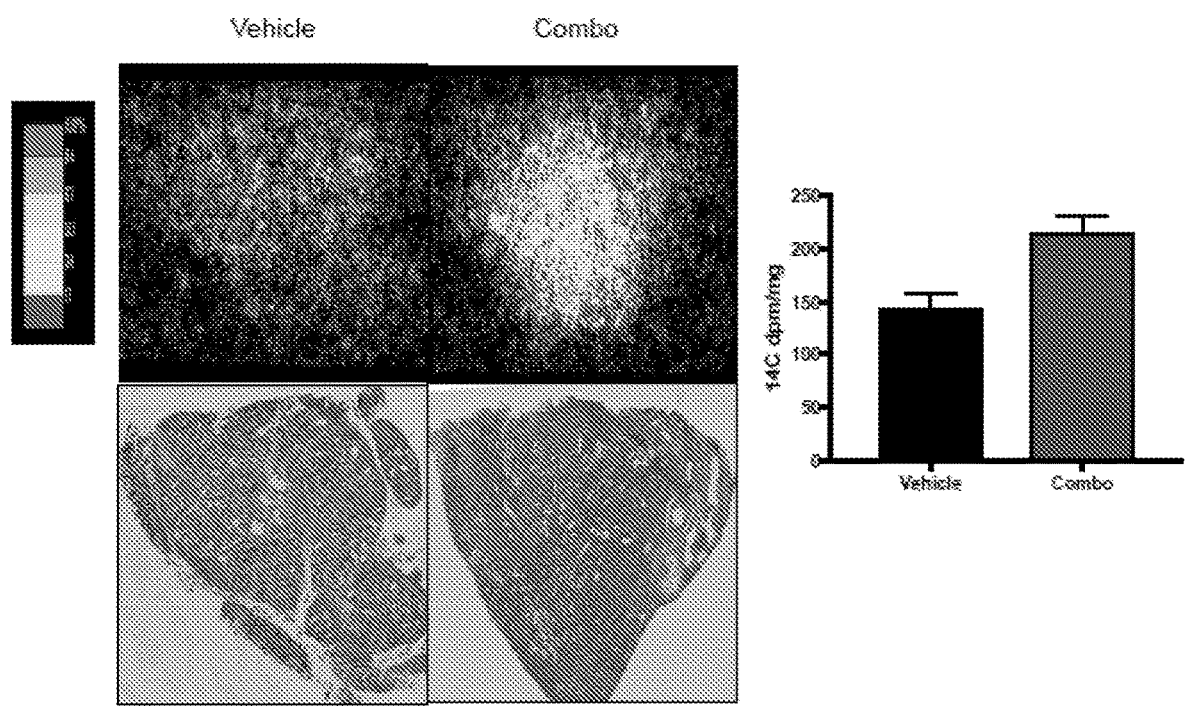

FIG. 31(B): Heat map representation of autoradiograph showing distribution of injected $^{14}$C-labeled gemcitabine in KPC GEMM tumors from mice pretreated with vehicle or combined trametinib (1 mg/kg and palbociclib (100 mg/kg body weight) for 2 weeks (scale bar, μm). Bottom, brightfield images of H&E stained tumor sections (scale bar, μm). Right, quantification $^{14}$C-labeled gemcitabine uptake into KPC GEMM tumors. Bars represent the mean±SEM.

Figure 31C:
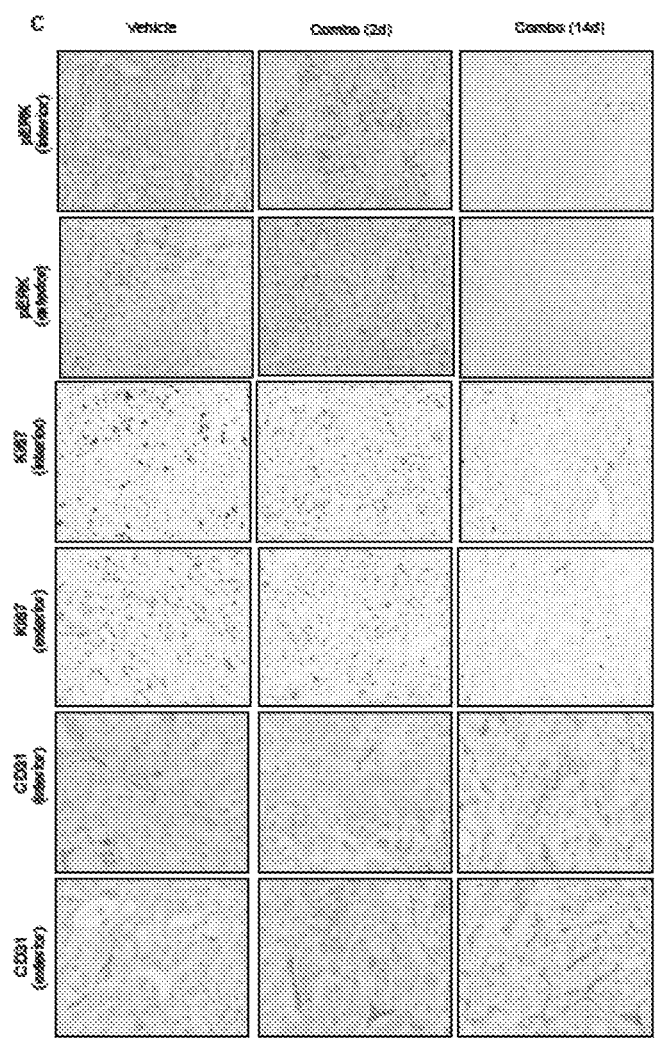

FIG. 31(C): Immunohistochemical staining of the interior and exterior of KPC$^{mut}$ PDAC organoid transplant tumors following 2 day or 2 week treatment with vehicle or combined trametinib (1 mg/kg and palbociclib (100 mg/kg body weight).

Figure 31D:
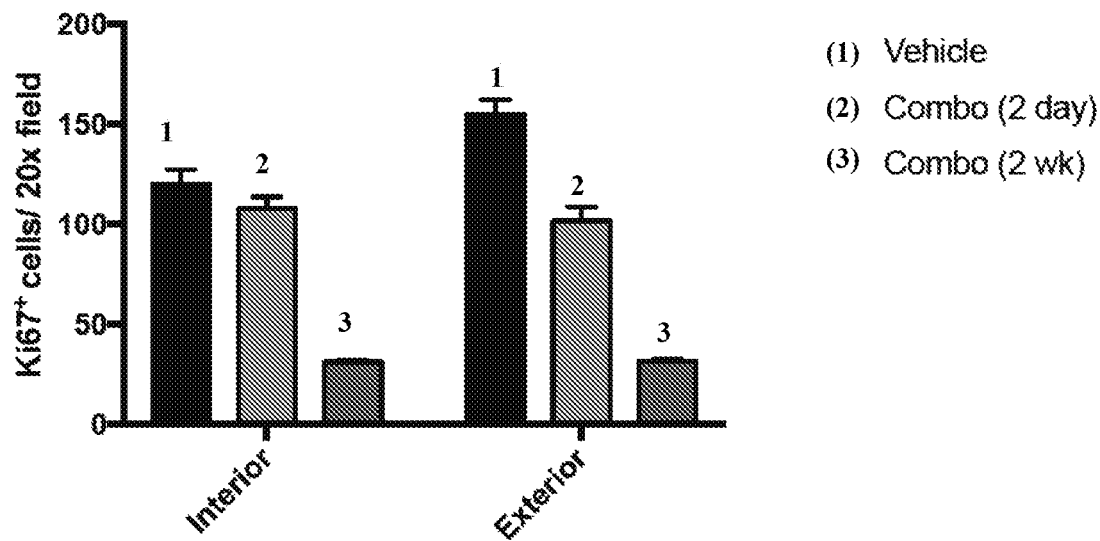

FIG. 31(D): Quantification of Ki67$^+$ proliferating cells per 20× field in KPC$^{mut}$ PDAC organoid transplant tumors following treatment as in FIG. 31(C). Bars represent the mean±SEM.

Figure 31E:
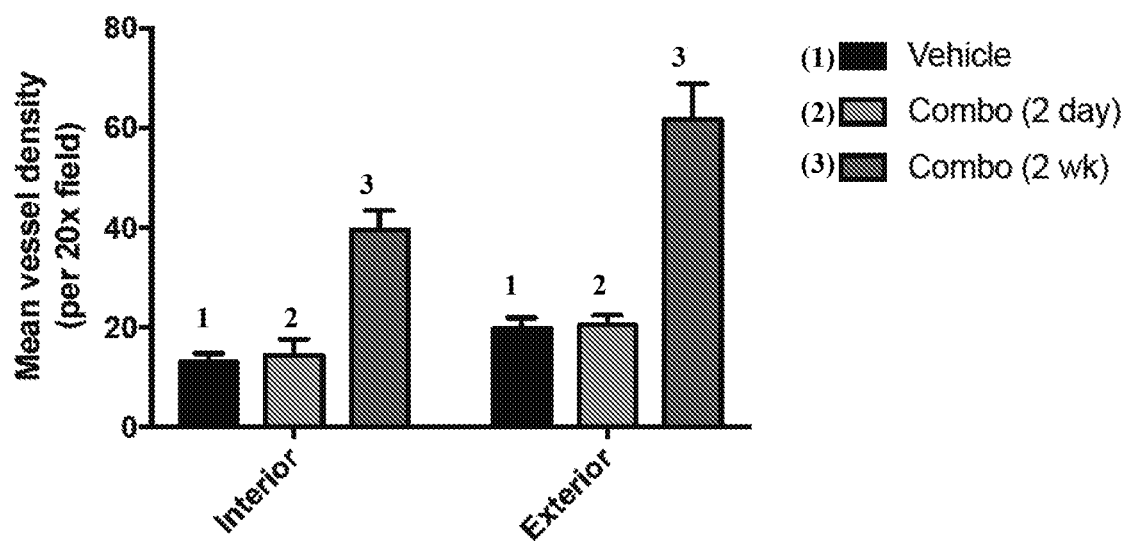

FIG. 31(E): Quantification of number of CD31$^+$ blood vessels per 20× field in KPC$^{mut}$ PDAC organoid transplant tumors following treatment as in FIG. 31(C). Bars represent the mean±SEM.

Figure 31F:
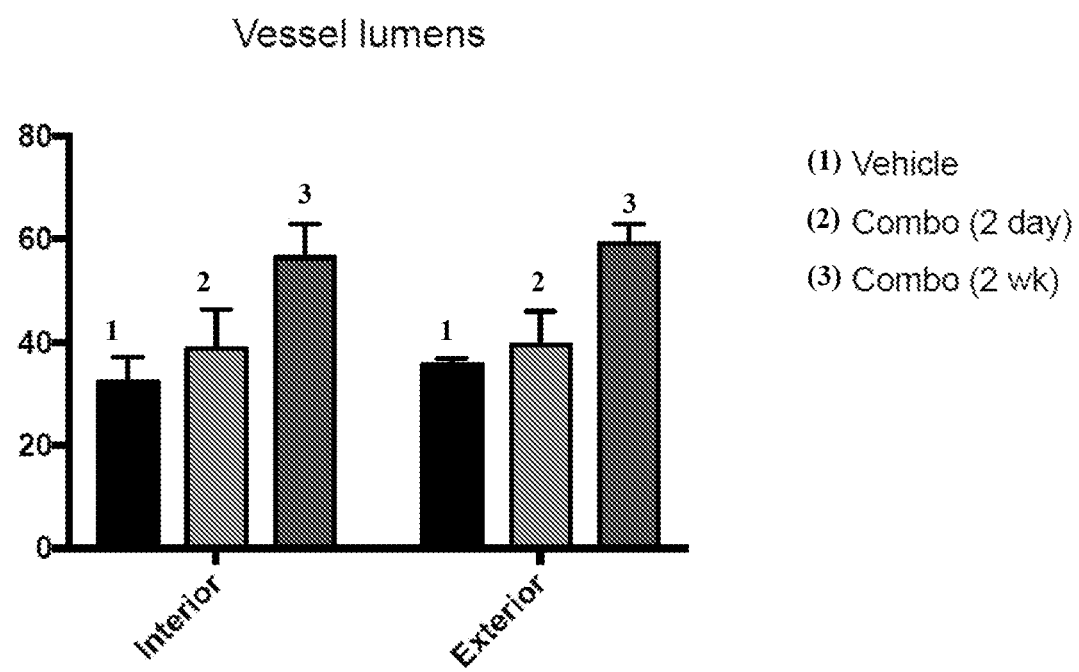

FIG. 31(F): Quantification of the percentage of CD31$^+$ blood vessels with visible/discernible lumens (see arrows in C) in KPC$^{mut}$ PDAC organoid transplant tumors following treatment in FIG. 31(C). Bars represent the mean±SEM.

Figure 32A:
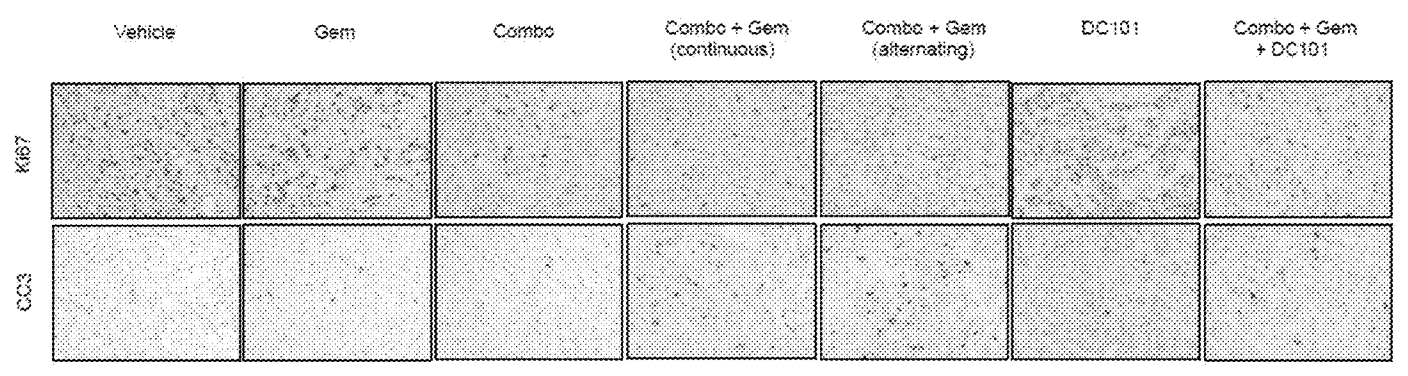

FIG. 32(A): Immunohistochemical staining of KPC$^{mut}$ PDAC organoid transplant tumors treated for 2 weeks with vehicle, trametinib (1 mg/kg body weight), palbociclib (100 mg/kg body weight), gemcitabine (100 mg/kg body weight), and/or a VEGFR2 blocking antibody (DC101; 800 μg per mouse).

Figure 32B:
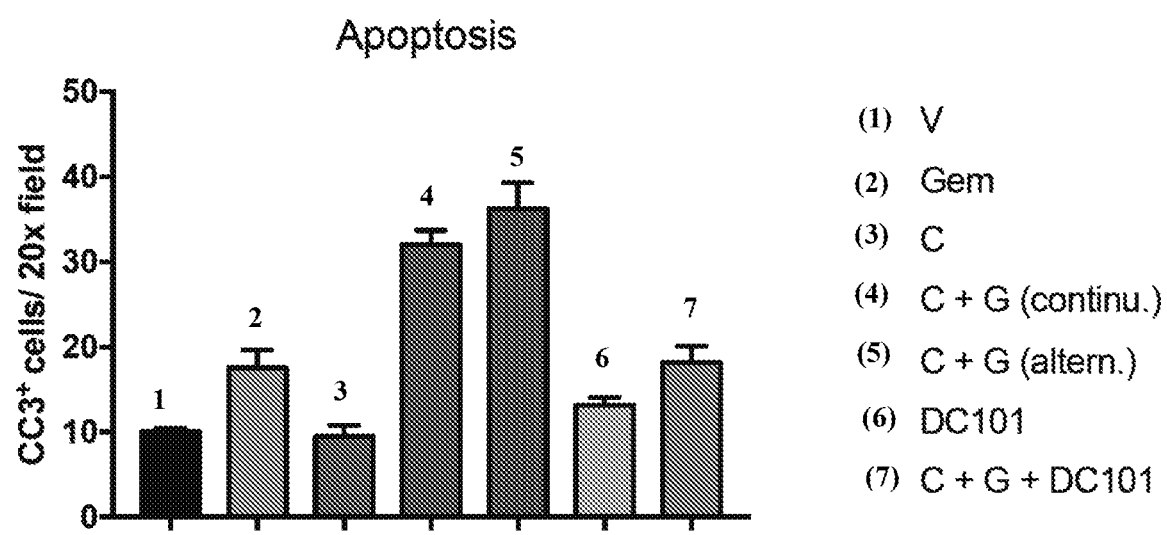
Figure 32:
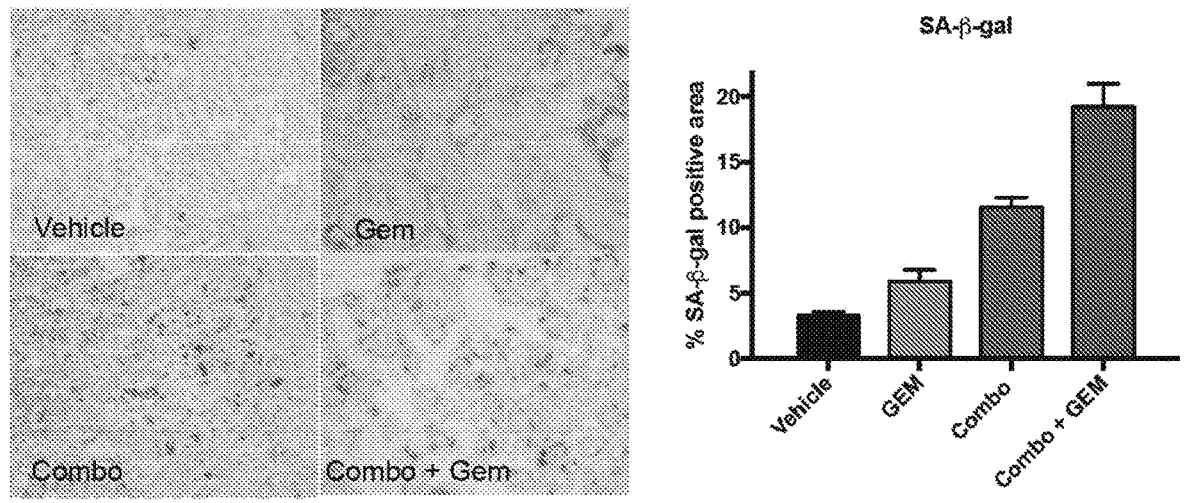

FIG. 32(B): Quantification of cleaved caspase-3 (CC3$^+$) tumor cells per 20× field in KPC$^{mut}$ PDAC organoid transplant tumors treated as in FIG. 32(A). Bars represent the mean±SEM.

FIG. 32(C): Representative SA-β-gal staining of KPC$^{mut}$ PDAC organoid transplant tumors treated as in FIG. 32(A). Right, quantification of SA-β-gal$^+$ staining. Bars represent the mean±SEM.

Figure 32D:
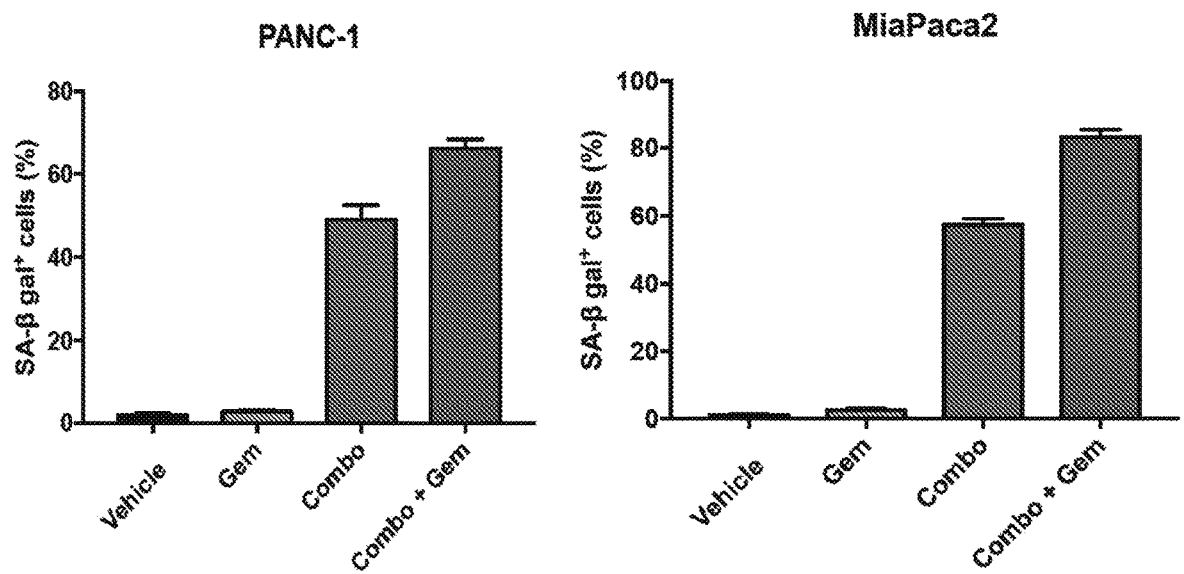

FIG. 32(D): Quantification of SA-β-gal$^+$ cells in human KRAS mutant PDAC cell lines (PANC-1, MiaPaCa2) treated with vehicle or combined trametinib (25 nM) and palbociclib (500 nM) for 6 days, followed by 2 day treatment with or without gemcitabine (1 uM). Bars represent the mean±SEM.

Figure 32E:
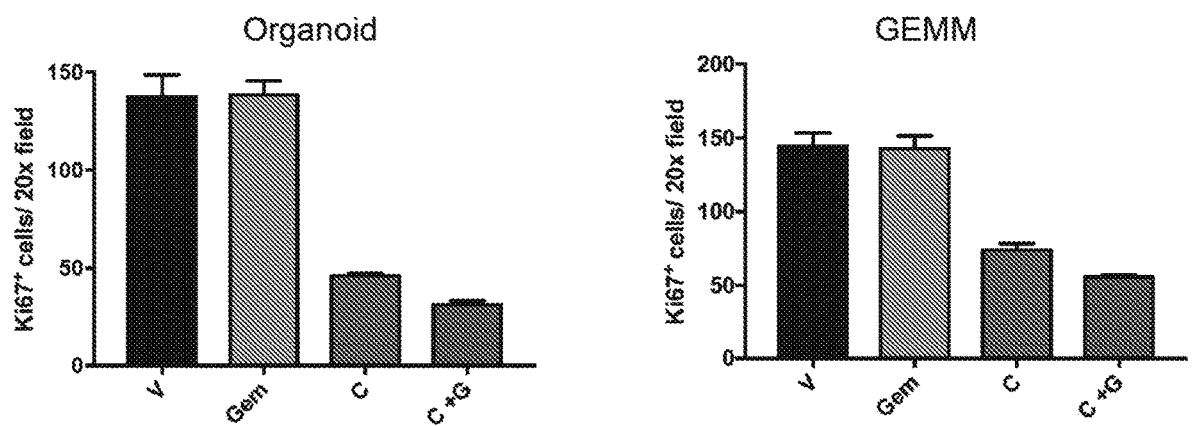

FIG. 32(E): Quantification of Ki67$^+$ proliferating cells per 20× field in KPC$^{mut}$ PDAC organoid transplant (left) or KPC GEMM (right) tumors following treatment as in FIG. 32(A). Bars represent the mean±SEM.

Figure 32F:
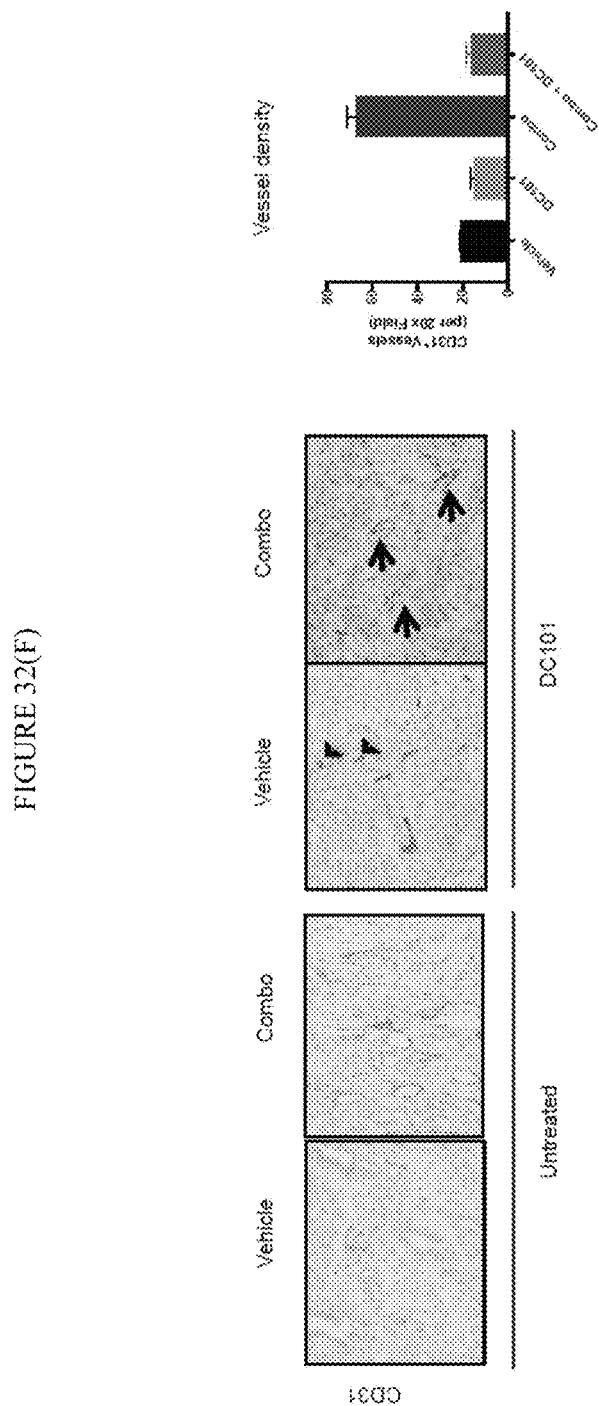

FIG. 32(F): Immunohistochemical staining of KPC$^{mut}$ PDAC organoid transplant tumors treated for 2 weeks with vehicle or combined trametinib (1 mg/kg body weight) and palbociclib (100 mg/kg body weight) in the presence or absence of a VEGFR2 blocking antibody (DC101; 800 μg per mouse). Right, quantification of number of CD31$^+$ blood vessels per 20× field. Bars represent the mean±SEM.

Figure 33A:
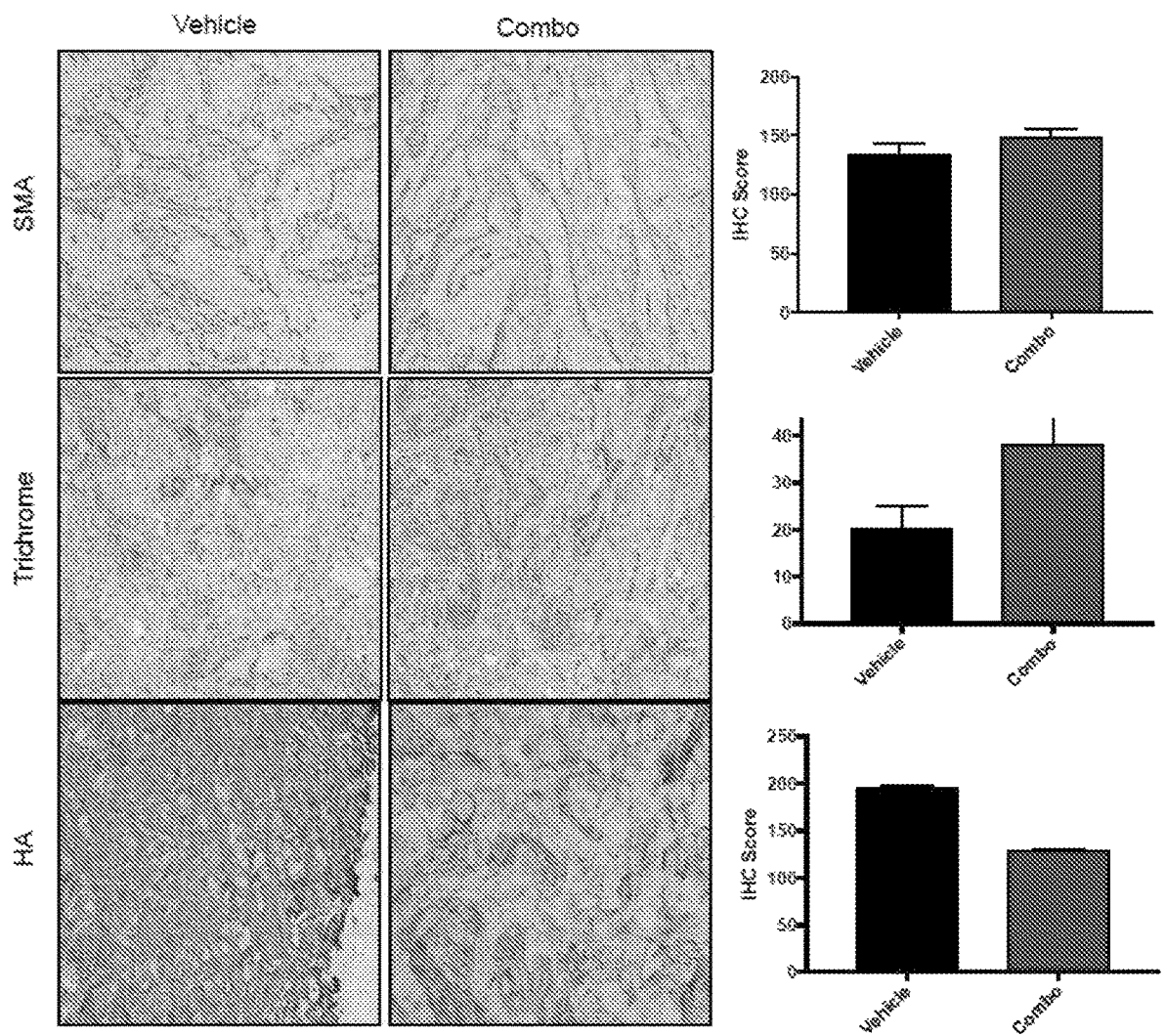

FIG. 33(A): Immunohistochemical staining of PR-07 PDAC PDX tumors treated with vehicle or combined trametinib (1 mg/kg body weight) and palbociclib (100 mg/kg body weight) for 2 weeks (scale bar, μm). Right, quantification of staining intensity of αSMA, collagen (trichrome), and hyaluronic acid (HA) in the TME. Bars represent the mean±SEM.

Figure 33B:
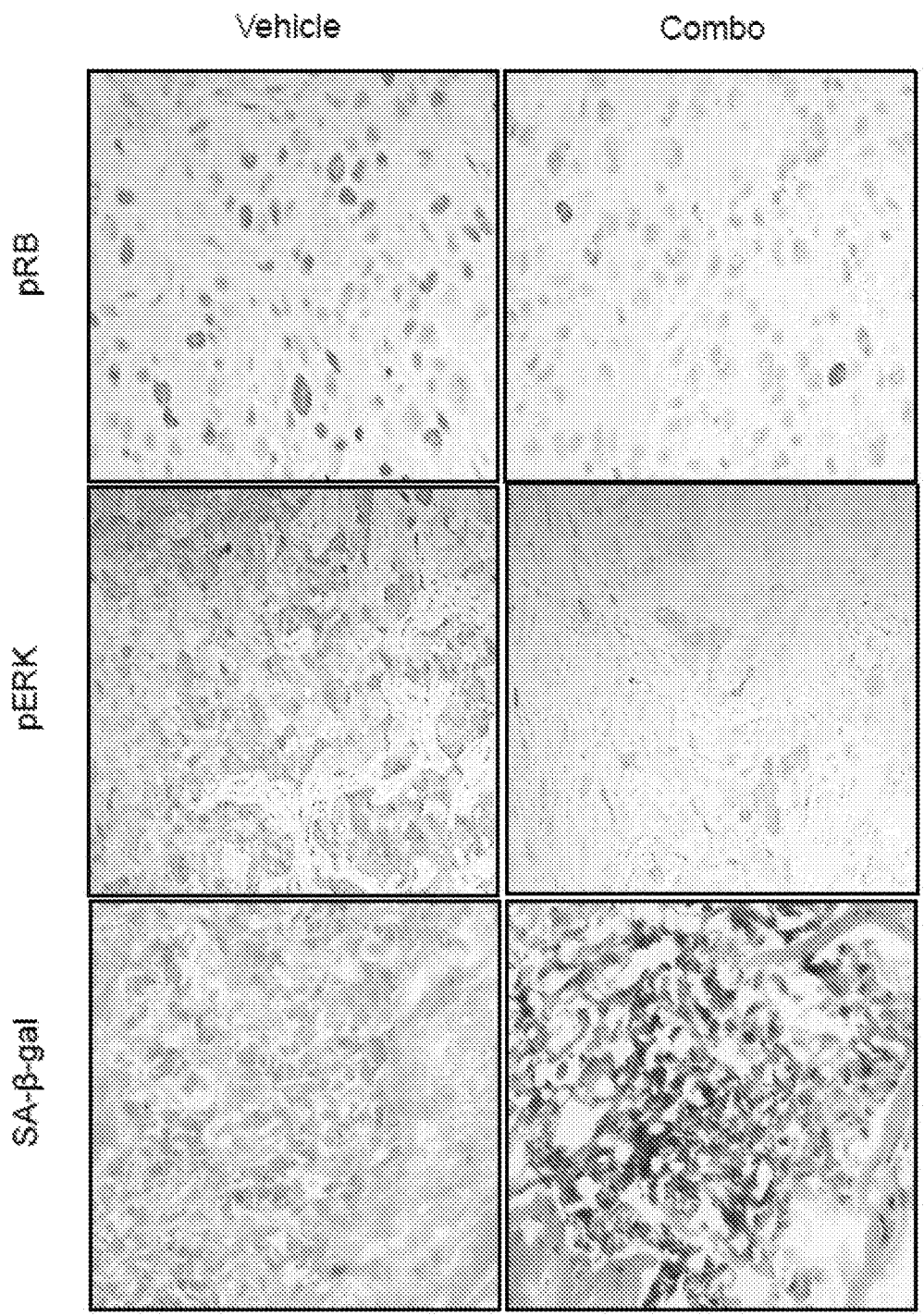

FIG. 33(B): Immunohistochemical staining of PR-07 PDAC PDX tumors treated as in FIG. 33(A) (scale bar, μm).

Figure 33C:
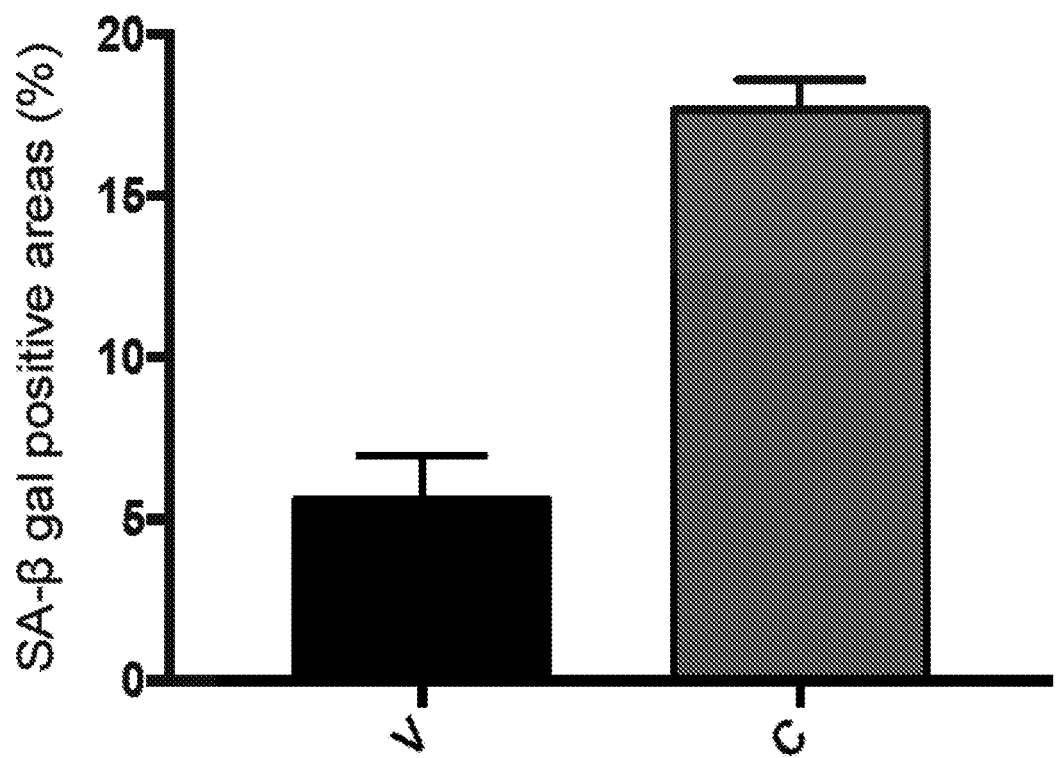

FIG. 33(C): Quantification of SA-β-gal staining in PR-07 PDAC PDX tumors treated as in FIG. 33(A). Bars represent the mean±SEM.

Figure 33D:
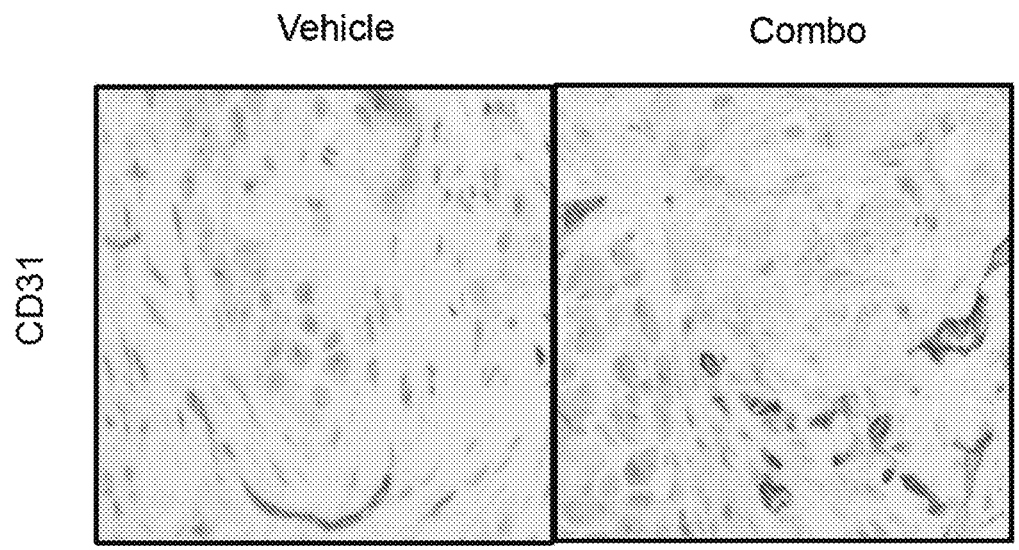

FIG. 33(D): CD31 immunohistochemical staining of PR-07 PDAC PDX tumors treated as in FIG. 33(A) (scale bar, μm). Arrowhead, collapsed vessel; Arrow, visible vessel lumen.

Figure 33E:
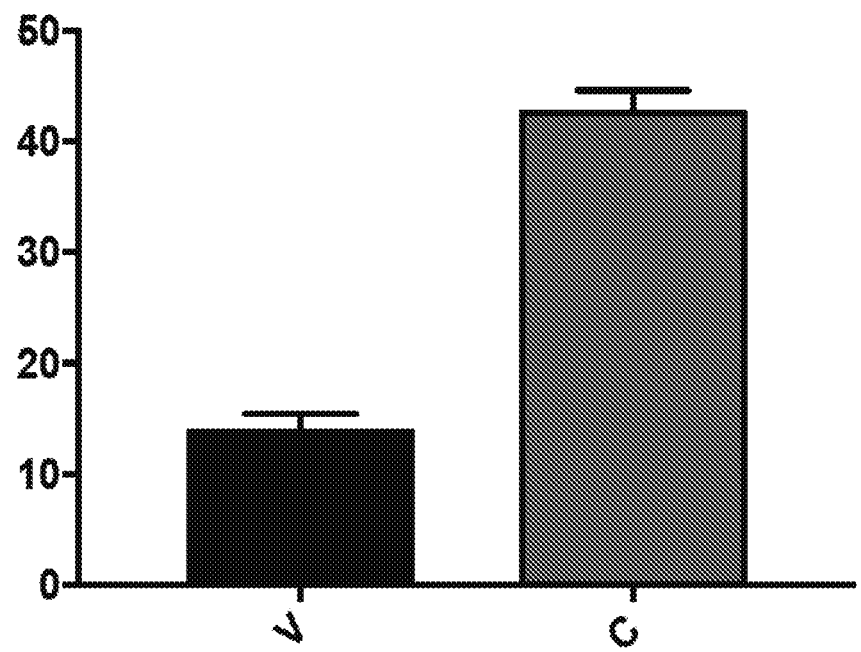

FIG. 33(E): Quantification of number of CD31$^+$ blood vessels per 20× field in PR-07 PDAC PDX tumors following treatment as in FIG. 33(A). Bars represent the mean±SEM.

Figure 33F:
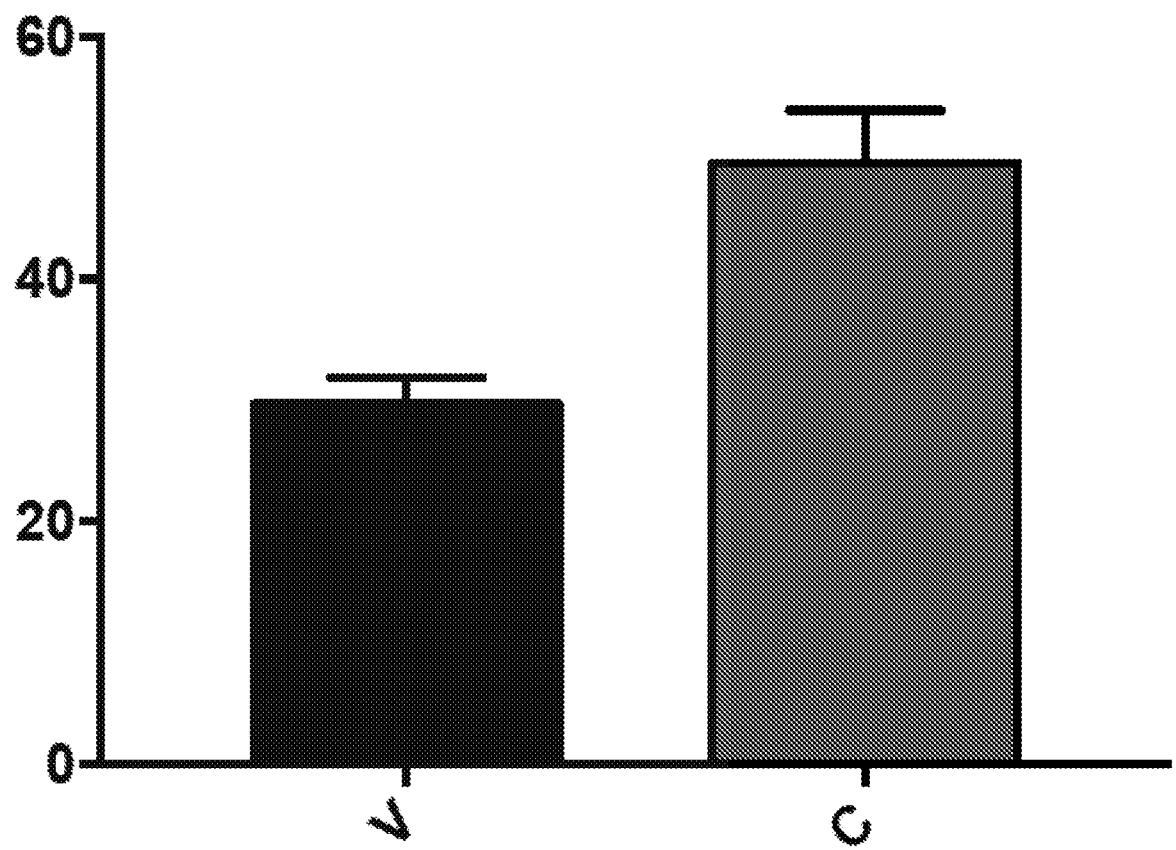

FIG. 33(F): Quantification of the percentage of CD31$^+$ blood vessels with visible/discernible lumens (see arrows in D) in PR-07 PDAC PDX tumors following treatment in FIG. 33(A). Bars represent the mean±SEM.

Figure 33G:
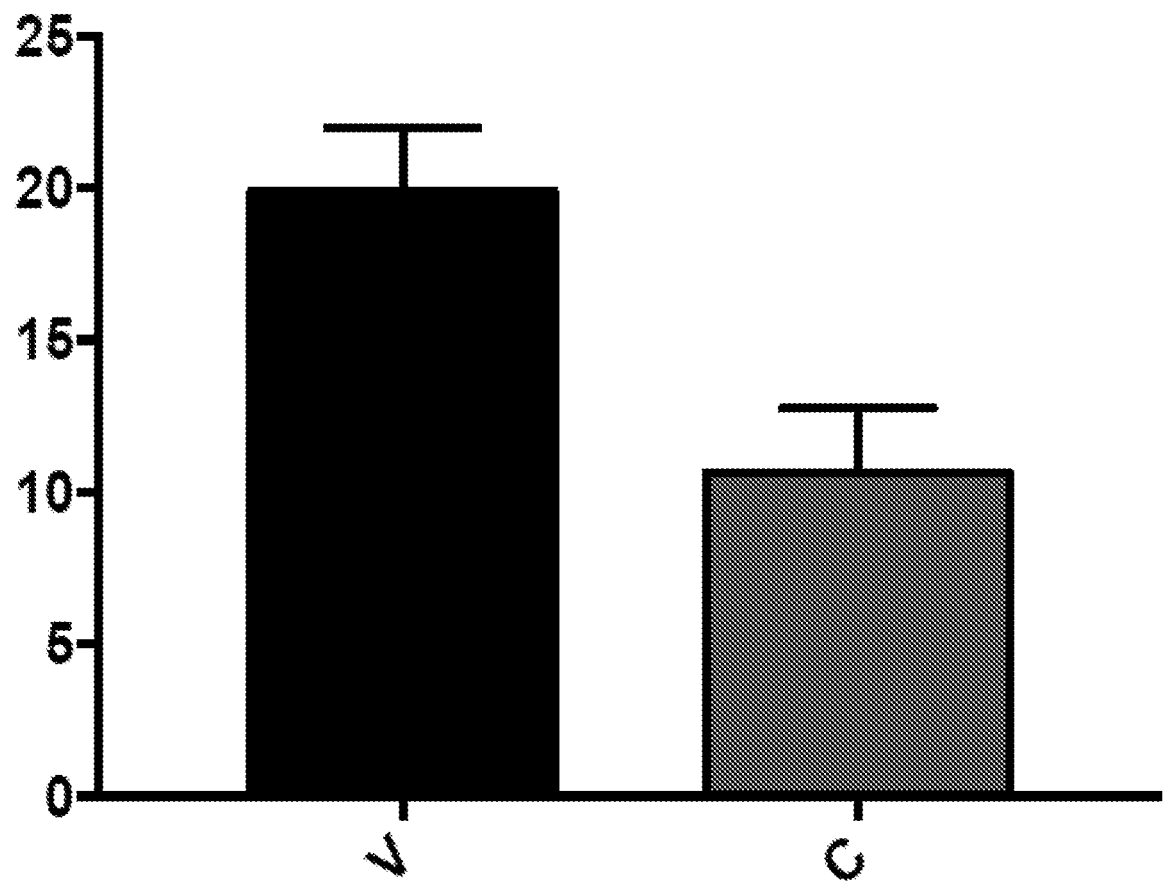

FIG. 33(G): Quantification of the average distance between a CD31$^+$ blood vessel and the 4 nearest tumor cells in PR-07 PDAC PDX tumors following treatment as in FIG. 33(A). Bars represent the mean±SEM.

Figure 34A:
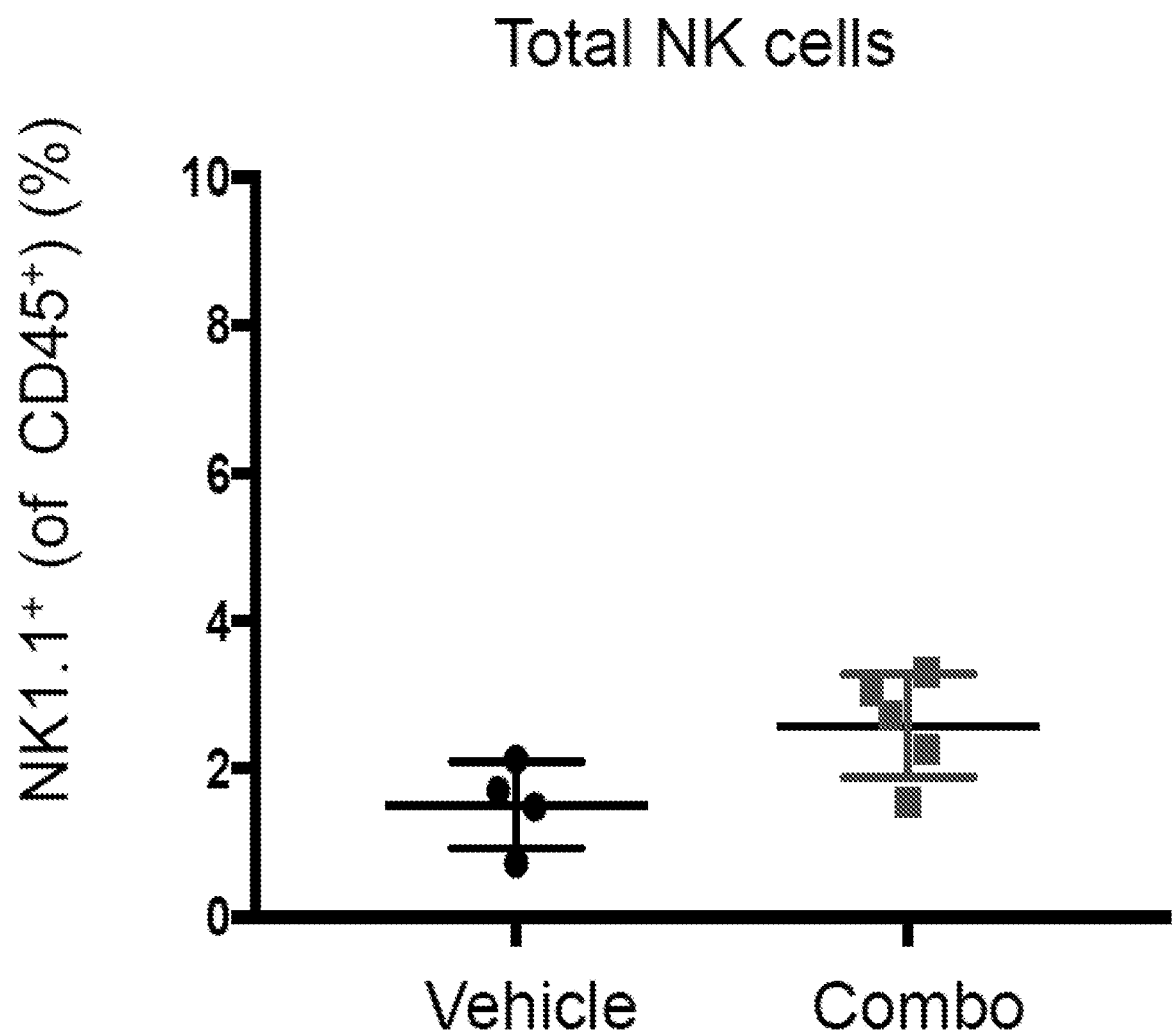

FIGS. 34(A)-34(B): Flow cytometry analysis of KPC$^{mut}$ cell line transplant PDAC tumors following 10-day treatment with vehicle or combined trametinib (1 mg/kg body weight) and palbociclib (100 mg/kg body weight), (n≥4 mice per group). FIG. 34(A): Percentage of total CD3$^−$ NK1.1$^+$ NK cells within the CD45$^+$ population. FIG. 34(B): Percentage of CD107a$^+$NK1.1$^+$ degranulating NK cells. Data represent the mean±SEM.

Figure 34C:
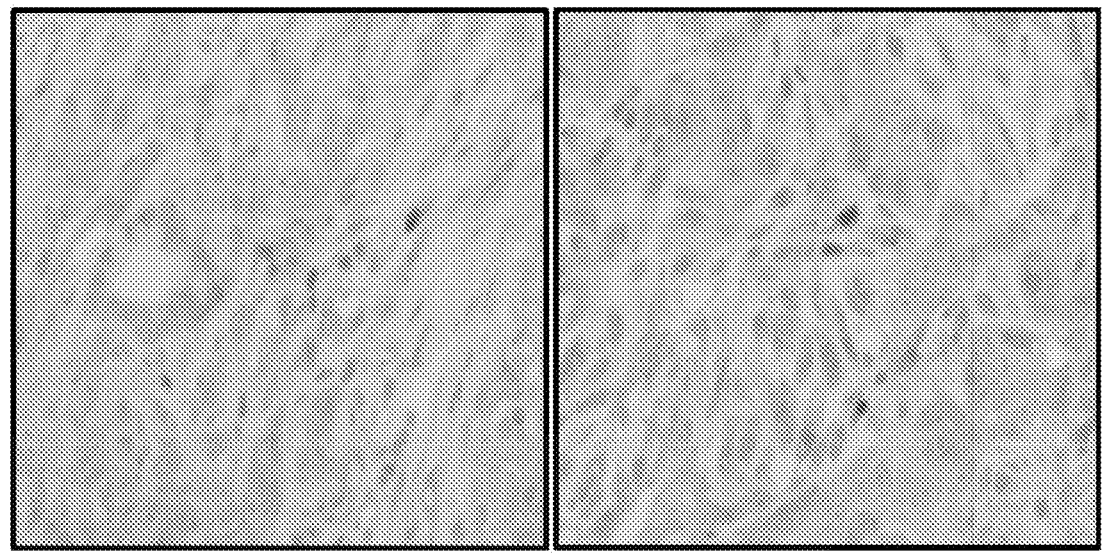

FIG. 34(C): Immunohistochemical staining KPC GEMM PDAC tumors treated for 2 weeks with vehicle or combined trametinib (1 mg/kg body weight) and palbociclib (100 mg/kg body weight) (scale bar, μm).

FIG. 34(D): Kaplan-Meier survival curve of KPC$^{mut}$ PDAC cell line transplant mice treated with vehicle or combined trametinib (1 mg/kg body weight) and palbociclib (100 mg/kg body weight) in the presence or absence of a NK1.1 depleting antibody (PK136) (250 μg per mouse) (n≥7 per group) (log-rank test).

Figure 34E:
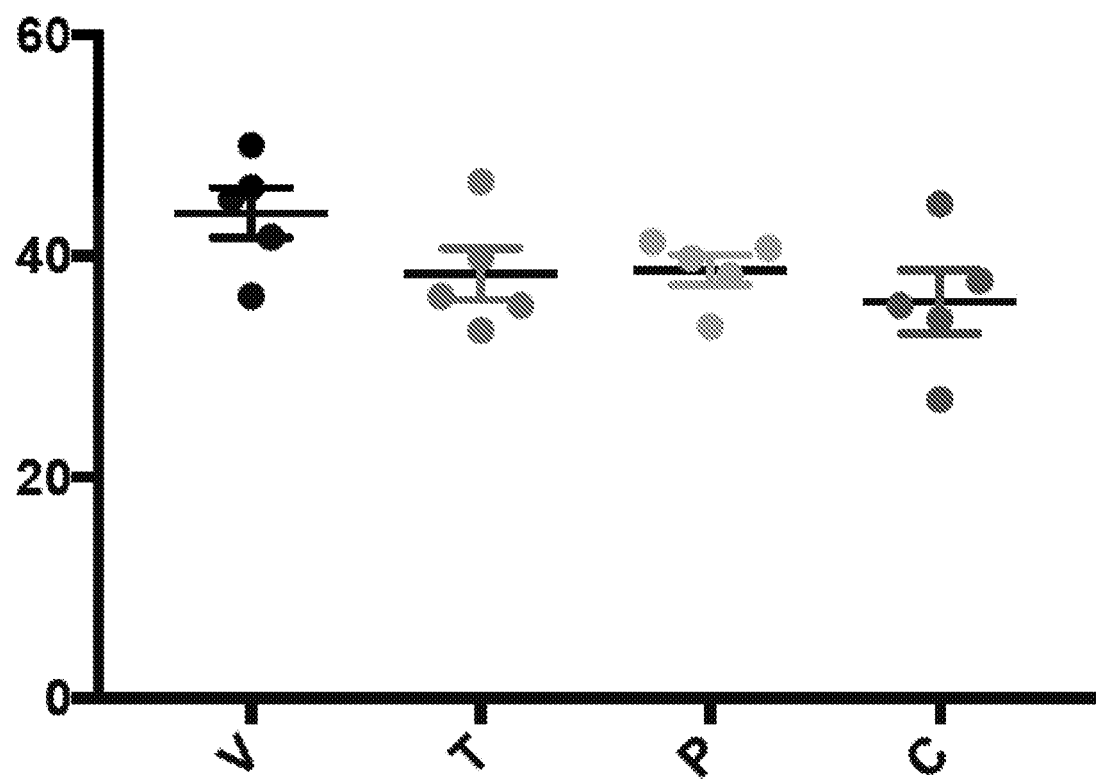
Figure 34F:
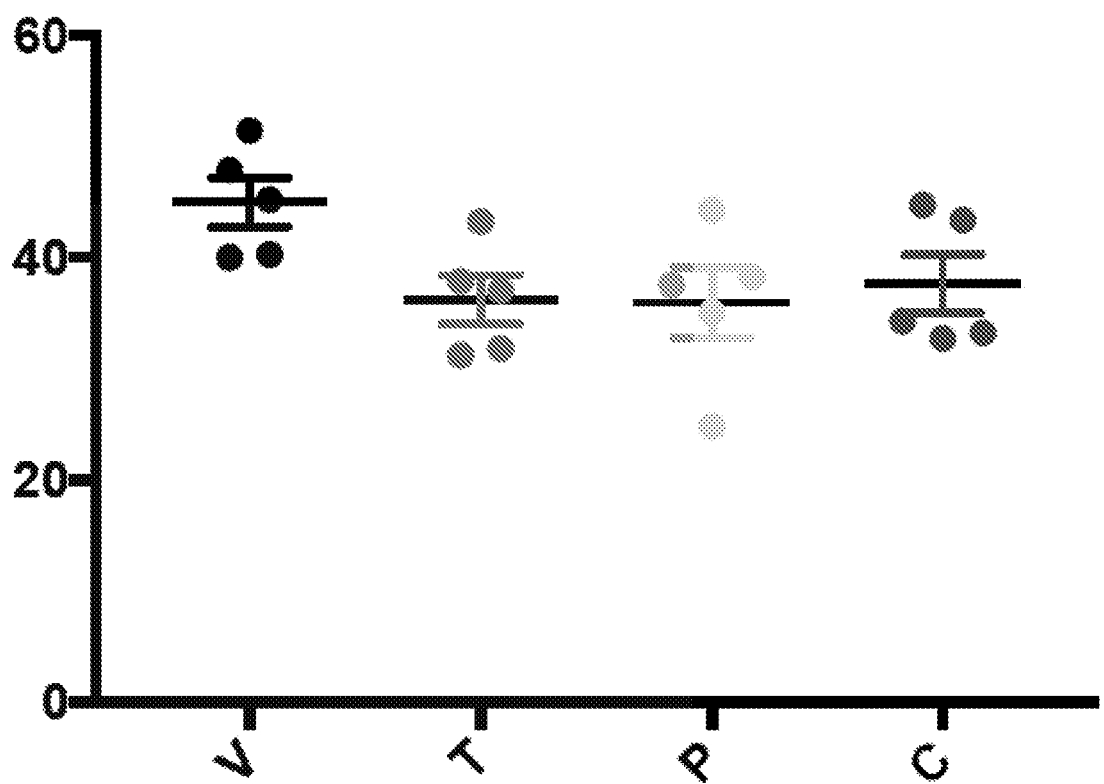
Figure 34G:
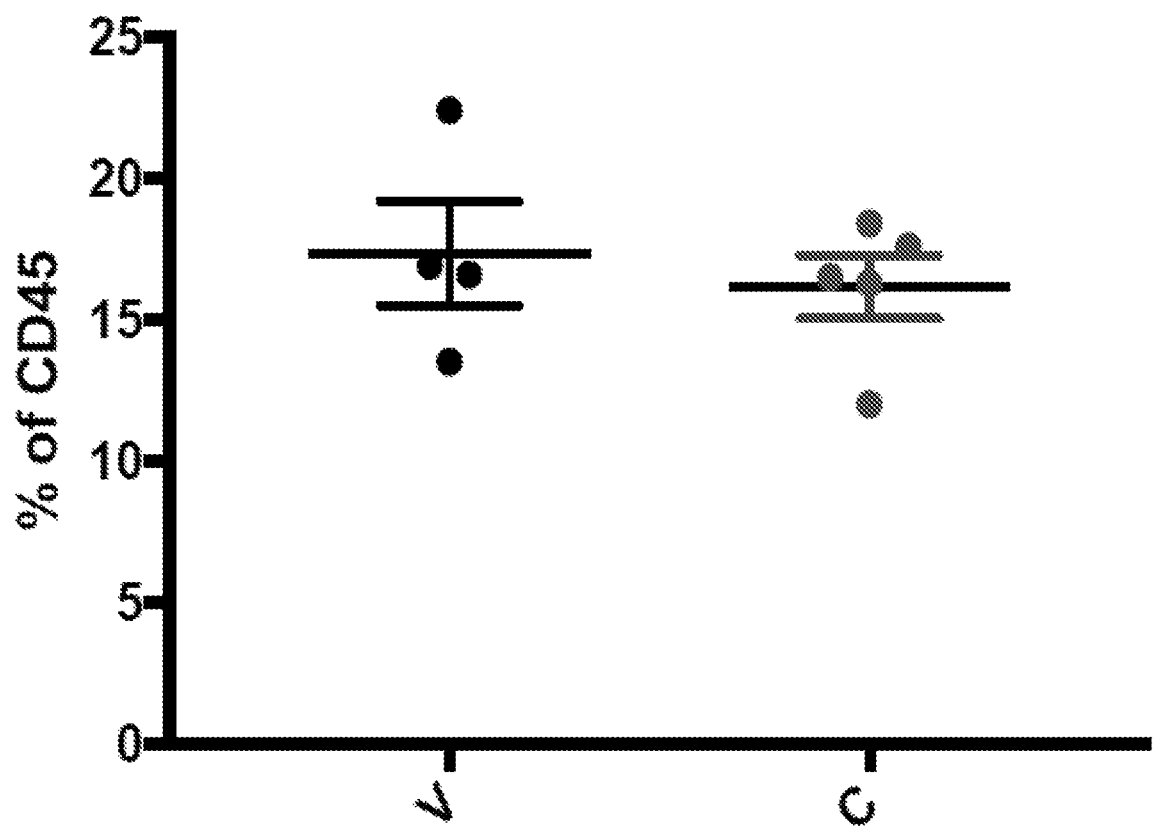
Figure 34H:
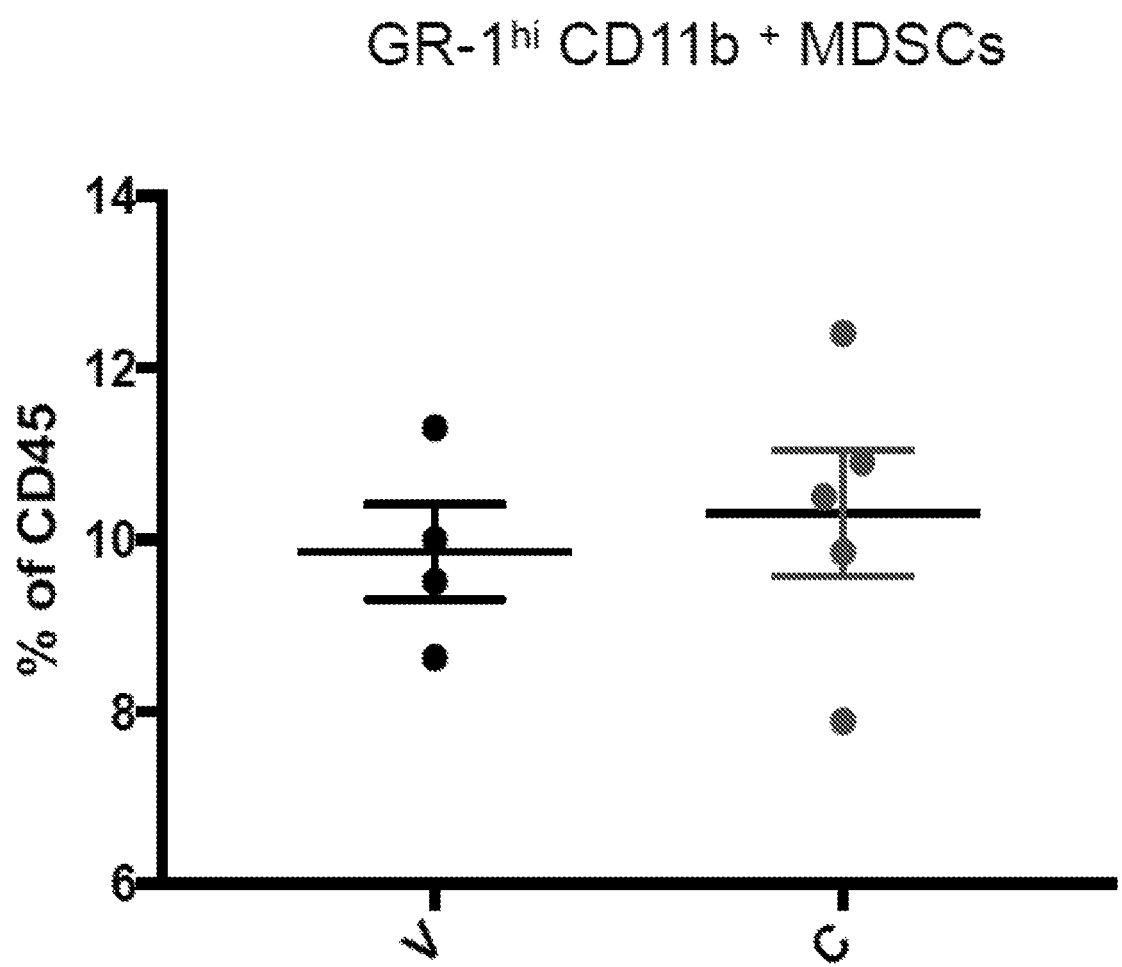

FIGS. 34(E)-34(H): Flow cytometry analysis of KPC$^{mut}$ cell line transplant PDAC tumors following 10-day treatment with vehicle or combined trametinib (1 mg/kg body weight) and palbociclib (100 mg/kg body weight), (n≥4 mice per group). FIG. 34(E): Percentage of CD69$^+$ CD4$^+$ T cells. FIG. 34(F): Percentage of CD44$^+$ CD4$^+$ T cells. FIG. 34(G) Percentage of F4/80$^+$ macrophages within the CD45$^+$ population. FIG. 34(H): Percentage of GR-1$^{hi}$CD11b$^+$ MDSCs within the CD45$^+$ population.

Figure 34I:
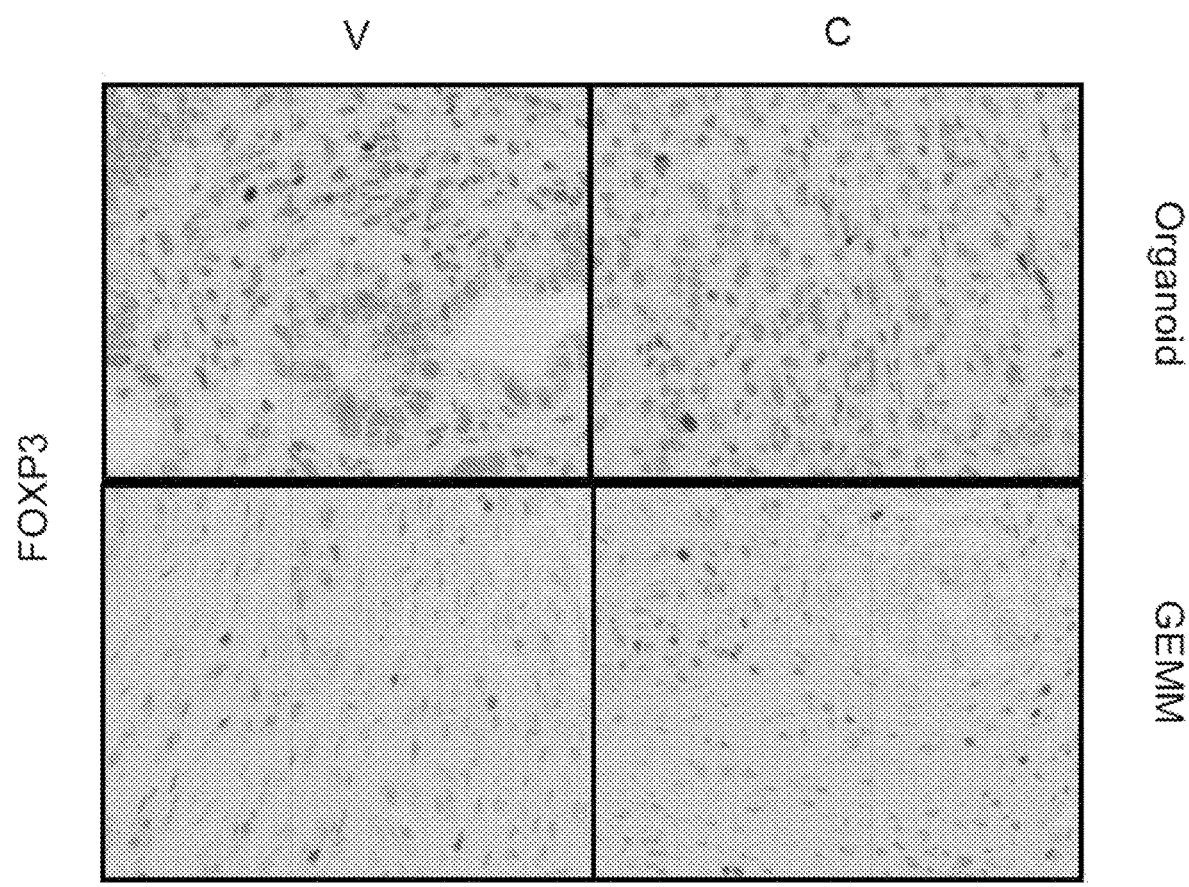

FIG. 34(I): Immunohistochemical staining KPC$^{mut}$ cell line transplant PDAC tumors treated as in FIG. 34(A) (scale bar, μm).

Figure 35A:
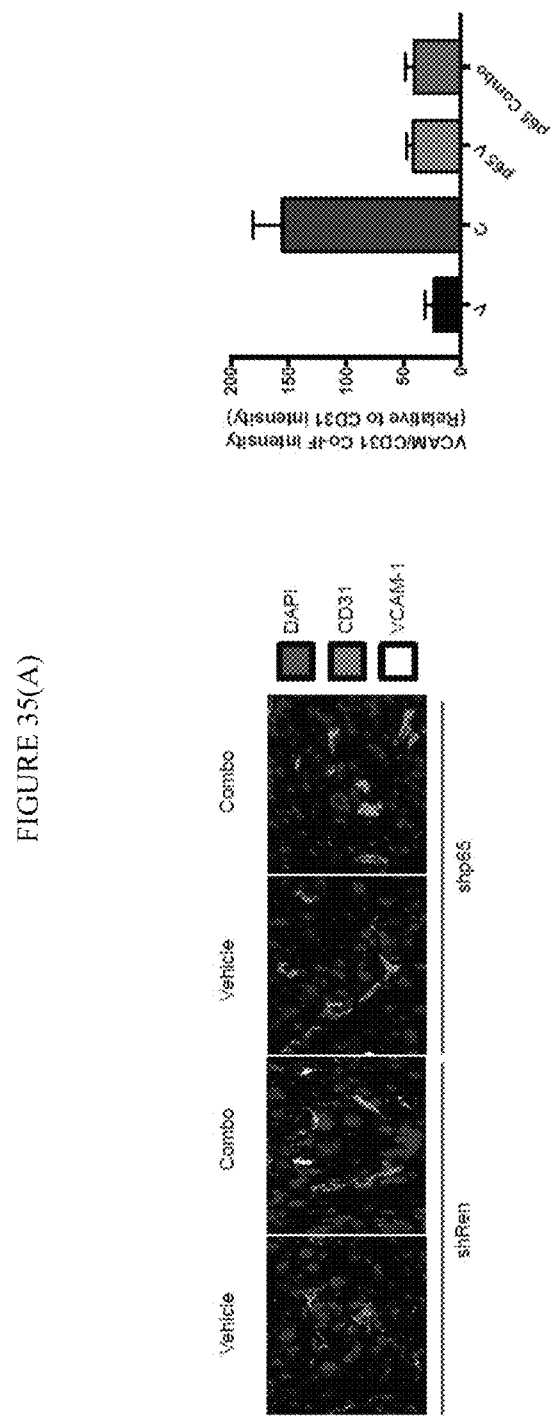

FIG. 35(A): Immunofluorescent images of VCAM-1 (white) co-localization with CD31$^+$ blood vessels (pink) in KPC PDAC organoid tumors harboring control Renilla (Ren) or p65-targeting shRNAs and treated with vehicle or combined trametinib (1 mg/kg body weight) and palbociclib (100 mg/kg body weight) for 2 weeks (scale bar, μm) (left).

Right, quantification of VCAM-1/CD31 co-immunofluorescence. Bars represent the mean±SEM.

Figure 35B:
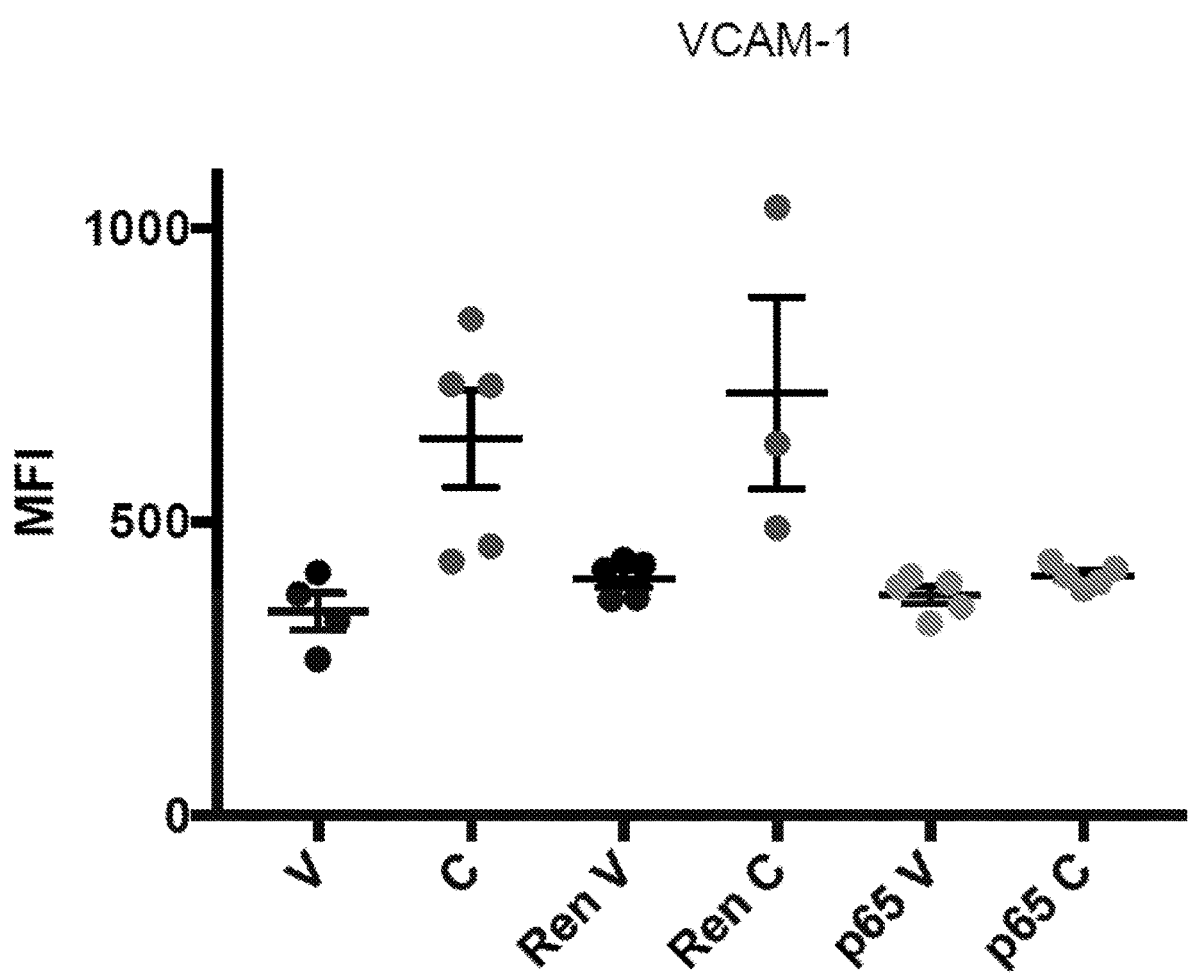
Figure 35C:
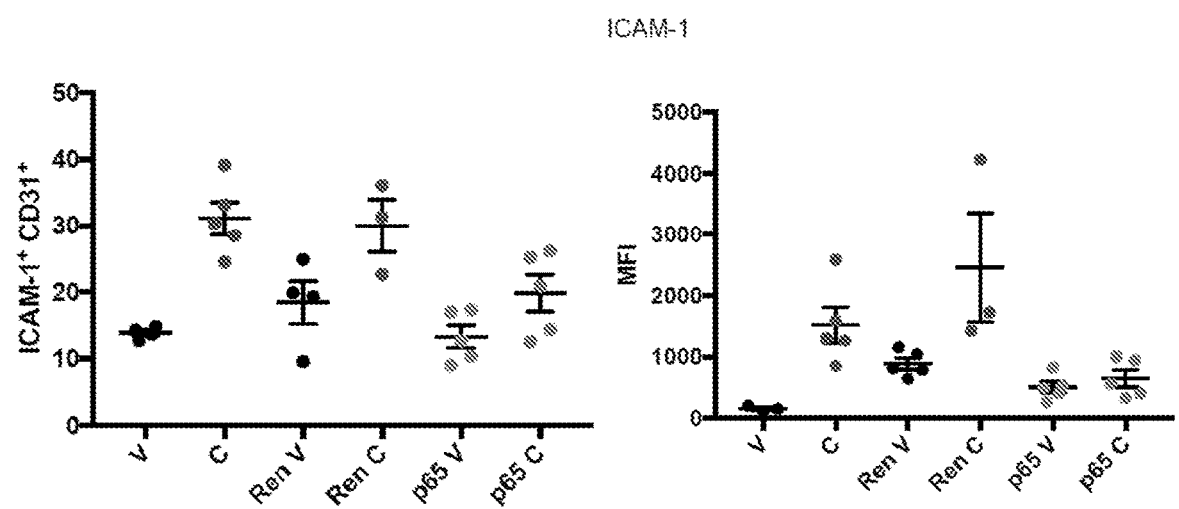

FIGS. 35(B)-35(C): Flow cytometry analysis of indicated KPC$^{mut}$ cell line transplant PDAC tumors following 10-day treatment with vehicle or combined trametinib (1 mg/kg body weight) and palbociclib (100 mg/kg body weight), (n≥3 mice per group). FIG. 35(B): Mean fluorescent intensity (MFI) of VCAM-1 expression on CD31$^+$ ECs. FIG. 35(C): Percentage of ICAM-1$^+$CD31$^+$ ECs (left). Right, MFI of ICAM-1 expression on CD31$^+$ ECs. Data represent the mean±SEM.

Figure 35D:
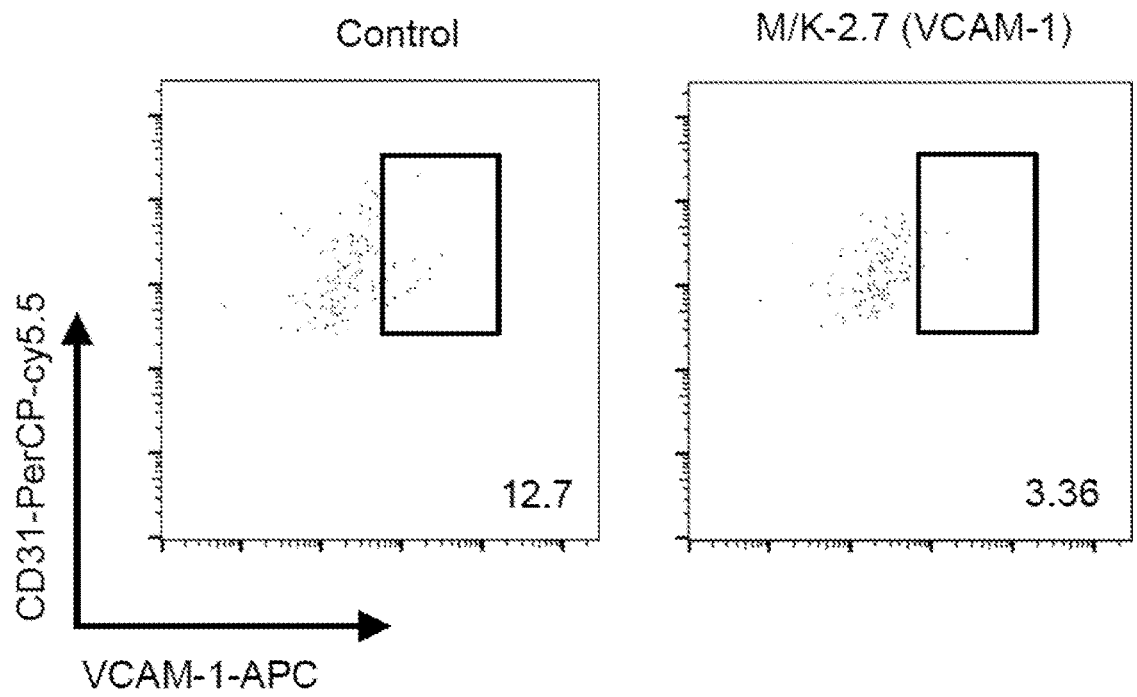

FIG. 35(D): Flow cytometry analysis of VCAM-1$^+$ expression on CD31$^+$ ECs from KPC$^{mut}$ cell line transplant PDAC tumors following 10-day treatment with a VCAM-1 neutralizing antibody (M/K-2.7; 200 µg per mouse).

Figure 35E:
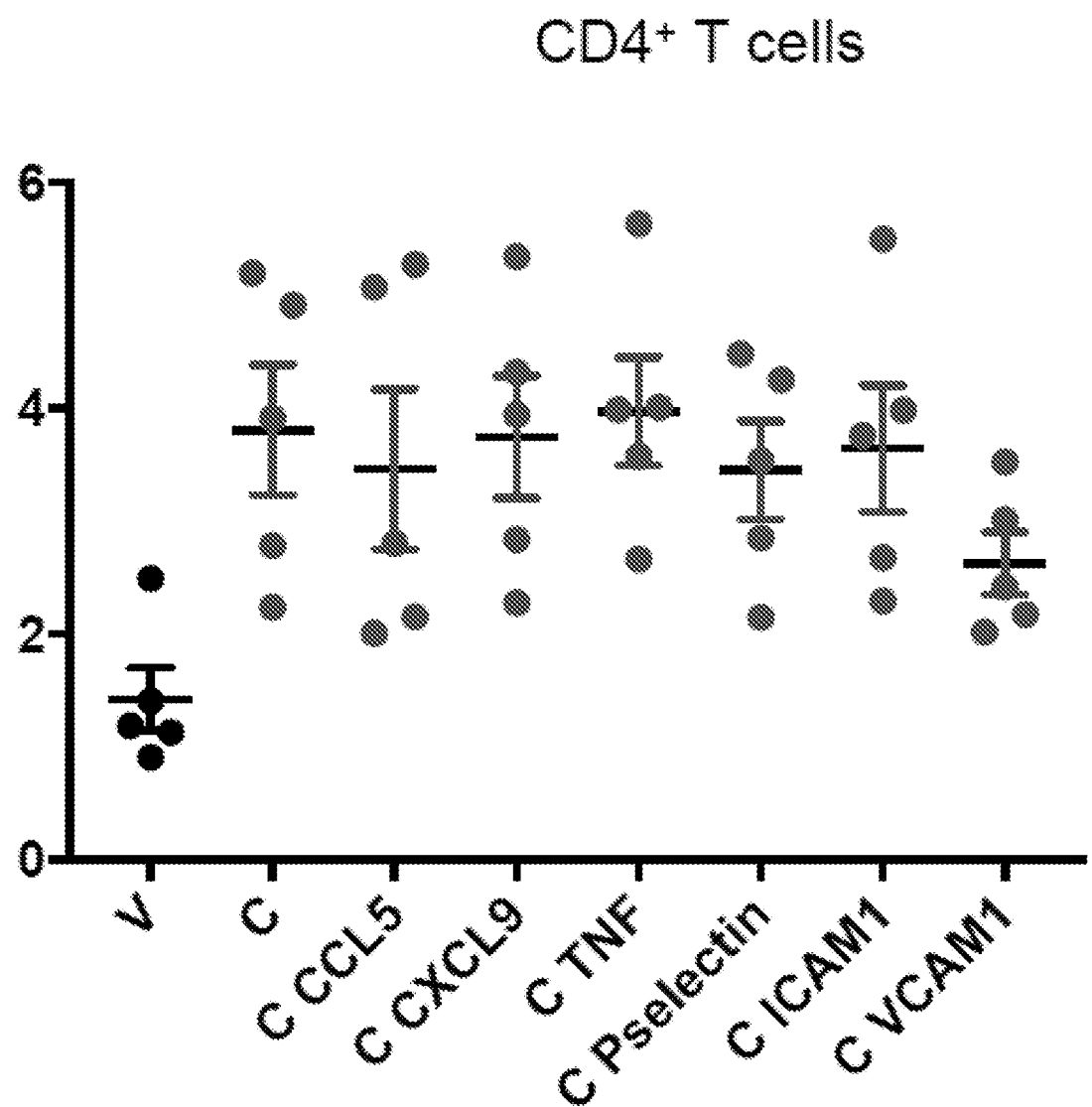

FIG. 35(E): Flow cytometry analysis of CD4$^+$ T cells within the CD45$^+$ population in KPC$^{mut}$ cell line transplant PDAC tumors following 10-day treatment with vehicle or combined trametinib (1 mg/kg body weight) and palbociclib (100 mg/kg body weight) and neutralizing mAbs targeting CCL5 (53405; 50 µg per mouse), CXCL9 (MIG-2F5.5; 500 µg per mouse), TNF-α (XT3.11; 200 µg per mouse), PSGL-1 (4RA10; 50 µg per mouse), ICAM-1 (YN1/1.7.4; 200 µg per mouse), or VCAM-1 (M/K-2.7; 200 µg per mouse) (n=5 mice per group). Data represent the mean±SEM.

Figure 35F:
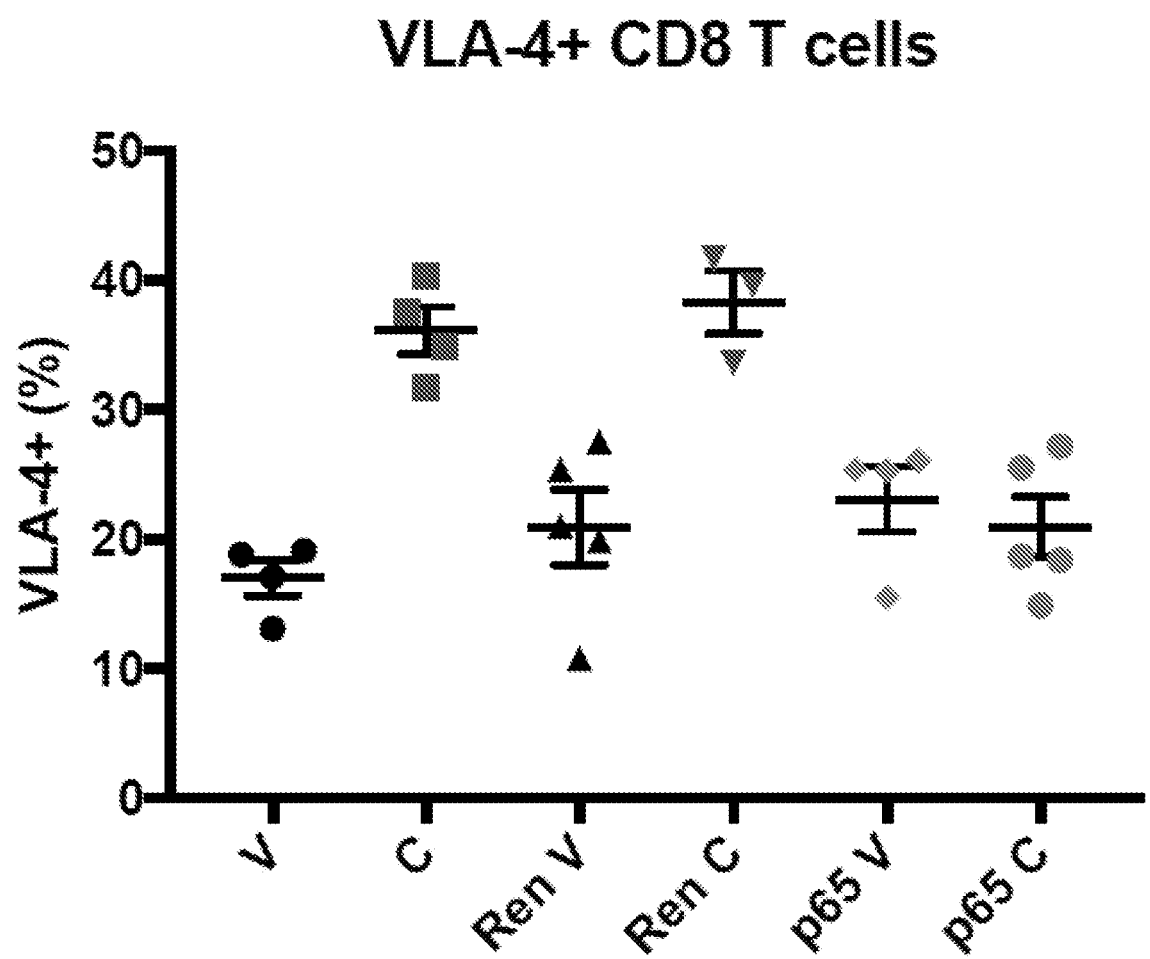
Figure 35G:
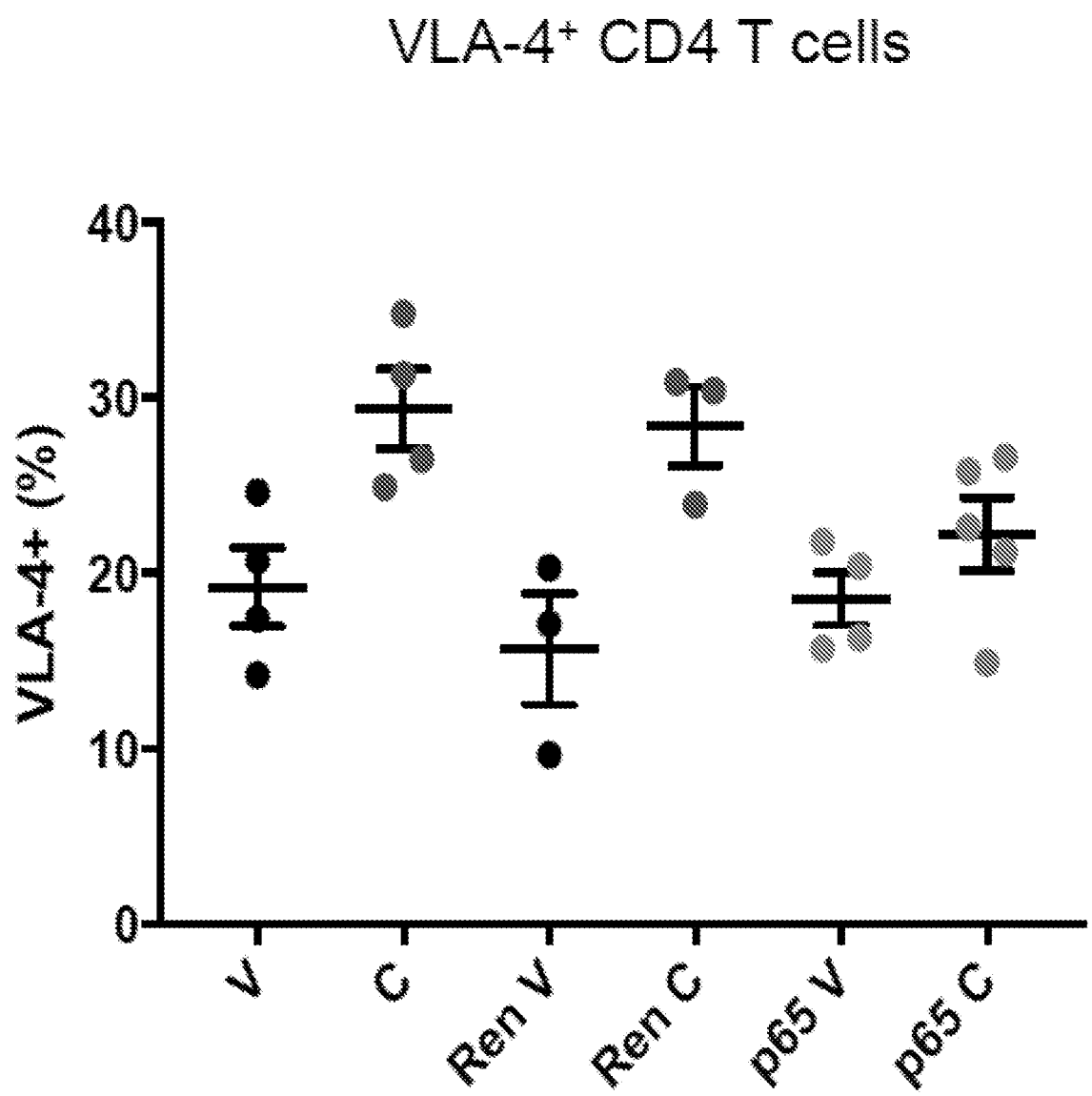

FIGS. 35(F)-35(G): Flow cytometry analysis of indicated KPC$^{mut}$ cell line transplant PDAC tumors following 10-day treatment with vehicle or combined trametinib (1 mg/kg body weight) and palbociclib (100 mg/kg body weight) (n≥3 mice per group). FIG. 35(F): Percentage of VLA-4$^+$ CD8$^+$ T cells. FIG. 35(G): Percentage of VLA-4$^+$ CD4$^+$ T cells. Data represent the mean±SEM.

Figure 35H:
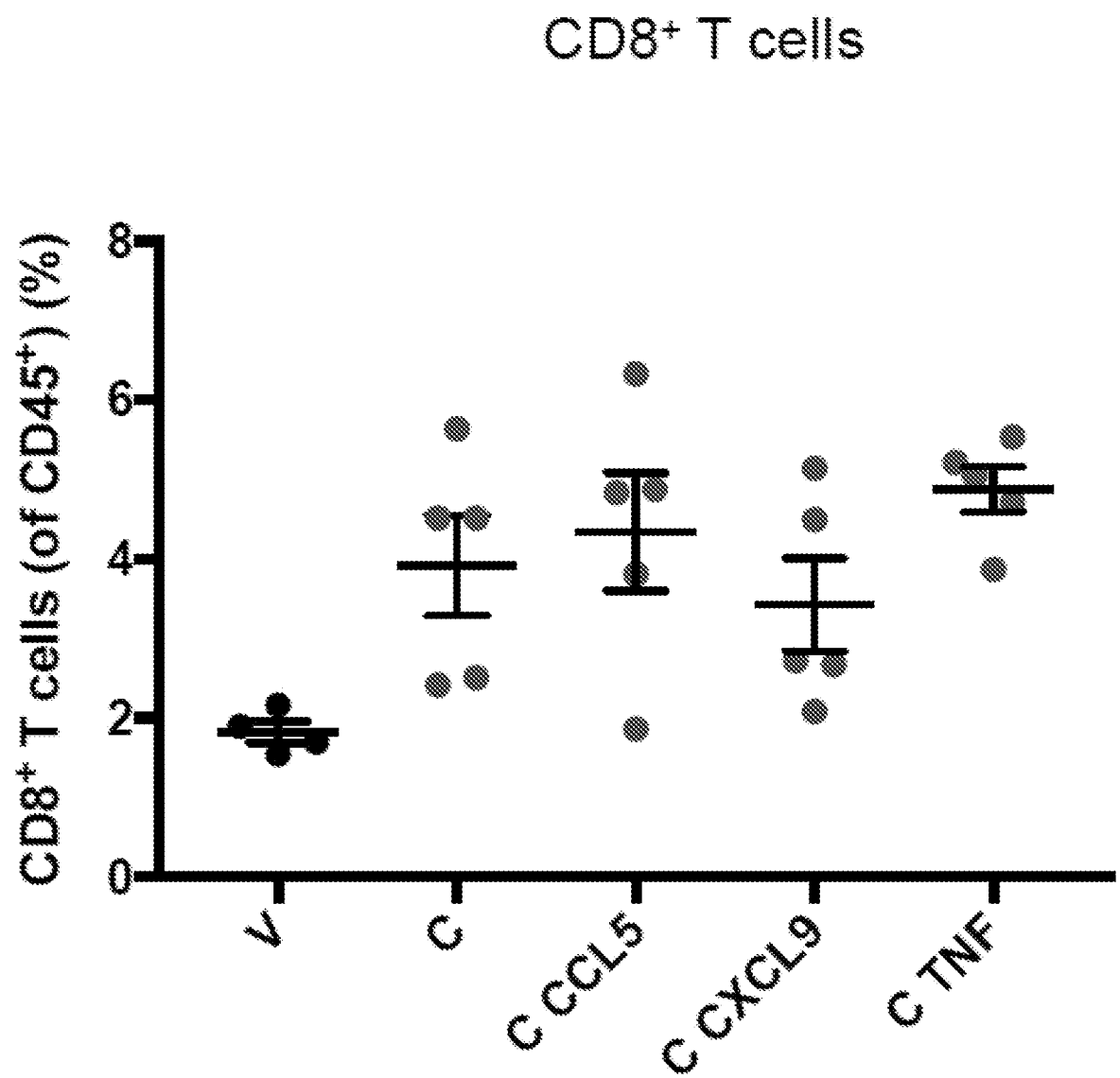
Figure 35I:
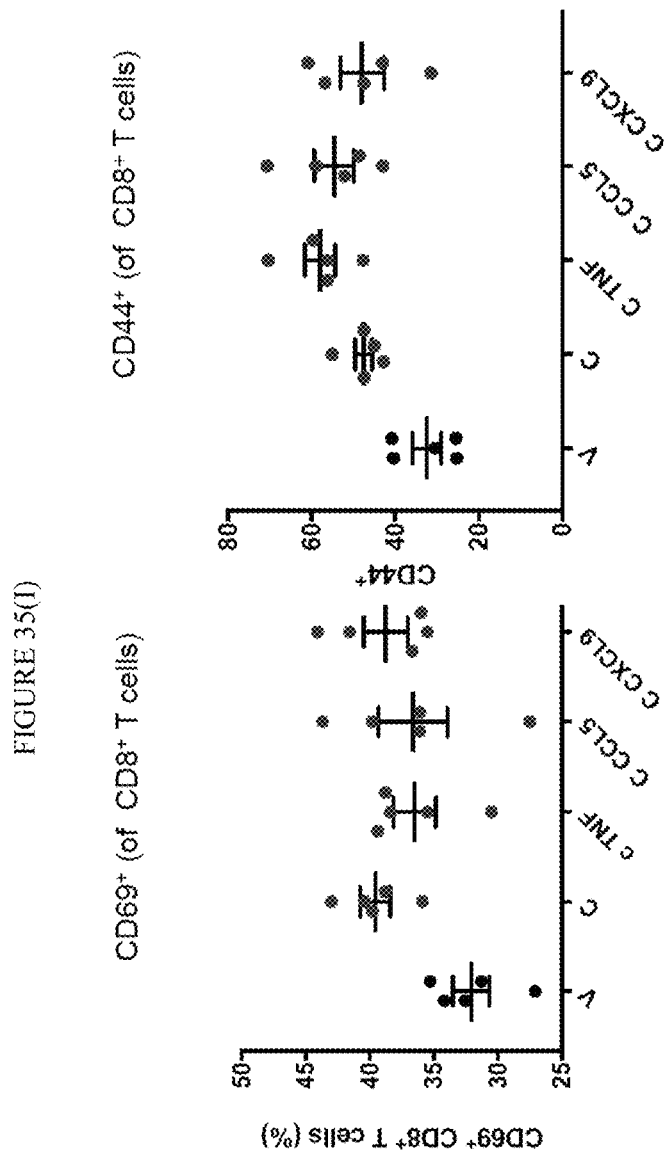

FIGS. 35(H)-35(I): Flow cytometry analysis of KPC$^{mut}$ cell line transplant PDAC tumors following 10-day treatment with vehicle or combined trametinib (1 mg/kg body weight) and palbociclib (100 mg/kg body weight) and neutralizing mAbs targeting CCL5 (53405; 50 µg per mouse), CXCL9 (MIG-2F5.5; 500 µg per mouse), TNF-α (XT3.11; 200 µg per mouse) (n≥4 mice per group). FIG. 35(H): Percentage of CD8$^+$ T cells within the CD45$^+$ population. FIG. 35(I): Percentage of CD69$^+$ CD8$^+$ T cells (left). Right, percentage of CD44$^+$ CD8$^+$ T cells. Data represent the mean±SEM.

Figure 36A:
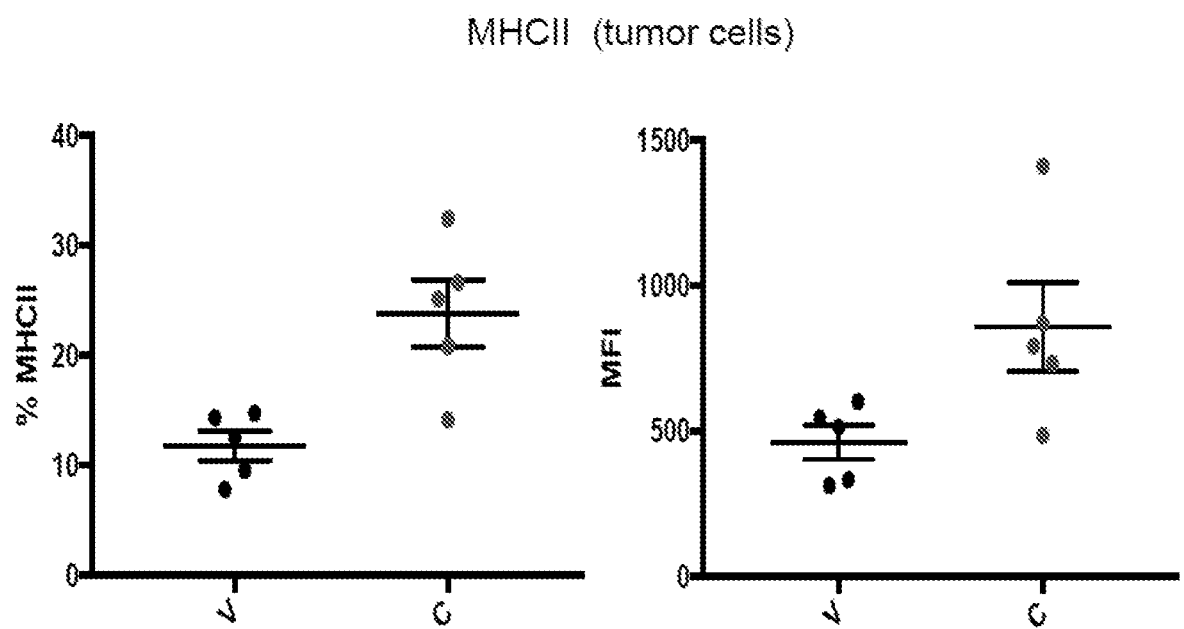
Figure 36B:
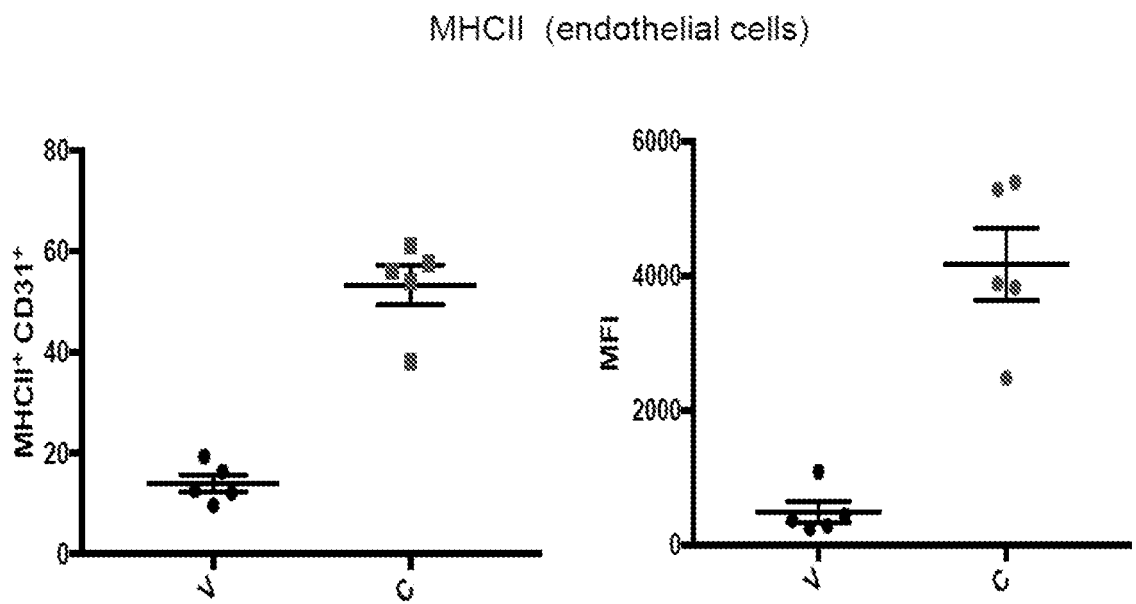
Figure 36C:
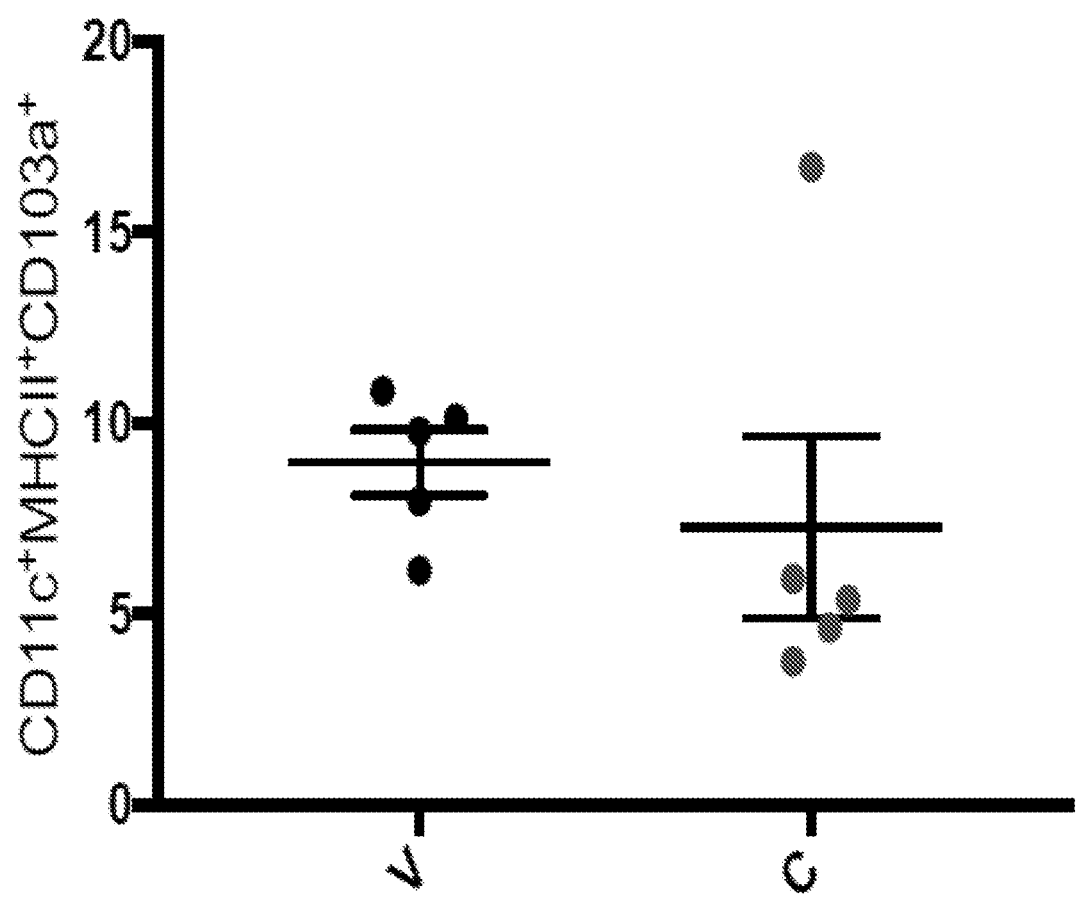
Figure 36D:
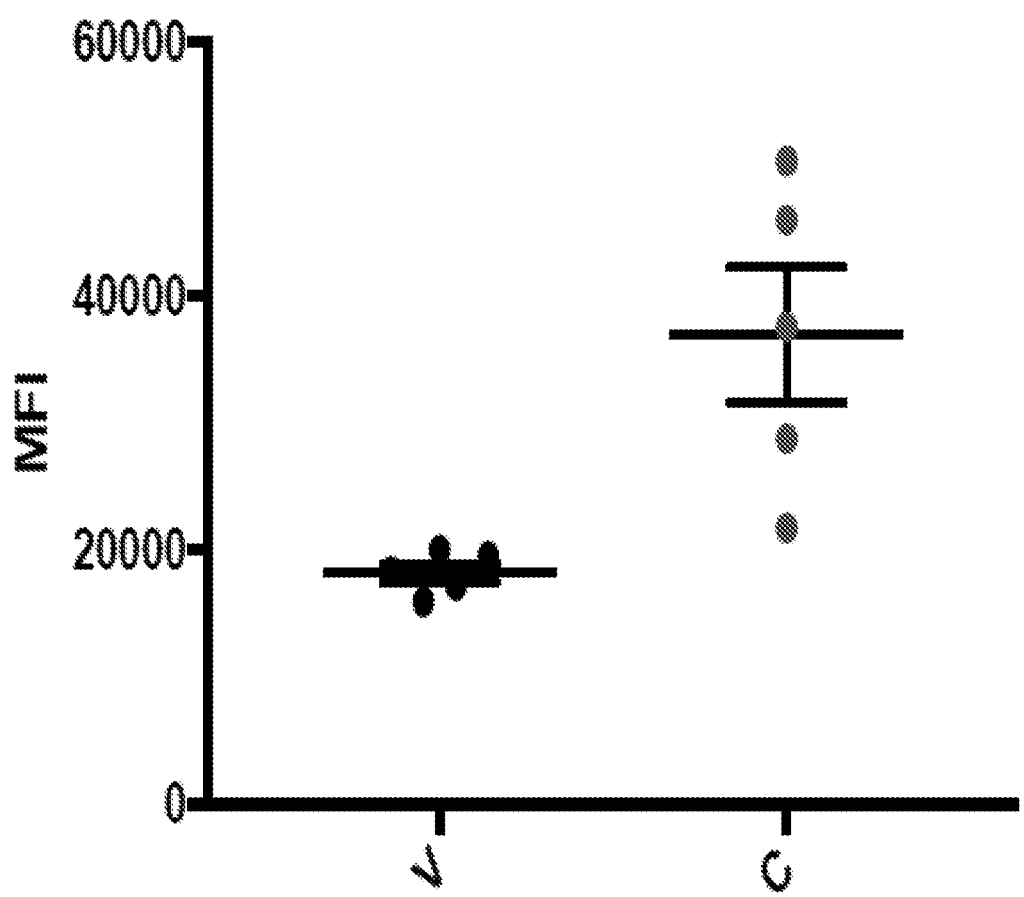

FIGS. 36(A)-36(D): Flow cytometry analysis of KPC$^{mut}$ cell line transplant PDAC tumors following 10-day treatment with vehicle or combined trametinib (1 mg/kg body weight) and palbociclib (100 mg/kg body weight), (n=5 mice per group). FIG. 36(A): Percentage of MHC-II$^+$ PDAC tumor cells (left). Right, MFI of MHC-II expression on PDAC tumor cells. FIG. 36(B): Percentage of MHC-II$^+$ CD31$^+$ ECs (left). Right, MFI of MHC-II expression on CD31$^+$ ECs. FIG. 36(C): Percentage of CD11b$^-$CD11c$^+$ MHC-II$^+$CD103a$^+$ DCs within the CD45$^+$ population. FIG. 36(D): MFI of MHC-II expression on CD11b$^-$CD11c$^+$ DCs. Data represent the mean±SEM.

Figure 36E:
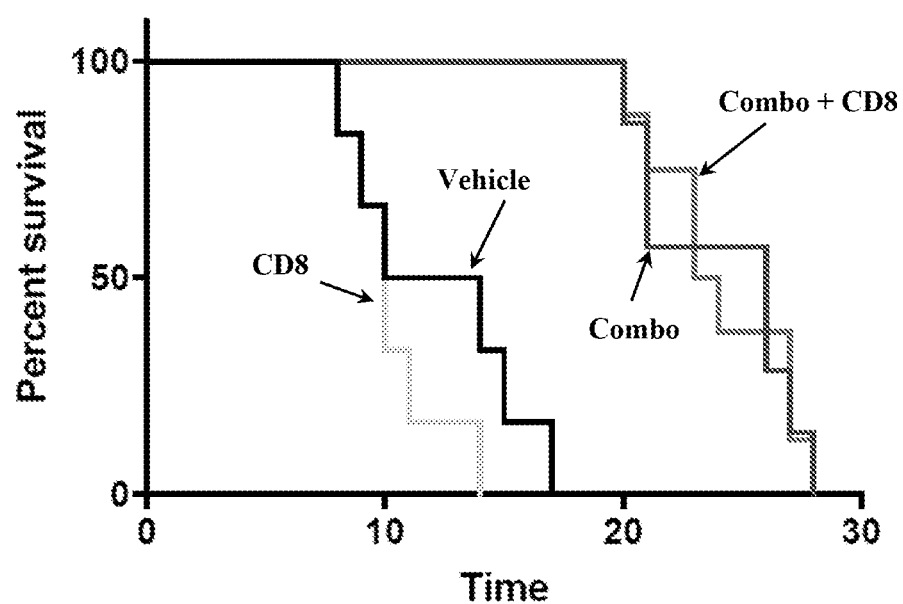

FIG. 36(E): Kaplan-Meier survival curve of KPC$^{mut}$ PDAC cell line transplant mice treated with vehicle or combined trametinib (1 mg/kg body weight) and palbociclib (100 mg/kg body weight) in the presence or absence of a CD8 depleting antibody (2.43; 200 per mouse) (n≥6 per group) (log-rank test).

Figure 36F:
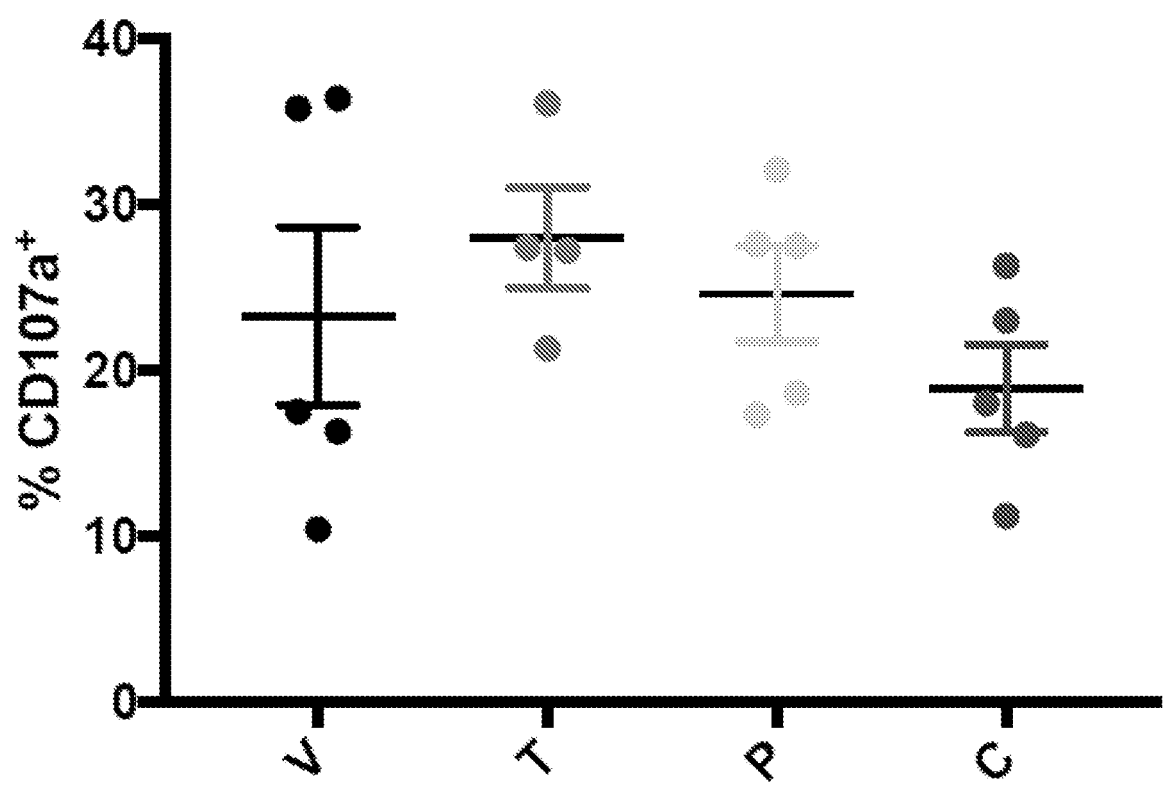
Figure 36G:
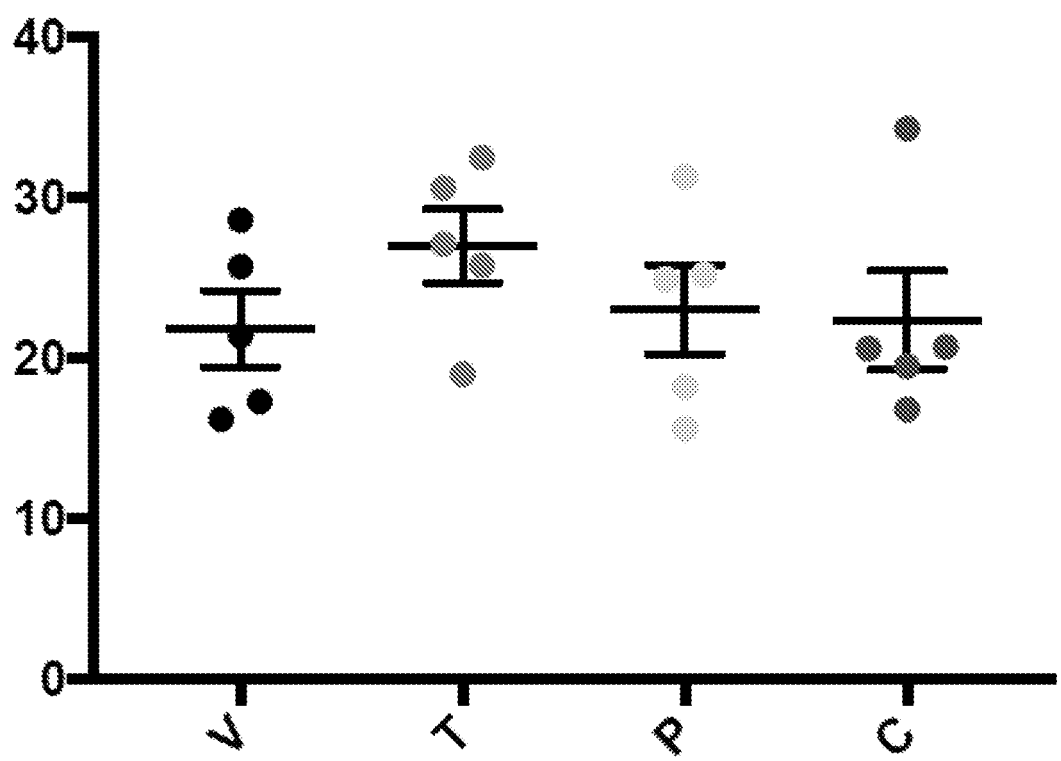
Figure 36H:
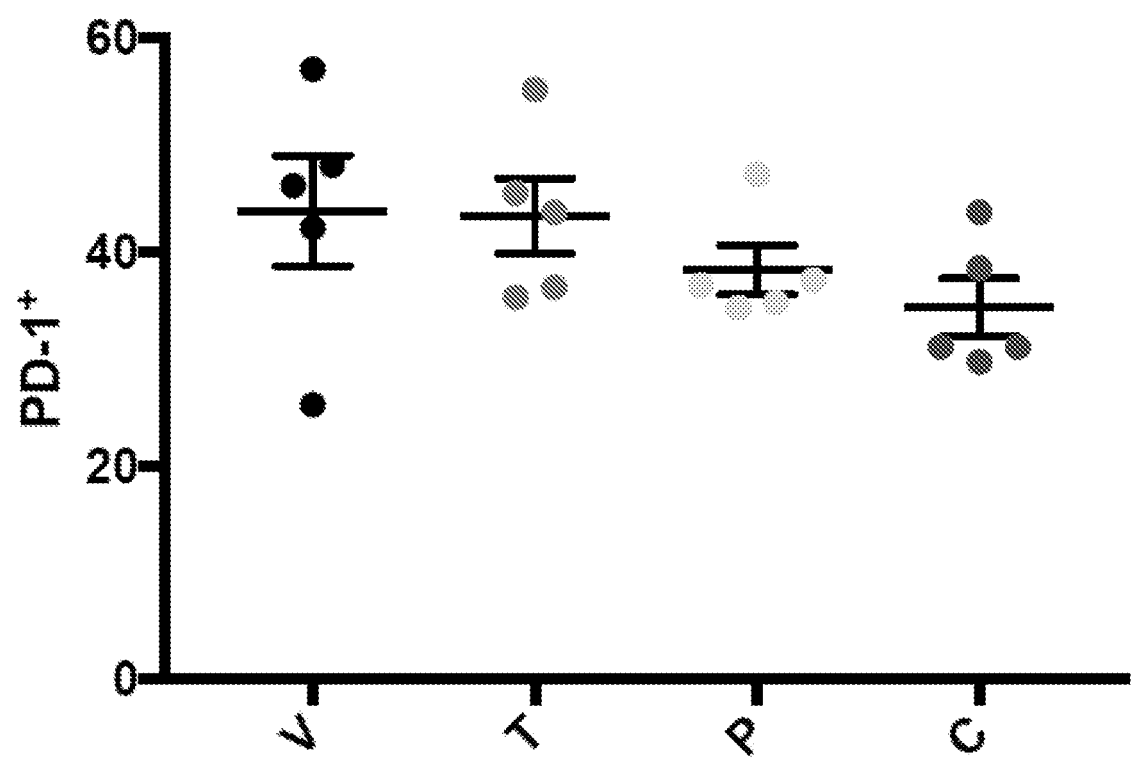
Figure 36I:
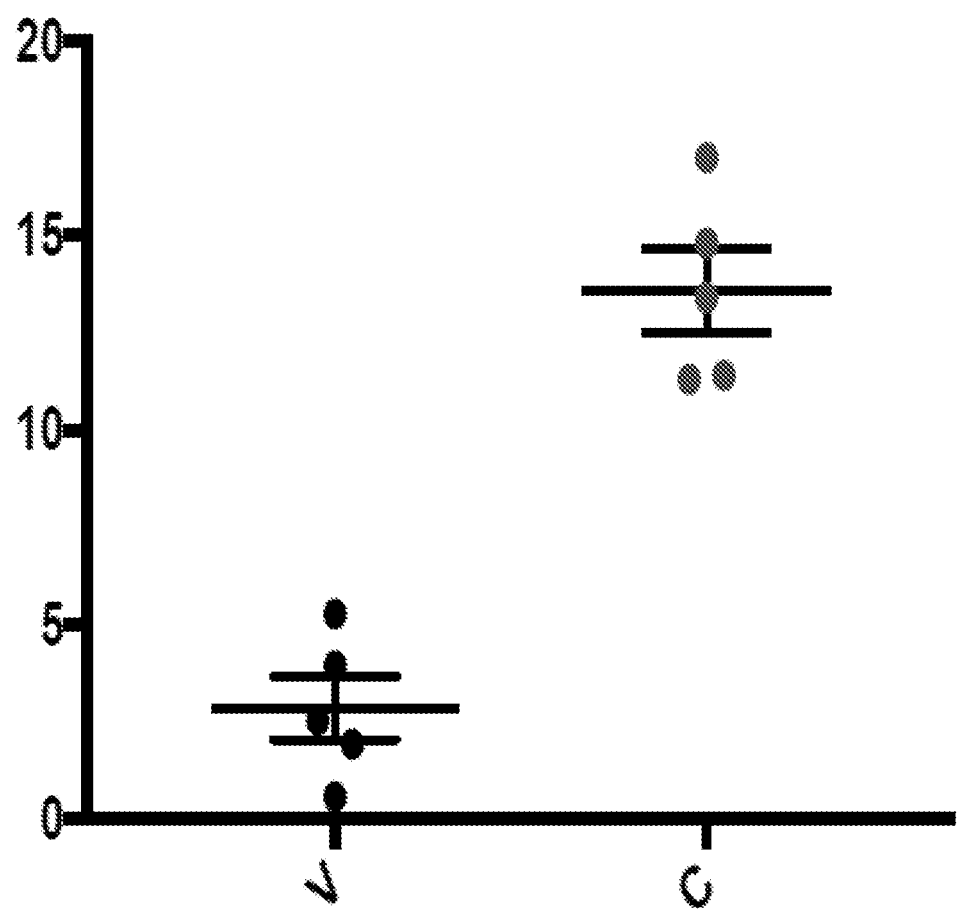

FIGS. 36(F)-36(I): Flow cytometry analysis of KPC$^{mut}$ cell line transplant PDAC tumors following 10-day treatment with vehicle, trametinib (1 mg/kg body weight), palbociclib (100 mg/kg body weight), or both in combination (n≥4 mice per group). FIG. 36(F): Percentage of CD107a$^+$ degranulating CD8$^+$ T cells. FIG. 36(G): Percentage of CD107a$^+$ degranulating CD4+ T cells. FIG. 36(H): Percentage of PD-1$^+$ CD4$^+$ T cells. FIG. 36(I): Percentage of PD-L1$^+$ CD31$^+$ ECs. Data represent the mean±SEM.

Figure 36J:
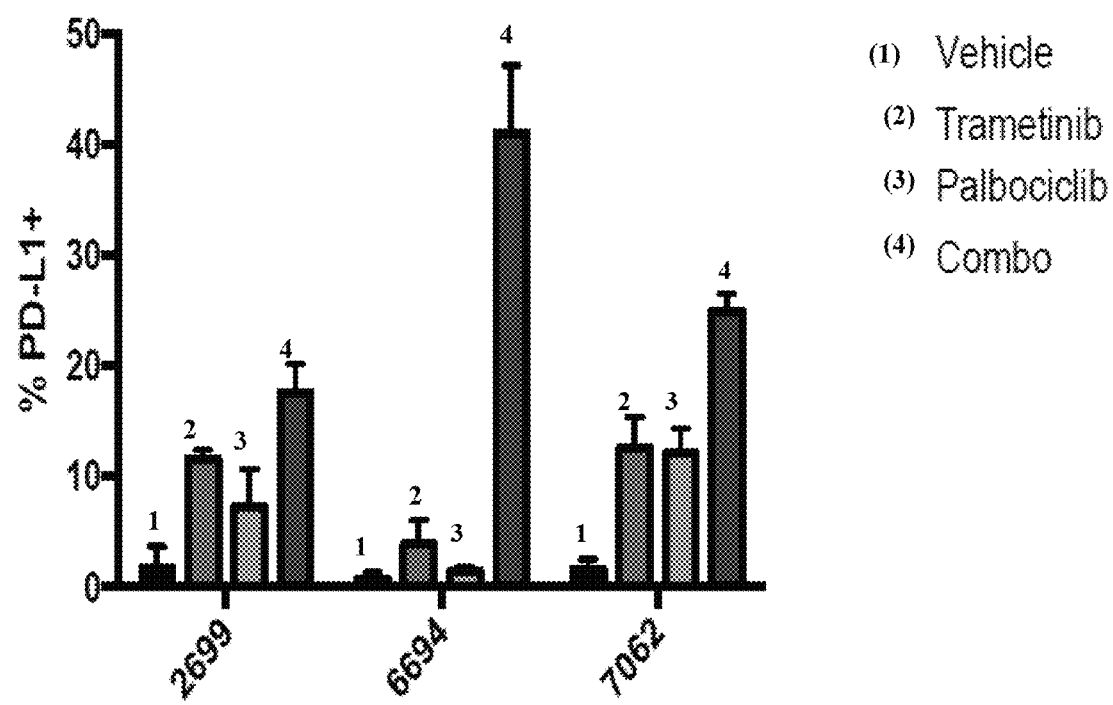

FIG. 36(J): Flow cytometry analysis of PD-L1 expression in 3 different KPC$^{mut}$ PDAC cell lines treated in culture with trametinib (25 nM) and/or palbociclib (500 nM) for 8 days. Bars represent the mean±SEM.

Figure 36K:
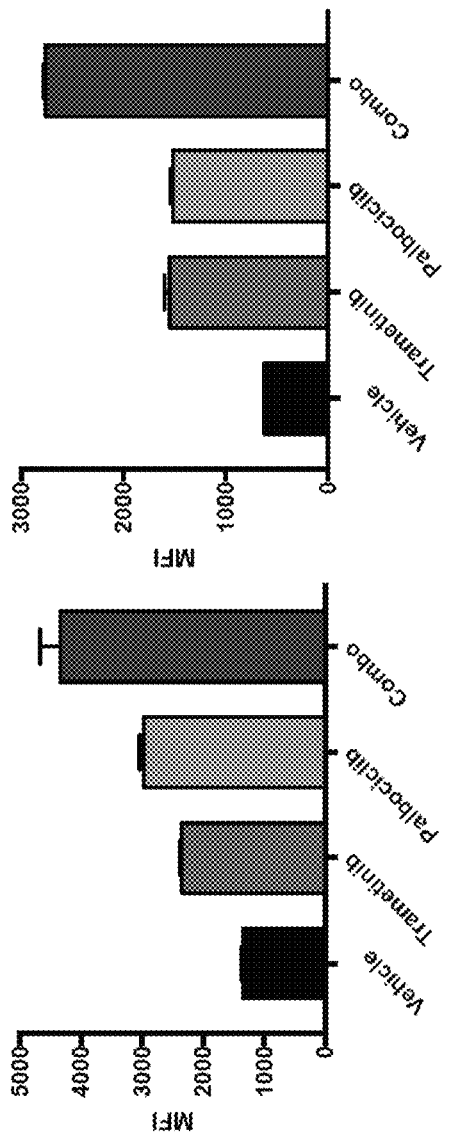

FIG. 36(K): Flow cytometry analysis of MFI of PD-L1 expression in human KRAS mutant PDAC cell lines (PANC-1, PU8988T) treated as in FIG. 36(J). Bars represent the mean±SEM.

Figure 37A:
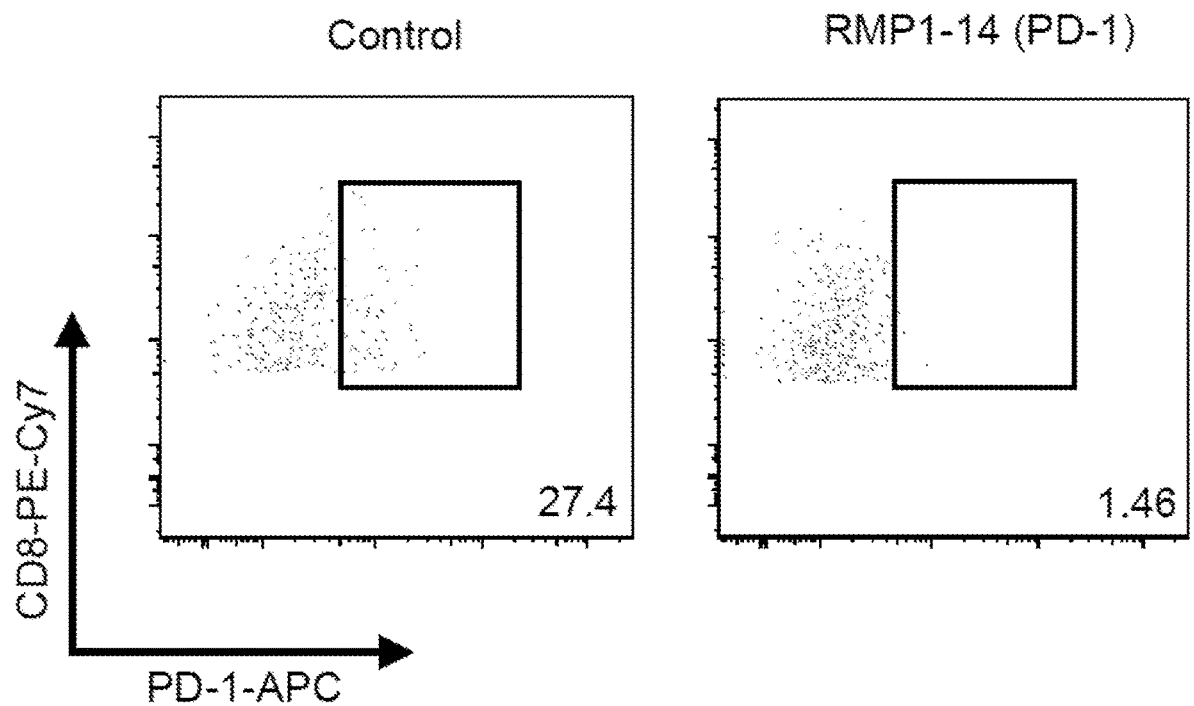

FIG. 37(A): Flow cytometry analysis of PD-1$^+$ expression in CD8$^+$ T cells from KPC$^{mut}$ cell line transplant PDAC tumors following 10-day treatment with a PD-1 blocking antibody (RMP1-14; 200 µg per mouse).

Figure 37B:
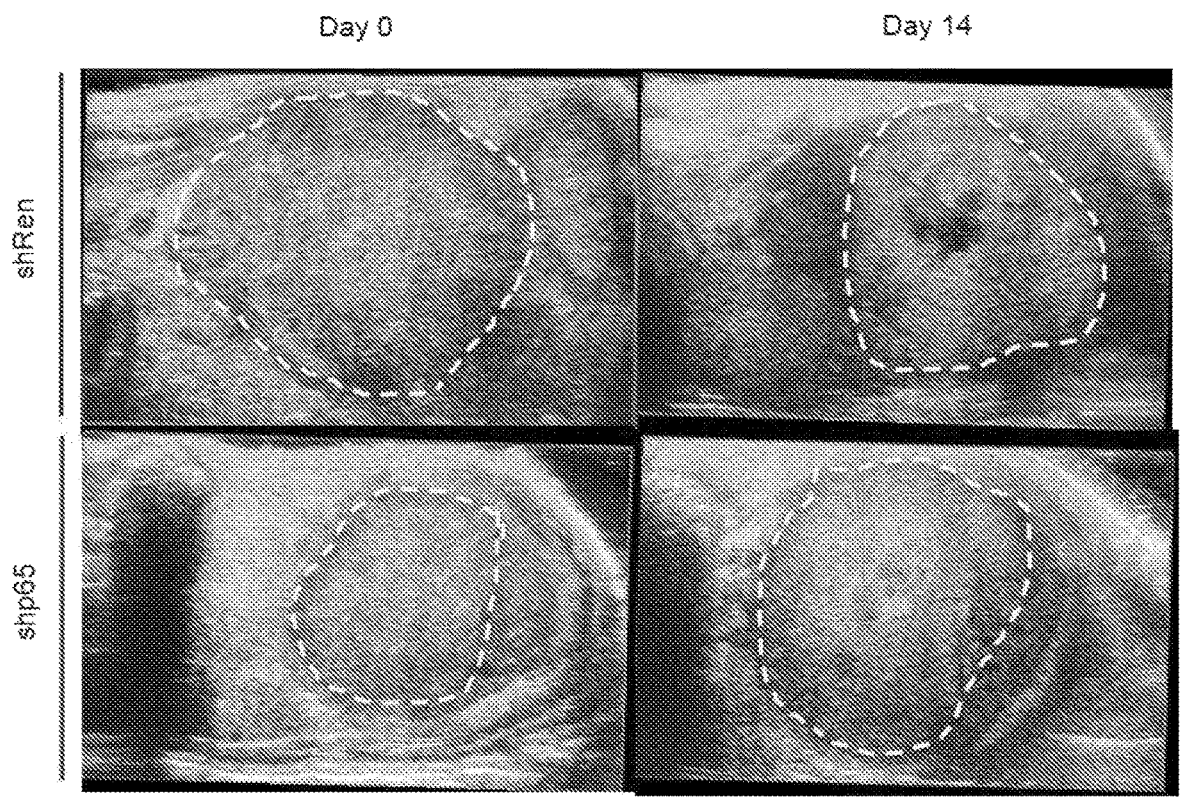

FIG. 37(B): Representative ultrasound images of a KPC$^{mut}$ PDAC organoid transplant tumors harboring control Renilla (Ren) or p65-targeting shRNAs (dashed yellow line) at pretreatment (day 0) and after 2 week treatment (day 14) with trametinib (1 mg/kg body weight), palbociclib (100 mg/kg body weight), and a PD-1 blocking antibody (RMP1-14; 200 µg per mouse). Arrows point to areas of tumor necrosis.

Figure 37C:
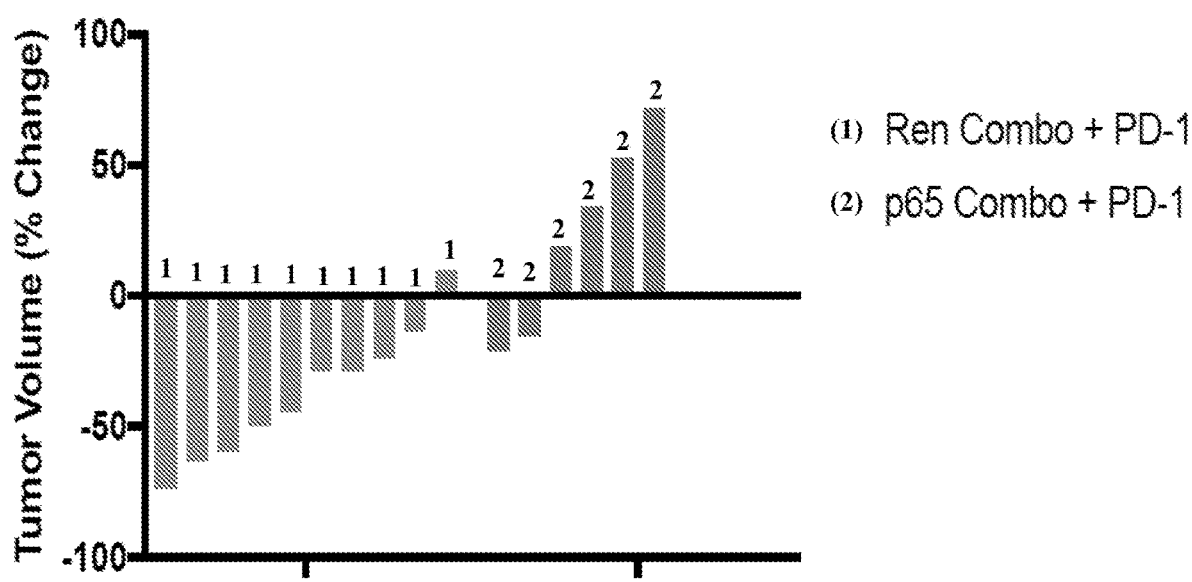

FIG. 37(C): A waterfall representation of the response of KPC$^{mut}$ PDAC organoid transplant tumors harboring control Renilla (Ren) or p65-targeting shRNAs and treated for 2 weeks with trametinib (1 mg/kg body weight), palbociclib (100 mg/kg body weight), and a PD-1 blocking antibody (RMP1-14; 200 µg per mouse) (n≥7 per group).

Figure 38:
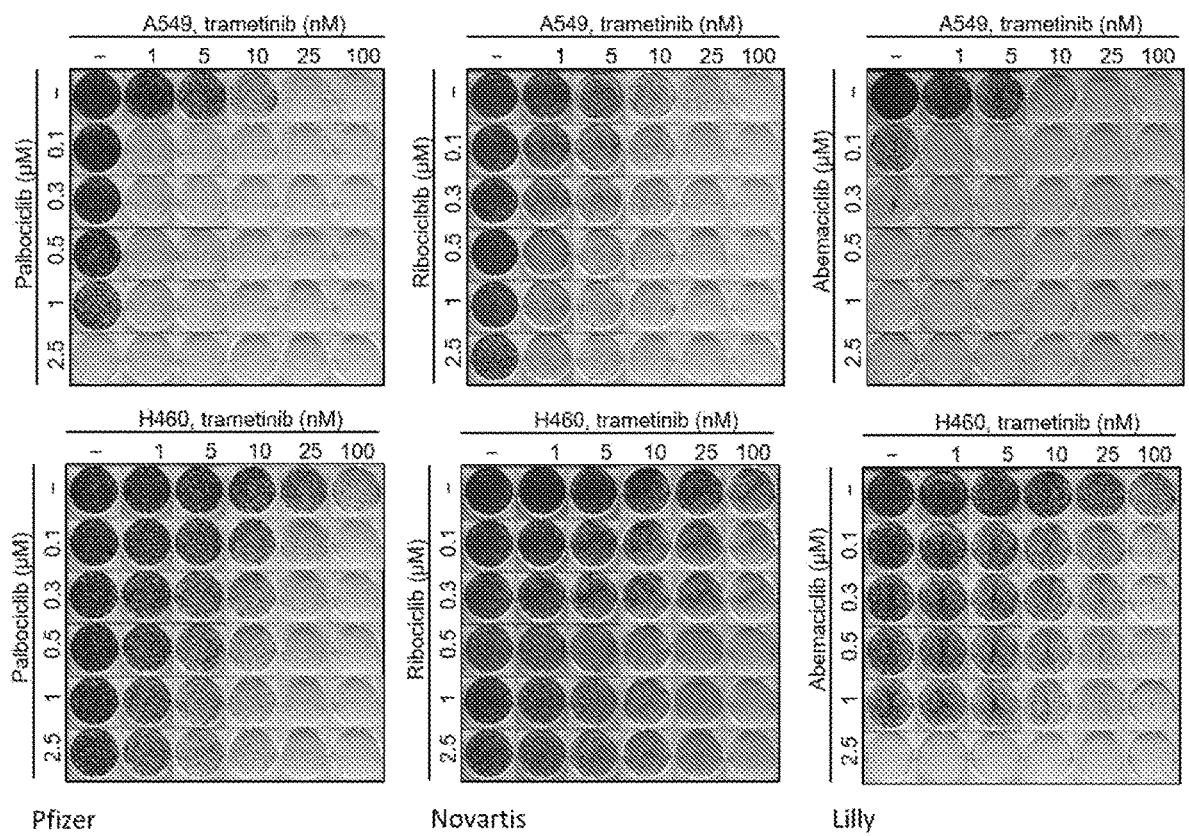

FIG. 38 shows the activity of three different CDK4/6 inhibitors in combination with trametinib at different doses. The human KRAS mutant lung cancer cell lines A549 and H460 were plated at a density of 10×10$^3$ cells per well and treated for 7-10 days with escalating doses of MEK (trametinib) and/or CDK4/6 inhibitors (palbociclib, ribociclib, abemaciclib). At endpoint cells were fixed, stained with crystal violet, and imaged.

DETAILED DESCRIPTION

PDAC is a deadly carcinoma with an overall 5-year survival rate of about 6%. For the 25% of patients who qualify for surgical resection, the only cure for the disease, the 5-year survival rate is only 20% (Jemal et al., CA Cancer J Clin. 60:277-3001 (2010)). The dire prognosis for PDAC patients is largely due to the inadequacy of the tools and treatments available for combating the disease, and advances in chemotherapy for PDAC patients have only marginally increased survival (Murakami K., World J Clin Oncol. 2, 229-236 (2011); Ballehaninna & Chamberlain, J Gastrointest Oncol. 3, 105-119 (2012)). KRAS mutant pancreatic ductal adenocarcinoma (PDAC) is characterized by a desmoplastic response that promotes hypovascularity, poor drug delivery, immunosuppression, and resistance to chemo- and immunotherapies.

The present disclosure demonstrates that combination therapy with a MEK inhibitor and a CDK 4/6 inhibitor is effective in treating pancreatic cancer, including PDAC, the most aggressive and malignant form of pancreatic cancer. In contrast, monotherapy with MEK inhibitors and CDK 4/6 inhibitors had no significant effect on subjects with pancreatic cancer.

Figure 1A:
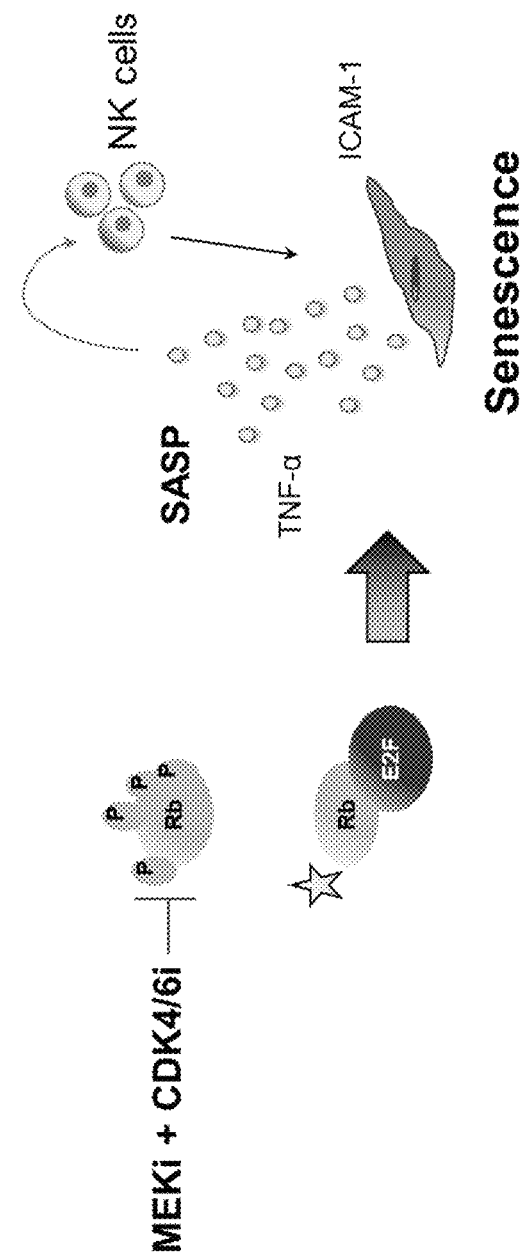
FIGS. 1(A)-1(B) show a model of senescence-associated secretory phenotype (SASP) modulation of tumor microenvironment to improve therapies for pancreatic cancer.
Figure 1B:
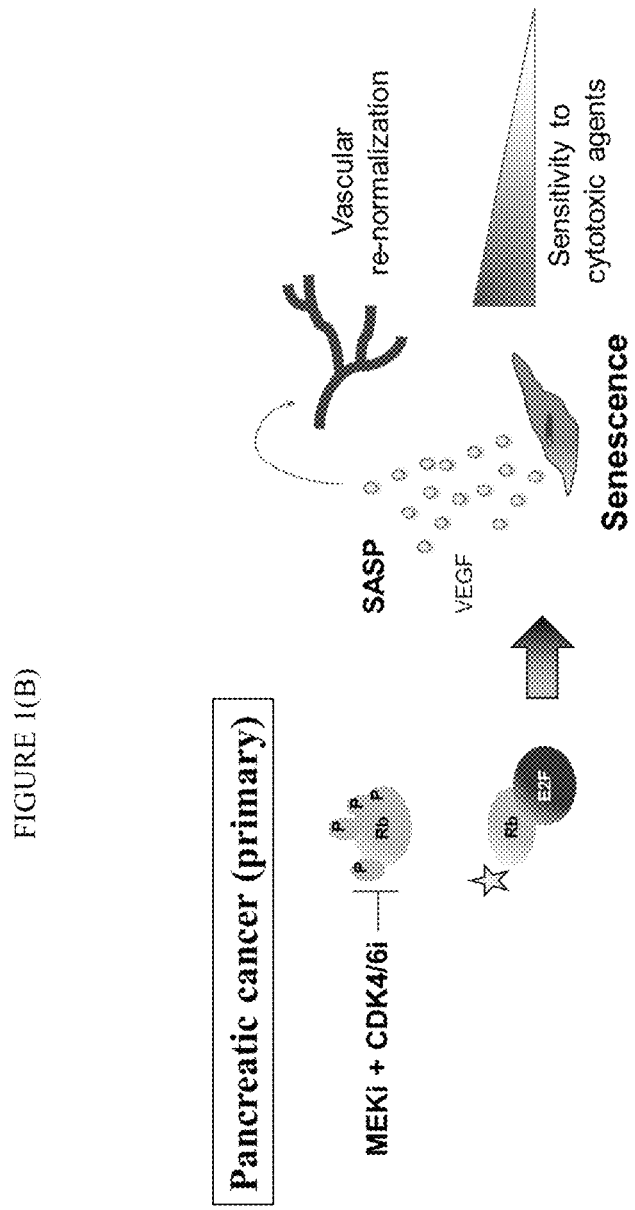

The Examples of the present disclosure demonstrate that combination therapy with a MEK inhibitor and a CDK 4/6 inhibitor (e.g., trametinib and palbociclib) induces RB-mediated cellular senescence and SASP in pancreatic cancer cells, increases pro-angiogenic SASP factor secretion, and reduces Hyaluronic Acid accumulation in the stroma following senescence induction. See FIGS. 1(A)-1(B). These findings were unexpected because previous studies have demonstrated that elevated angiogenesis actually promotes cancer progression, and results in poor patient prognosis (Hanahan, D. and Weinberg, R. A., Cell 144 (5): 646-674 (2011); Jain, R. K., Science 307 (5706): 58-62 (2005); Long, V. et al., Oncotarget 7(36): 58649-58658 (2016)). The present disclosure shows that pancreatic cancer patients (including those that are refractory to chemotherapy alone) receiving MEK inhibitor/CDK4/6 inhibitor combination therapy displayed vascular re-normalization and increased uptake and responsiveness to cytotoxic agents such as gemcitabine and abraxane or immune checkpoint inhibitors. Without wishing to be bound by theory, it is believed that the effects of combination therapy with senescence-inducing agents (e.g., a MEK inhibitor and a CDK 4/6 inhibitor) can be attributed at least in part to the induction of vascular re-normalization in pancreatic cancer patients, which consequently increases drug permeability and improves anti-tumor responses at metastatic sites. In addition, increased antigen presentation and SASP-mediated vascular remodeling upon treatment mediates $CD8^+$ T cell accumulation and activation, sensitizing PDAC to PD-1 checkpoint blockade. These results demonstrate that therapy-induced senescence confers susceptibilities to otherwise ineffective chemo- and immunotherapies in PDAC through SASP-dependent, non-cell autonomous effects on the tumor vasculature and immune system.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), intratumorally, or topically. Administration includes self-administration and the administration by another.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of pancreatic cancer. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the terms "individual", "patient", or "subject" are used interchangeably and refer to an individual organism, a vertebrate, a mammal, or a human. In certain embodiments, the individual, patient or subject is a human.

As used herein, the term "MEK" refers to members of the MAPK kinase family, which are dual specificity enzymes that phosphorylate threonine and tyrosine residues within the activation loop of their MAP kinase substrates. Enzymes in this family include MEK1, MEK2, MEK3, MEK4, MEK5, MEK6, and MEK7.

The term "MEK inhibitor" refers to a compound that is capable of interacting with inhibiting the enzymatic activity of a MEK. As used herein, inhibiting MEK enzymatic activity means reducing the ability of MEK to phosphorylate a substrate peptide or protein. In some embodiments, the MEK inhibitor reduces MEK enzymatic activity by at least about 50%, at least about 75%, at least about 90%, at least about 95%, or at least about 99%. In various embodiments, the concentration of MEK inhibitor required to reduce MEK enzymatic activity is less than about 1 µM, less than about 500 nM, less than about 100 nM, or less than about 50 nM. In some embodiments, the MEK inhibitor is selective, e.g., the MEK inhibitor reduces the ability of MEK to phosphorylate a substrate peptide or protein at a concentration that is lower than the concentration of the inhibitor that is required to produce another, unrelated biological effect, e.g., reduction of the enzymatic activity of a different kinase. In some embodiments, the MEK inhibitor also reduces the enzymatic activity of a MAPK kinase that is implicated in cancer.

As used herein, a "sample" or "biological sample" refers to a body fluid or a tissue sample isolated from a subject. In some cases, a biological sample may consist of or comprise whole blood, platelets, red blood cells, white blood cells, plasma, sera, urine, feces, epidermal sample, vaginal sample, skin sample, cheek swab, sperm, amniotic fluid, cultured cells, bone marrow sample, tumor biopsies, aspirate and/or chorionic villi, cultured cells, endothelial cells, synovial fluid, lymphatic fluid, ascites fluid, interstitial or extracellular fluid and the like. The term "sample" may also encompass the fluid in spaces between cells, including gingival crevicular fluid, bone marrow, cerebrospinal fluid (CSF), saliva, mucus, sputum, semen, sweat, urine, or any other bodily fluids. Samples can be obtained from a subject by any means including, but not limited to, venipuncture, excretion, ejaculation, massage, biopsy, needle aspirate, lavage, scraping, surgical incision, or intervention or other means known in the art. A blood sample can be whole blood or any fraction thereof, including blood cells (red blood cells, white blood cells or leukocytes, and platelets), serum and plasma.

As used herein, the term "separate" therapeutic use refers to an administration of at least two active ingredients at the same time or at substantially the same time by different routes.

As used herein, the term "sequential" therapeutic use refers to administration of at least two active ingredients at different times. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

MEK Inhibitors

The mitogen-activated protein kinase (MAPK) signaling pathway plays critical roles in the regulation of diverse cellular activities, including cell proliferation, survival, differentiation, and motility (Karin, L. C. M. *Nature*, 410, 37-40 (2001)). Dysregulation of the MAPK pathway occurs in more than one-third of all malignancies. The classical MAPK pathway consists of Ras (a family of related proteins which is expressed in all animal cell lineages and organs), Raf (a family of three serine/threonine-specific protein kinases that are related to retroviral oncogenes), MEK (mitogen-activated protein kinase kinase), and ERK (extracellular signal-regulated kinases), sequentially relaying proliferative signals generated at the cell surface receptors into the nucleus through cytoplasmic signaling. MEK inhibitors target the Ras/Raf/MEK/ERK signaling pathway, inhibiting cell proliferation and inducing apoptosis.

Figure 19:
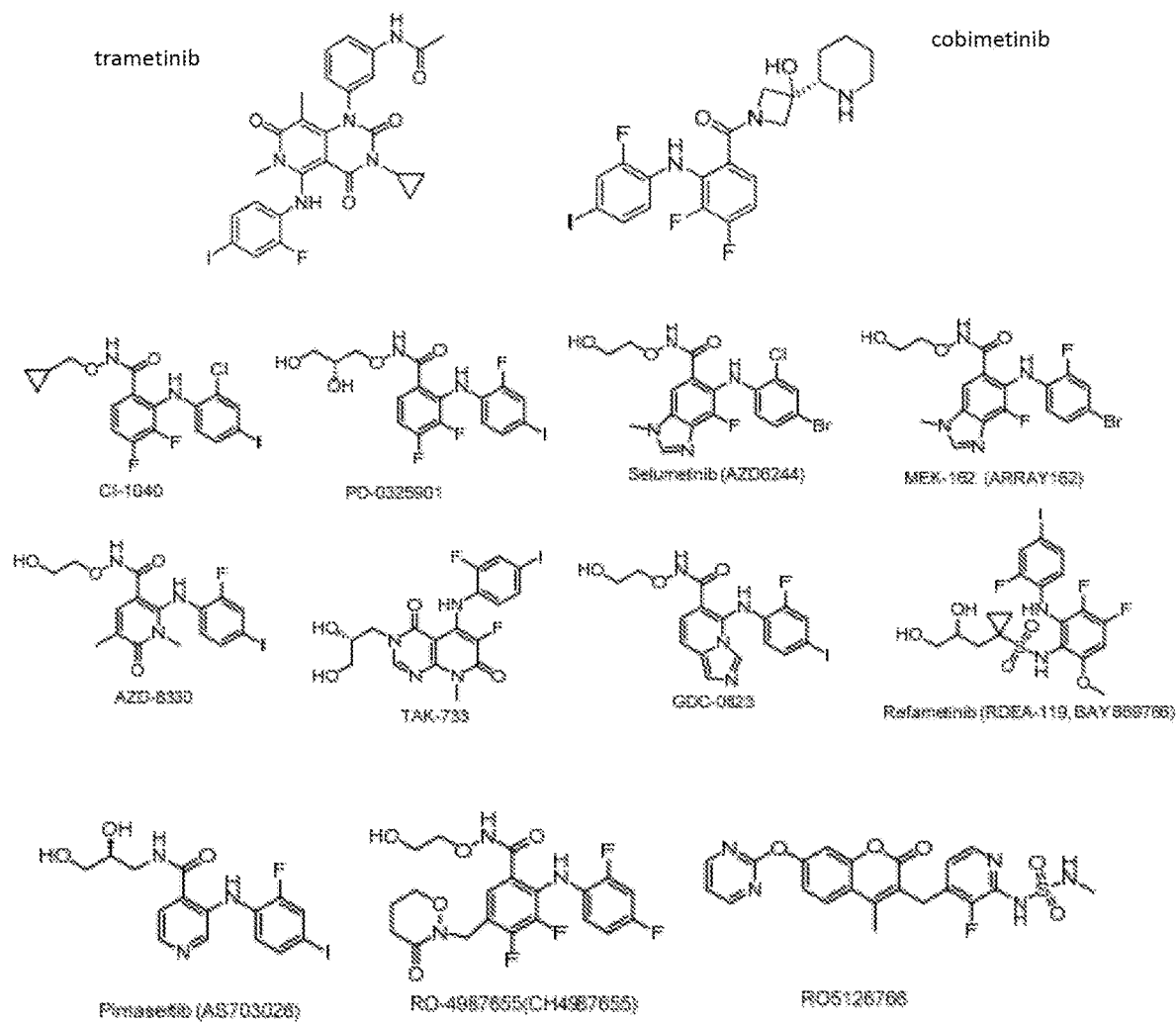
FIG. 19 shows exemplary structures of some of the MEK inhibitors disclosed herein.

Examples of MEK inhibitors include trametinib, cobimetinib, binimetinib, selumetinib, PD-325901, TAK-733, CI-1040 (PD184352), PD0325901, MEK162, AZD8330, GDC-0623, refametinib, pimasertib, RO4987655, RO5126766, WX-554, HL-085, CInQ-03, G-573, PD184161, PD318088, PD98059, RO5068760, U0126, and SL327. Examples of CDK4/6 inhibitors include palbociclib, ribociclib, and abemaciclib. The properties, efficacy, and therapeutic indications of the various MEK inhibitors are described in Cheng & Tian, *Molecules* 22, 1551 (2017). Exemplary structures of some of the MEK inhibitors disclosed herein are show in FIG. 19. Thus far, no MEK inhibitors been clinically approved for the treatment of pancreatic cancer.

CDK4/CDK6 Inhibitors

CDK4 and CDK6 are cyclin-dependent kinases that control the transition between the G1 and S phases of the cell cycle. The S phase is the period during which the cell synthesizes new DNA and prepares itself to divide during mitosis. CDK4/6 activity is typically deregulated and overactive in cancer cells. Some cancers exhibit amplification or overexpression of the genes encoding cyclins or the CDKs themselves.

A major target of CDK4 and CDK6 during cell-cycle progression is the retinoblastoma protein (RB). When RB is phosphorylated, its tumor-suppressive properties are inactivated. Selective CDK4/6 inhibitors deactivate CDK4 and CDK6 and dephosphorylate RB, resulting in cell-cycle arrest. In some cases, the arrested cells enter a state of senescence. Examples of CDK4/6 inhibitors include palbociclib, ribociclib, and abemaciclib.

Formulations Including the MEK Inhibitors and/or the CDK4/6 Inhibitors of the Present Technology The pharmaceutical compositions of the present technology can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired. In certain embodiments, the compositions disclosed herein are formulated for administration to a mammal, such as a human.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition that they release the active ingredient(s) only, or in a certain part of the intestinal tract, optionally, in a delayed manner. Examples of embedding compositions that can be used include polymeric substances and waxes.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or in a certain part of the intestinal tract, optionally, in a delayed manner. Examples of embedding compositions that can be used include polymeric substances and waxes.

Methods of Treatment of the Present Technology

In one aspect, the present disclosure provides a method for preventing or treating pancreatic cancer in a subject in need thereof comprising administering to the subject an effective amount of a MEK inhibitor and an effective amount of a CDK4/6 inhibitor. The pancreatic cancer may be an exocrine pancreatic cancer or an endocrine pancreatic cancer. Examples of pancreatic cancers include, but are not limited to PDAC, acinar cell carcinoma, solid pseudopapillary neoplasms, pancreatoblastoma, pancreatic neuroendocrine tumors (PNETs), gastrinomas, insulinomas, glucagonomas, somatostatinomas and VIPomas. Additionally or alternatively, in some embodiments, the pancreatic cancer comprises a KRAS mutation such as G12D, G12V, G12C, G12R, G12A, G13D, Q61L, Q61H etc. In certain embodiments, the subject is human. Additionally or alternatively, in some embodiments, the subject is non-responsive to at least one prior line of cancer therapy such as chemotherapy or immunotherapy.

Examples of MEK inhibitors include trametinib, cobimetinib, binimetinib, selumetinib, PD-325901, TAK-733, CI-1040 (PD184352), PD0325901, MEK162, AZD8330, GDC-0623, refametinib, pimasertib, RO4987655, RO5126766, WX-554, HL-085, CInQ-03, G-573, PD184161, PD318088, PD98059, RO5068760, U0126, and SL327. Examples of CDK4/6 inhibitors include palbociclib, ribociclib, and abemaciclib.

Additionally or alternatively, in some embodiments, the subject exhibits an increase in one or more of (a) NK cell immune surveillance, (b) senescent tumor cell clearance, or (c) vascular re-normalization after administration of the MEK inhibitor and the CDK4/6 inhibitor. In any of the above embodiments, the subject exhibits a delay in metastatic onset and/or tumor growth after administration of the MEK inhibitor and the CDK4/6 inhibitor compared to that observed in an untreated control subject diagnosed with pancreatic cancer. Additionally or alternatively, in some embodiments of the combination therapy methods disclosed herein, the time to response and/or duration of response is improved relative to that observed with MEK inhibitor monotherapy or CDK4/6 inhibitor monotherapy.

In one aspect, the present disclosure provides a method for increasing the efficacy of at least one chemotherapeutic agent in a patient with pancreatic cancer comprising administering to the patient an effective amount of a MEK inhibitor and an effective amount of a CDK4/6 inhibitor. Examples of chemotherapeutic agents include abraxane, capecitabine, erlotinib, fluorouracil (5-FU), gemcitabine, irinotecan, leucovorin, nab-paclitaxel, cisplatin, irinotecan, docetaxel, oxaliplatin, tipifarnib, everolimus, sunitinib, dovitinib, ruxolitinib, pegylated-hyaluronidase, pemetrexed, folinic acid, paclitaxel, MK2206, GDC-0449, IPI-926, gamma secretase/RO4929097, M402, and LY293111.

In another aspect, the present disclosure provides a method for increasing the efficacy of at least one immunotherapeutic agent in a patient with pancreatic cancer comprising administering to the patient an effective amount of a MEK inhibitor and an effective amount of a CDK4/6 inhibitor. Examples of immunotherapeutic agents include immune checkpoint inhibitors (e.g., antibodies targeting CTLA-4, PD-1, PD-L1), ipilimumab, 90Y-Clivatuzumab tetraxetan, pembrolizumab, nivolumab, trastuzumab, cixutumumab, ganitumab, demcizumab, cetuximab, nimotuzumab, dalotuzumab, sipuleucel-T, CRS-207, and GVAX.

Examples of MEK inhibitors include trametinib, cobimetinib, binimetinib, selumetinib, PD-325901, TAK-733, CI-1040 (PD184352), PD0325901, MEK162, AZD8330, GDC-0623, refametinib, pimasertib, RO4987655, RO5126766, WX-554, HL-085, CInQ-03, G-573, PD184161, PD318088, PD98059, RO5068760, U0126, and SL327. Examples of CDK4/6 inhibitors include palbociclib, ribociclib, and abemaciclib.

Additionally or alternatively, in some embodiments of the methods disclosed herein, the pancreatic cancer is an exocrine pancreatic cancer or an endocrine pancreatic cancer. Examples of pancreatic cancers include, but are not limited to PDAC, acinar cell carcinoma, solid pseudopapillary neoplasms, pancreatoblastoma, pancreatic neuroendocrine tumors (PNETs), gastrinomas, insulinomas, glucagonomas, somatostatinomas and VIPomas. In certain embodiments, the pancreatic cancer comprises a KRAS mutation such as G12D, G12V, G12C, G12R, G12A, G13D, Q61L, Q61H etc. In some embodiments of the methods disclosed herein, the patient is human.

Additionally or alternatively, in some embodiments of the methods disclosed herein, the MEK inhibitor and the CDK4/6 inhibitor are administered sequentially, simultaneously, or separately. The MEK inhibitor and/or the CDK4/6 inhibitor may be administered orally, parenterally, by inhalation spray, intranasally, buccally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intravenously, or subcutaneously. Formulations including any MEK inhibitor and/or CDK4/6 inhibitor disclosed herein may be designed to be short-acting, fast-releasing, or long-acting. In other embodiments, compounds can be administered in a local rather than systemic means, such as administration (e.g., by injection) at a tumor site.

Additionally or alternatively, in some embodiments of the methods disclosed herein, the MEK inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), simultaneously with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a CDK4/6 inhibitor to a patient with pancreatic cancer.

In some embodiments, the MEK inhibitor and CDK4/6 inhibitor are administered to a patient, for example, a mammal, such as a human, in a sequence and within a time interval such that the inhibitor that is administered first acts together with the inhibitor that is administered second to provide greater benefit than if each inhibitor were administered alone. For example, the MEK inhibitor and CDK4/6 inhibitor can be administered at the same time or sequentially in any order at different points in time; however, if not administered at the same time, the MEK inhibitor and CDK4/6 inhibitor are administered sufficiently close in time so as to provide the desired therapeutic or prophylactic effect of the combination of the two inhibitors. In one embodiment, the MEK inhibitor and CDK4/6 inhibitor exert their effects at times which overlap. In some embodiments, the MEK inhibitor and CDK4/6 inhibitor each are administered as separate dosage forms, in any appropriate form and by any suitable route. In other embodiments, the MEK inhibitor and CDK4/6 inhibitor are administered simultaneously in a single dosage form.

It will be appreciated that the frequency with which any of these therapeutic agents can be administered can be once or more than once over a period of about 2 days, about 3 days, about 4 days, about 5 days, about 6 days, about 7 days, about 8 days, about 9 days, about 10 days, about 11 days, about 12 days, about 13 days, about 14 days, about 20 days, about 28 days, about a week, about 2 weeks, about 3 weeks, about 4 weeks, about a month, about every 2 months, about every 3 months, about every 4 months, about every 5 months, about every 6 months, about every 7 months, about every 8 months, about every 9 months, about every 10 months, about every 11 months, about every year, about every 2 years, about every 3 years, about every 4 years, or about every 5 years.

For example, a MEK inhibitor or CDK4/6 inhibitor may be administered daily, weekly, biweekly, or monthly for a particular period of time. A MEK inhibitor or CDK4/6 inhibitor may be dosed daily over a 14 day time period, or twice daily over a seven day time period. A MEK inhibitor or CDK4/6 inhibitor may be administered daily for 7 days.

Alternatively, a MEK inhibitor or CDK4/6 inhibitor may be administered daily, weekly, biweekly, or monthly for a particular period of time followed by a particular period of non-treatment. In some embodiments, the MEK inhibitor or CDK4/6 inhibitor can be administered daily for 14 days followed by seven days of non-treatment, and repeated for two more cycles of daily administration for 14 days followed by seven days of non-treatment. In some embodiments, the MEK inhibitor or CDK4/6 inhibitor can be administered twice daily for seven days followed by 14 days of non-treatment, which may be repeated for one or two more cycles of twice daily administration for seven days followed by 14 days of non-treatment.

In some embodiments, the MEK inhibitor or CDK4/6 inhibitor is administered daily over a period of 14 days. In another embodiment, the MEK inhibitor or CDK4/6 inhibitor is administered daily over a period of 12 days, or 11 days, or 10 days, or nine days, or eight days. In another embodiment, the MEK inhibitor or CDK4/6 inhibitor is administered daily over a period of seven days. In another embodiment, the MEK inhibitor or CDK4/6 inhibitor is administered daily over a period of six days, or five days, or four days, or three days.

In some embodiments, individual doses of the MEK inhibitor and the CDK4/6 inhibitor are administered within a time interval such that the two inhibitors can work together (e.g., within 1 hour, 2 hours, 4 hours, 6 hours, 12 hours, 24 hours, 48 hours, 72 hours, 96 hours, 5 days, 6 days, 1 week, or 2 weeks). In some embodiments, the treatment period during which the therapeutic agents are administered is then followed by a non-treatment period of a particular time duration, during which the therapeutic agents are not administered to the patient. This non-treatment period can then be followed by a series of subsequent treatment and non-treatment periods of the same or different frequencies for the same or different lengths of time. In some embodiments, the treatment and non-treatment periods are alternated. It will be understood that the period of treatment in cycling therapy may continue until the patient has achieved a complete response or a partial response, at which point the treatment may be stopped. Alternatively, the period of treatment in cycling therapy may continue until the patient has achieved a complete response or a partial response, at which point the period of treatment may continue for a particular number of cycles. In some embodiments, the length of the period of treatment may be a particular number of cycles, regardless of patient response. In some other embodiments, the length of the period of treatment may continue until the patient relapses.

In some embodiments, the MEK inhibitor and the CDK4/6 inhibitor are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In some embodiments, the MEK inhibitor is administered for a particular length of time prior to administration of the CDK4/6 inhibitor. For example, in a 21-day cycle, the MEK inhibitor may be administered on days 1 to 5, days 1 to 7, days 1 to 10, or days 1 to 14, and the CDK4/6 inhibitor may be administered on days 6 to 21, days 8 to 21, days 11 to 21, or days 15 to 21. In other embodiments, the CDK4/6 inhibitor is administered for a particular length of time prior to administration of the MEK inhibitor. For example, in a 21-day cycle, the CDK4/6 inhibitor may be administered on days 1 to 5, days 1 to 7, days 1 to 10, or days 1 to 14, and the MEK inhibitor may be administered on days 6 to 21, days 8 to 21, days 11 to 21, or days 15 to 21.

In one embodiment, the administration is on a 21-day dose schedule in which a once daily dose of MEK inhibitor is administered beginning on day eight for seven days, followed by seven days of non-treatment, in combination with twice-daily administration of the CDK4/6 inhibitor for seven days followed by 14 days of non-treatment (e.g., the MEK inhibitor is administered on days 8-14 and the CDK4/6 inhibitor is administered on days 1-7 of the 21-day schedule). In another embodiment, the administration is on a 21-day dose schedule in which a once daily dose of CDK4/6 inhibitor is administered beginning on day eight for seven days, followed by seven days of non-treatment, in combination with twice-daily administration of the MEK inhibitor for seven days followed by 14 days of non-treatment (e.g., the CDK4/6 inhibitor is administered on days 8-14 and the MEK inhibitor is administered on days 1-7 of the 21-day schedule).

In some embodiments, the MEK inhibitor and CDK4/6 inhibitor each are administered at a dose and schedule typically used for that agent during monotherapy. In other embodiments, when the MEK inhibitor and CDK4/6 inhibitor are administered concomitantly, one or both of the agents can advantageously be administered at a lower dose than typically administered when the agent is used during monotherapy, such that the dose falls below the threshold that an adverse side effect is elicited.

The therapeutically effective amounts or suitable dosages of the MEK inhibitor and the CDK4/6 inhibitor in combination depends upon a number of factors, including the nature of the severity of the condition to be treated, the particular inhibitor, the route of administration and the age, weight, general health, and response of the individual patient. In certain embodiments, the suitable dose level is one that achieves a therapeutic response as measured by tumor regression or other standard measures of disease progression, progression free survival, or overall survival. In other embodiments, the suitable dose level is one that achieves this therapeutic response and also minimizes any side effects associated with the administration of the therapeutic agent.

Suitable daily dosages of MEK inhibitors can generally range, in single or divided or multiple doses, from about 10% to about 120% of the maximum tolerated dose as a single agent. In certain embodiments, the suitable dosages of MEK inhibitors are from about 20% to about 100% of the maximum tolerated dose as a single agent. In other embodiments, the suitable dosages of MEK inhibitors are from about 25% to about 90% of the maximum tolerated dose as a single agent. In some embodiments, the suitable dosages of MEK inhibitors are from about 30% to about 80% of the maximum tolerated dose as a single agent. In other embodiments, the suitable dosages of MEK inhibitors are from about 40% to about 75% of the maximum tolerated dose as a single agent. In some embodiments, the suitable dosages of MEK inhibitors are from about 45% to about 60% of the maximum tolerated dose as a single agent. In other embodiments, suitable dosages of MEK inhibitors are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, or about 120% of the maximum tolerated dose as a single agent.

Suitable daily dosages of CDK4/6 inhibitors can generally range, in single or divided or multiple doses, from about 10% to about 120% of the maximum tolerated dose as a single agent. In certain embodiments, the suitable dosages of CDK4/6 inhibitors are from about 20% to about 100% of the maximum tolerated dose as a single agent. In some other embodiments, the suitable dosages of CDK4/6 inhibitors are from about 25% to about 90% of the maximum tolerated dose as a single agent. In some other embodiments, the suitable dosages of CDK4/6 inhibitors are from about 30% to about 80% of the maximum tolerated dose as a single agent. In some other embodiments, the suitable dosages of CDK4/6 inhibitors are from about 40% to about 75% of the maximum tolerated dose as a single agent. In some other embodiments, the suitable dosages of CDK4/6 inhibitors are from about 45% to about 60% of the maximum tolerated dose as a single agent. In other embodiments, suitable dosages of CDK4/6 inhibitors are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, or about 120% of the maximum tolerated dose as a single agent.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the MEK inhibitor or CDK4/6 inhibitor, sufficient for achieving a therapeutic or prophylactic effect, may range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of MEK inhibitor or CDK4/6 inhibitor ranges from 0.001-10,000 micrograms per kg body weight. In one embodiment, MEK inhibitor or CDK4/6 inhibitor concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of a MEK inhibitor or CDK4/6 inhibitor may be defined as a concentration of the MEK inhibitor or CDK4/6 inhibitor at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Kits

The present disclosure provides kits for treating pancreatic cancer comprising a MEK inhibitor disclosed herein, a CDK4/CDK6 inhibitor disclosed herein, and instructions for treating pancreatic cancer. When simultaneous administration is contemplated, the kit may comprise a MEK inhibitor and a CDK 4/6 inhibitor that has been formulated into a single pharmaceutical composition such as a tablet, or as separate pharmaceutical compositions. When the MEK inhibitor and the CDK 4/6 inhibitor are not administered simultaneously, the kit may comprise a MEK inhibitor and a CDK 4/6 inhibitor that has been formulated as separate pharmaceutical compositions either in a single package, or in separate packages.

Additionally or alternatively, in some embodiments, the kits further comprise at least one chemotherapeutic agent and/or at least one immunotherapeutic agent that are useful for treating pancreatic cancer. Examples of such chemotherapeutic agents include abraxane, capecitabine, erlotinib, fluorouracil (5-FU), gemcitabine, irinotecan, leucovorin, nab-paclitaxel, cisplatin, irinotecan, docetaxel, oxaliplatin, tipifarnib, everolimus, sunitinib, dovitinib, ruxolitinib, pegylated-hyaluronidase, pemetrexed, folinic acid, paclitaxel, MK2206, GDC-0449, IPI-926, gamma secretase/RO4929097, M402, and LY293111. Examples of such immunotherapeutic agents include immune checkpoint inhibitors (e.g., antibodies targeting CTLA-4, PD-1, PD-L1), ipilimumab, 90Y-Clivatuzumab tetraxetan, pembrolizumab, nivolumab, trastuzumab, cixutumumab, ganitumab, demcizumab, cetuximab, nimotuzumab, dalotuzumab, sipuleucel-T, CRS-207, and GVAX.

The kits may further comprise pharmaceutically acceptable excipients, diluents, or carriers that are compatible with one or more kit components described herein. Optionally, the above described components of the kits of the present technology are packed in suitable containers and labeled for the treatment of pancreatic cancer. Examples of pancreatic cancers include, but are not limited to PDAC, acinar cell carcinoma, solid pseudopapillary neoplasms, pancreatoblastoma, pancreatic neuroendocrine tumors (PNETs), gastrinomas, insulinomas, glucagonomas, somatostatinomas and VIPomas. The kits may optionally include instructions customarily included in commercial packages of therapeutic products, that contain information about, for example, the indications, usage, dosage, manufacture, administration, contraindications and/or warnings concerning the use of such therapeutic products.

EXAMPLES

The present technology is further illustrated by the following Examples, which should not be construed as limiting in any way. For each of the examples below, any MEK inhibitor or CDK4/6 inhibitor described herein could be used.

Example 1: General Methods and Procedures

Cell Lines, Organoids and Compounds.

PANC-1, PU-8988T, MiaPaca-2, CF-PAC, 3B11, H2030, H460, A549, and HCC15 cells were purchased from the American Type Culture Collection (ATCC, Manassas Va.). YT cells were purchased from DSMZ (Braunschweig, Germany). Murine KPC cell lines and organoids were generated from P48-Cre; Kras$^{+/LSL-G12D}$; Trp53$^{fl/+}$ (KPC) mice. All cells were maintained in a humidified incubator at 37° C. with 5% $CO_2$, and grown in RPMI 1640 or DMEM supplemented with 10% FBS and 100 IU ml$^{-1}$ penicillin/streptomycin. All cell lines used were negative for *mycoplasma*.

To generate pancreas organoids from KPC mouse tumors, pancreas tumors were first minced and dissociated with 0.012% (w/v) collagenase XI (Sigma, St. Louis Mo.) and 0.012% (w/v) dispase (Gibco, Thermo Fisher Scientific, Waltham Mass.) in DMEM media containing 1% FBS (Gibco, Thermo Fisher Scientific, Waltham Mass.) at 37° C. with mild agitation for up to 1 hour. The material was further digested with TrypLE (Gibco, Thermo Fisher Scientific, Waltham Mass.) for 15 minutes at 37° C. Dissociated tissue was then seeded in growth factor-reduced (GFR) Matrigel (BD Biosciences, Franklin Lakes N.J.) and cultured in advanced DMEM/F12 supplemented with the following: 1% penicillin/streptomycin, HEPES 10 mM, Glutamax 1×, A83-01 500 nM, hEGF 50 ng/mL, mNoggin 100 ng/mL, hFGF10 100 ng/mL, hGastrin I 0.01 µM, N-acetylcysteine 1.25 mM, Nicotinamide 10 mM, B27 supplement 1× final, and R-spondin1 conditioned media (10% final). Organoids were passaged every 3-4 days and maintained in 48-well dishes.

Trametinib (S2673) and palbociclib (S1116) were all purchased from Selleck Chemicals (Houston, Tex.) for in vitro studies. Drugs for in vitro studies were dissolved in DMSO (vehicle) to yield 10 mM stock solutions and stored at –80° C. For in vitro studies, growth media with or without drugs was changed every 2-3 days. For in vivo studies, trametinib (T-8123) and palbociclib (P-7744) were purchased from LC Laboratories (Woburn Mass.). Trametinib was dissolved in a 5% hydroxypropyl methylcellulose and 2% Tween-80 solution (Sigma, St. Louis Mo.), and palbociclib in sodium lactate buffer (pH 4). Gemcitabine and Abraxane were purchased from MSKCC (New York N.Y.).

For visualizing KPC tumor cell lines with luciferase and GFP, Luciferase (Luc)-GFP constructs were cloned into MSCV-based vectors and retroviruses were packaged by co-transfection of Gag-Pol expressing 293 T cells with expression constructs and envelope vectors (VSV-G) using the calcium phosphate method. Following transduction, cells were purified by FACS sorting the GFP$^+$ population on a FACSAria (BD Biosciences, Franklin Lakes N.J.).

Senescence assays. SA-β-gal staining was performed as previously described at pH 6.0 for human cells and 5.5 for mouse cells and tissue (V. Krizhanovsky et al., *Cell* 134, 657-667 (2008)). Fresh frozen sections of pancreas tumor tissue, or adherent cells plated in 6-well plates, were fixed with 0.5% Gluteraldehyde in PBS for 15 min, washed with PBS supplemented with 1 mM $MgCl_2$, and stained for 5-8 hours in PBS containing 1 mM $MgCl_2$, 1 mg/ml X-Gal, and 5 mM each of Potassium ferricyanide and Potassium ferrocyanide. Tissue sections were counterstained with eosin. 5 high power fields per well/section were counted and averaged.

For drug withdrawal assays, cells ($5×10^3$ to $10×10^3$ cells per well of 6-well plate) were pre-treated for 8 days with vehicle (DMSO) or indicated drugs, and then re-plated ($5×10^3$ cells per well of 6-well plate) in the absence of drugs for 7 to 14 days. Remaining cells were fixed with methanol (1%) and formaldehyde (1%), stained with 0.5% crystal violet, and photographed using a digital scanner. Relative growth was quantified by densitometry after extracting crystal violet from the stained cells using 10% of acetic acid.

Immunoblotting.

Cell lysis was performed using RIPA buffer (Cell Signaling Technology, Danvers Mass.) supplemented with phosphatase inhibitors (5 mM sodium fluoride, 1 mM sodium orthovanadate, 1 mM sodium pyrophosphate, 1 mM (3-glycerophosphate) and protease inhibitors (Protease Inhibitor Cocktail Tablets, Roche, Basel, Switzerland). Protein concentration was determined using a Bradford Protein Assay kit (Biorad, Hercules Calif.). Proteins were separated by SDS-PAGE and transferred to polyvinyl difluoride (PVDF) membranes (Millipore, Burlington Mass.) according to standard protocols. Membranes were immunoblotted with antibodies against: pRB$^{S780}$ (9307) from Cell Signaling Technology (Danvers Mass.), and total RB from Santa Cruz Biotechnology (Dallas Tex.) in 5% BSA in TBS blocking buffer. After primary antibody incubation, membranes were probed with an ECL anti-rabbit IgG or anti-mouse IgG secondary antibody (1:10,000) from GE Healthcare Life Sciences (Pittsburgh, Pa.) and imaged using a FluorChem M system (Protein Simple, Minneapolis, Minn.). Protein loading was measured using a monoclonal β-actin antibody directly conjugated to horseradish peroxidase (1:20,000) from Sigma-Aldrich (St. Louis Mo.) and imaged as described above.

qRT-PCR.

Total RNA was isolated using the RNeasy Mini Kit (Qiagen, Hilden, Germany), and complementary DNA (cDNA) was obtained using the TaqMan reverse transcription reagents (Applied Biosystems, Foster City Calif.). Real-time PCR was performed in triplicate using SYBR Green PCR Master Mix (Applied Biosystems, Foster City Calif.) on the ViiA 7 Real-Time PCR System (Invitrogen, Carlsbad Calif.). β-actin served as endogenous normalization controls.

High Throughput RNA-Sequencing (RNA-Seq).

Total RNA was extracted using the RNeasy Mini Kit (Qiagen, Hilden, Germany) from cell lines following 8 day treatment with vehicle (DMSO) or indicated drugs. PolyA mRNA was selected using beads coated with polyT oligonucleotides. Purified polyA mRNA was subsequently fragmented, and first and second strand cDNA synthesis performed using standard Illumina mRNA TruSeq library preparation protocols. Double stranded cDNA was subsequently processed for TruSeq dual-index Illumina library generation. For sequencing, pooled multiplexed libraries were run on a HiSeq 2500 machine on RAPID mode. Approximately 10 million 76 bp single-end reads were retrieved per replicate condition. Resulting RNA-Seq data was analyzed by removing adaptor sequences using Trimmomatic (A. M. Bolger, M. Lohse, B. Usadel, *Bioinformatics* 30, 2114-2120 (2014)), aligning sequencing data to GRCh37.75(hg19) with STAR (A. Dobin et al., *Bioinformatics* 29, 15-21 (2013)), and genome wide transcript counting using HTSeq (S. Anders, P. T. Pyl, W. Huber, *Bioinformatics* 31, 166-169 (2015)) to generate a RPKM matrix of transcript counts. Differential expression was analyzed by looking at fold changes between experimental conditions.

The GEO accession number for gene expression data reported in this study is GSE110397.

Immunohistochemistry and Immunofluorescence.

Tissues were fixed overnight in 10% formalin, embedded in paraffin, and cut into 5 μm sections. Haematoxylin and eosin (H&E), Masson's trichrome (collagen in blue), and immunohistochemical/immunofluorescence staining were performed using standard protocols. The following primary antibodies were used: pERK$^{T202/Y204}$ (4370), cleaved caspase-3 (CC3) (9664) (Cell Signaling Technology, Danvers Mass.), Ki67 (AB16667), CD31 (AB28364), α-smooth muscle actin (SMA) (AB5694, Abcam, Cambridge, UK), pRB$^{S807/S811}$ (Sc-16670, Santa Cruz Biotechnology, Dallas Tex.), and biotinylated hyaluronic acid binding protein (HABP) (AMS.HKD-BC41, Amsbio, Abingdon, UK). For quantification of CD31$^+$ vessels, 5 high power fields per section were counted and averaged. Metastatic burden in the lungs and liver of KPC Genetically Engineered Mouse Model (GEMM) mice was quantified from H&E stained sections.

Flow Cytometry.

For analysis of NK cell ligand expression in cell lines, cells were treated for 8 days with vehicle (DMSO), trametinib (25 nM), palbociclib (500 nM), or their combination and then trypsinized, resuspended in PBS supplemented with 2% FBS, and stained with the following antibodies for 30 minutes on ice: ICAM-1/CD54 (HA58, BioLegend, San Diego Calif.), ULBP-2/5/6 (165903), and MICA (159227) (R&D Systems, Minneapolis, Minn.). Flow cytometry was performed on an LSRFortessa, and data were analyzed using FlowJo (TreeStar).

For in vivo sample preparation, lungs were isolated, flushed with PBS, and allocated for 10% formalin fixation (1 lobe), OCT frozen blocks (1 lobe), and FACS (remaining 3 lobes) following 1-week treatment. To prepare single cell suspensions for flow cytometry analysis, lung lobes were placed in 5 ml of collagenase buffer (1×HBSS with calcium and magnesium (Gibco Thermo Scientific, Waltham Mass.), 1 mg/ml Collagenase A (Roche, Basel, Switzerland), and 0.1 mg/ml DNase I) in C tubes and then processed using program 37C_m_LDK_1 on a gentleMACS Octo dissociator with heaters (Miltenyi Biotec, Bergisch Gladbach, Germany). Dissociated tissue was passed through a 70 μm cell strainer and centrifuged at 1:500 rpm×5 minutes. Red blood cells were lysed with ACK lysis buffer (Quality Biological, Gaithersburg Md.) for 5 minutes, and samples were centrifuged and resuspended in PBS supplemented with 2% FBS. Samples were blocked with anti-CD16/32 (FC block, 131) Biosciences, Franklin Lakes N.J.) for 20 minutes and then incubated with the following antibodies (purchased from BioLegend, San Diego Calif.) for 30 minutes on ice: CD45 (30-F11), NK1.1 (Pk136), CD3 (17A2), CD8 (53-6.7), CD4 (GK1.5), Gr-1 (RB6-8C5), and CD11b (M1/70, BD Biosciences, Franklin Lakes N.J.). NK cells were gated from the CD45$^+$CD3$^-$NK1.1$^+$ population. DAPI was used to distinguish live/dead cells, and tumor cells were gated as GFP$^+$. Flow cytometry was performed on an LSRFortessa, and data were analyzed using FlowJo (TreeStar).

NK Cell Degranulation Assays.

Mice were injected i.v. with 250 μl of a solution containing 25 μg anti-CD107a PE (ID4B, BioLegend, San Diego Calif.) and 10 μg monensin (BioLegend, San Diego Calif.) in 1×PBS 4 hours before mice were euthanized. Lung lobes were then isolated, dissociated, stained with cell surface antibodies, and analyzed by flow cytometry as described above.

Cytokine Array.

Cells were plated in triplicate in 6-well plates and treated for 6 days in the presence or absence of drug. On day 6, 2 mL of new media was added to each well and cells were incubated an additional 48 hours in the presence or absence of drugs. Conditioned media was then collected and the cells were trypsinized and counted using a cellometer (Nexcelom Biosciences, Lawrence Mass.). Media samples were then normalized based on cell number by diluting with culture media. Aliquots (50 μl) of the conditioned media were analyzed using multiplex immunoassays (Human Cytokine/Chemokine Array 42-Plex Discovery Assay) from Eve Technologies (Calgary, Canada). Biological replicates were averaged to determine cytokine levels. Heat maps display relative cytokine expression values normalized to vehicle-treated samples.

In Vitro Endothelial Growth Assays.

KPC tumor cells were treated with vehicle or combined trametinib (25 nM) and palbociclib (500 nM) for 6 days, and conditioned serum-free DMEM media with 100 IU ml$^{-1}$ penicillin/streptomycin was collected as described above. Filtered conditioned media (CM) or normal serum-free media was then applied to 5,000 3B11 murine endothelial cells plated in 24-well dishes. Cells were counted daily in quadruplicate using a Guava Easycyte (Millipore, Burlington Mass.) to determine growth.

NK Cell Co-Culture Assays.

The YT cell line or primary human NK cells were used for co-culture assays with human tumor cells. Buffy coats from 2 different healthy volunteer donors were obtained from the New York Blood Center and peripheral blood mononuclear cells were isolated by density gradient centrifugation. Subsequently, NK cells were purified using the human NK cell isolation kit (Miltenyi Biotec, Bergisch Gladbach, Germany) according to the manufacturer's instructions. 80% or greater NK cell purity was confirmed by flow cytometry analysis of CD3$^-$ and CD56$^+$ (HCD56, BioLegend, San Diego Calif.) populations.

Human NK cell co-culture assays were performed as previously described (N. Tasdemir et al., *Cancer Discov* 6, 612-629 (2016)). Briefly, human KRAS-mutant tumor cells were pre-treated for 8 days in the presence or absence of drugs. Tumor cells were then trypsinized and stained with CellTracker Green CMFDA dye (Thermo Fisher Scientific, Waltham Mass.) according to the manufacturer's instructions. Tumor cells were seeded in 96-well plates and allowed to adhere overnight in regular growth media. The NK cells were stained with CellTracker red CMPTX dye (Thermo Fisher Scientific, Waltham Mass.) according to the manufacturer's instructions. NK cells were then added to the 96-well plates containing labeled tumor cells at an effector-to-target cell ratio of 10:1. Some wells only received media alone without NK cells as controls. For the co-culture assay, cells were maintained in $CO_2$ independent media (Life Technologies, Carlsbad Calif.) supplemented with 10% FBS, 100 IU/ml penicillin/streptomycin, and 1.5 μM DRAQ7 (Biostatus, Loughborough UK) in the presence or absence of drugs. Co-cultures were imaged every 30 minutes at a 10× objective in a temperature-controlled incubation chamber for a total of 24 hours using an INCell 6000 high-content imager (GE Healthcare Life Sciences, Pittsburgh, Pa.). 4 fields per each well were imaged. Images for each channel were analyzed using GE Developer image analysis software (GE Healthcare Life Sciences, Pittsburgh, Pa.). Cell viability of both tumor cells and NK cells was determined by DRAQ7 positivity. NK cell cytotoxicity was assessed by the percent change in total tumor cell numbers and DRAQ7+ tumor cells in the presence of NK cells as compared to control wells lacking NK cells for each condition (run in triplicate) after 20 hour co-culture. ICAM-1 blockade was achieved through administration of a human ICAM-1 blocking antibody to the co-culture (25 µg/ml; R&D Systems, Minneapolis, Minn.).

Animal Models.

All mouse experiments were approved by the Memorial Sloan-Kettering Cancer Center (MSKCC) Internal Animal Care and Use Committee. Mice were maintained under specific pathogen-free conditions, and food and water were provided ad libitum.

Patient-Derived Xenograft (PDX) Models.

5-7 week old female NOD-scid IL2Ry$^{null}$ (NSG) mice were used for animal experiments with patient-derived xenografts (PDXs). MSK-PR07 is pancreatic ductal adenocarcinoma harboring mutations in KRAS (G12D) and p53 (L344Q), and is derived from a patient treated with gemcitabine and abraxane. MSK-PC69 is pancreatic ductal adenocarcinoma harboring a mutation in KRAS (G12D) and p53 deletion, and is derived from a previously untreated patient. MSK-PR002 is pancreatic ductal adenocarcinoma harboring a mutation in KRAS (G12V) but is p53 intact, and is derived from a patient treated with first with gemcitabine and abraxane, and then with 5-FU/liposomal irinotecan. Tumors were cut into pieces and inserted into a pocket in the subcutaneous space as previously described (J. T. Poirier et al., Oncogene 34, 5869-5878 (2015)). Following inoculation, mice were monitored daily, weighed twice weekly, and caliper measurements begun when tumors became visible. Tumor volume was calculated using the following formula: tumor volume=(D×d$^2$)/2, in which D and d refer to the long and short tumor diameter, respectively. When tumors reached a size of 100-200 mm$^3$, mice were randomized based on starting tumor volume (caliper measurements) and treated with vehicle, trametinib (1 mg/kg body weight), and/or palbociclib (100 mg/kg body weight) per os for 4 consecutive days followed by 3 days off treatment. Gemcitabine was administered once a week (100 mg/kg body weight) by intraperitoneal injection. Tumor size and mouse weights were recorded twice weekly. No obvious toxicities were observed in the vehicle- or drug-treated animals as assessed by changes in body weight (taking tumor size into account). Experimental endpoints were achieved when tumors reached 2000 mm$^3$ or became ulcerated.

KPC Organoid transplant models.

For the orthotopic engraftment of KPC pancreas cancer organoids derived from P48-Cre; Kras$^{+/LSL-G12D}$; Trp53$^{fl/+}$ mice, 8-10 week old Athymic Nude or C57BL/6 female mice (Charles River Laboratories, Wilmington Mass.) were first anesthetized using Isoflurane. An incision was made in the left abdominal side. Organoids (approximately 5×10$^4$ cells/mouse) were prepared from cultures. Organoids were washed with ice-cold PBS, physically broken into pieces by triturating through fire-polished glass Pasteur pipettes, and finally resuspended in 25 µl of Matrigel (Matrigel, BD Biosciences, Franklin Lakes N.J.) diluted 1:1 with cold PBS. The organoid suspension was injected into the tail region of the pancreas using a Hamilton Syringe. Successful injection was verified by the appearance of a fluid bubble without signs of intraperitoneal leakage. The abdominal wall was sutured with absorbable Vicryl suture (Ethicon Inc., Somerville, N.J.), and the skin was closed with wound clips (CellPoint Scientific Inc., Gaithersburg, Md.). Mice were monitored for tumor development by ultrasound, and enrolled and randomized into treatment groups once tumors reached 100-300 mm$^3$. Mice were treated with vehicle, trametinib (1 mg/kg body weight), and/or palbociclib (100 mg/kg body weight) per os for 4 consecutive days followed by 3 days off treatment. Gemcitabine and Abraxane (nab-paclitaxel) were administered once a week (100 mg/kg body weight) by intraperitoneal injection. Ultrasound imaging was repeated every 2 weeks during treatment to assess changes in pancreas tumor burden. Upon sacrifice, pancreas tumor tissue was allocated for 10% formalin fixation and OCT frozen blocks.

Electroporation-Based Models.

For pancreas in vivo electroporation, 8-10 week old C57BL/6 female mice were anesthetized with isofluorane and the surgical site (right hemi-abdomen) was prepared as described above. 50 µl of a plasmid mix containing a) 1 µg of Sleeping Beauty transposase (SB13), b) 5 µg of a transposon vector containing a KRAS$^{G12D}$ cDNA and GFP, and c) 20 µg of a pX330 vector containing a p53-targeting sgRNA and Cas9 nuclease was injected into the tail region of the pancreas using a 27.5 gauge syringe and tweezer electrodes were tightly placed around the injection bubble. Two pulses of electrical current (35V) were applied using an in vivo electroporator (NEPAGENE NEPA21 Type II electroporator). After electroporation, the peritoneum cavity was rinsed with 0.5 ml of pre-warmed saline. Subsequently the peritoneum and muscles were sutured with absorbable sutures and the skin closed with skin staples. The mice were kept at 37° C. until they awoke and post surgery pain management was done with injections of buprenorphine for the three following days. This procedure efficiently generates KRAS$^{G12D}$; Trp53$^{-/-}$ pancreas tumors in 3-5 weeks. Mice were monitored for tumor development by ultrasound, and enrolled and randomized into treatment groups once tumors reached 300-500 mm$^3$. Mice were treated with vehicle, trametinib (1 mg/kg body weight), and/or palbociclib (100 mg/kg body weight) per os for 4 consecutive days followed by 3 days off treatment. Ultrasound imaging was repeated every 2 weeks during treatment to assess changes in pancreas tumor burden. Upon sacrifice pancreas tumor tissue was allocated for 10% formalin fixation and OCT frozen blocks.

Pancreas Cancer Lung Metastasis/Dissemination Model.

Figure 5A:
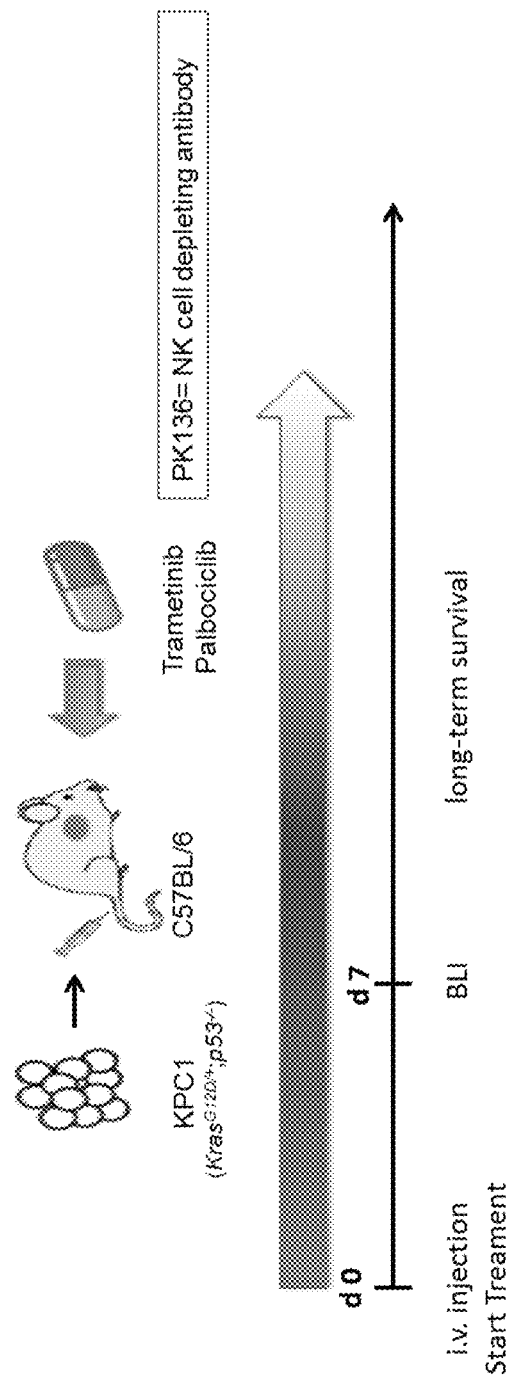
FIG. 5(A) shows a schematic of pancreas cancer lung metastasis model. $5 \times 10^5$ luciferase-expressing $Kras^{G12D/+}$; $Trp53^{-/-}$ (KPC) pancreas tumor cells were tail vein injected into C57BL/6 mice. Treatment with vehicle, a NK1.1 depleting antibody (PK136, 250 µg), and/or trametinib (1 mg/kg) and palbociclib (100 mg/kg) was initiated the same day as transplantation.

To generate experimental pancreas cancer lung metastases, 5×10$^5$ KPC pancreas tumor cells expressing luciferase and GFP (LUC-GFP) were transplanted by tail injection into 8-10 week old C57BL/6 female mice. Mice were monitored for tumor development (and progression over time) by bioluminescence imaging (BLI) on a Xenogen IVIS (Caliper Life Sciences, Waltham Mass.). Starting the same day as transplantation (Day 0) or following lung metastasis formation (6-8 days post-transplantation), mice were evaluated by BLI to quantify lung tumor burden before being randomized into various study cohorts and treated with vehicle, trametinib (1 mg/kg body weight), and/or palbociclib (100 mg/kg body weight) per os for 4 consecutive days followed by 3 days off treatment. For NK cell depletion, mice were injected intraperitoneally with either an α-NK1.1 antibody (250 µg; PK136, BioXcell) or isotype control (250 µg; C1.18.4, BioXcell) twice per week. See FIG. 5(A). NK cell depletion was confirmed by flow cytometry analysis of lung tumor tissue, spleen, and/or peripheral blood following 1-week of treatment. For immunohistochemical and flow cytometry analysis, mice were treated for 1 week with indicated drugs. Upon sacrifice lung lobes were allocated for 10% formalin fixation (1 lobe), OCT frozen blocks (1 lobe), and FACS (remaining 3 lobes).

KPC GEMM Model.

Trp53$^{fl/+}$, Kras$^{+/LSL-G12D}$ and Pdx1-Cre strains on a C57Bl/6 background were interbred to obtain Pdx1-Cre;

Kras$^{+/LSL-G12D}$; Trp53$^{fl/+}$ (KPC) mice. Mice were monitored for tumor development by ultrasound, and enrolled and randomized into treatment groups once tumors reached 100-300 mm$^3$. Mice were treated with vehicle, trametinib (1 mg/kg body weight), and/or palbociclib (100 mg/kg body weight) per os for 4 consecutive days followed by 3 days off treatment. Gemcitabine was administered once a week (100 mg/kg body weight) by intraperitoneal injection. Ultrasound imaging was repeated every 2 weeks during treatment to assess changes in pancreas tumor burden.

Ultrasound Imaging.

High-contrast ultrasound imaging was performed on a Vevo 2100 System with a MS250 13- to 24-MHz scanhead (VisualSonics, Toronto Canada) to stage and quantify pancreas tumor burden. Tumor volume was analyzed using Vevo 2100 software.

Gemcitabine Tracer In Vivo.

Figure 13A:
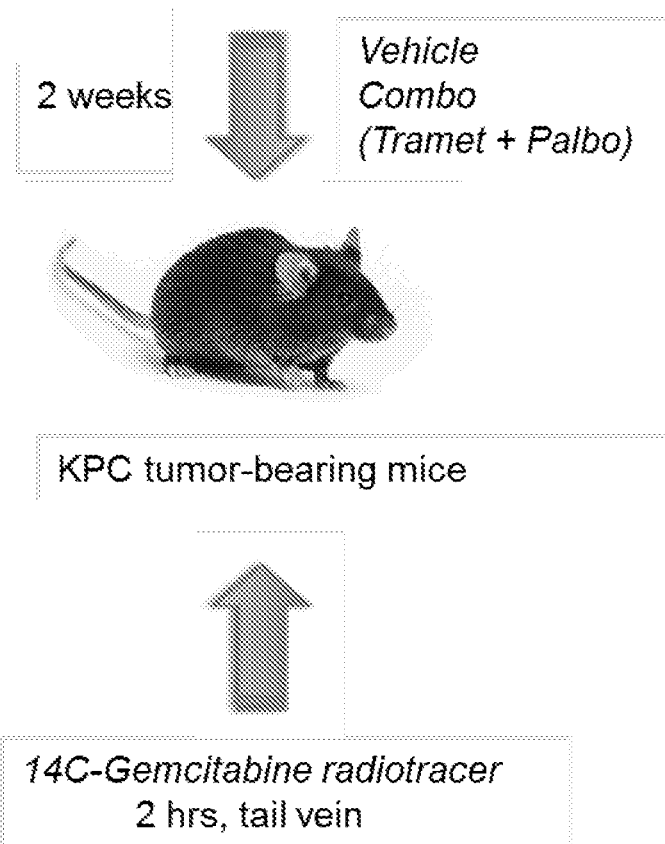
FIG. 13(A) shows gemcitabine uptake into pancreatic tumors following MEK/CDK4/6 inhibition. To assess gemcitabine uptake into pancreas tumors, a radiolabeled $^{14}$C-gemcitabine analog was tail vein injected into pancreas tumor-bearing mice following 2 week i.p. treatment with vehicle or combined trametinib (1 mg/kg) and palbociclib (100 mg/kg). Mice were sacrificed 2 hours after $^{14}$C-gemcitabine administration.

To assess gemcitabine uptake into pancreas tumors in vivo, KPC organoid transplant and GEMM mice harboring pancreas tumors were first treated for 2 weeks with vehicle or combined trametinib (1 mg/kg body weight) and palbociclib (100 mg/kg body weight) per os for 4 consecutive days followed by 3 days off treatment. See FIG. 13(A). $^{14}$C-gemcitabine (specific activity 58.8 mCi/mmol; Moravek Biochemicals, Brea Calif.) was then administered in sterile saline by intraperitoneal (i.p.) injection at 5 µCi/animal. Fluorescein isothiocyanate-dextran (MW 2,000,000, Sigma-Aldrich, St. Louis Mo.) was intravenously given in the lateral tail vein 30 minutes before sacrifice. Animals were euthanized 1 hour after $^{14}$C-gemcitabine administration.

Autoradiographs of tumor sections were exposed for 7 days and read with the Typhoon FLA 7000 laser scanner (GE Healthcare Life Sciences, Pittsburgh, Pa.). Before exposure, slides were marked with clear nail polish containing $^{14}$C to serve as a fiduciary marker for registration of autoradiographic images. The absolute amount of activity in tumor sections was quantified by use of $^{14}$C standards (ARC, St. Louis, Mo.) in terms of µCi/g. A subset of tumor sections was washed in phosphate-buffered saline (PBS) after autoradiography, and a second exposure was performed. Disintegrations per minute (dpm) were then normalized to tumor weight to calculate gemcitabine uptake.

Statistical Analysis.

Statistical analyses were performed as described in the figure legend for each experiment. Data are expressed as mean±s.e.m. Group size was determined on the basis of the results of preliminary experiments and no statistical method was used to predetermine sample size. The indicated sample size (n) represents biological replicates. Group allocation and outcome assessment were not performed in a blinded manner. All samples that met proper experimental conditions were included in the analysis. Survival was measured using the Kaplan-Meier method. Statistical significance was determined by one- and two-way ANOVA, Student's t-test, log-rank test, and Pearson's correlation using Prism 6 software (GraphPad Software) as indicated. Significance was set at $P<0.05$.

Example 2: Use of Combination Therapy with MEK Inhibitor and CDK 4/6 Inhibitor to Prevent or Treat Pancreatic Cancer This Example demonstrates that the combination therapy methods disclosed herein are useful to prevent or treat pancreatic cancer in subjects in need thereof.

Synergistic Therapeutic Effects of Trametinib and Palbociclib in Pancreatic Cancer Models.

Beyond its role in cell cycle control, RB is a potent mediator of cellular senescence, a stress-induced program that limits the proliferation of damaged cells. In contrast to quiescence, senescence can be characterized by durable (if not permanent) proliferative arrest and insensitivity to mitogenic stimuli. Senescent cells acquire changes in cell morphology, expression of senescence-associated beta-galactosidase (SA-β-gal) activity, a higher order chromatin reorganization associated with a distinct transcriptional profile and stable repression of cell cycle regulatory genes, and secretion of a wide-range of growth factors, proteases, chemokines, and cytokines collectively known as the senescence-associated secretory phenotype (SASP).

Figure 2A:
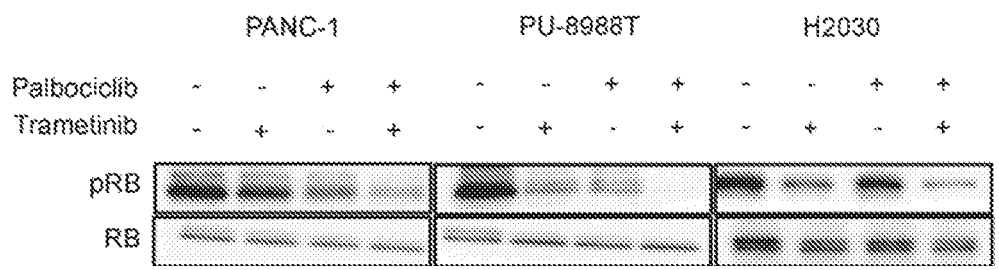
FIG. 2(A) shows an immunoblot of human KRAS-mutant lung (H2030) and pancreatic (PANC-1, PU-8988T) tumor cells treated with trametinib (25 nM) and/or palbociclib (500 nM) for 48 hours.
Figure 2B:
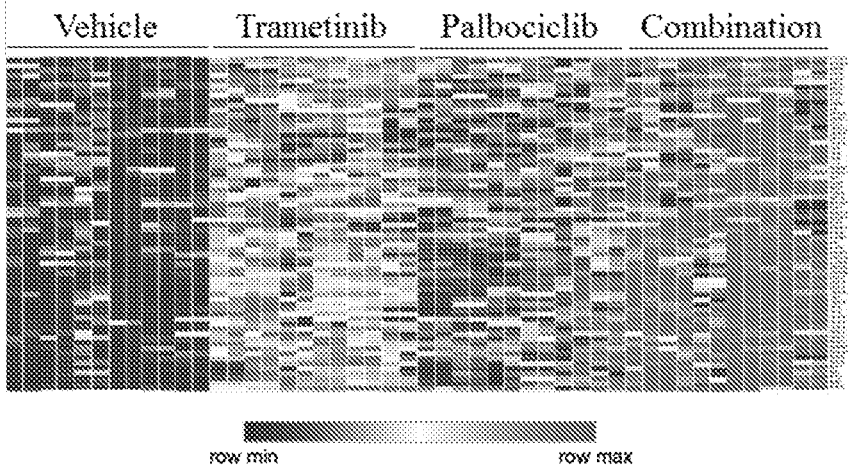
FIG. 2(B) shows a heat map of SASP gene expression in 3 human KRAS-mutant lung cancer cell lines (A549, H460, H2030) and 3 pancreatic cancer cell lines (PANC-1, PU-8988T, MiaPaca2) following treatment as described in FIG. 2(C) as assessed by RNA-seq. Two biological replicates per cell line are shown.
Figure 2C:
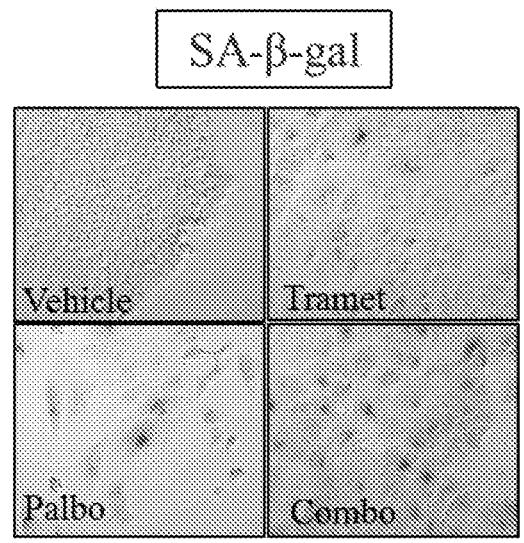
FIG. 2(C) shows representative senescence-associated beta-galactosidase (SA-β-gal) staining following 8 day treatment of human CF-PAC pancreatic cancer cells with trametinib (25 nM) and/or palbociclib (500 nM).
Figure 2D:
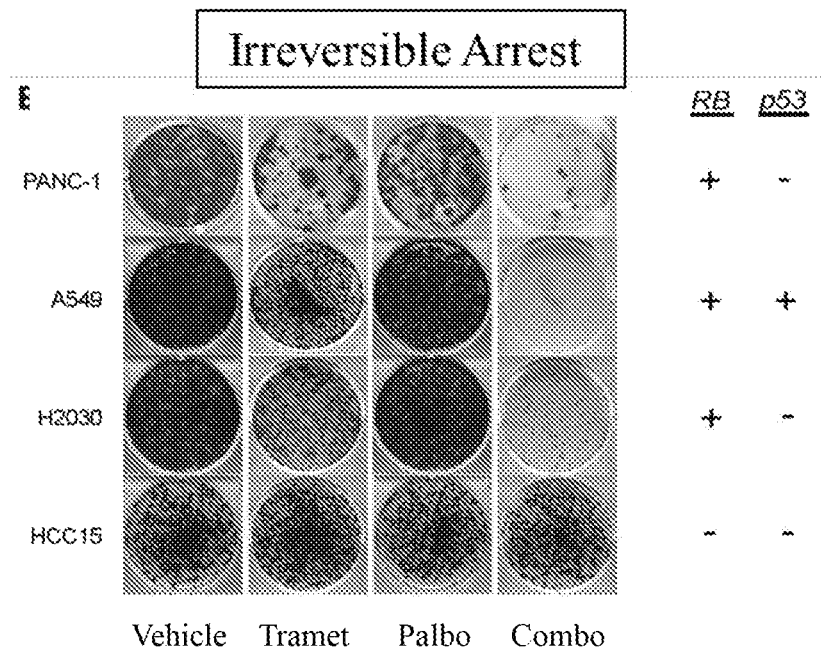
FIG. 2(D) shows a clonogenic assay of human KRAS-mutant lung and pancreas cancer cells re-plated in the absence of drugs following 8 day pre-treatment with trametinib (25 nM) and/or palbociclib (500 nM). RB and p53 genomic status indicated on right.

Lung cancer cell lines treated with both trametinib and palbociclib served as positive controls for RB-dependent senescence and SASP. See FIGS. 2(A)-2(B) and 2(D). As shown in FIGS. 2(A)-2(D), pancreatic tumor cells exhibited an induction in RB-dependent senescence and SASP when treated with a combination of trametinib and palbociclib. FIG. 2(A) shows that pancreatic tumor cell lines (PANC-1 and PU-8988T) treated with both trametinib and palbociclib displayed a reduction in RB phosphorylation compared to that observed in pancreatic tumor cells treated with the single agents. Induction of SASP genes occurred exclusively in pancreatic cancer cells that treated with both trametinib and palbociclib, and not in cells treated with trametinib or palbociclib alone. See FIG. 2(B) and FIG. 18. SA-β-gal staining was observed in the majority of pancreatic tumor cells that were exposed to the MEK inhibitor and CDK 4/6 inhibitor. See FIG. 2(C). As shown in FIG. 2(D), combination therapy with trametinib and palbociclib induced irreversible arrest (a hallmark of senescence) in pancreatic cancer cells in a RB-dependent yet p53-independent manner. No irreversible arrest was observed in pancreatic cancer cells that were treated with only trametinib or palbociclib.

Figure 3A:
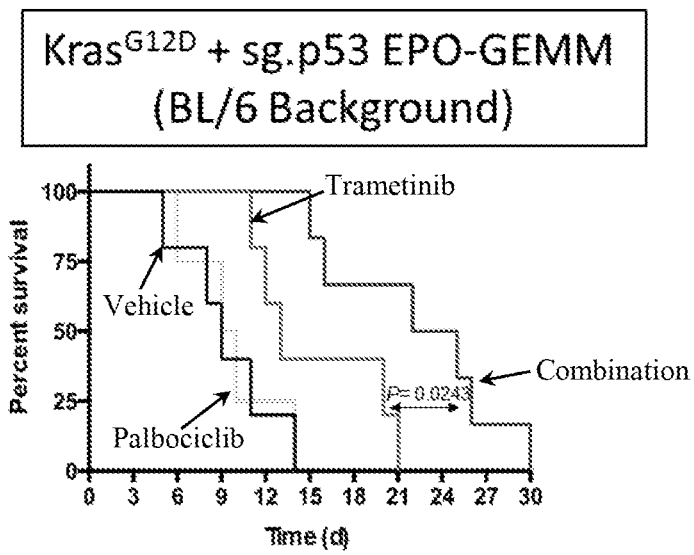
FIG. 3(A) shows a Kaplan-Meier survival curve of $Kras^{G12D/+}$; $Trp53^{-/-}$ electroporation-based EPO-GEMM pancreas cancer mice (C57BL/6) treated with vehicle, trametinib (1 mg/kg), palbociclib (100 mg/kg), or both following tumor formation (log-rank test).
Figure 3B:
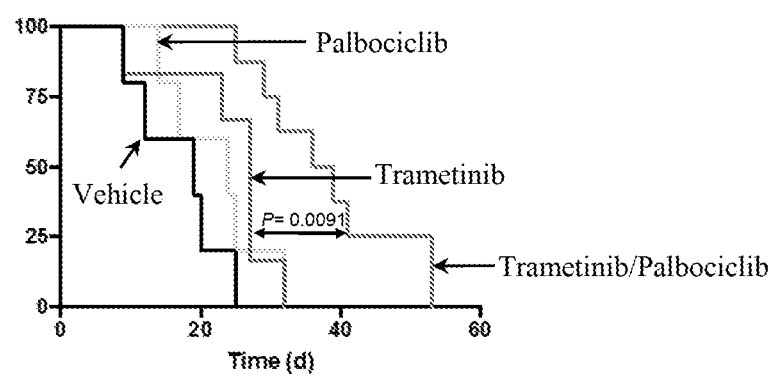
FIG. 3(B) shows a Kaplan-Meier survival curve of nude mice that were orthotopically transplanted with $Kras^{G12D/+}$; $Trp53^{-/-}$ (KPC) pancreas tumor organoids and treated as described in FIG. 3(A) (log-rank test).
Figure 3C:
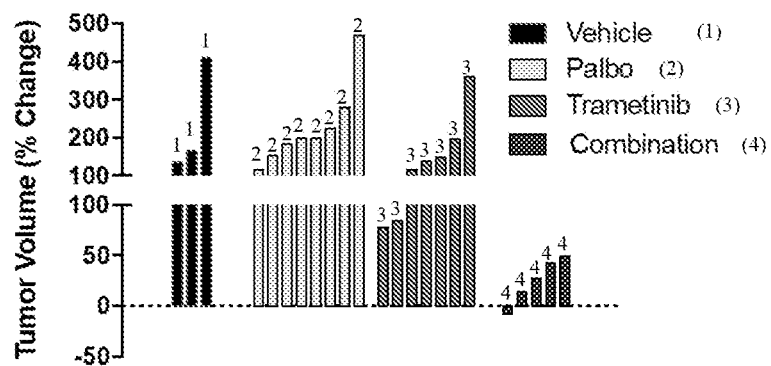
FIG. 3(C) shows a waterfall representation of the response of each tumor after 2 weeks of treatment as shown in FIG. 3(B).
Figure 3D:
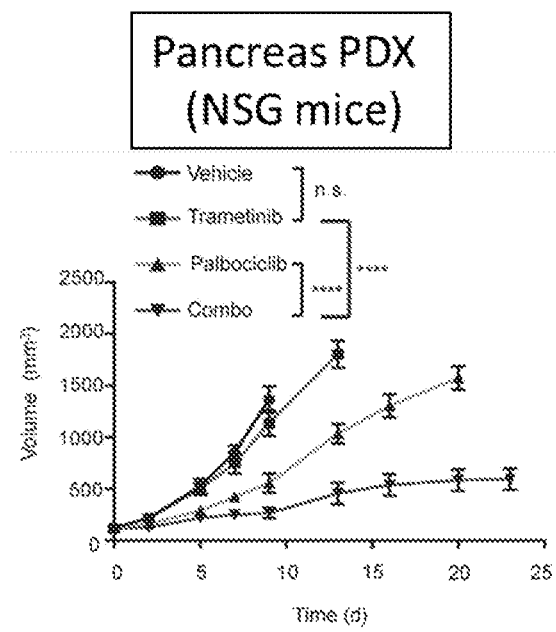
FIG. 3(D) shows tumor volumes of mice bearing KRAS-mutant MSK-PR07 patient-derived xenograft (PDX) pancreas tumors treated with vehicle, trametinib (1 mg/kg body weight), palbociclib (100 mg/kg body weight), or a combination of trametinib and palbociclib for indicated times. Two-way ANOVA. Error bars, mean±s.e.m. n.s., not significant.  $P<0.01$, * $P<0.001$, **** $P<0.0001$.
Figure 3E:
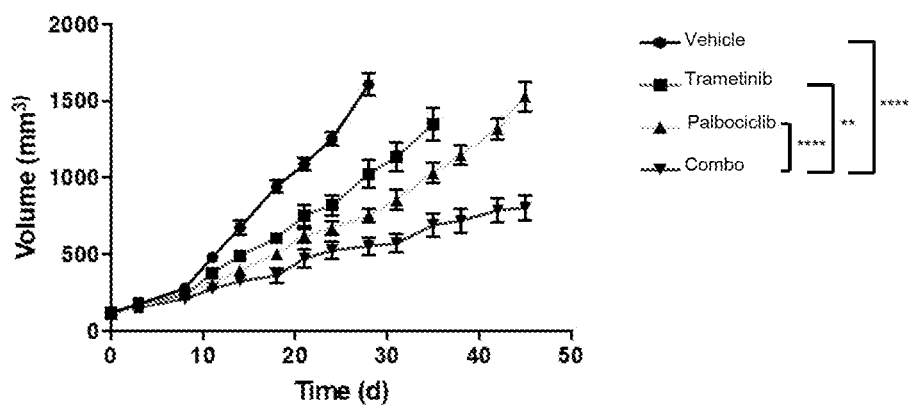
FIG. 3(E) shows tumor volumes of mice bearing KRAS-mutant MSK-PC69 patient-derived xenograft (PDX) pancreas tumors treated with vehicle, trametinib (1 mg/kg body weight), palbociclib (100 mg/kg body weight), or a combination of trametinib and palbociclib for indicated times. Two-way ANOVA. Error bars, mean±s.e.m. n.s., not significant.  $P<0.01$, * $P<0.001$, **** $P<0.0001$.
Figure 3F:
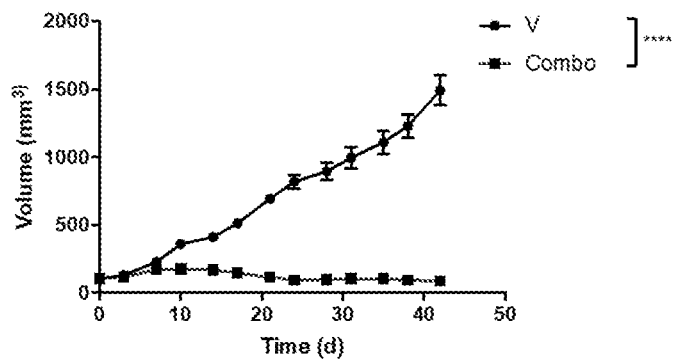
FIG. 3(F) shows tumor volumes of mice bearing KRAS-mutant MSK-PR002 patient-derived xenograft (PDX) pancreas tumors treated with vehicle, trametinib (1 mg/kg body weight), palbociclib (100 mg/kg body weight), or a combination of trametinib and palbociclib for indicated times. Two-way ANOVA. Error bars, mean±s.e.m. n.s., not significant.  $P<0.01$, * $P<0.001$, **** $P<0.0001$.
Figure 4A:
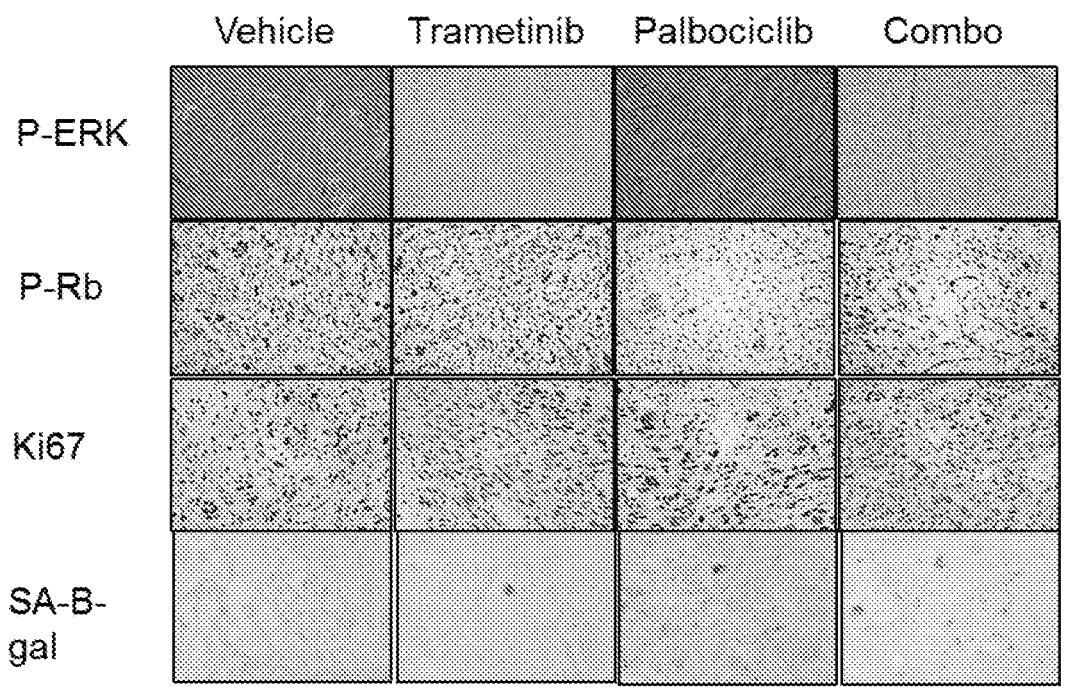
FIG. 4(A) shows immunohistochemical staining of pancreas tumor sections from $Kras^{G12D/+}$; $Trp53^{-/-}$ electroporation-based EPO-GEMM mice (C57BL/6) following 1 week treatment with vehicle, trametinib (1 mg/kg body weight), palbociclib (100 mg/kg body weight), or a combination of trametinib and palbociclib.
Figure 4B:
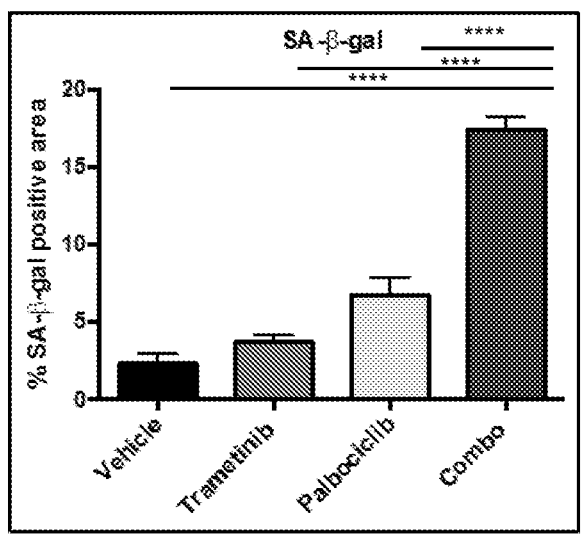
FIG. 4(B) shows the quantification of SA-β-gal staining. One-Way ANOVA. Error bars, mean±s.e.m. **** $P<0.0001$.
Figure 5C:
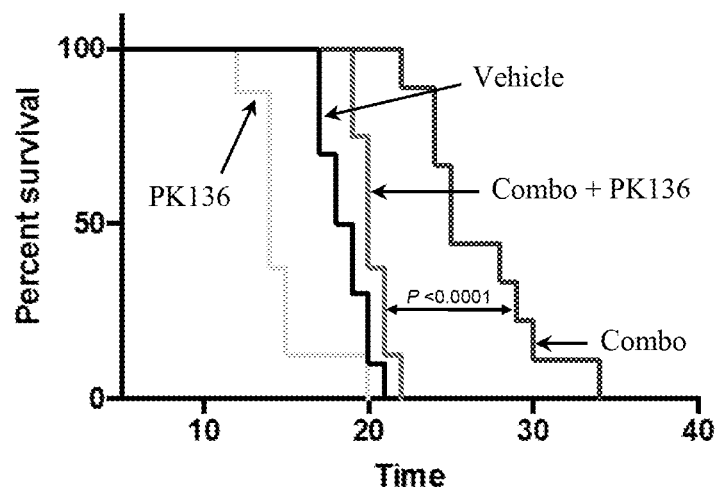
FIG. 5(C) shows the Kaplan-Meier survival curve analysis of C57BL/6 mice transplanted with KPC pancreas tumor cells by tail vein injection as described in FIG. 5(A) (log-rank test). PK136=NK1.1 depleting antibody.
Figure 6A:
FIG. 6(A) shows $5 \times 10^5 Kras^{G12D/+}$; $Trp53^{-/-}$ (KPC) pancreas tumor cells were tail vein injected into C57BL/6 mice, and treatment with vehicle, a NK1.1 depleting antibody (PK136, 250 µg), and/or trametinib (1 mg/kg) and palbociclib (100 mg/kg) was initiated 7 days post-transplantation. Kaplan-Meier survival curve analysis of these mice following treatment initiation is shown (log-rank test).
Figure 6A:
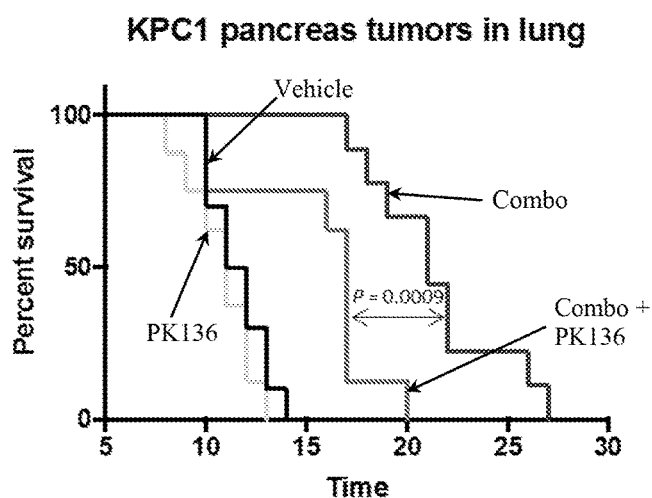
Figure 6B:
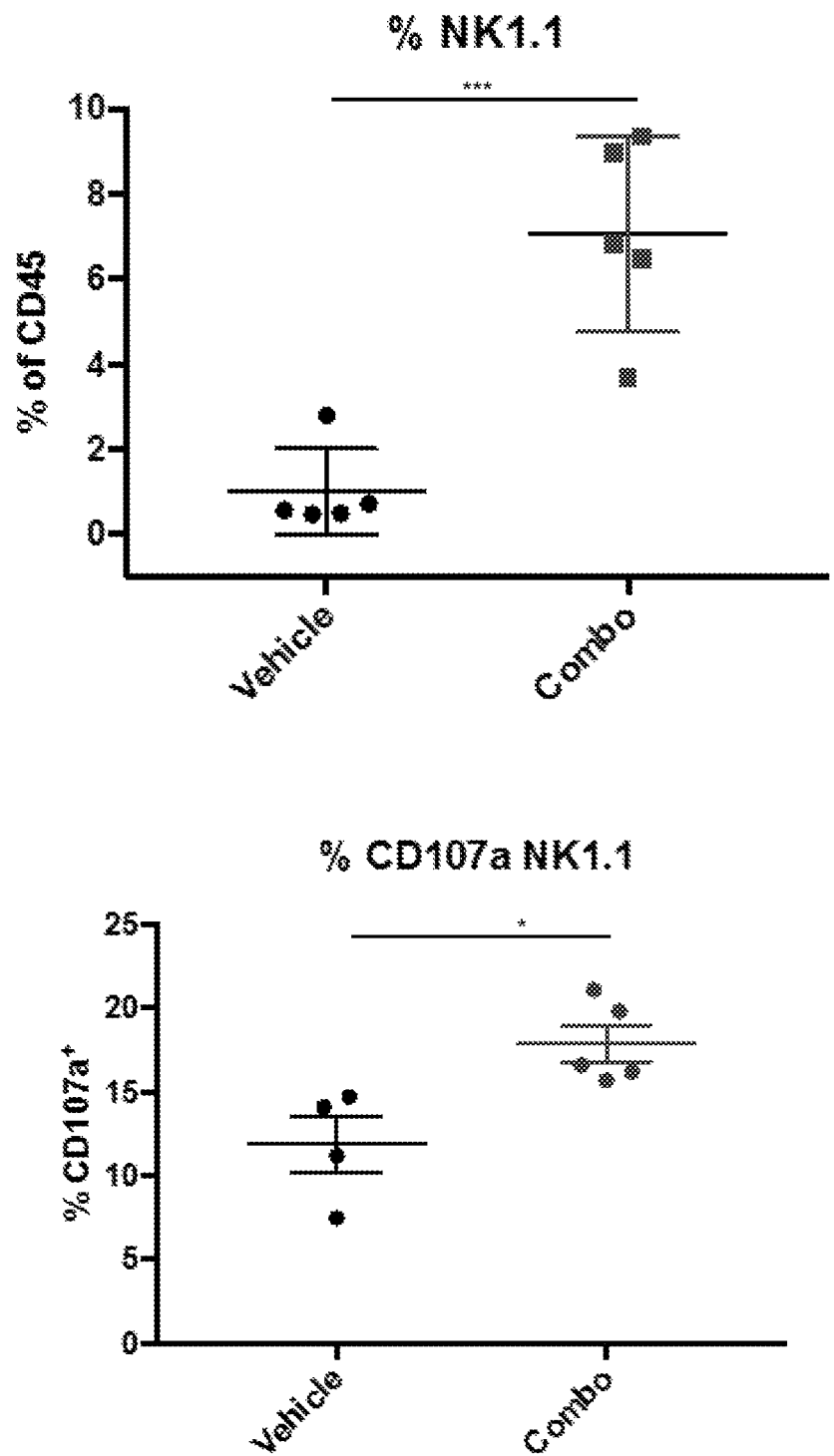
FIG. 6(B) shows the percentage of total NK cells within the $CD45^+$ population (top) and $CD107a^+$ degranulating NK cells (bottom) in the lungs following 1 week treatment of lung metastasis-bearing mice. Unpaired two-tailed t-test. Error bars, mean±s.e.m. * $P<0.05$, *** $P<0.001$.

Combination therapy with trametinib and palbociclib also induced senescence in in vivo pancreatic models. See FIGS. 4(A)-4(B) (showing a significant increase in SA-β-gal staining in animals that received both trametinib and palbociclib relative to that observed in animals that received the single agents). Further, combination therapy with trametinib and palbociclib significantly increased survival and reduced tumor progression in Kras$^{G12D/+}$; Trp53$^{-/-}$ electroporation-based EPO-GEMM pancreas cancer mice as well as nude mice orthotopically transplanted with Kras$^{G12D/+}$; Trp53$^{-/-}$ (KPC) pancreas tumor organoids compared to animals that were treated with the single agents. See FIGS. 3(A)-3(C). Likewise, combination therapy with trametinib and palbociclib significantly reduced tumor growth in mice bearing KRAS-mutant patient-derived xenograft (PDX) pancreas tumors compared to animals treated with the single agents. See FIGS. 3(D)-3(F). Combination therapy with trametinib and palbociclib significantly increased the survival of mice harboring established pancreas cancer lung metastases in an NK cell-dependent manner. See FIGS. 5(C) and 6(A). As shown in FIG. 6(B), combination therapy with trametinib and palbociclib led to a significant increase in both the number of NK cells and NK cell activation.

As shown in FIG. 38, different combinations of MEK inhibitors and CDK4/6 inhibitors exhibited synergistic inhibition of tumor cell growth at low concentrations of these inhibitors relative to that observed with MEK inhibitors or CDK4/6 inhibitors alone (which only achieve growth inhibitory effects at high concentrations). Thus, the synergistic effects of trametinib and palbociclib in PDAC models can be logically extended to other distinct combinations of MEK inhibitors and CDK4/6 inhibitors.

Synergistic Prophylactic Effects of Trametinib and Palbociclib in Pancreatic Cancer Models.

Figure 5B:
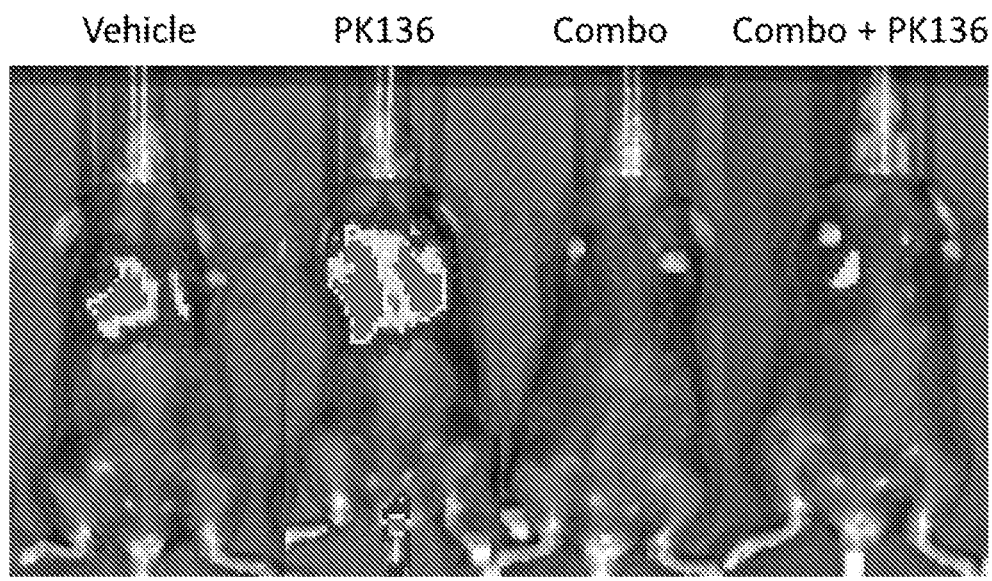
FIG. 5(B) shows bioluminescent imaging (BLI) of tumor burden in lung following 1-week treatment.

As shown in FIG. 5(B), combination therapy with trametinib and palbociclib significantly delayed the onset of pancreas tumor lung metastases in NK cell-dependent manner.

NK Cells Directly Target and Kill Senescent Pancreatic Tumor Cells Following Combination Therapy with Trametinib and Palbociclib Through Induction of Cell Surface SASP Factor ICAM-1.

Figure 7A:
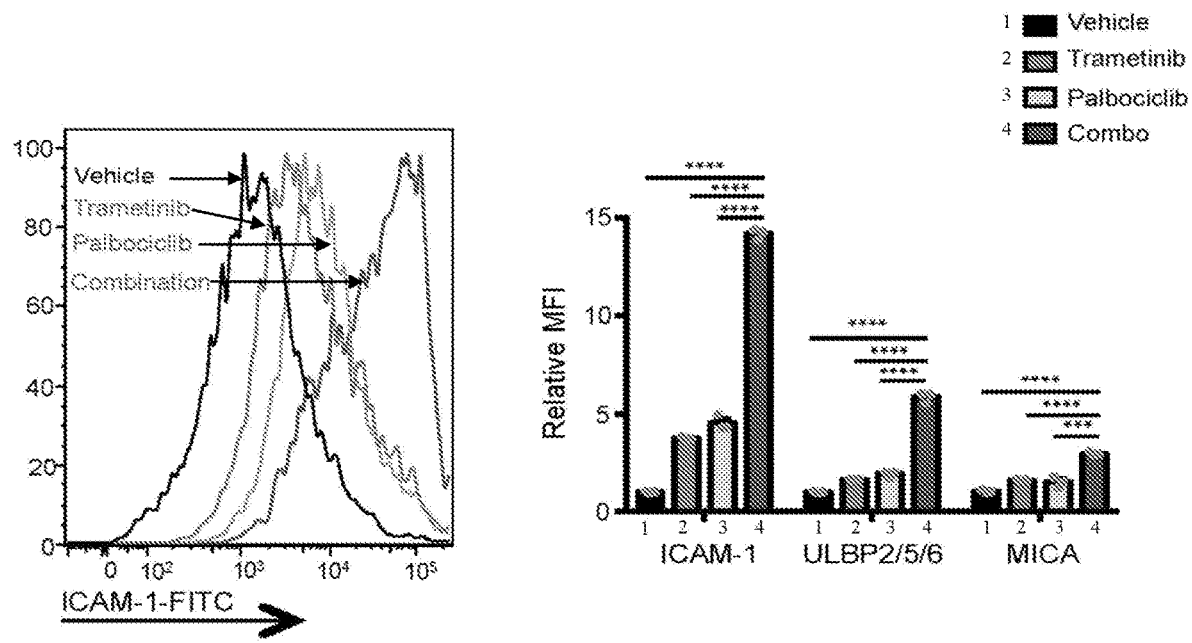
FIG. 7(A) shows the flow cytometry analysis of ICAM-1 expression and levels of other NK cell activating ligands following 8 day treatment of human PANC-1 tumor cells with trametinib (25 nM) and/or palbociclib (500 nM) (left).
Figure 7B:
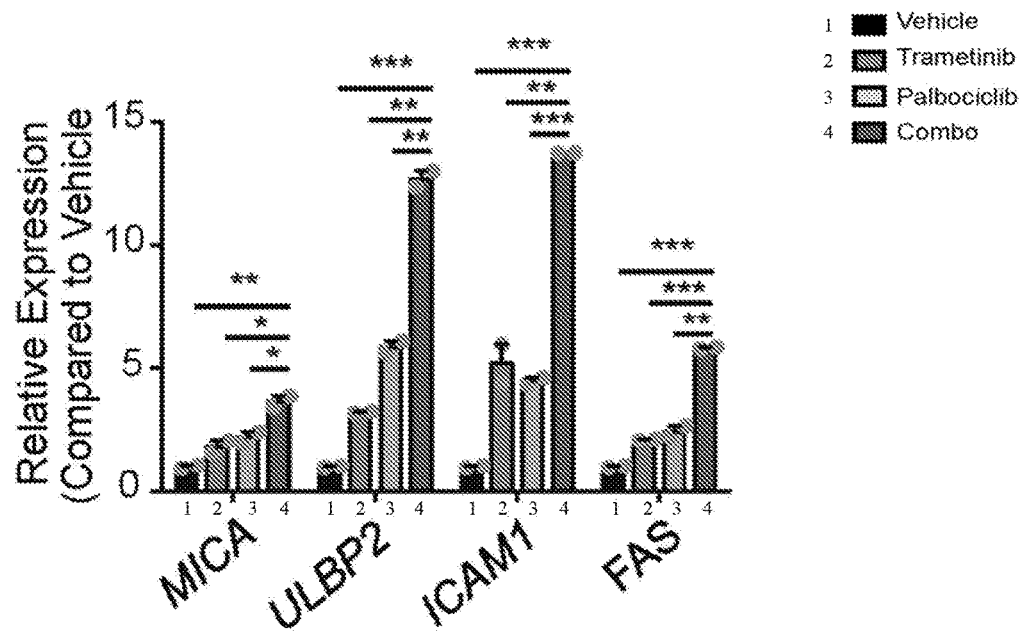
FIG. 7(B) shows qRT-PCR analysis of NK cell ligand expression following 8 day treatment of human pancreas PANC-1 tumor cell lines in vitro with trametinib (25 nM) and/or palbociclib (500 nM). One-way ANOVA. Error bars, mean±s.e.m. * $P<0.05$,  $P<0.01$, * $P<0.001$, **** $P<0.0001$.
Figure 7C:
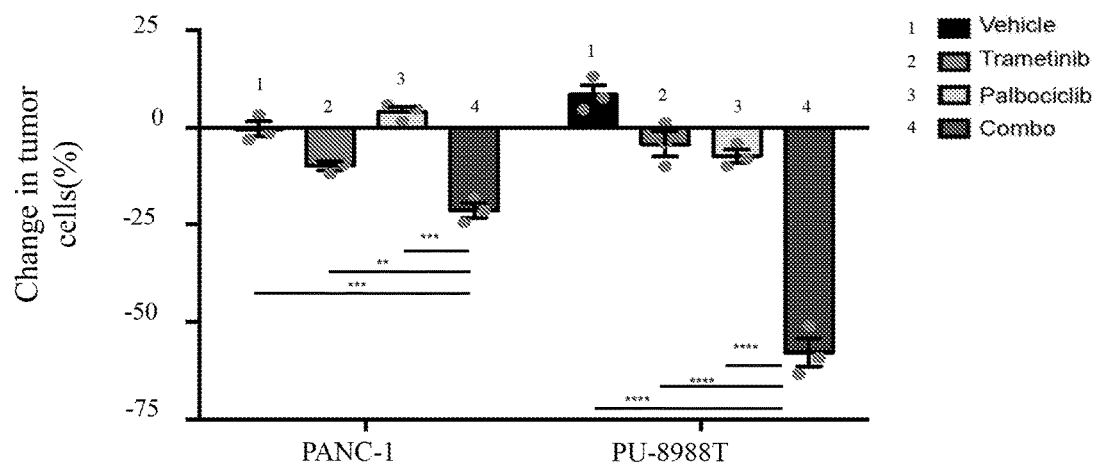
FIG. 7(C) shows the quantification of NK cell cytotoxicity following pre-treatment of PANC-1 and PU-8988T pancreas tumor cell lines with indicated drugs for 8 days and co-culturing with the YT NK cell line at a 10:1 effector:target (E:T) ratio for 20 hours. Change in tumor cells is normalized to control wells lacking NK cells. One-way ANOVA. Error bars, mean±s.e.m. * P<0.05,  P<0.01, * P<0.001,**** P<0.0001.
Figure 7D:
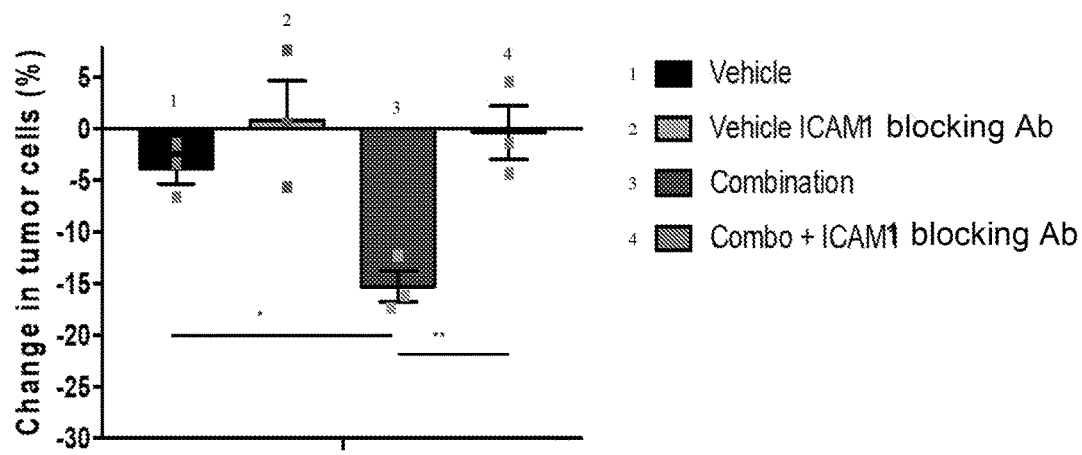
FIG. 7(D) shows the quantification of NK cell cytotoxicity following pre-treatment of human pancreas PANC-1 tumor cells with indicated drugs for 8 days and co-culturing with primary human NK cells (in the presence or absence of ICAM-1 (25 µg/ml) blocking mAbs) at a 10:1 E:T ratio for 20 hours. One-way ANOVA. Error bars, mean±s.e.m. * P<0.05,  P<0.01,* P<0.001,**** P<0.0001.
Figure 8:
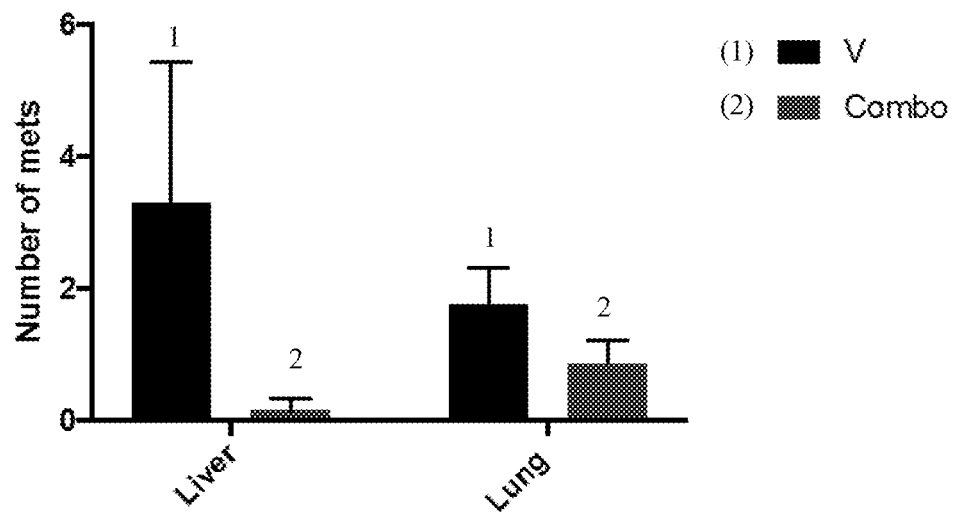
FIG. 8 shows the metastatic burden of Pdx1-Cre; Kras$^{LSL-G12D/+}$; Trp53fl$^{/+}$ (KPC) GEMM mice were treated with vehicle or trametinib (1 mg/kg)+palbociclib (100 mg/kg) following confirmation of pancreas tumor formation by ultrasound. Following 2-week treatment, liver and lungs were harvested from animals, and metastatic burden was assessed by quantifying the number of metastases from H&E stained tissue sections.

As shown in FIGS. 7(A)-7(B), combination therapy with trametinib and palbociclib led to enhanced expression of ICAM-1 and other activating NK cell ligands in pancreatic tumor cells compared to that observed in pancreatic tumor cells that received single agent treatment. The degree of NK cell cytotoxicity observed with PANC and PU8988T tumor cells pretreated with both trametinib and palbociclib was significantly greater than that observed with single agent treatment. See FIG. 7(C). Combination therapy with trametinib and palbociclib significantly increased NK cell cytotoxicity in an ICAM-1 dependent manner (FIG. 7(D)) and reduced metastatic burden in KPC GEMM pancreas cancer mice.

Taken together, these results demonstrate that combination therapy with a MEK inhibitor and a CDK 4/6 inhibitor increases NK cell immune surveillance and promotes senescent tumor cell clearance in subjects with pancreatic cancer. Accordingly, the combination therapy methods disclosed herein are useful for preventing or treating pancreatic cancer in a subject in need thereof.

Example 3: Use of Combination Therapy with MEK Inhibitor and CDK 4/6 Inhibitor to Promote Vascular Re-Normalization in Subjects with Pancreatic Cancer This Example demonstrates that the combination therapy methods disclosed herein are useful to prevent or treat pancreatic cancer in subjects in need thereof.

Combination Therapy with Trametinib and Palbociclib Induces Vascular Re-Normalization.

Figure 9A:
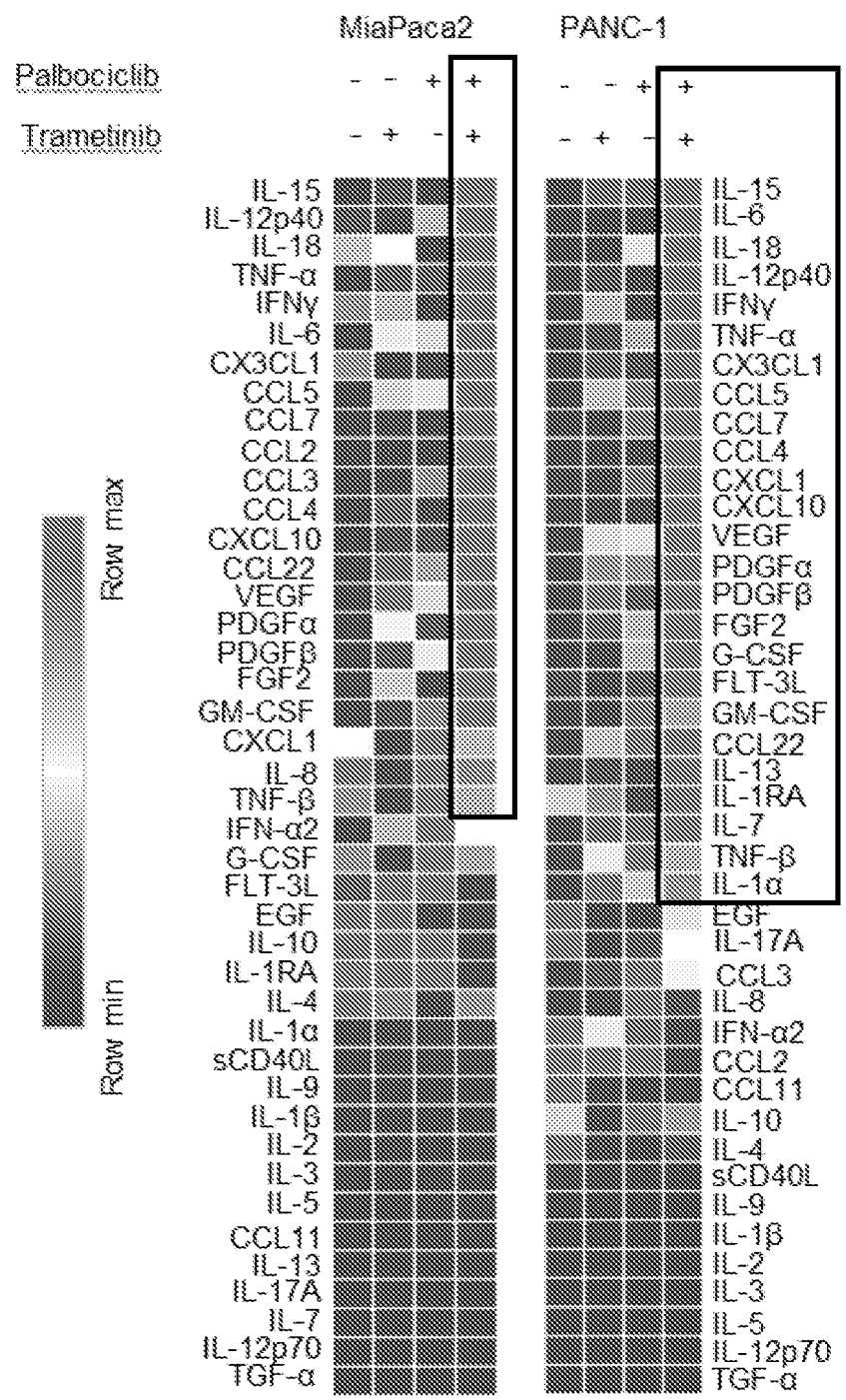
FIG. 9(A) shows a heat map of cytokine array results from human KRAS-mutant pancreas tumor cell lines treated with trametinib (25 nM) and/or palbociclib (500 nM) for 8 days. Data presented as mean of three biological replicates. Boxes highlight cytokines that were elevated in the two pancreas tumor cell lines that were treated with both trametinib and palbociclib.
Figure 9B:
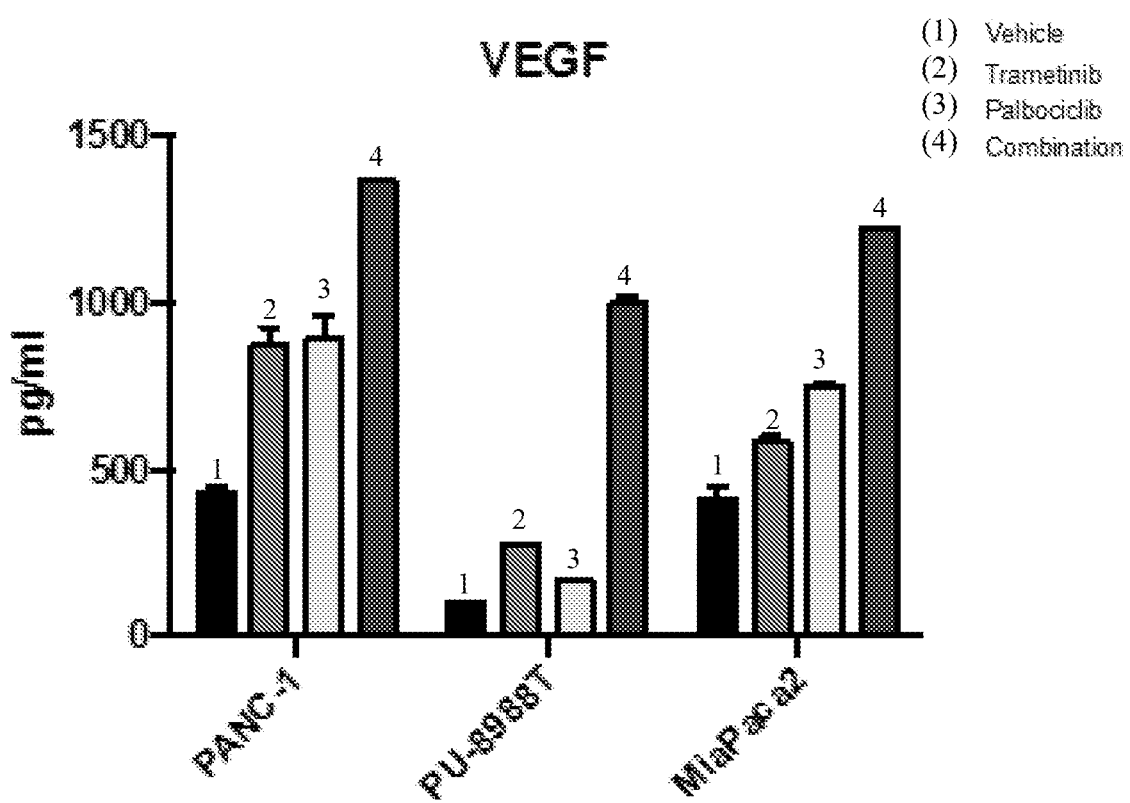
FIG. 9(B) shows the quantification of secreted VEGF levels from human pancreas tumor cell lines treated with indicated drugs for 8 days as measured by cytokine array as described in FIG. 9(A).
Figure 9C:
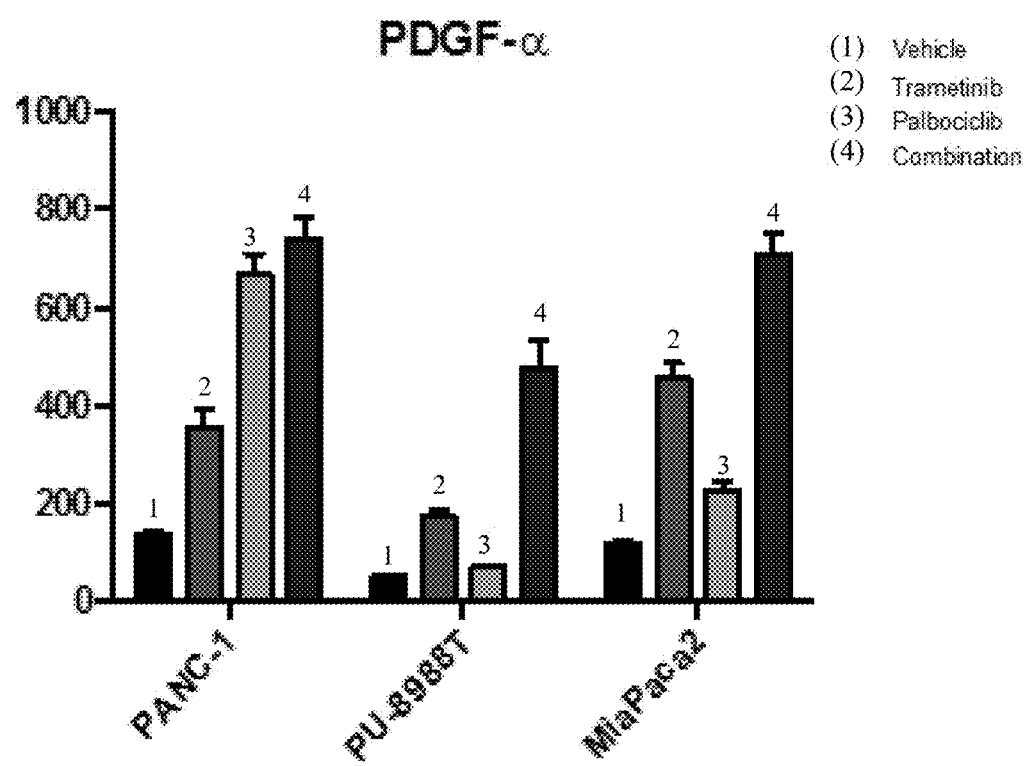
FIG. 9(C) shows the quantification of secreted PDGF-α levels from human pancreas tumor cell lines treated with indicated drugs for 8 days as measured by cytokine array as described in FIG. 9(A).
Figure 9D:
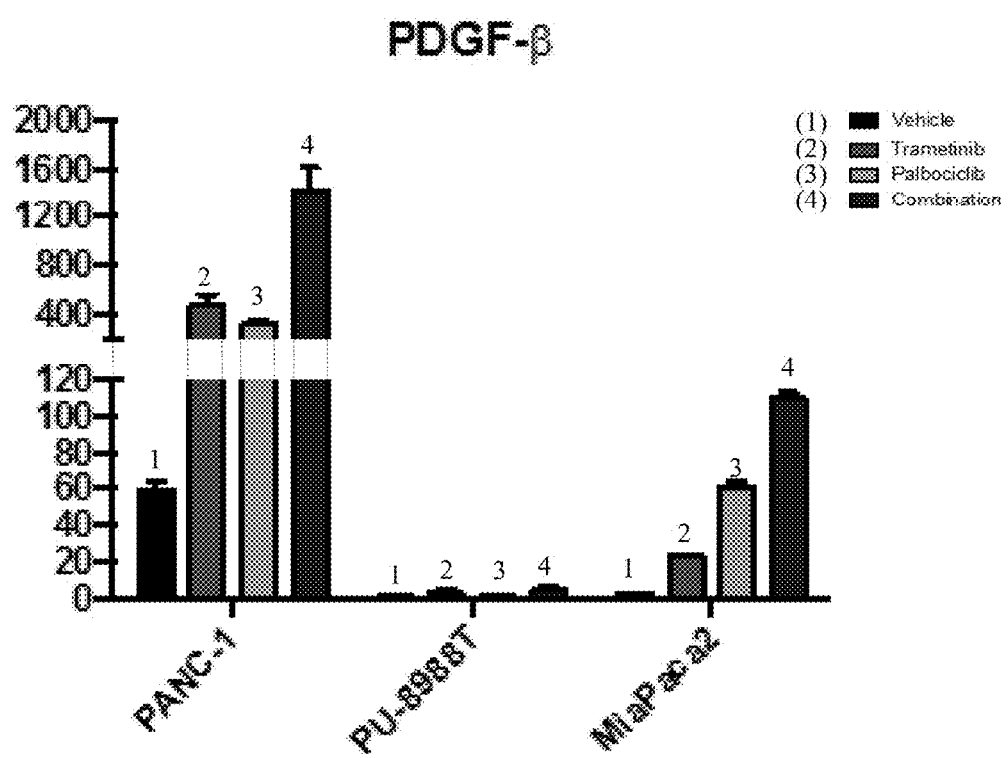
FIG. 9(D) shows the quantification of secreted PDGF-β levels from human pancreas tumor cell lines treated with indicated drugs for 8 days as measured by cytokine array as described in FIG. 9(A).
Figure 9E:
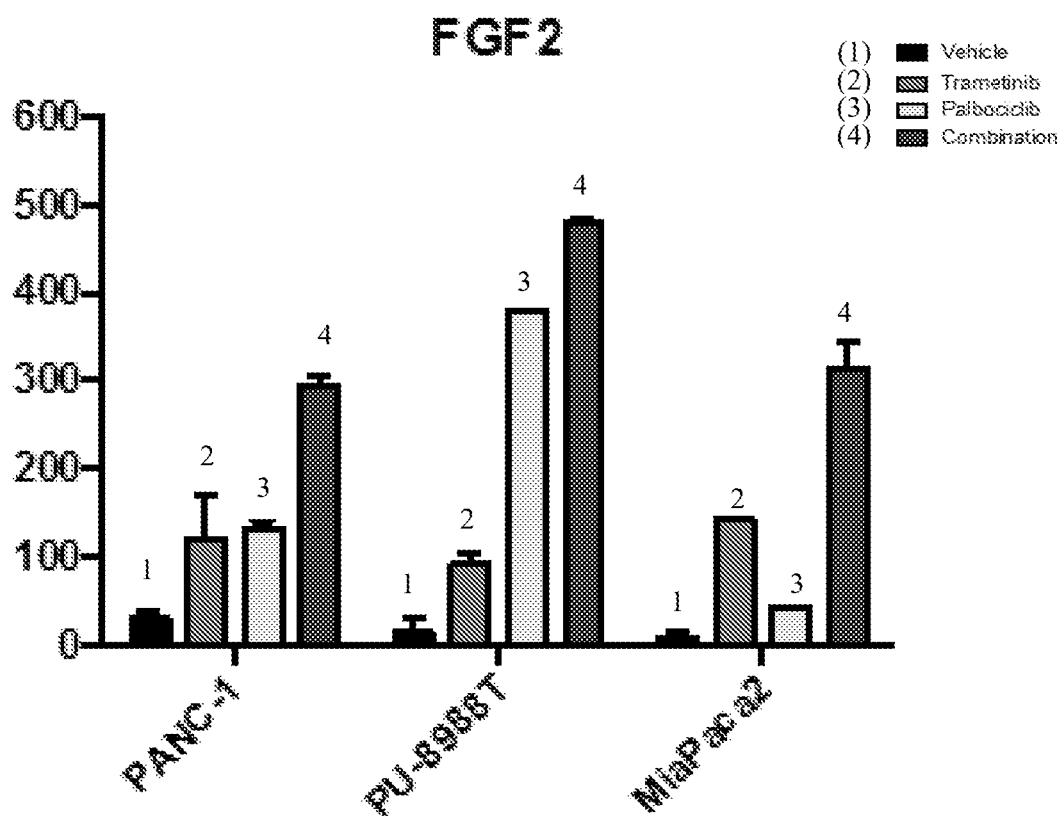
FIG. 9(E) shows the quantification of secreted FGF2 levels from human pancreas tumor cell lines treated with indicated drugs for 8 days as measured by cytokine array as described in FIG. 9(A).
Figure 9F:
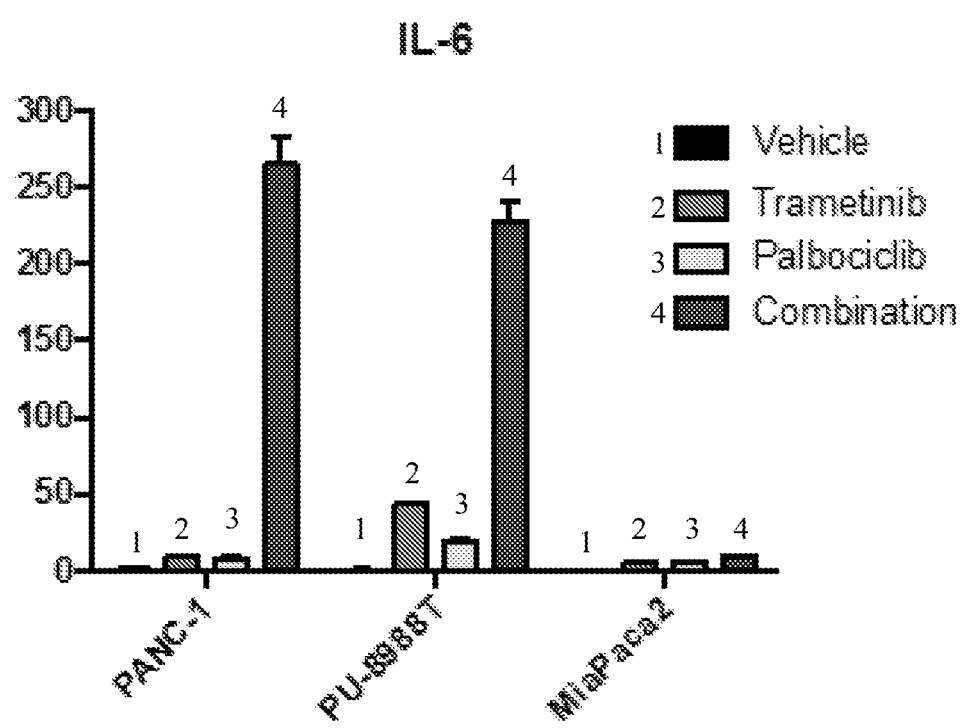
FIG. 9(F) shows the quantification of secreted IL-6 levels from human pancreas tumor cell lines treated with indicated drugs for 8 days as measured by cytokine array as described in FIG. 9(A).
Figure 11:
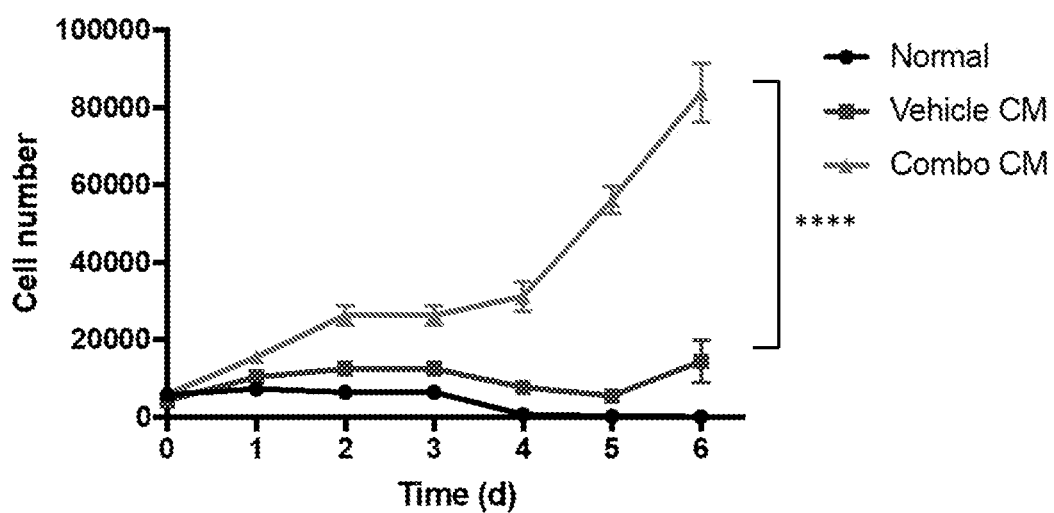
FIG. 11 shows survival of 3B11 mouse endothelial cells that were cultured in normal serum-free or conditioned media (CM) at Day 0. Serum-free CM was collected from mouse KPC pancreas tumor cells following 6 day vehicle or combined trametinib (25 nM) and palbociclib (500 nM) treatment. Cells were counted daily in quadruplicate to determine growth. Two-way ANOVA. Error bars, mean±s.e.m. **** P<0.0001.

As shown in FIG. 9(A), human pancreas cancer cell lines treated with both trametinib and palbociclib displayed pro-angiogenic SASP as evidenced by cytokine array analysis. Pro-angiogenic SASP factors were expressed at significantly higher levels in tumor cells treated with both trametinib and palbociclib compared to those receiving single agents. See FIGS. 9(B)-9(F). Further, conditioned media (SASP) obtained from pancreas tumor cells that received trametinib+palbociclib combination therapy promoted endothelial cell survival and growth in vitro. See FIG. 11

Figure 10A:
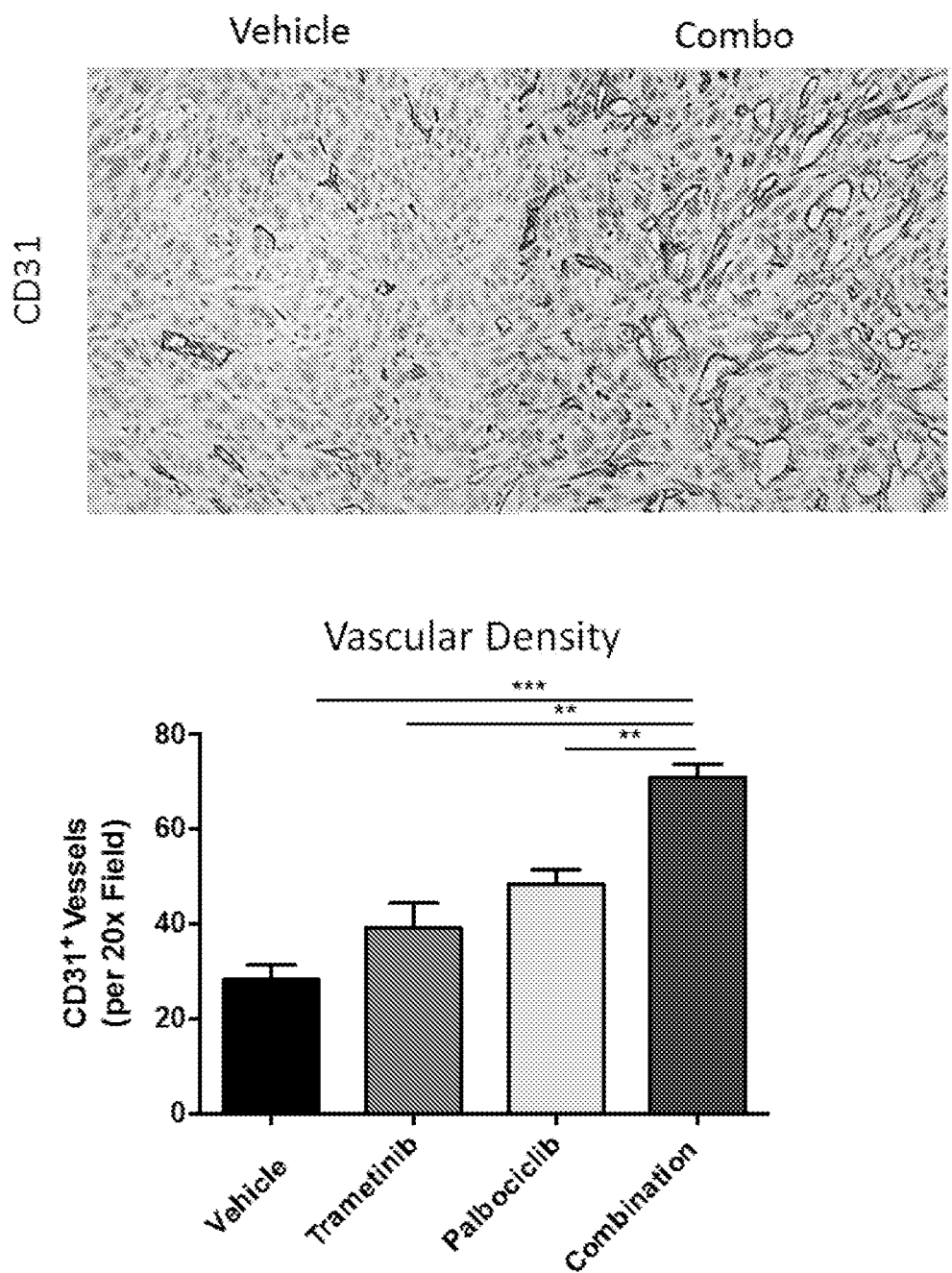
FIG. 10(A) shows immunohistochemical staining of sections from KPC pancreas organoid transplant tumors in C57BL/6 mice following 2 week treatment with vehicle or combined trametinib (1 mg/kg) and palbociclib (100 mg/kg) (top). Arrowhead, collapsed vessel; Arrow, visible vessel lumen following treatment.
Figure 10B:
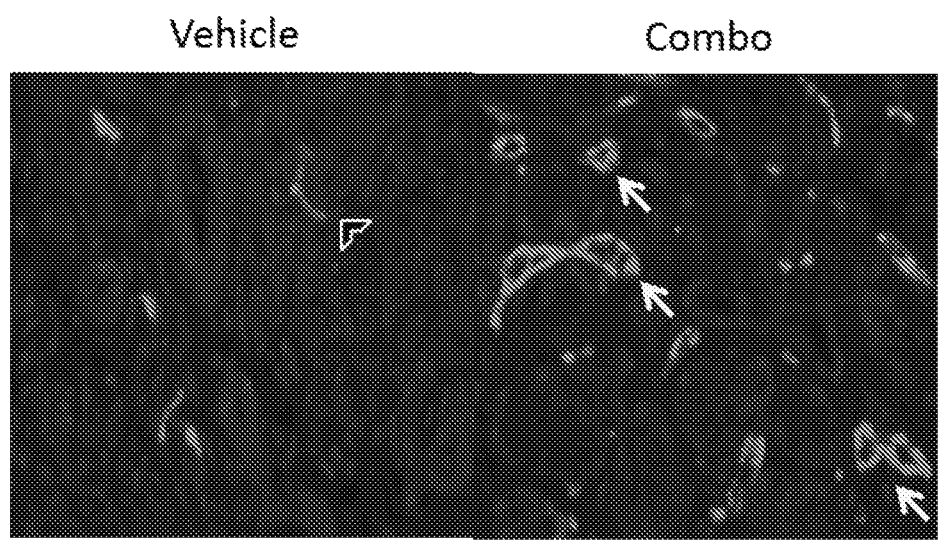
FIG. 10(B) shows immunohistochemical staining of KPC GEMM pancreas tumor sections following 2 week treatment. Arrowhead, collapsed vessel; Arrow, visible vessel lumen following treatment.
Figure 12:
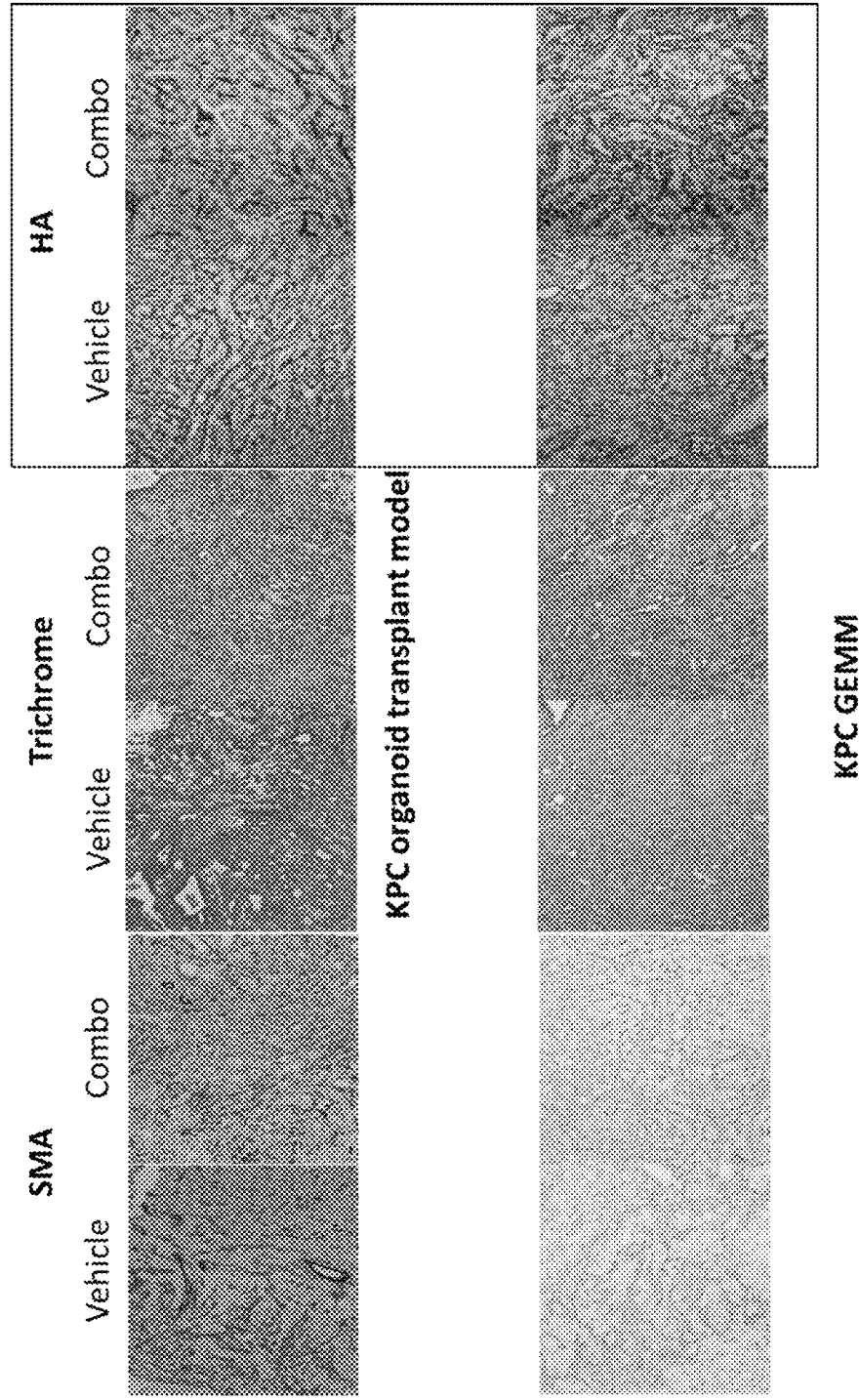
FIG. 12 shows the immunohistochemical staining of sections from KPC pancreas organoid transplant tumors in C57BL/6 mice (Top) and KPC GEMM pancreas tumors (Bottom) following 2 week treatment with vehicle or combined trametinib (1 mg/kg) and palbociclib (100 mg/kg).

Moreover, combination therapy with trametinib and palbociclib significantly increased the number and size of blood vessels in vivo in both the KPC organoid transplant model and KPC GEMM model. See FIGS. 10(A)-(B). No increase in blood vessel number or size was observed in animals that were treated with the single agents. According to FIG. 12, combination therapy with trametinib and palbociclib did not lead to stromal depletion in the pancreas (as measured by no change in SMA+fibroblast numbers or collagen deposition from trichrome staining). Rather, treatment with trametinib and palbociclib reduced Hyaluronic Acid (HA) accumulation, a molecule that has been shown to contribute significantly to vascular collapse in PDAC tumors. See FIG. 12.

These results demonstrate that combination therapy with a MEK inhibitor and a CDK 4/6 inhibitor promotes vascular re-normalization in subjects with pancreatic cancer. Accordingly, the combination therapy methods disclosed herein are useful for preventing or treating pancreatic cancer in a subject in need thereof.

Example 4: Use of Combination Therapy with MEK Inhibitor and CDK 4/6 Inhibitor to Increase the Uptake and Efficacy of Chemotherapeutic Agents in Patients with Pancreatic Cancer This Example demonstrates that the combination therapy methods disclosed herein are useful for increasing the efficacy of chemotherapeutic agents in patients with pancreatic cancer.

Increased Chemotherapeutic Drug Uptake into Pancreatic Tumors Following MEK/CDK4/6 Inhibition.

Figure 13B:
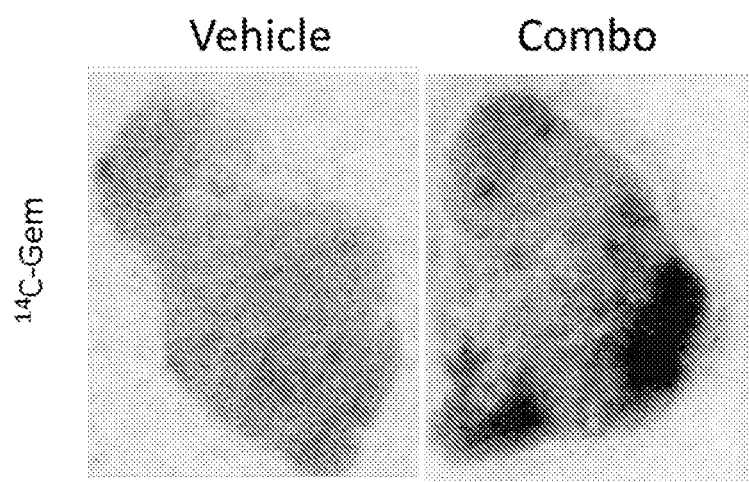
FIG. 13(B) shows an autoradiograph showing distribution of $^{14}$C-labeled gemcitabine in KPC organoid transplant pancreas tumors in C57BL/6 mice after 2 hour incubation and 2 week pre-treatment with indicated compounds.
Figure 13C:
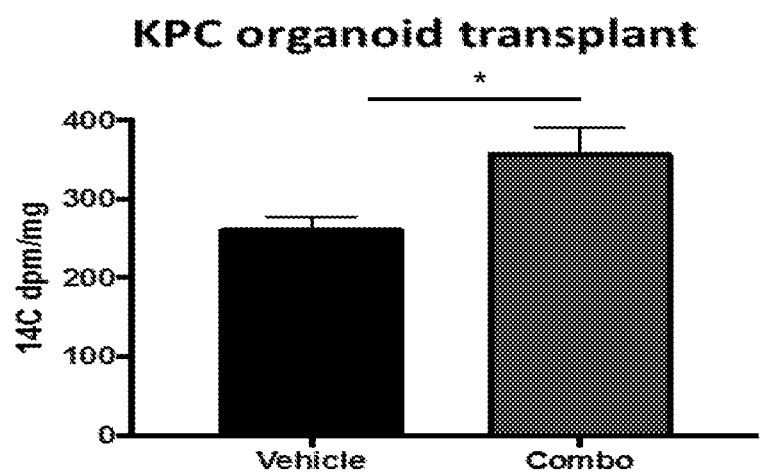
FIG. 13(C) shows the quantification of $^{14}$C-gemcitabine uptake in pancreas tumor tissue from KPC organoid transplant. Unpaired two-tailed t-test. Error bars, mean±s.e.m. * P<0.05.
Figure 13D:
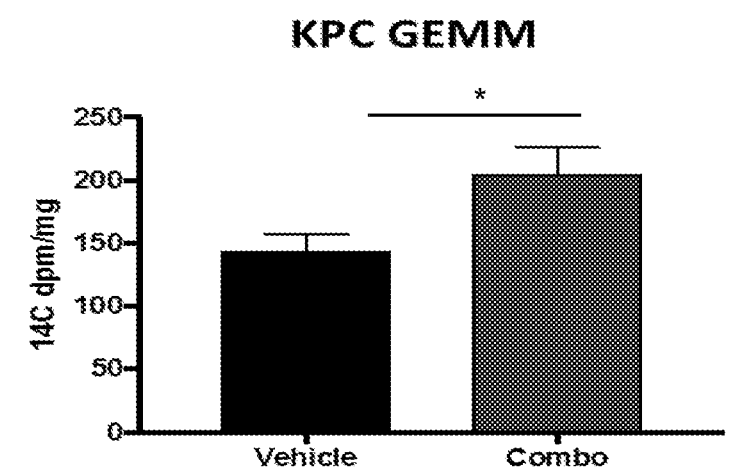
FIG. 13(D) shows the quantification of $^{14}$C-gemcitabine uptake in pancreas tumor tissue from GEMM mice. Unpaired two-tailed t-test. Error bars, mean±s.e.m. * P<0.05.
Figure 14A:
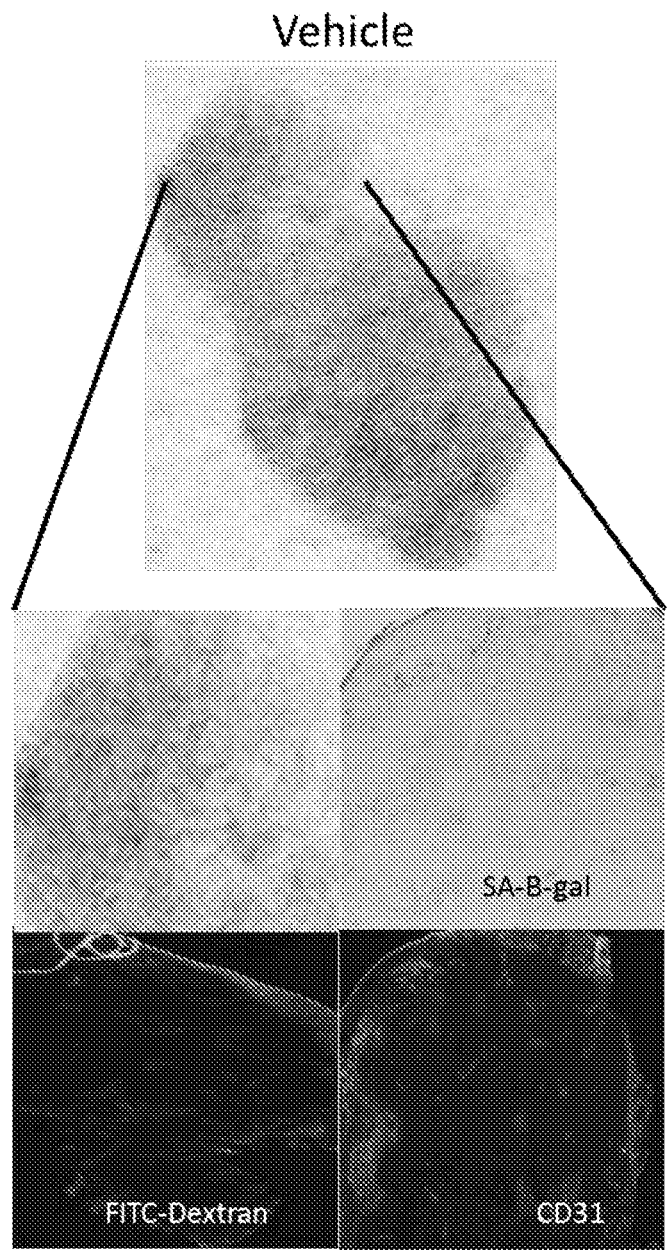
FIG. 14(A) shows an autoradiograph showing distribution of $^{14}$C-labeled gemcitabine in KPC organoid transplant pancreas tumors in C57BL/6 mice after 2 hour incubation and 2 week pre-treatment with vehicle (top) and an overlay of autoradiographs with immunohistochemical staining of consecutive sections for markers of senescence (SA-β-gal), blood vessels (CD31), and vascular perfusion (dextran).
Figure 14B:
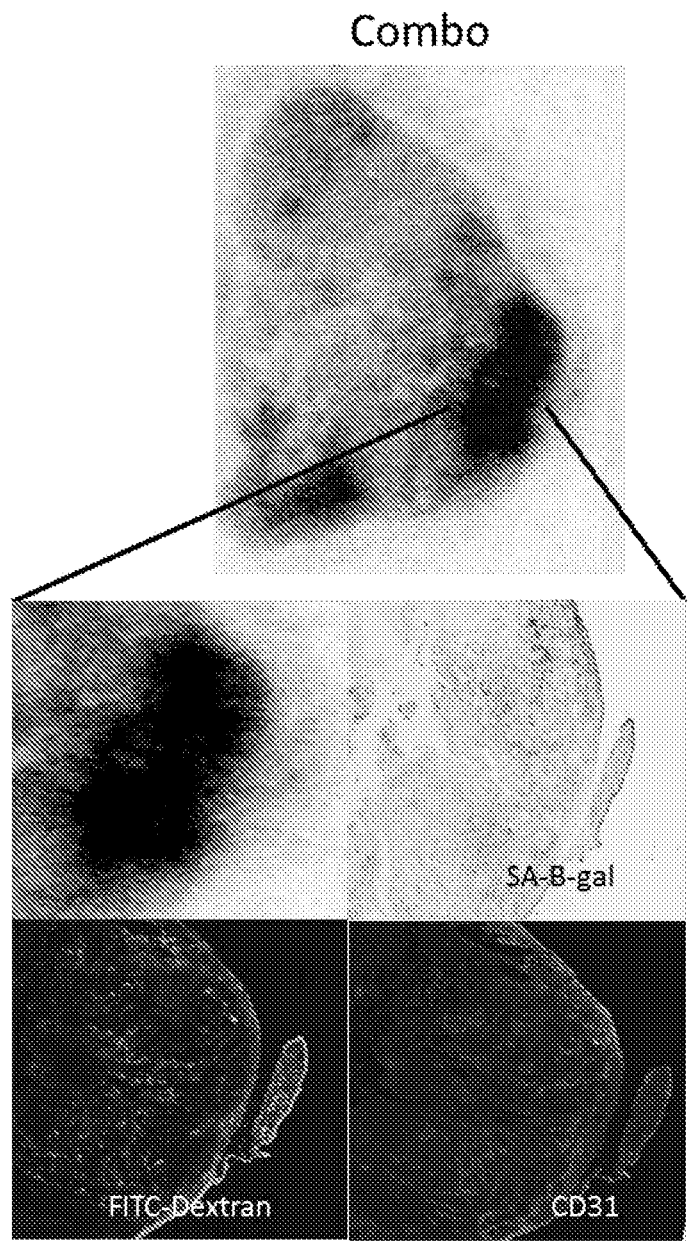
FIG. 14(B) shows an autoradiograph showing distribution of $^{14}$C-labeled gemcitabine in KPC organoid transplant pancreas tumors in C57BL/6 mice after 2 hour incubation and 2 week pre-treatment with combined trametinib and palbociclib (top) and an overlay of autoradiographs with immunohistochemical staining of consecutive sections for markers of senescence (SA-β-gal), blood vessels (CD31), and vascular perfusion (dextran).

As shown in FIGS. 13(B)-13(D), combination therapy with trametinib and palbociclib resulted in enhanced accumulation of gemcitabine in pancreas tumors in both the KPC organoid transplant model and the KPC GEMM model. Animals receiving both trametinib and palbociclib displayed high gemcitabine uptake, which was associated with elevated vessel density, vascular perfusion, and senescence induction (as measured by SA-$\beta$-gal staining). See FIGS. 14(A)-(B).

Combination Therapy with Trametinib and Palbociclib Increases the Efficacy of Chemotherapeutic Agents in Non-Responsive Patients with Pancreatic Cancer.

Figure 15A:
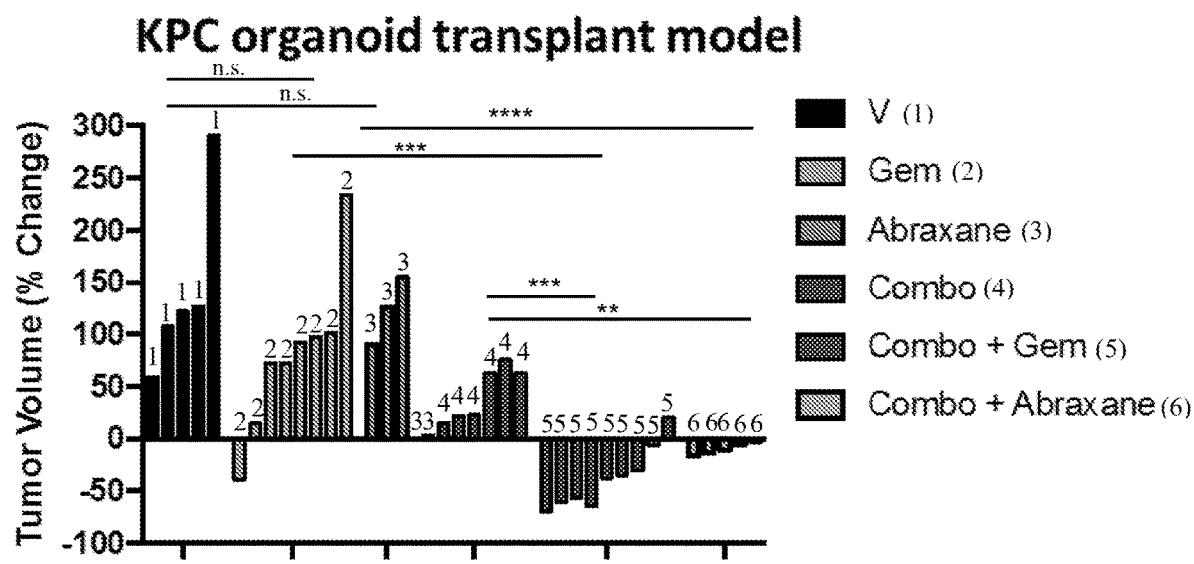
FIG. 15(A) shows a waterfall representation of the response of each orthotopically transplanted KPC organoid pancreas tumor after 2 weeks of treatment. C57BL/6 mice with orthotopically transplanted KPC organoid pancreas tumors were treated for 2 weeks with vehicle, gemcitabine (100 mg/kg), abraxane (100 mg/kg), and/or combined trametinib (1 mg/kg) and palbociclib (100 mg/kg). One-way ANOVA. Error bars, mean±s.e.m. n.s, not significant, * P<0.05,  P<0.01, * P<0.001.
Figure 15B:
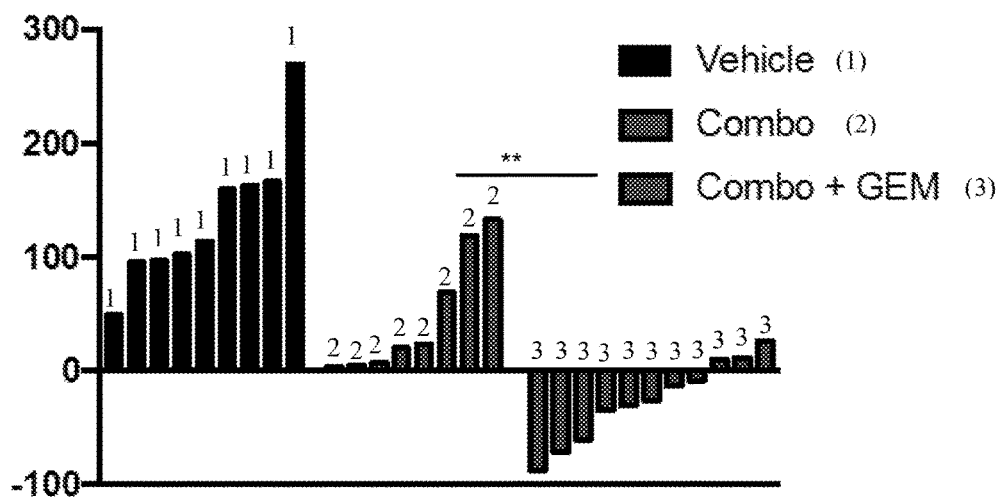
FIG. 15(B) shows a waterfall representation of the response of KPC GEMM pancreas tumors after 2 weeks of treatment. KPC GEMM mice were treated for 2 weeks with vehicle, gemcitabine (100 mg/kg), and/or combined trametinib (1 mg/kg) and palbociclib (100 mg/kg). One-way ANOVA. Error bars, mean±s.e.m. n.s, not significant, * P<0.05,  P<0.01, * P<0.001.
Figure 15C:
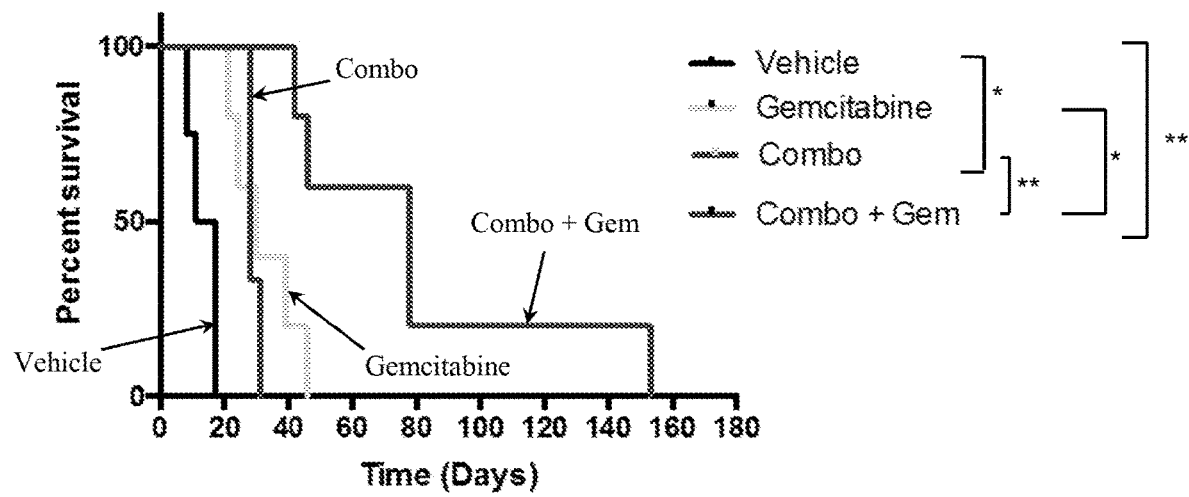
FIG. 15(C) shows Kaplan-Meier survival curve analysis of C57BL/6 mice with orthotopically transplanted KPC organoid pancreas tumors receiving indicated treatments (log-rank test). One-way ANOVA. Error bars, mean±s.e.m. n.s, not significant, * P<0.05,  P<0.01,* P<0.001.
Figure 15D:
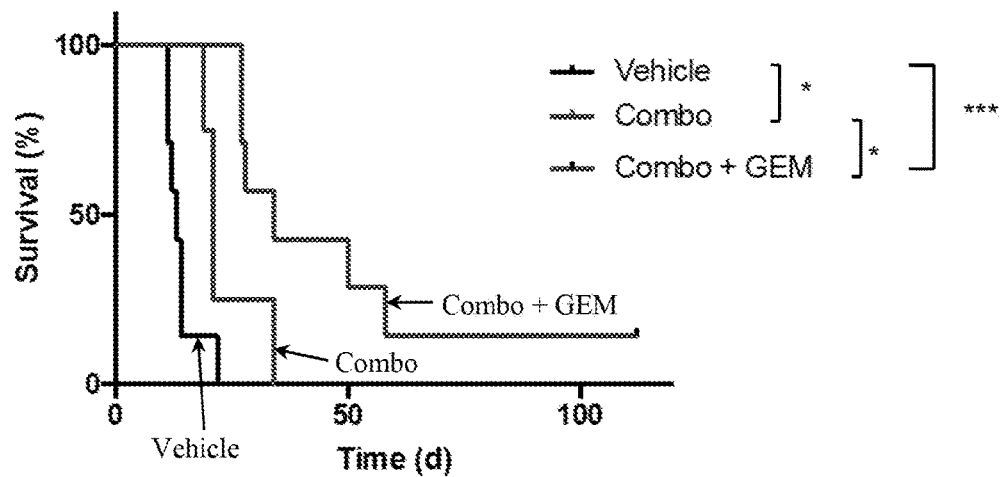
FIG. 15(D) shows Kaplan-Meier survival curve analysis of KPC GEMM mice receiving indicated treatments (log-rank test). One-way ANOVA. Error bars, mean±s.e.m. n.s, not significant, * P<0.05,  P<0.01,* P<0.001.
Figure 17A:
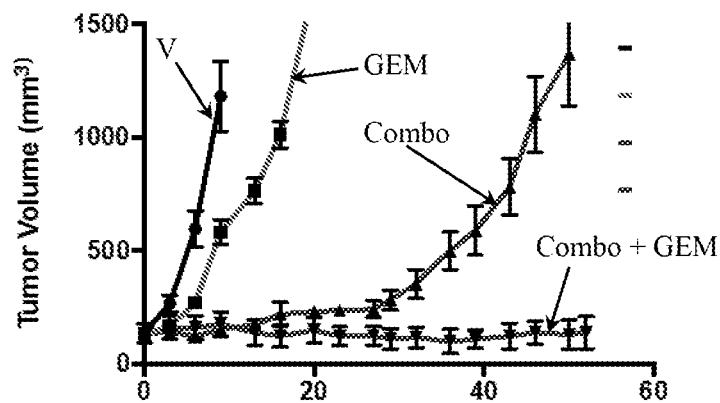
FIG. 17(A) shows tumor volumes of mice bearing KRAS-mutant MSK-PR07 patient-derived xenograft (PDX) pancreas tumors treated with vehicle, gemcitabine (100 mg/kg body weight), and/or trametinib (1 mg/kg body weight) and palbociclib (100 mg/kg body weight) for indicated times.
Figure 17B:
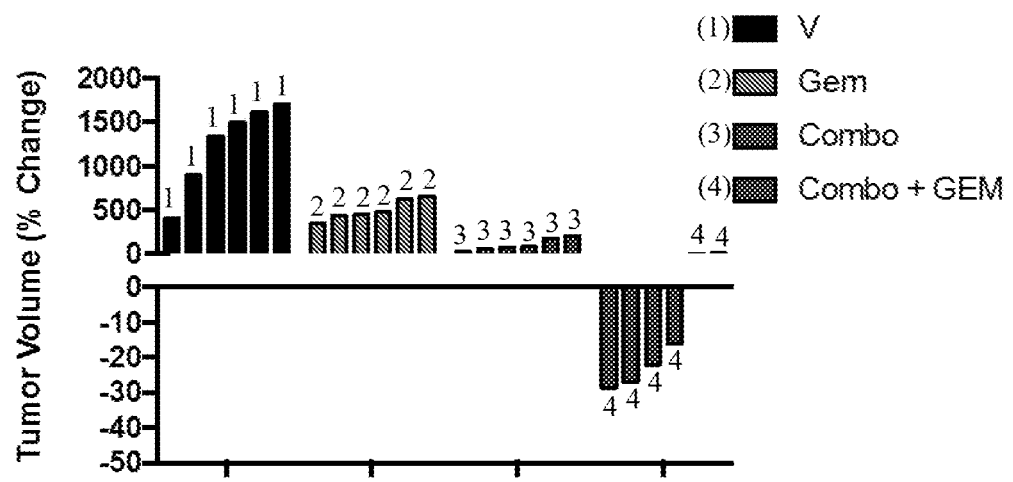
FIG. 17(B) shows a waterfall representation of the response of each tumor described in FIG. 17(A) after 2 weeks of treatment.

As shown in FIGS. 15(A) and 15(C), combination therapy with trametinib and palbociclib significantly enhanced the efficacy of gemcitabine and abraxane in the KPC organoid transplant model (as measured by the regression of pancreas tumors and enhanced long-term survival) compared to that observed in control animals that did not the combination therapy. Likewise, combination therapy with trametinib and palbociclib significantly enhanced the efficacy of gemcitabine in the KPC GEMM model (as measured by the regression of pancreas tumors and enhanced long-term survival) compared to that observed in control animals that did not the combination therapy. See FIGS. 15(B) and 15(D). Further, combining trametinib and palbociclib with gemcitabine significantly reduced tumor volumes in animals bearing a PDAC PDX from a gemcitabine refractory patient compared to that observed in animals that received gemcitabine only or trametinib+palbociclib only. See FIGS. 17(A)-17(B).

Figure 16:
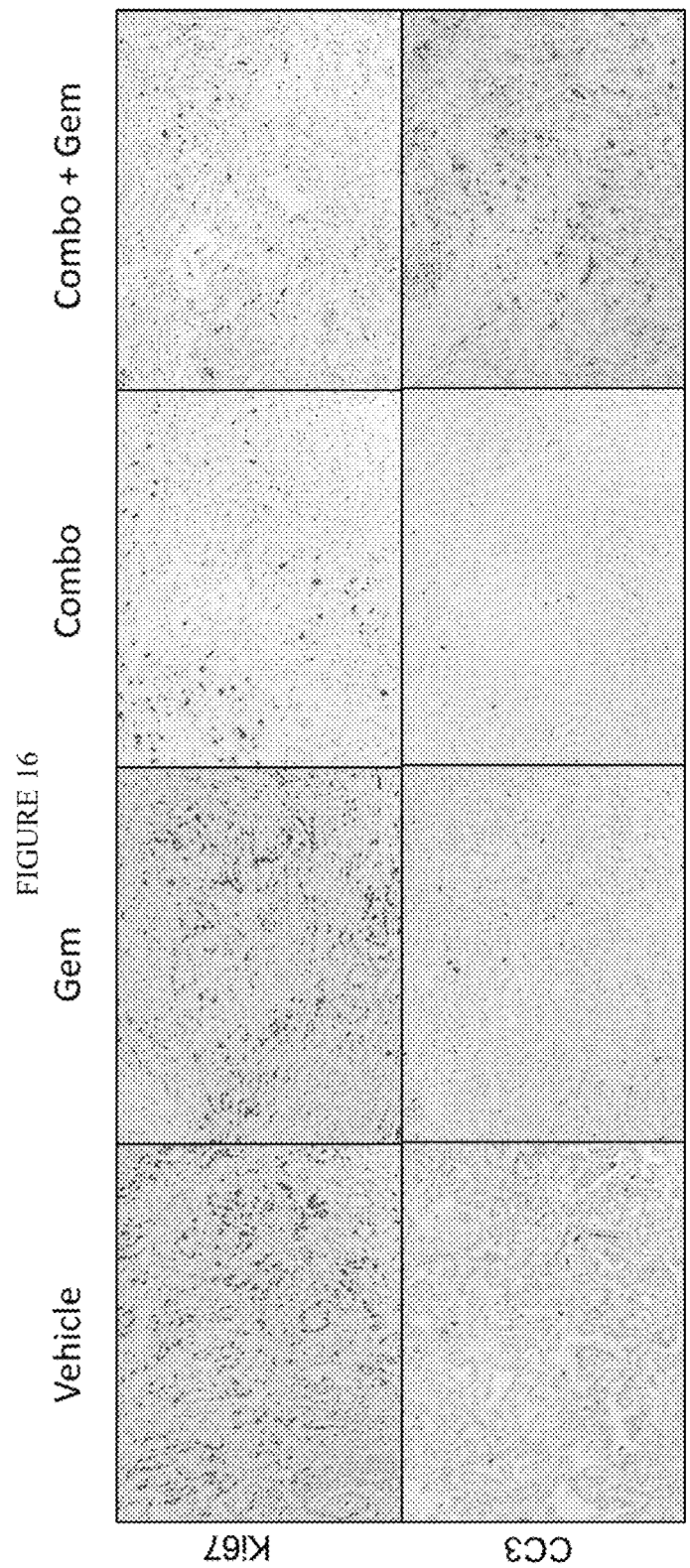
FIG. 16 shows immunohistochemical staining of KPC GEMM pancreas tumor sections following 2 week treatment. CC3, Cleaved Caspase-3.
Figure 17C:
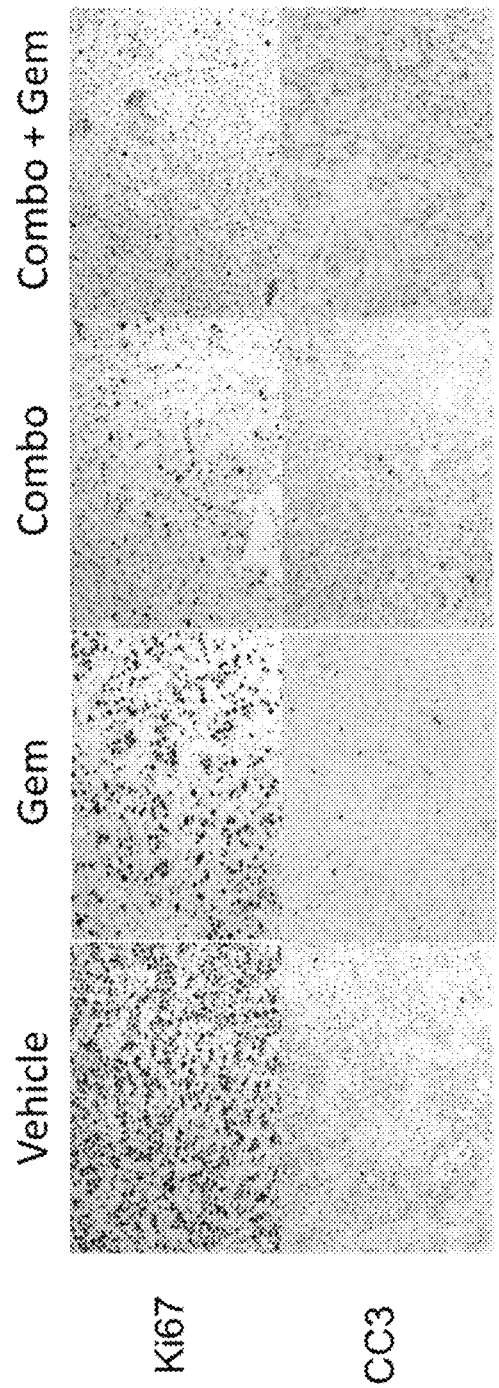
FIG. 17(C) shows immunohistochemical staining of pancreas PDX tumor sections following 2 week treatment. CC3, Cleaved Caspase-3.

Combination therapy with trametinib and palbociclib enhanced gemcitabine-mediated cell death (as measured by increased CC3 staining) in both KPC GEMM pancreas tumors and PDAC PDX tumors. See FIGS. 16 and 17(C).

Taken together, these results demonstrate that combination therapy with a MEK inhibitor and a CDK 4/6 inhibitor increases the uptake and efficacy of chemotherapeutic agents in non-responsive patients with pancreatic cancer. Accordingly, the combination therapy methods disclosed herein are useful for increasing the efficacy of chemotherapeutic agents in patients with pancreatic cancer.

Figure 20A:
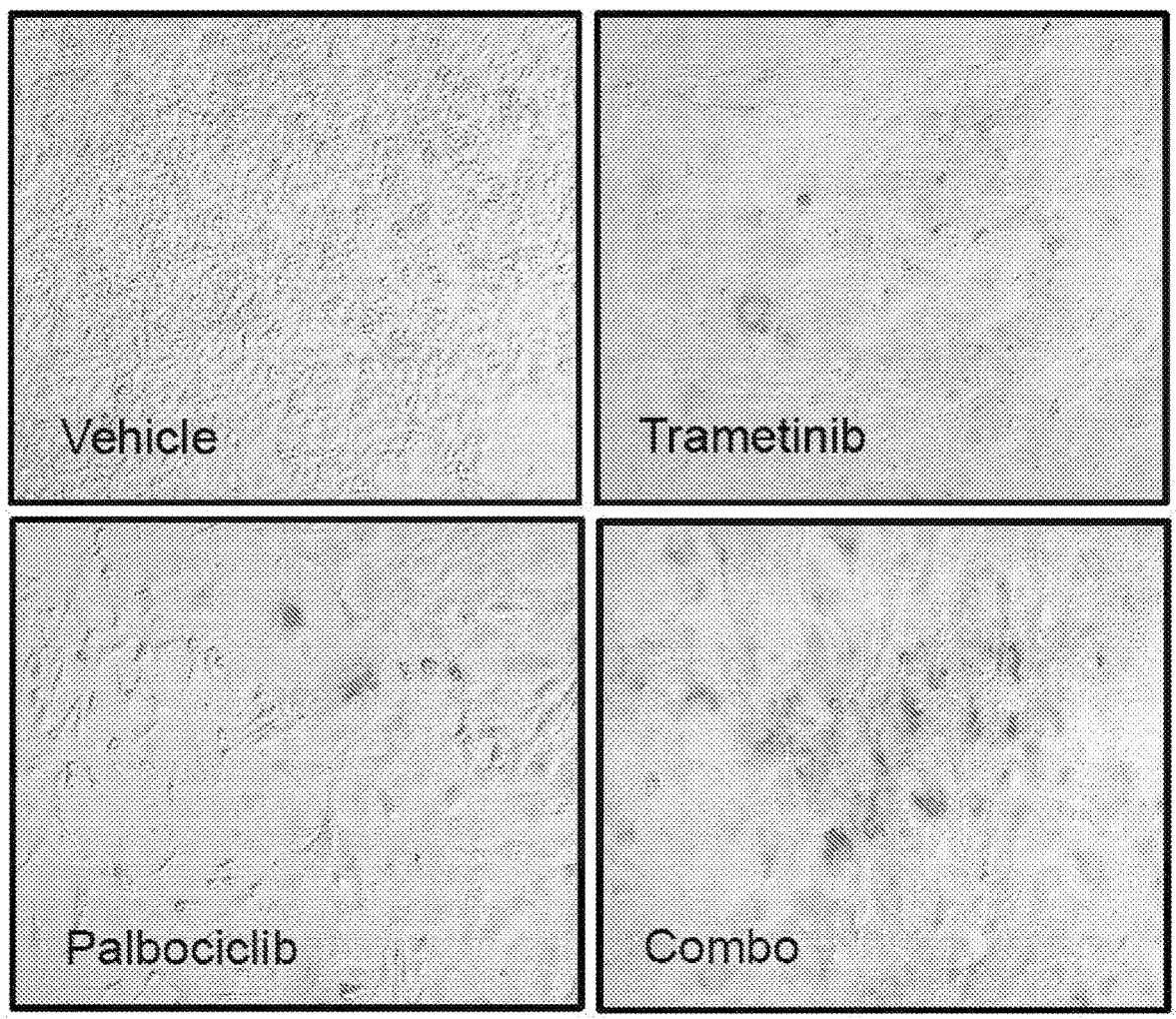
FIG. 20(A) shows representative SA-β-gal staining of KPC PDAC tumor cells treated with trametinib (25 nM) and/or palbociclib (500 nM) for 8 days (scale bar, μm).
Figure 20B:
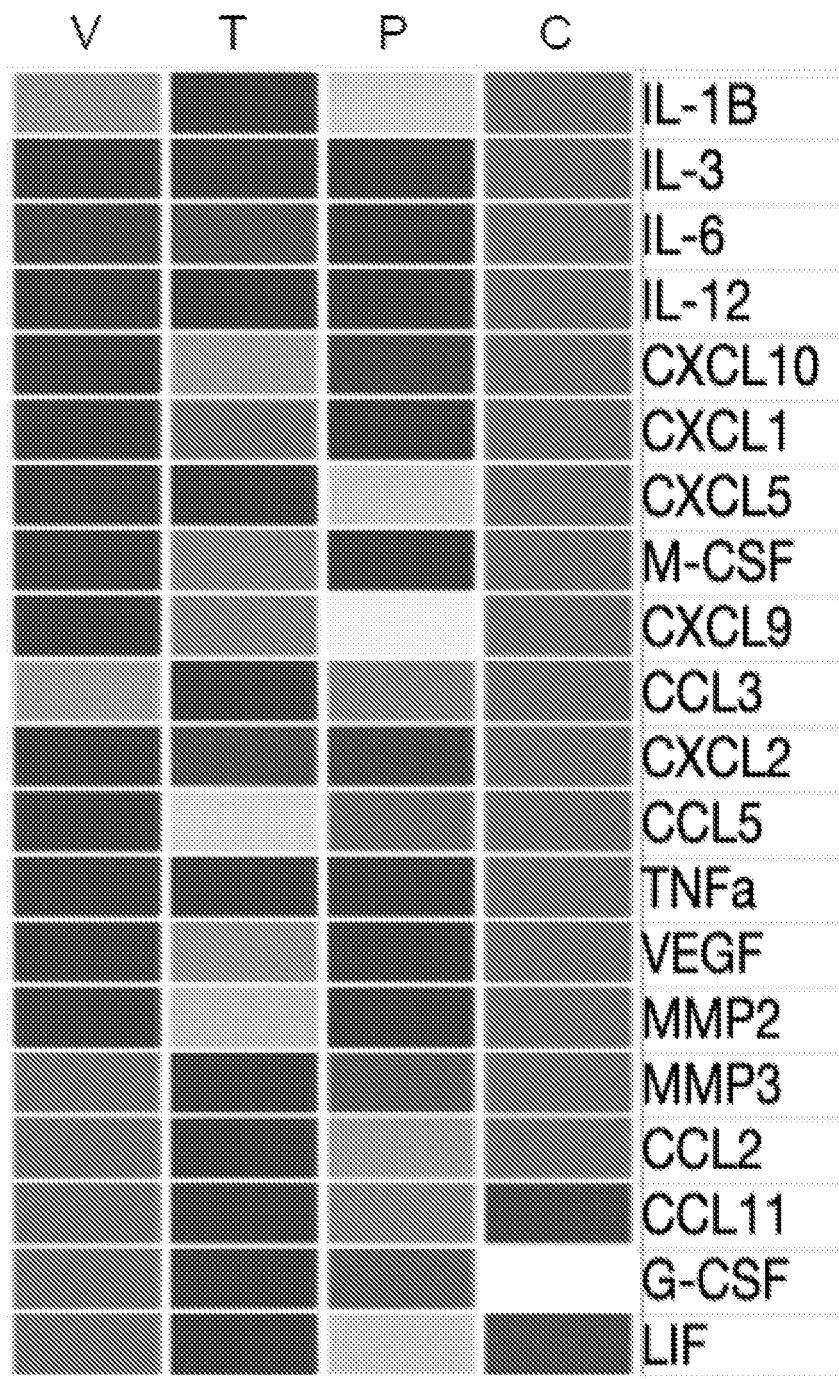
FIG. 20(B) shows a heat map of cytokine array results from KPC PDAC tumor cells treated as in FIG. 20(A). Data presented as mean of three biological replicates.

Example 5: Combination Therapy with MEK Inhibitor and CDK 4/6 Inhibitor Triggers Pro-Angiogenic SASP and Vascular Remodeling in PDAC While trametinib (T) and palbociclib (P) as single agents induce a reversible, quiescent growth arrest, the combination of both inhibitors (T/P) in human KRAS mutant PDAC cell lines leads to a senescent-like growth arrest characterized by a) stable arrest following drug withdrawal, b) increased senescence-associated betagalactosidase (SA-β-gal) expression and heterochromatin foci (SAHF) formation, and c) a SASP transcriptional signature. Cytokine array analysis of these PDAC cell lines following T/P treatment revealed enhanced secretion not only of SASP-associated pro-inflammatory cytokine and chemokines, but also pro-angiogenic factors (VEGF, PDGFA/B, FGF2) and matrix metalloproteineases (MMP2/3/7/9/10) (FIG. 27(A)). T/P combination treatment also induced senescence and secretion of both pro-inflammatory and pro-angiogenic SASP factors in murine PDAC cell lines derived from the Pdx1-Cre; LSL-KRAS$^{G12D}$; Trp53$^{fl/wt}$ (KPC) genetically engineered mouse model (GEMM) (FIGS. 20(A) and 20(B)).

Figure 20C:
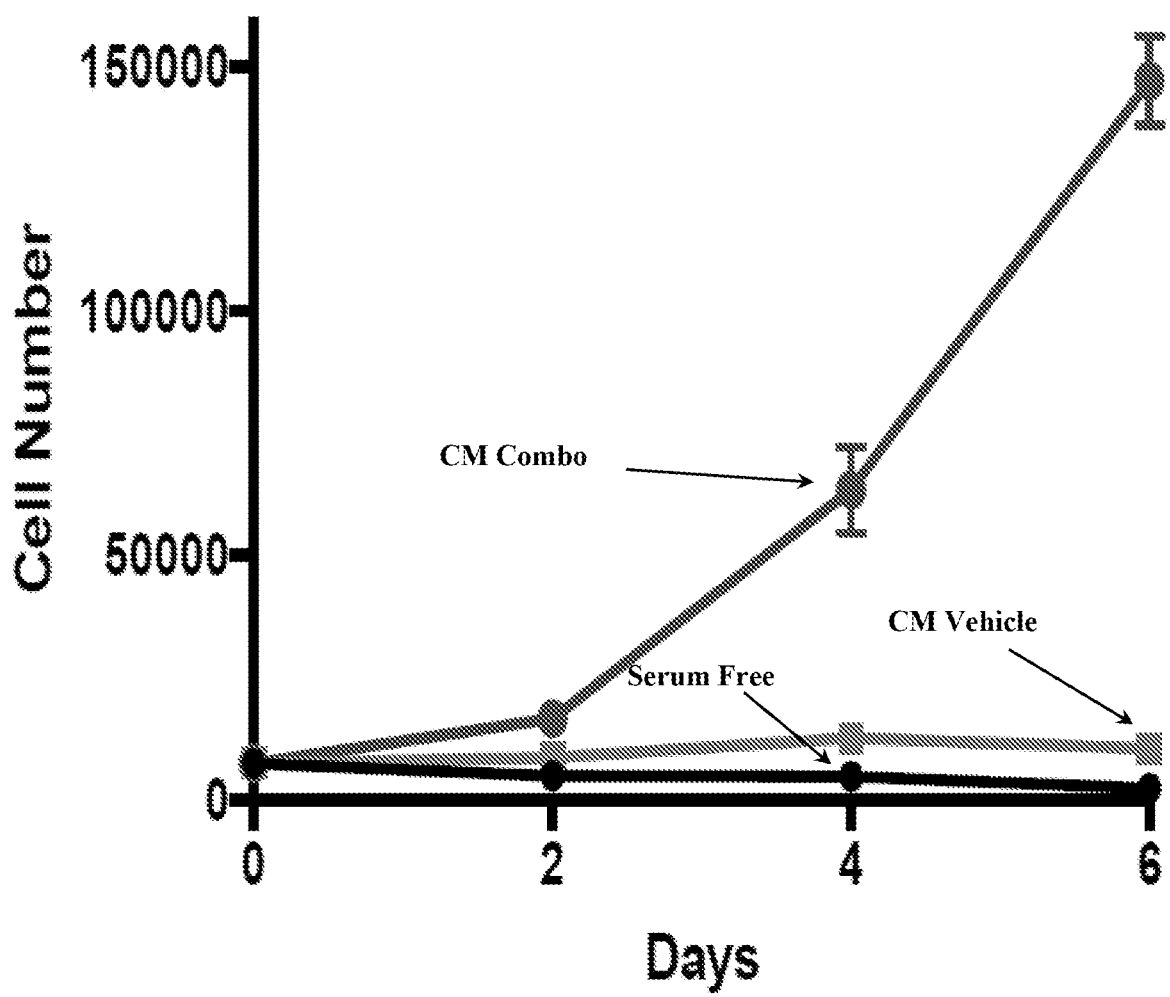
FIG. 20(C) shows cell growth analysis of 3B-11 endothelial cells cultured in serum-free media or conditioned media from KPC$^{mut}$ PDAC tumor cells treated for 8 days as in FIG. 20(A). Data represent the mean±SEM.
Figure 20D:
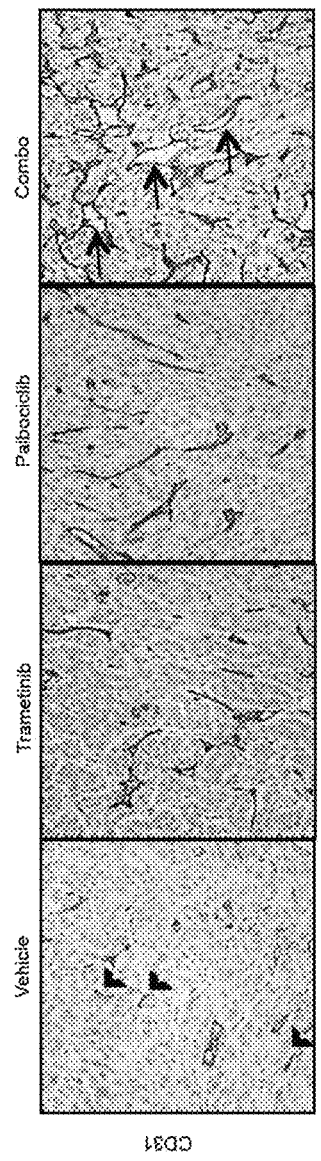
FIG. 20(D): CD31 immunohistochemical staining of KPC$^{mut}$ PDAC organoid transplant tumors treated with vehicle, trametinib (1 mg/kg body weight), palbociclib (100 mg/kg body weight), or both for 2 weeks (scale bar, μm). Arrowhead, collapsed vessel; Arrow, visible vessel lumen.
Figure 20E:
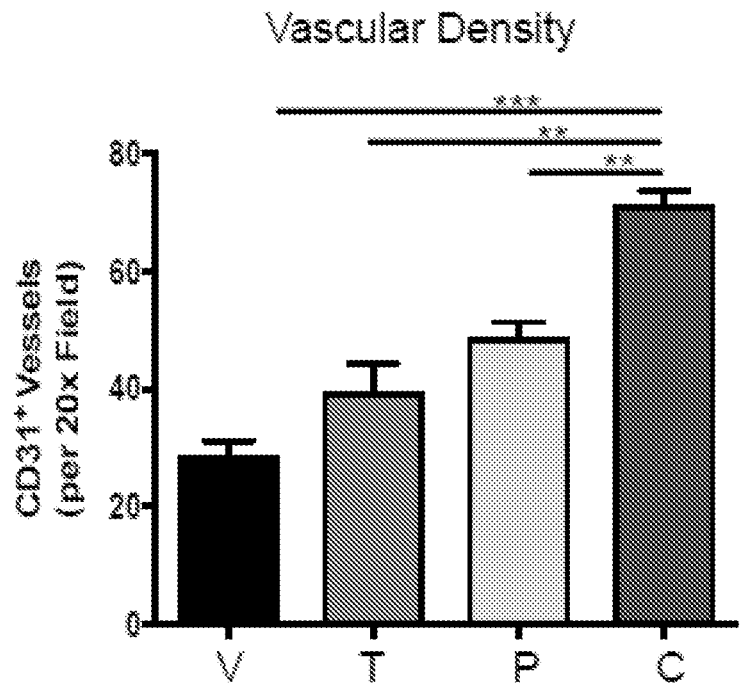
FIG. 20(E): Quantification of number of CD31$^+$ blood vessels per 20× field in KPC$^{mut}$ PDAC organoid transplant tumors following treatment as in FIG. 20(D). Bars represent the mean±SEM.
Figure 20F:
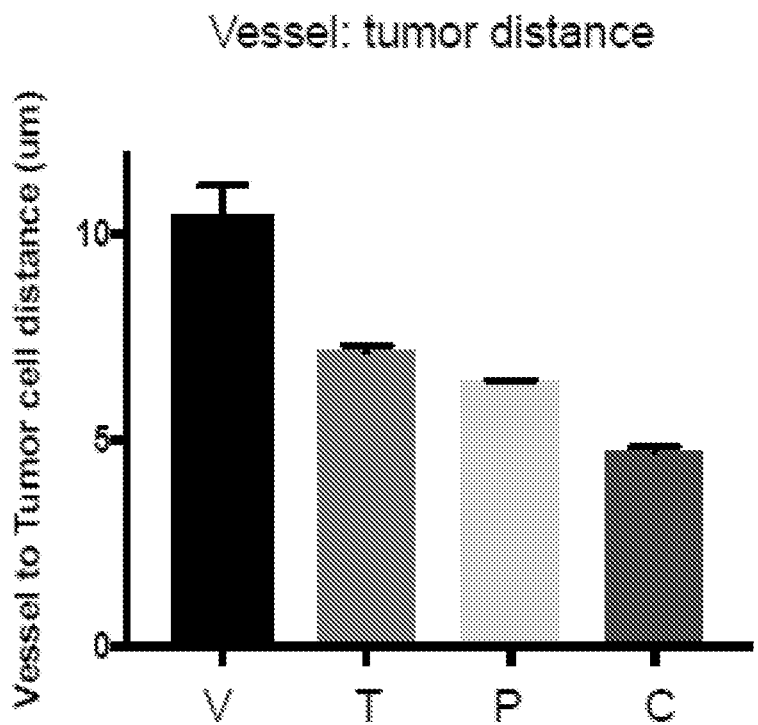
FIG. 20(F): Quantification of the average distance between a CD31$^+$ blood vessel and the 4 nearest tumor cells in KPC$^{mut}$ PDAC organoid transplant tumors following treatment as in FIG. 20(D). Bars represent the mean±SEM.
Figure 20G:
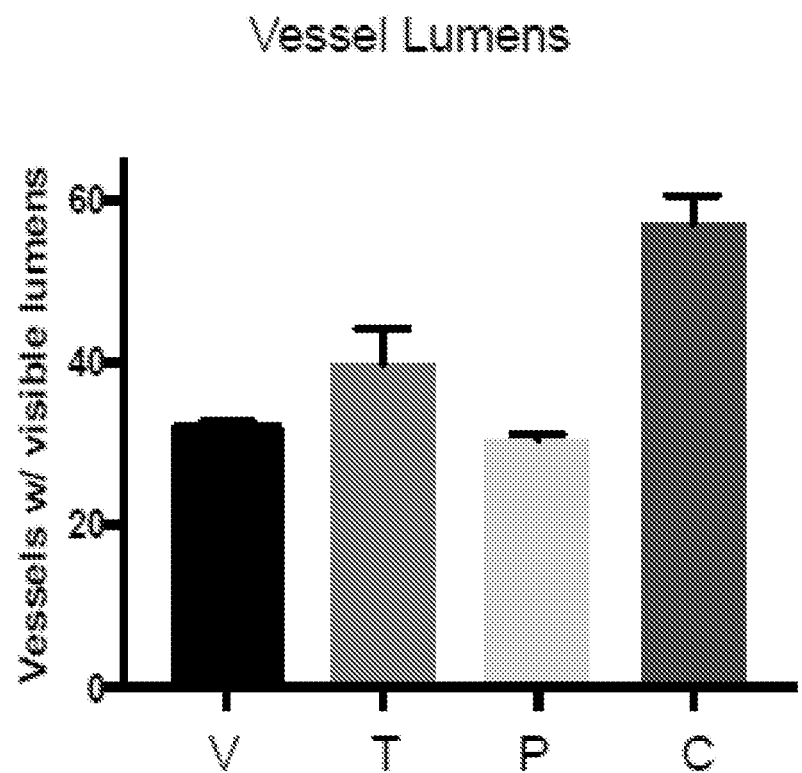
FIG. 20(G): Quantification of the percentage of CD31$^+$ blood vessels with visible/discernible lumens (see arrows in FIG. 20(D)) in KPC$^{mut}$ PDAC organoid transplant tumors following treatment in FIG. 20(D). Bars represent the mean±SEM.

To first interrogate whether pro-angiogenic SASP could functionally influence endothelial cell (EC) growth and blood vessel formation, conditioned media from senescent KPC PDAC tumor cells treated with vehicle or T/P was collected and applied to primary pancreatic and transformed ECs in culture. Conditioned media from T/P-treated PDAC cells distinctly supported EC growth compared to conditioned media from actively proliferating vehicle-treated PDAC cells (FIGS. 20(C) and 27(B)). Conditioned media from T/P-treated PDAC cells also promoted the formation of tube-like structures, reminiscent of vascular networks in vivo, when ECs were grown on a three-dimensional basement membrane (FIGS. 27(C)). These results demonstrate that therapy-induced senescence (TIS) triggers secretion of factors that can alter endothelial cell phenotypes.

Next, to investigate whether TIS could remodel PDAC associated vasculature in vivo, two different mouse models of PDAC that recapitulate the histopathology and stromal response observed in the human disease were utilized: (1) the Pdx1-Cre; LSL-KRAS$^{G12D}$; Trp53$^{fl/wt}$ (KPC) GEMM, where tumors form autochthonously in the pancreas (Herreros-Villanueva et al., *World J Gastroenterol* 18, 1286-1294 (2012)); and (2) syngeneic transplantation of PDAC organoids harvested from Pdx1-Cre; LSL-KRAS$^{G12D}$; Trp53$^{R172H/wt}$, (KPC$^{mut}$) tumors into immunocompetent C57BL/6 mice (Boj et al., *Cell* 160, 324-338 (2015); Hingorani et al., *Cancer cell* 4, 437-450 (2003)). Two-week T/P treatment in both models led to decreased proliferation, inhibition of ERK and RB phosphorylation, and induction of SA-β-gal in absence of apoptosis, indicative of senescence induction in vivo (FIGS. 28(A)-28(C)).

Figure 20H:
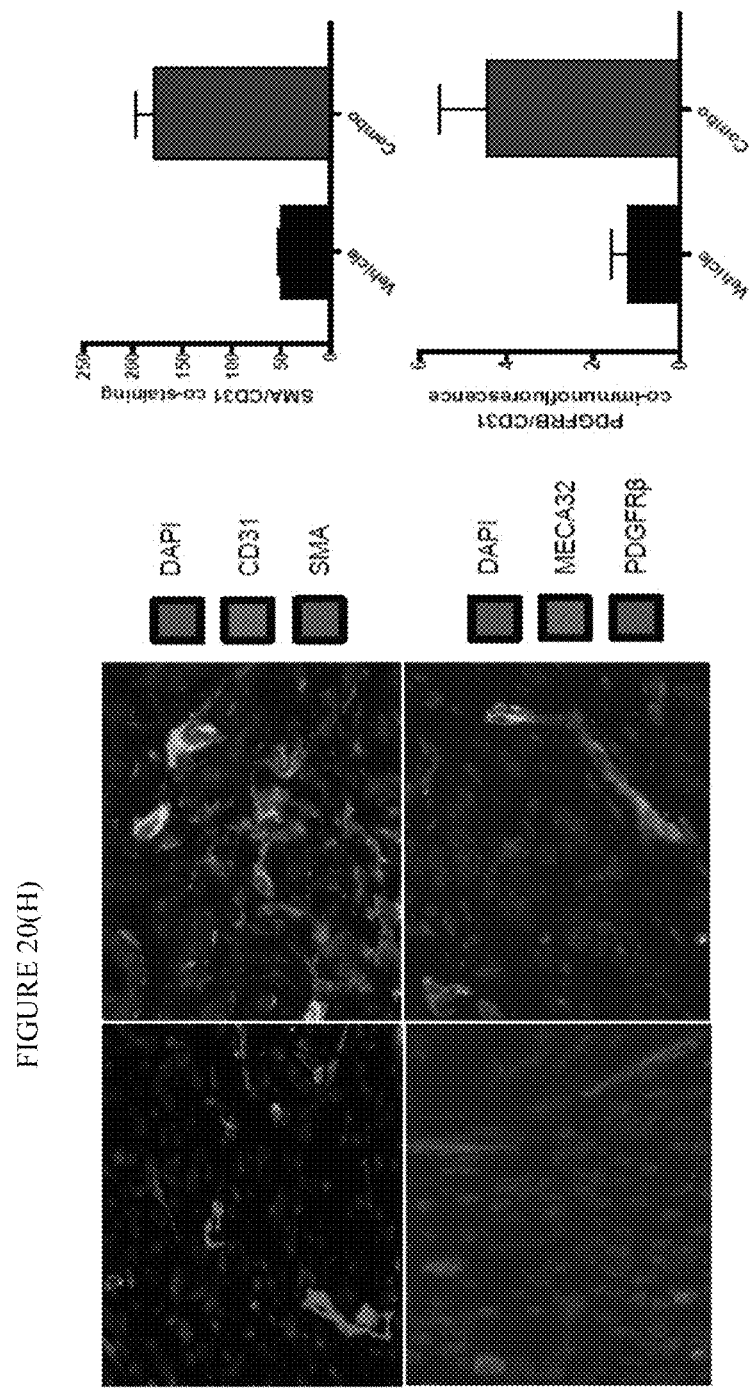
FIG. 20(H): Immunofluorescent images of αSMA (top, green) or PDGFRβ (bottom, green) co-localization with CD31$^+$/MECA32$^+$ blood vessels (red) in KPC GEMM PDAC tumors treated with vehicle or combined trametinib (1 mg/kg body weight) and palbociclib (100 mg/kg body weight) for 2 weeks (scale bar, μm). (left). Right, quantification of αSMA/CD31 (top) or PDGFRβ/MECA32 (bottom) co-immunofluorescence. Bars represent the mean±SEM. See also FIGS. 27-30.

Strikingly, the senescence-inducing T/P combination, but not T or P alone, led to an increase in blood vessel density as well as closer proximity of vessels to tumor cells in both PDAC models (FIGS. 20(D)-20(F) and FIGS. 28(D)-28(F)). Moreover, while many blood vessels in vehicle-treated PDAC tumors lacked an apparent lumen and appeared collapsed, those in T/P-treated tumors had open and readily discernible lumens (FIGS. 20(D), 20(G), 28(D), and 28(G)). In addition, blood vessels in PDAC tumors following TIS were found to be associated with higher levels of α-smooth muscle actin (αSMA) and the pericyte marker PDGFRβ, indicative of a mature and normalized vasculature (FIGS. 20(H) and 28(H)). Although angiogenesis can facilitate tumor invasion into blood vessels and formation distant metastases (Zetter, *Annu Rev Med* 49, 407-424 (1998)), a reduction (rather than increase) in metastasis to the lungs and liver was observed at end-point following combination treatment of KPC GEMM PDAC-bearing mice (FIG. 28(I)). Together, these results demonstrate that TIS can induce vascular remodeling in hypovascular PDAC models in the absence of acute pro-metastatic adaptation.

Previous work has demonstrated that vascular normalization can also be achieved in PDAC models through stromal remodeling and myofibroblast ablation (Olive et al., *Science* 324, 1457-1461 (2009); Provenzano et al., *Cancer Cell* 21, 418-429 (2012); Rhim et al., *Cancer Cell* 25, 735-747 (2014)). T/P treatment did not affect collagen production or impair myofibroblast accumulation in either PDAC transplant or GEMM models, which had similar levels of stromal reactivity (FIGS. 29(A) and 29(B)). T/P drug treatment did lead, however, to a significant reduction in the levels of hyaluronic acid (HA) that accumulates in the PDAC stroma during disease progression and generates high interstitial pressures that culminate in vessel collapse and poor perfusion (FIG. 29(C)). HA degradation upon T/P combination treatment may therefore also contribute to the opening of vessel lumens and vascular maturation in these PDAC models.

Other stromal subtypes in the PDAC TME, most prominently fibroblasts and macrophages, can also secrete factors that promote angiogenesis. However, conditioned media from senescent tumor cells had no impact on proliferation of these cell types, and did not promote the secretion of angiogenic factors from pancreatic fibroblasts or VEGF transcription in bone marrow-derived macrophages (FIGS. 29(D)-29(G)). Moreover, no changes in in vitro macrophage polarization were observed following treatment with SASP-conditioned media (FIG. 29(H)). Together, these results demonstrate that senescent tumor cells are the primary source of these pro-angiogenic factors in the PDAC TME.

Vascular remodeling in PDAC is not limited to TIS, but may represent a pancreas specific response to the SASP. First, although TIS through T/P treatment leads to secretion of similar angiogenic factors in Kras mutant, p53 deficient (KP) lung cancer cell lines, T/P treatment did not appear to induce vascular remodeling in KP GEMM lung tumors in vivo (FIG. 30(A)). Second, induction of senescence via restoration of p53 in a PDAC mouse model driven by a mutant KRAS$^{G12D}$ allele and a doxycycline (dox)-inducible p53-targeting short hairpin (shRNA) leads to expression of pro-angiogenic factors in vitro, and increased vascular density and vessel lumen size in vivo (FIGS. 30(B)-30(D)). Therefore, senescence induction through multiple mechanisms can lead to PDAC-specific vascular remodeling.

Accordingly, the combination therapy methods disclosed herein are useful for preventing or treating pancreatic cancer in a subject in need thereof.

Figure 21A:
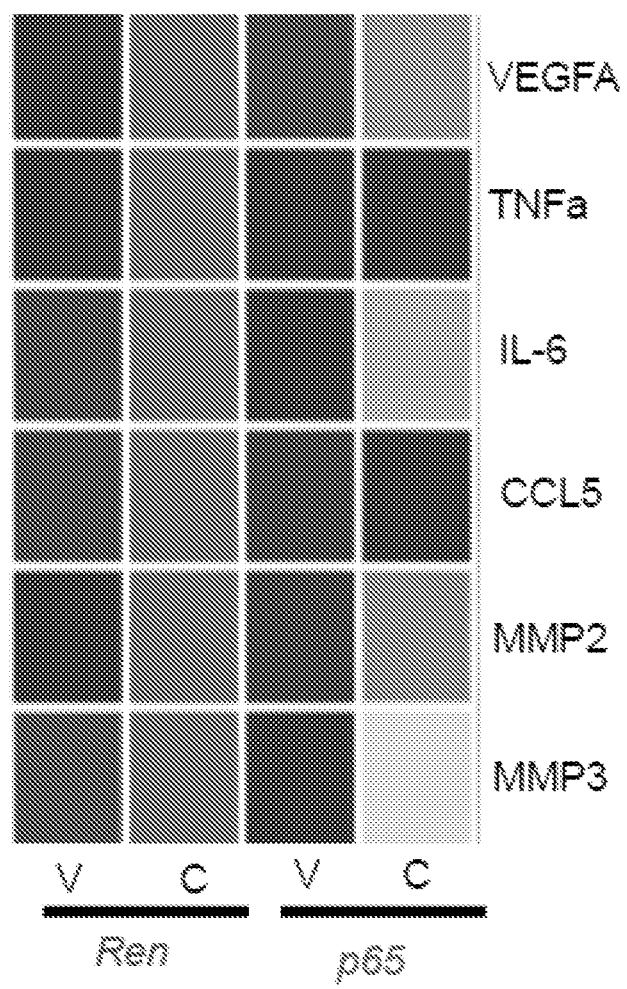
FIG. 21(A): Heat map of cytokine array results from KPC PDAC tumor cells harboring control *Renilla* (Ren) or p65 shRNAs and treated for 8 days with trametinib (25 nM) and/or palbociclib (500 nM). Data presented as mean of three biological replicates.
Figure 21B:
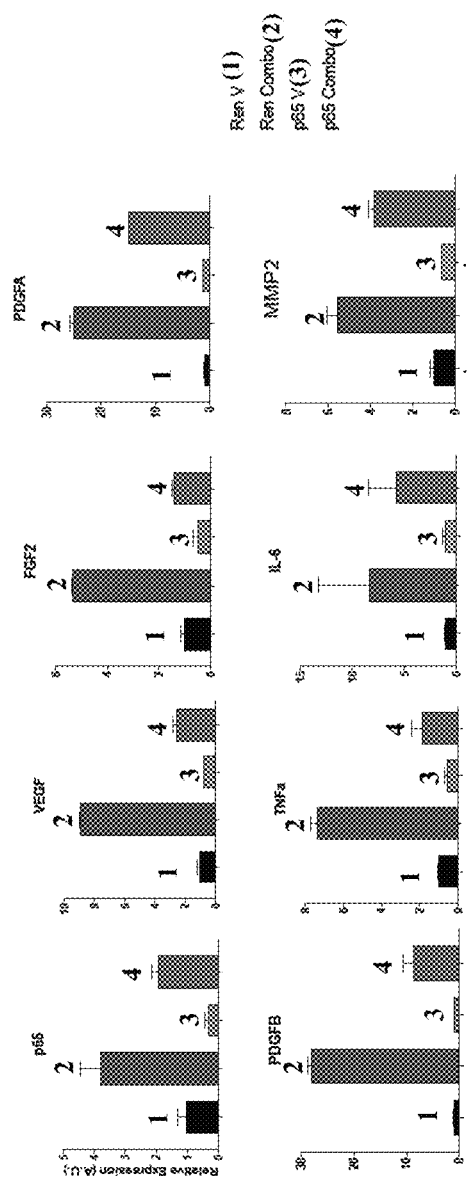
FIG. 21(B): qRT-PCR analysis of SASP gene expression in KPC PDAC tumor cells transduced with indicated shRNAs following treatment as in FIG. 21(A). Bars presented as mean of three biological replicates.
Figure 21C:
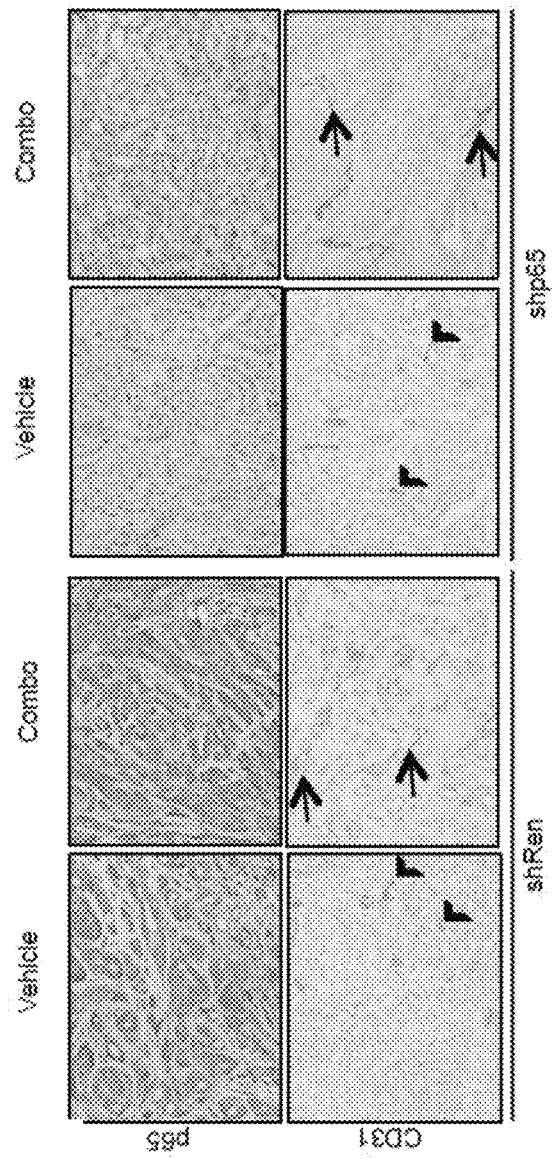
FIG. 21(C): CD31 immunohistochemical staining of KPC$^{mut}$ PDAC organoid transplant tumors harboring *Renilla* (Ren) or p65 shRNAs and treated for 2 weeks with treated with vehicle or combined trametinib (1 mg/kg and palbociclib (100 mg/kg body weight) (scale bar, μm).
Figure 21D:
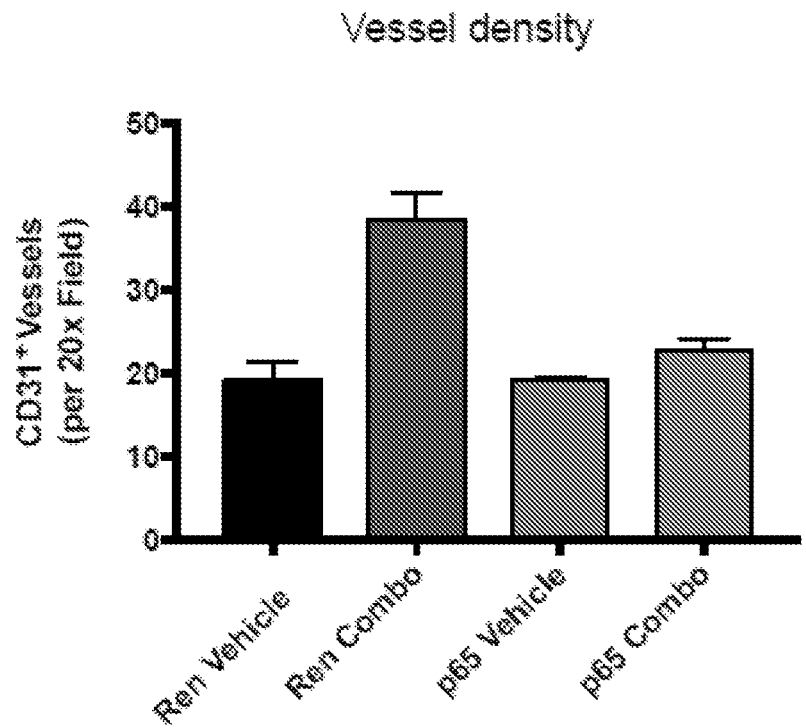
FIG. 21(D): Quantification of number of CD31$^+$ blood vessels per 20× field in KPC$^{mut}$ PDAC organoid transplant tumors harboring *Renilla* (Ren) or p65 shRNAs and treated as in FIG. 21(C). Bars represent the mean±SEM.
Figure 21E:
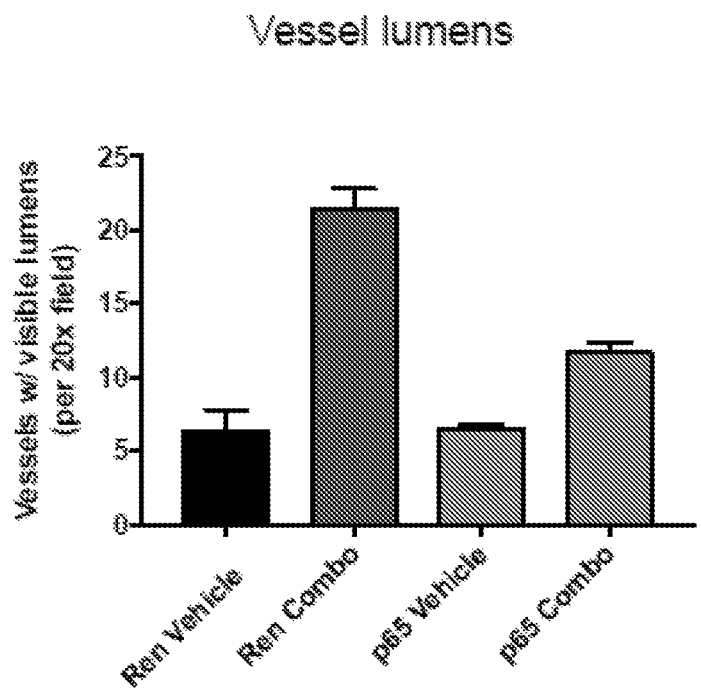
FIG. 21(E): Quantification of number of CD31$^+$ blood vessels with visible/discernible lumens (see arrows in FIG. 21(D)) in KPC$^{mut}$ PDAC organoid transplant tumors harboring *Renilla* (Ren) or p65 shRNAs and treated as in FIG. 21(C). Bars represent the mean±SEM.
Figure 21F:
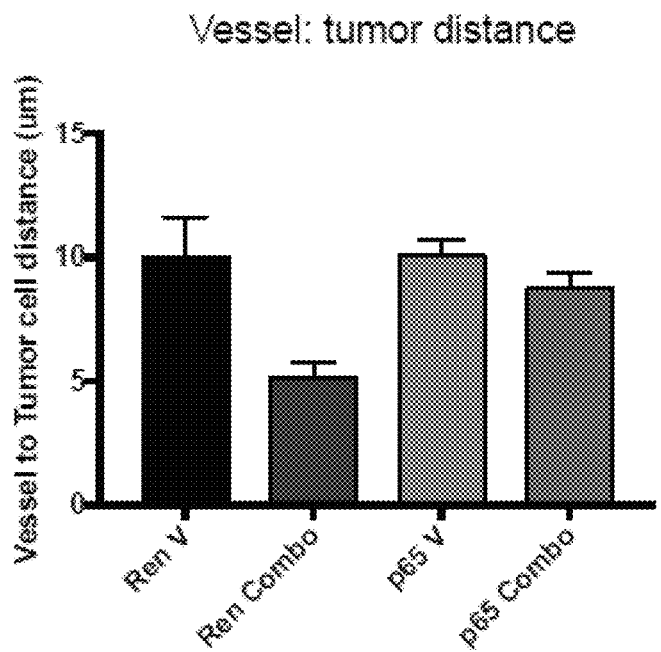
FIG. 21(F): Quantification of the average distance between a CD31$^+$ blood vessel and the 4 nearest tumor cells in KPC$^{mut}$ PDAC organoid transplant tumors harboring *Renilla* (Ren) or p65 shRNAs and treated as in FIG. 21(C). Bars represent the mean±SEM.
Figure 21G:
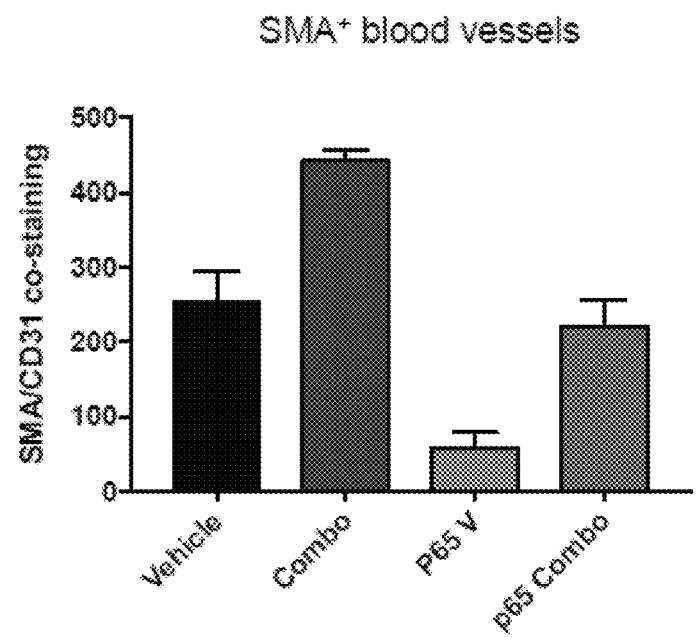
FIG. 21(G): Quantification of αSMA/CD31 co-immunofluorescence in KPC$^{mut}$ PDAC organoid transplant tumors harboring *Renilla* (Ren) or p65 shRNAs and treated as in FIG. 21(C). Bars represent the mean±SEM.
Figure 21H:
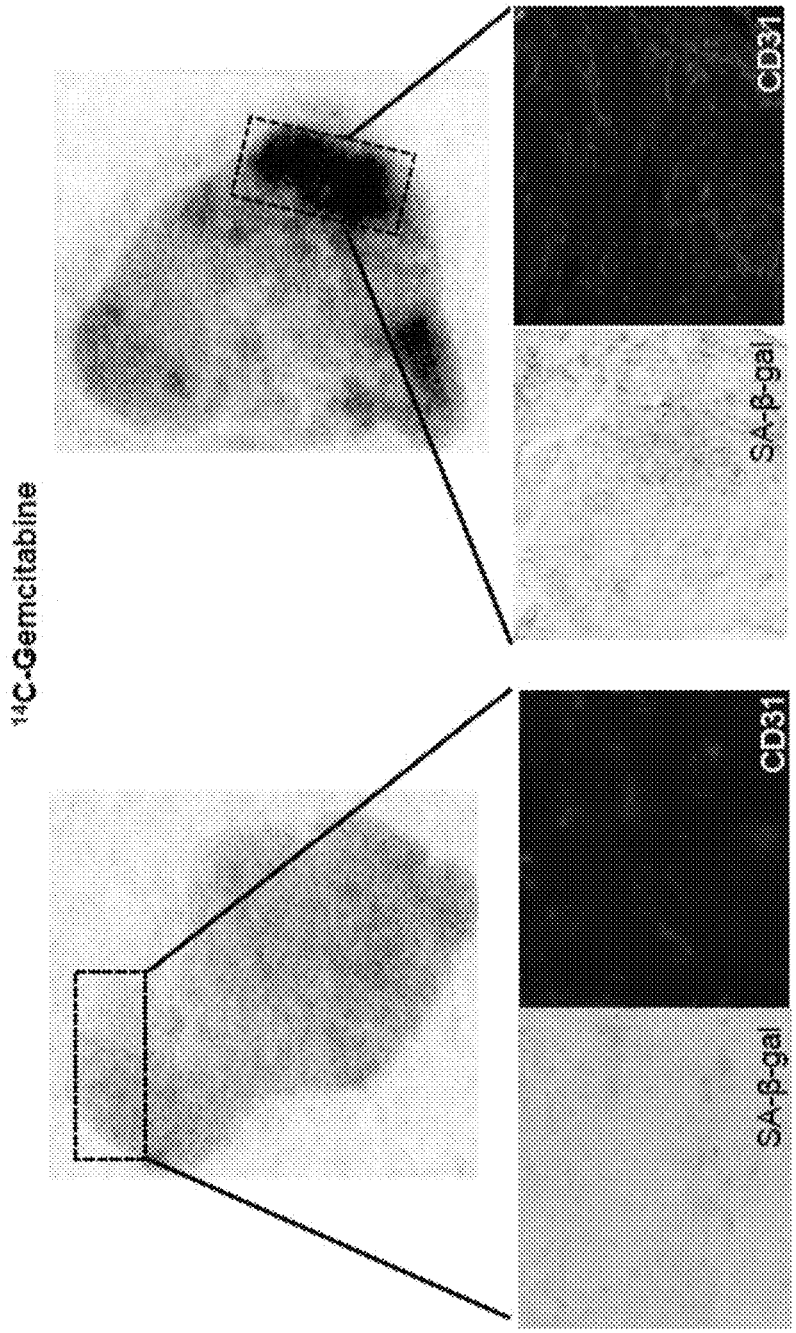
FIG. 21(H): Autoradiograph showing distribution of injected $^{14}$C-labeled gemcitabine in KPC PDAC organoid transplant tumors from mice pretreated with vehicle or combined trametinib (1 mg/kg and palbociclib (100 mg/kg body weight) for 2 weeks (scale bar, μm). Inset, overlay of autoradiographs with immunohistochemical staining of consecutive sections (scale bar, μm).

Example 6: Vascular Remodeling Following Therapy-Induced Senescence is SASP-Dependent and Leads to Enhanced Drug Delivery into PDAC Tumors To assess whether vascular remodeling following T/P treatment is SASP-dependent, shRNAs were introduced into KPC$^{mut}$ PDAC organoids to knockdown expression of the p65 subunit of NF-KB, which was previously shown to be a transcriptional mediator of the SASP but dispensable for senescence-mediated growth arrest (Chien et al., *Genes Dev* 25, 2125-2136 (2011); Tasdemir et al., *Cancer Discov* 6, 612-629 (2016)). Indeed, expression of pro-angiogenic factors following T/P treatment was SASP-dependent, as p65 knockdown significantly inhibited their induction after treatment (FIGS. 21(A)-21(B)). Upon transplantation of p65-deficient KPC$^{mut}$ PDAC organoids into C57BL/6 mice, the increase in vessel density and proximity to tumor cells, as well as the presence of mature and normalized αSMA+ vessels with open lumens following T/P treatment was abolished (FIGS. 21(C)-21(H)). Thus, T/P treatment-induced vascular remodeling is SASP-dependent.

Figure 21I:
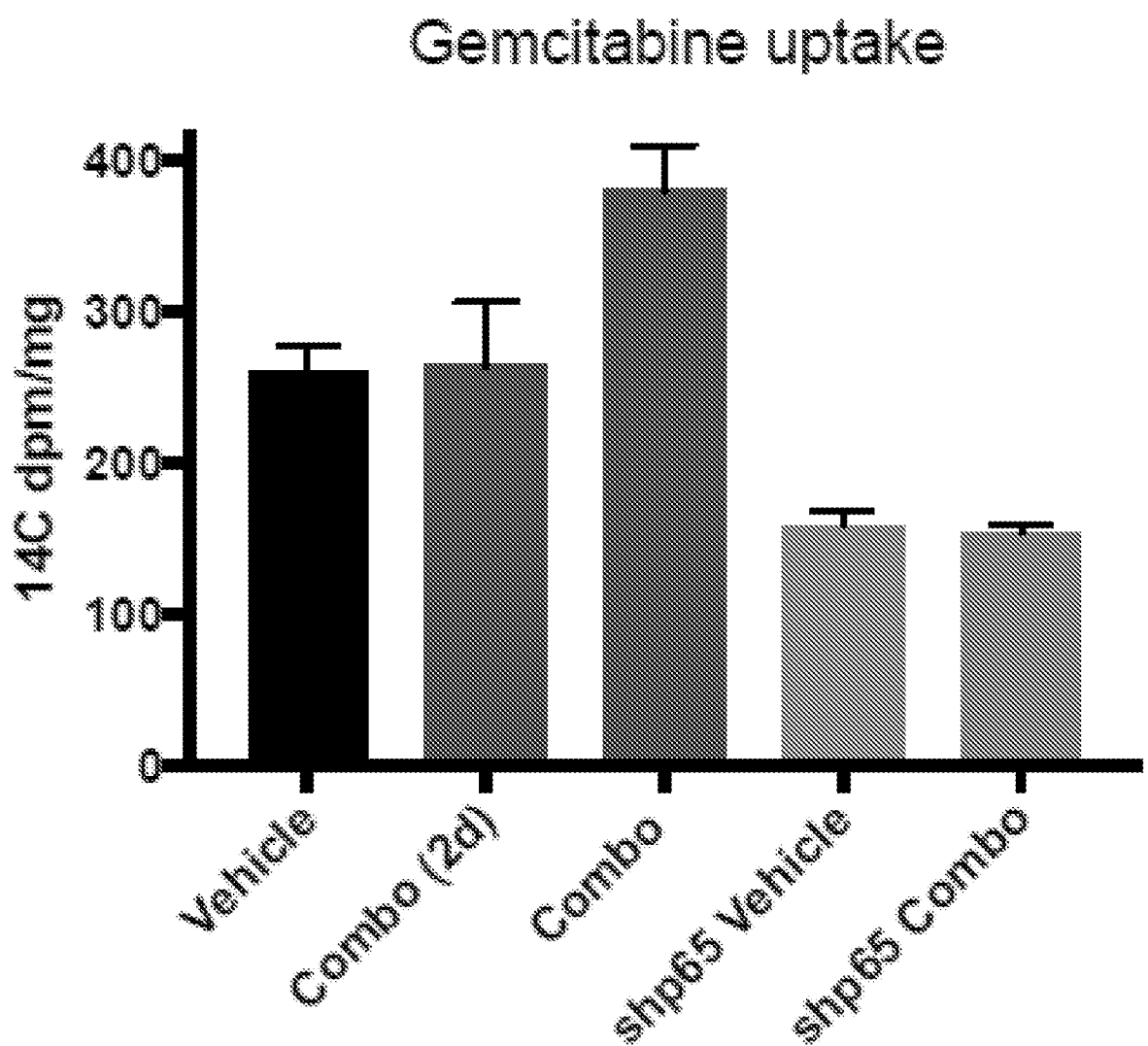
FIG. 21(I): Quantification of $^{14}$C-labeled gemcitabine in indicated KPC PDAC organoid transplant tumors treated for 2 days or 2 weeks with vehicle or combined trametinib (1 mg/kg and palbociclib (100 mg/kg body weight). See also FIG. 31.

To test whether blood vessel maturation and normalization following senescence induction facilitates drug delivery, PDAC tumor-bearing mice were pretreated for two weeks with vehicle or T/P and then given one dose of a $^{14}$C-labeled gemcitabine radiotracer to quantify the uptake of the chemotherapeutic agent into the tumor. Strikingly, pretreatment with the senescence-inducing T/P drug combination led to increased gemcitabine penetration into the tumor (but not into the normal pancreas or other organs), particularly in focal regions containing high densities of SA-β-gal+ senescent cells and blood vessels (FIGS. 21(I), 31(A), and 31(B)). This increase in gemcitabine uptake following T/P treatment was significantly reduced upon p65 knockdown, indicating that SASP-mediated vascular remodeling is critical for increased drug delivery. These effects were observed after two-week treatment, whereas 48-hour T/P treatment did not result in increased gemcitabine uptake. T/P treatment inhibited ERK phosphorylation and cell proliferation, as well as increased blood vessel numbers and size, in both the periphery and interior of these PDAC tumors more potently after two-weeks compared to a 48-hour treatment (FIGS. 31(C)-31(F)), suggesting that a) long-term T/P treatment is required for vascular remodeling and b) that these targeted therapies achieve better on-target tumor inhibition as well once senescence-associated vascular remodeling has been induced. Therefore, vascular remodeling following TIS is SASP-dependent and functionally leads to better vessel perfusion and drug uptake.

Accordingly, the combination therapy methods disclosed herein are useful for preventing or treating pancreatic cancer in a subject in need thereof.

Figure 22A:
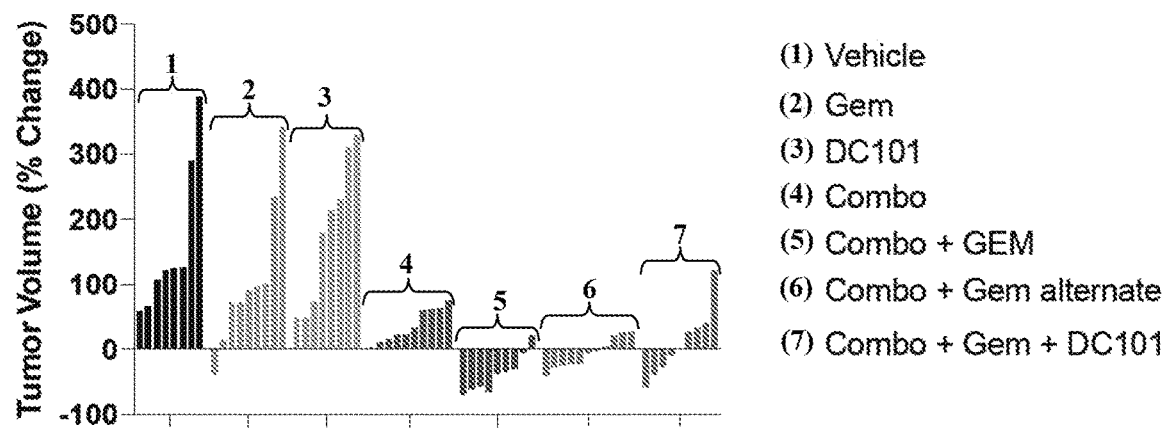
FIG. 22(A): A waterfall representation of the response of KPC$^{mut}$ PDAC organoid transplant tumors after 2 weeks of treatment with vehicle, trametinib (1 mg/kg body weight), palbociclib (100 mg/kg body weight), gemcitabine (100 mg/kg body weight), and/or a VEGFR2 blocking antibody (DC101; 800 μg per mouse) either continuously or on an alternating weekly schedule (n≥8 per group).
Figure 22B:
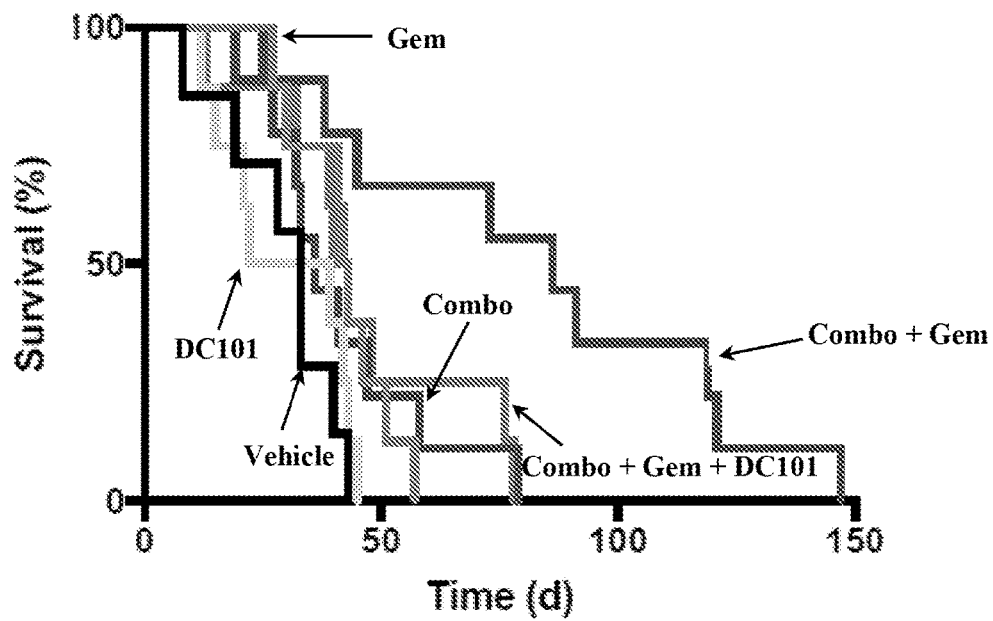
FIG. 22(B): Kaplan-Meier survival curve of KPC$^{mut}$ PDAC organoid transplant mice treated as in FIG. 22(A) (n≥7 per group) (log-rank test).
Figure 22C:
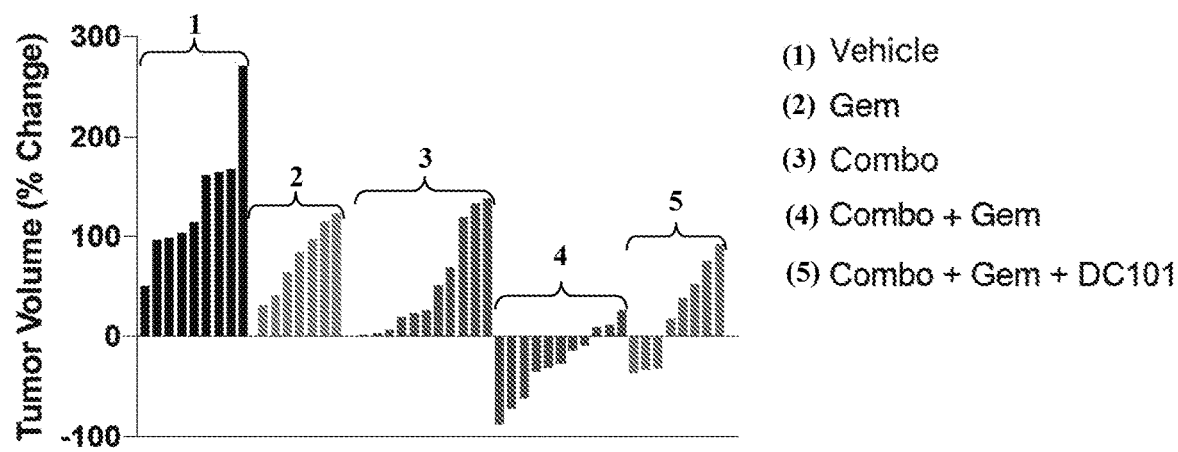
FIG. 22(C): A waterfall representation of the response of KPC GEMM PDAC tumors after 2 weeks of treatment with vehicle, trametinib (1 mg/kg body weight), palbociclib (100 mg/kg body weight), gemcitabine (100 mg/kg body weight), and/or a VEGFR2 blocking antibody (DC101; 800 μg per mouse) (n≥7 per group).
Figure 22D:
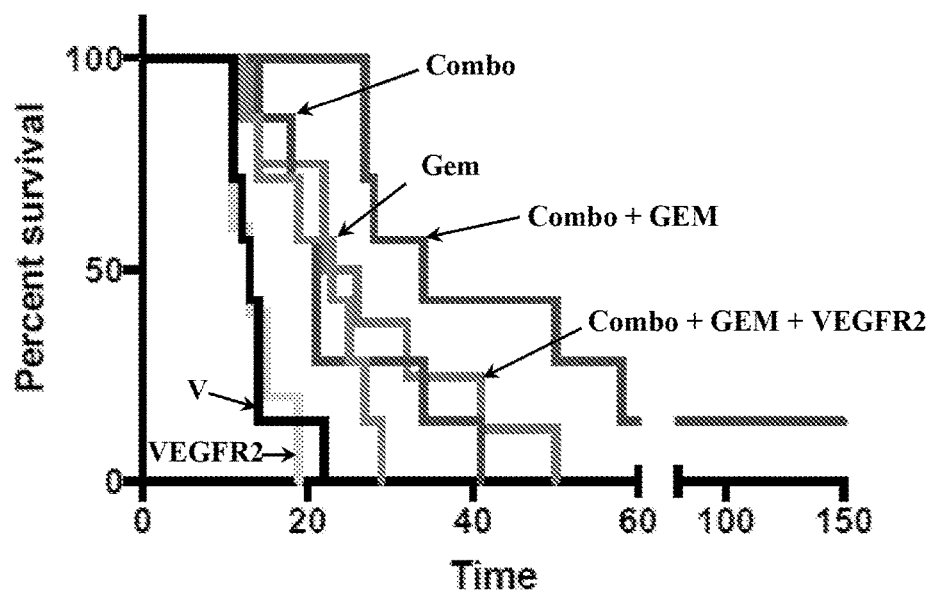
FIG. 22(D): Kaplan-Meier survival curve of KPC GEMM PDAC mice treated as in FIG. 22(C) (n≥5 per group) (log-rank test).
Figure 22E:
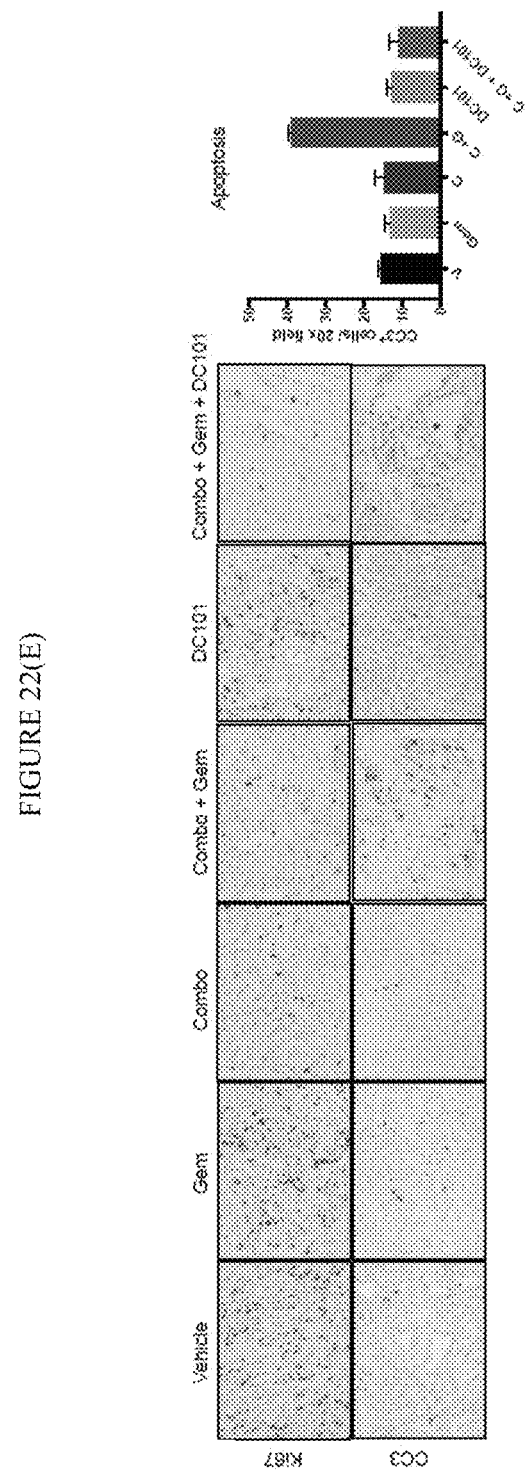
FIG. 22(E): Immunohistochemical staining of KPC GEMM PDAC tumors treated for 2 weeks as in FIG. 22(C). Right, quantification of cleaved caspase-3 (CC3$^+$) tumor cells per 20× field. Bars represent the mean±SEM.

Example 7: Senescence-Inducing Therapies Lead to Enhanced Sensitivity to Cytotoxic Chemotherapy Given the increased uptake of gemcitabine into PDAC tumors following TIS and SASP-mediated vascular remodeling, the effects of combining trametinib and palbociclib treatment with gemcitabine (T/P/G) on gemcitabine efficacy was assessed. In the KPC$^{mut}$ PDAC organoid transplant model, gemcitabine alone had no effect on tumor growth and limited impact on overall survival (FIGS. 22(A)-22(B)), similar to what was observed in human patients (Carmichael et al., *Br J Cancer* 73, 101-105 (1996)). While T/P treatment led to some reduction in tumor growth and a marginal increase in the survival of PDAC-bearing animals, adding gemcitabine to this regimen led to potent tumor regressions and long-term survival in this model (FIGS. 22(A)-22(B)). Similar effects were also observed in the autochthonous KPC GEMM model following the triple T/P/G therapy, including a notable number of tumor regressions and long-term survivors (FIGS. 22(C)-22(D)). Mechanistically, while gemcitabine treatment alone was unable to induce tumor cell death, T/P/G treatment led to tumor cell apoptosis along with significantly reduced proliferation (FIGS. 22(E), 32(A), and 32(B)). Cell death was likely occurring in tumor cells that continue to proliferate in the presence of T/P treatment, as an increased accumulation of SA-β-gal+ senescent cells and a decrease in Ki67+ proliferating cells was observed following T/P/G therapy in both murine PDAC models (FIGS. 22(E) and 32(A)-32(F)). Tumor regressions and similar levels of apoptosis were also achieved when giving T/P and G sequentially on an alternating weekly schedule instead of continuously (FIGS. 22(A), 32(A), and 32(B)), demonstrating that T/P pretreatment could set the stage for increased gemcitabine efficacy through its vascular remodeling effects.

To understand if vascular remodeling is critical for the enhanced efficacy of T/P/G triple therapy, high doses of a VEGFR2 blocking antibody (DC101) were used as a tool to specifically prevent neo-vascularization following senescence induction in the PDAC models. Indeed, high doses of DC101 significantly reduced new blood vessel formation following T/P treatment but not in the control vehicle setting (FIG. 33(F)). Accordingly, VEGFR2 blockade with DC101 significantly inhibited T/P/G treatment-mediated tumor responses by mitigating tumor cell apoptosis, culminating in a reduced overall survival similar to that of T/P treatment alone (FIGS. 22(A)-22(E), 32(A), and 32(B)). Thus, SASP-mediated neo-vascularization is critical for tumor regressions and long-term survival in PDAC-tumor bearing animals following T/P/G treatment.

These findings were further validated in the human setting. Despite being implanted subcutaneously into the flank of immunodeficient NOD-scid IL2Rγ$^{null}$ (NSG) mice, some patient-derived xenograft (PDX) tumors from PDAC patients contained a robust and dense stroma characterized by collagen, myofibroblast, and HA accumulation (FIG. 33(A)). As was observed in murine PDAC models, T/P treatment of human PDAC PDX tumors led to reduced RB and ERK phosphorylation, induction of SA-β-gal expression, increased vascular density and lumen diameter, and degradation of HA (FIGS. 33(A)-33(G)). Given these human models are necessarily transplanted into immunodeficient mice, this further demonstrates that the vascular remodeling induced by T/P therapy is immune-independent.

Figure 22F:
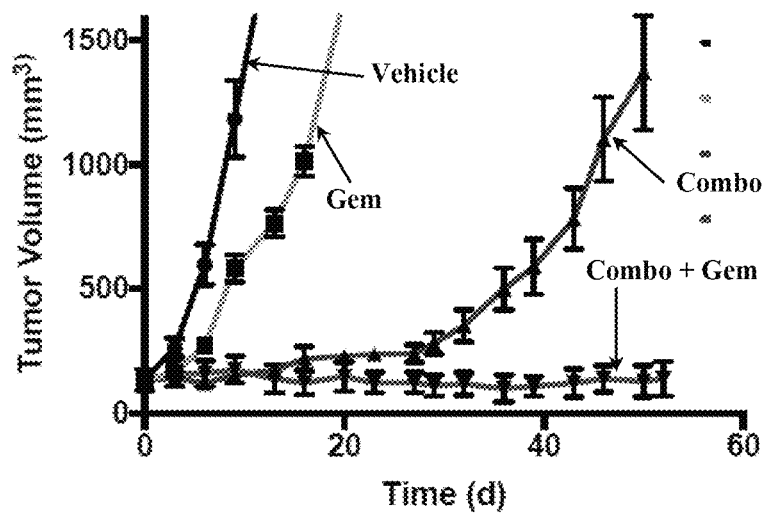
FIG. 22(F): Tumor volumes of mice bearing KRAS-mutant PR-07 patient-derived xenograft (PDX) PDAC tumors treated with vehicle, trametinib (1 mg/kg body weight), palbociclib (100 mg/kg body weight), and/or gemcitabine (100 mg/kg body weight) for indicated times (n=7 per group).
Figure 22G:
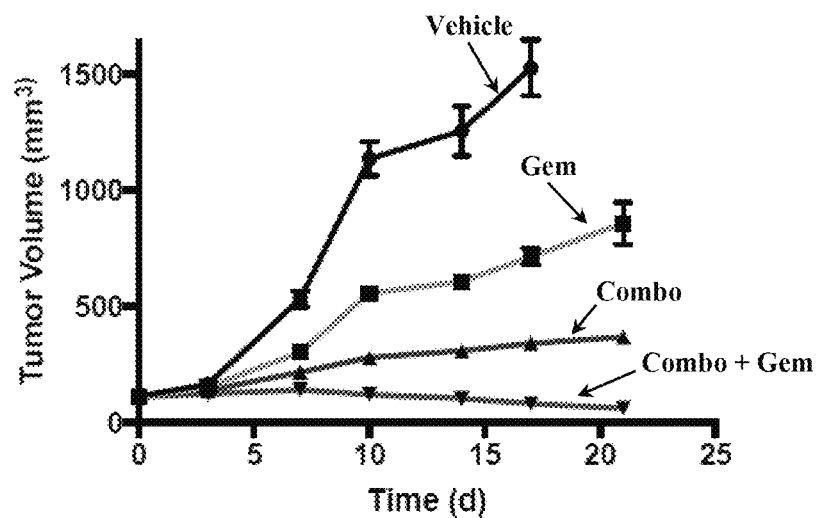
FIG. 22(G): Tumor volumes of mice bearing KRAS-mutant PR-05 patient-derived xenograft (PDX) PDAC tumors treated with vehicle, trametinib (1 mg/kg body weight), palbociclib (100 mg/kg body weight), and/or gemcitabine (100 mg/kg body weight) for indicated times (n=7 per group).
Figure 22H:
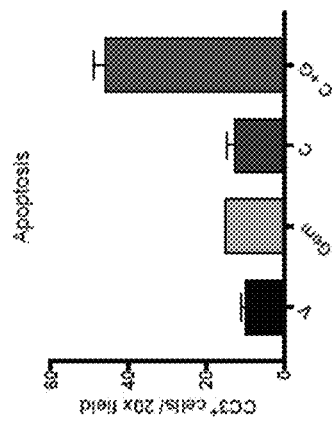
FIG. 22(H): Immunohistochemical staining of KRAS-mutant PR-07 patient-derived xenograft (PDX) PDAC tumors treated as in FIG. 22(C). Right, quantification of cleaved caspase-3 (CC3$^+$) tumor cells per 20× field. Bars represent the mean±SEM. See also FIGS. 32 and 33.
Figure 22H:
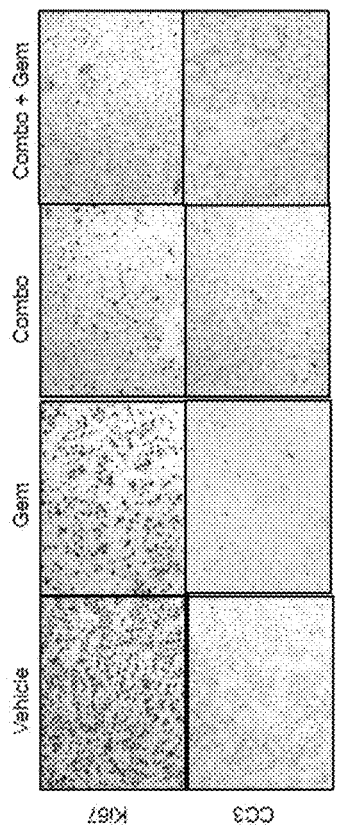

The two tested preclinical PDX models were derived from PDAC tumors of patients who had relapsed on gemcitabine treatment in combination with abraxane (PR-07) or abraxane+PEGPH20 (PR-05), an HA degrading agent. While both PDX tumors remained gemcitabine refractory, combining T/P treatment with gemcitabine led to sustained inhibition of tumor growth and in some mice partial tumor regressions through a combination of reduced proliferation and induction of apoptosis (FIGS. 22(F)-22(H)). Thus, T/P combination treatment, through vascular remodeling, can re-sensitize gemcitabine refractory patient-derived PDAC tumors to gemcitabine and lead to sustained tumor control.

Accordingly, the combination therapy methods disclosed herein are useful for increasing the efficacy of chemotherapeutic agents in patients with pancreatic cancer.

Example 8: MEK Inhibitor and CDK4/6 Inhibitor Treatment Makes T Cell "Cold" PDAC Tumors "Hot" in SASP-Dependent Manner Without wishing to be bound by theory, it is believed that SASP-mediated vascular remodeling may not only promote enhanced drug delivery and efficacy, but also facilitate better lymphocyte infiltration into "cold" PDAC tumors. Therefore, the effect of treatment on NK and other immune cells was interrogated following syngeneic transplantation of a KPC PDAC cell line engineered to express luciferase and GFP into C57BL/6 mice, which allows for the rapid assessment of changes in the PDAC immune milieu in an immunocompetent setting. Unexpectedly, T/P treatment did not increase NK cell numbers or induce NK cell degranulation in the PDAC TME in both KPC cell line transplant and KPC GEMM models, and depletion of NK cells did not reduce the survival benefit of T/P treatment (FIGS. 34(A)-34(C)).

Figure 23A:
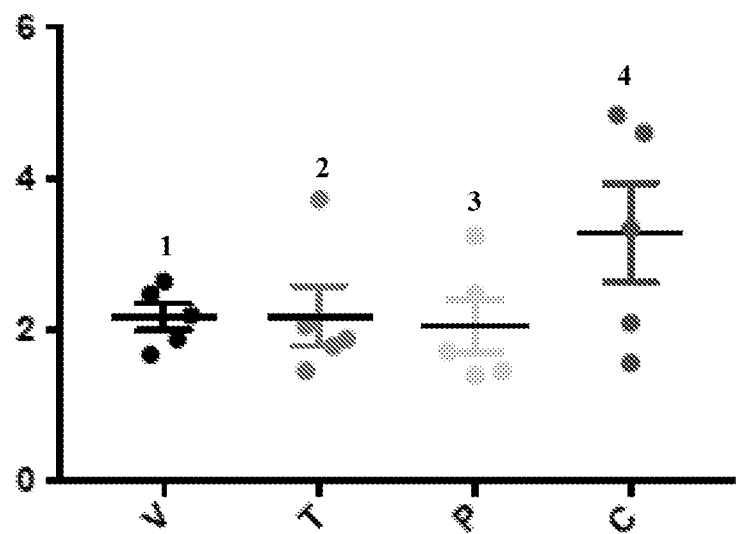
FIG. 23(A)-23(B): Flow cytometry analysis of KPC$^{mut}$ cell line transplant PDAC tumors following 10-day treatment with vehicle, trametinib (1 mg/kg body weight), palbociclib (100 mg/kg body weight), or both in combination (n=5 mice per group).
Figure 23B:
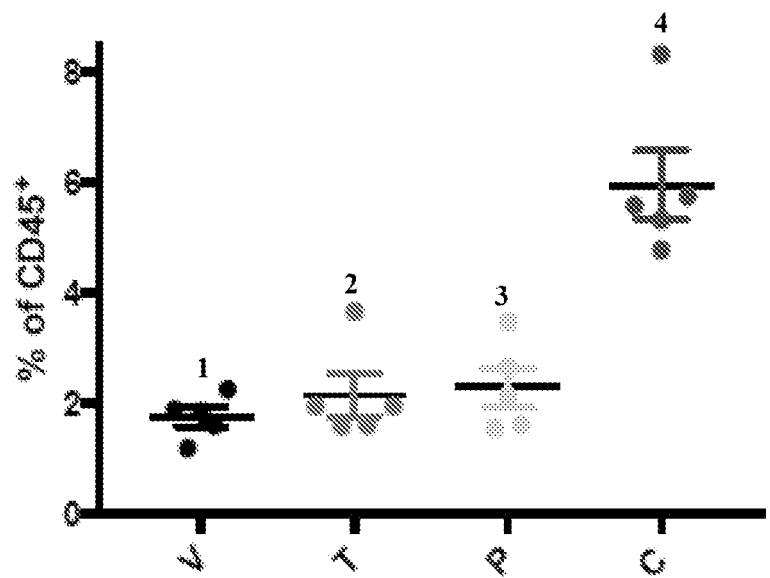
Figure 23C:
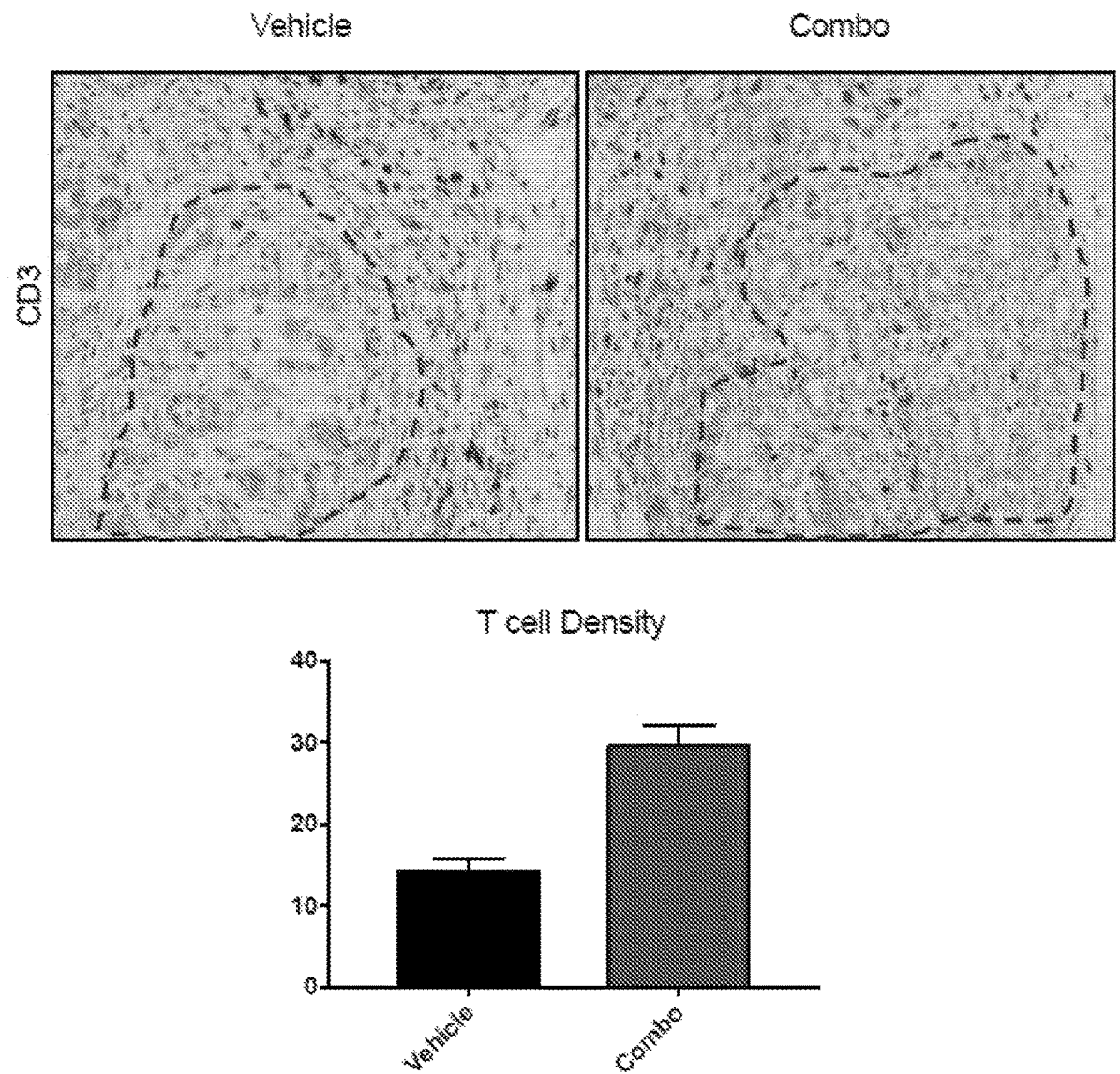
FIG. 23(C): CD3 immunohistochemical staining of KPC PDAC GEMM tumors treated with vehicle or combined trametinib (1 mg/kg body weight) and palbociclib (100 mg/kg body weight) for two weeks (scale bar, μm). Dashed red line outlines tumor region. Bottom, quantification of intratumoral CD3$^+$ T cells per 20× field. Bars represent the mean±SEM.
Figure 23D:
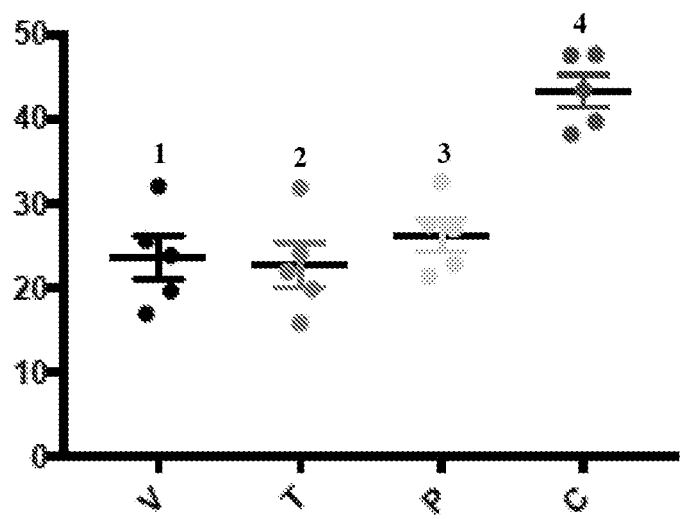
FIG. 23(D)-23(E): Flow cytometry analysis of KPC$^{mut}$ cell line transplant PDAC tumors following 10-day treatment with vehicle, trametinib (1 mg/kg body weight), palbociclib (100 mg/kg body weight), or both in combination (n=5 mice per group).
Figure 23E:
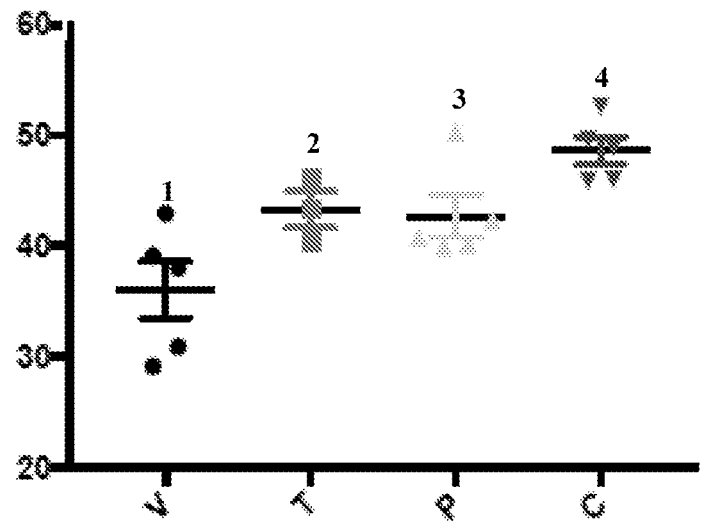
Figure 23F:
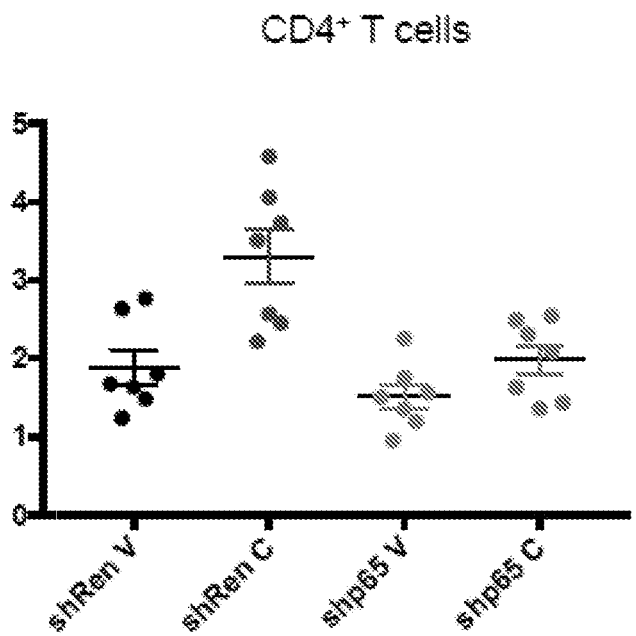
FIG. 23(F)-23(I): Flow cytometry analysis of KPC$^{mut}$ cell line transplant PDAC tumors harboring control *Renilla* (Ren) or p65-targeting shRNAs and treated as in FIG. 23(A) (n=5 mice per group).
Figure 23G:
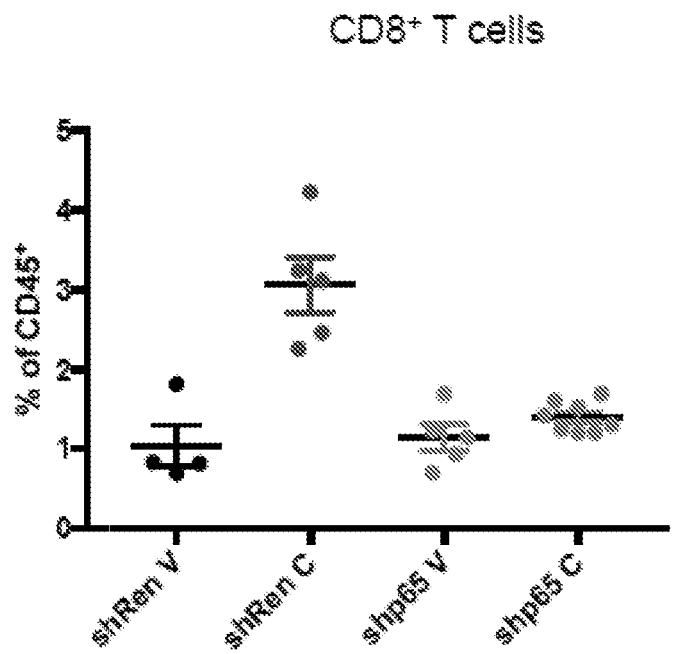
Figure 23H:
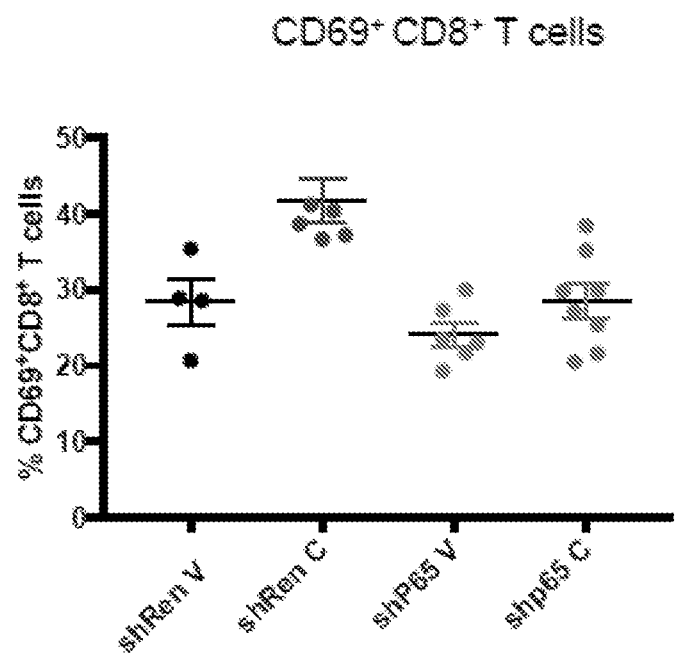
Figure 23I:
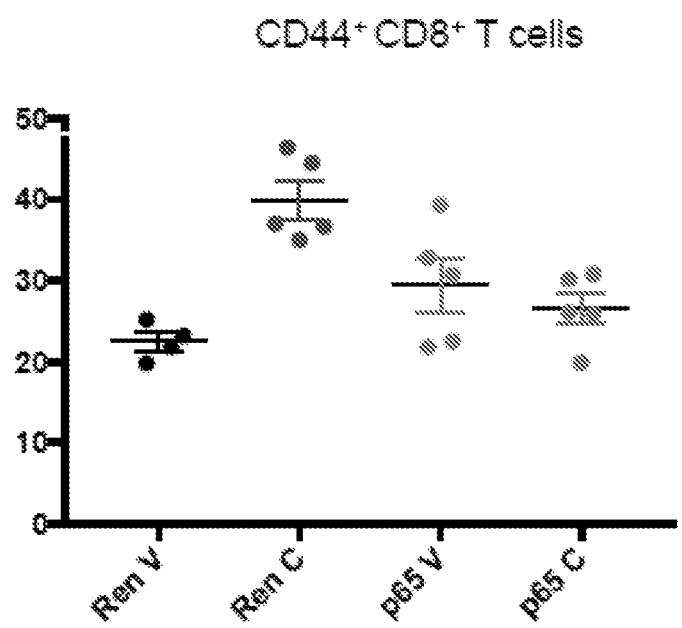
Figure 23J:
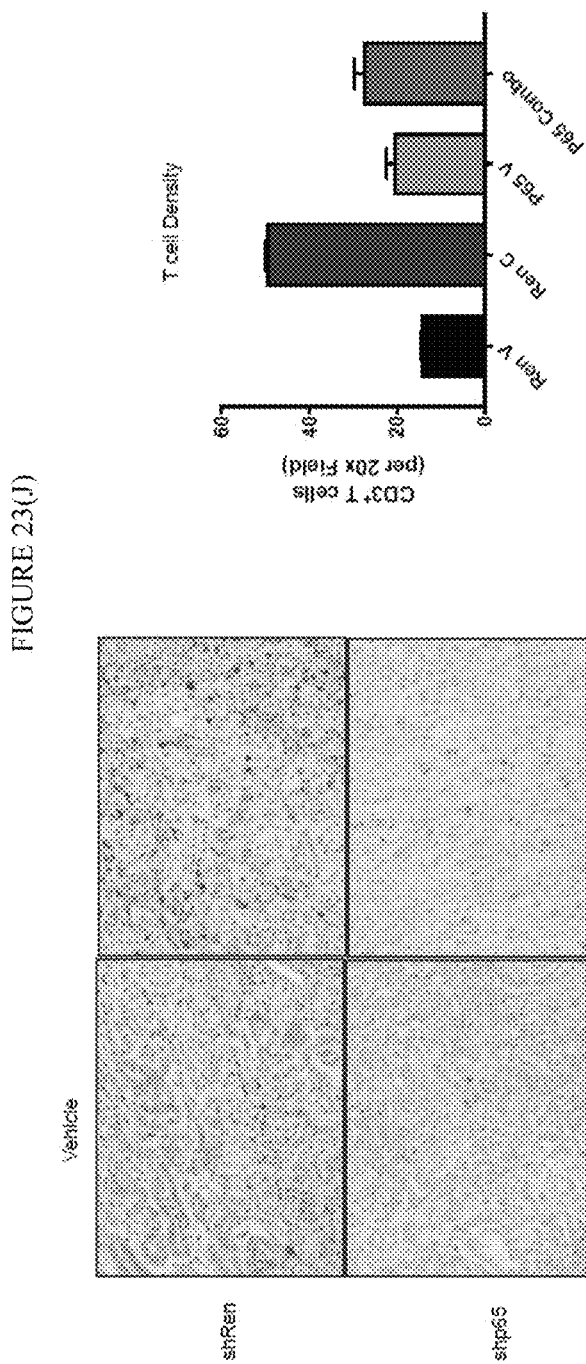
FIG. 23(J): CD3 immunohistochemical staining of KPC PDAC organoid tumors harboring control *Renilla* (Ren) or p65-targeting shRNAs and treated as in FIG. 23(E) (scale bar, μm). Right, quantification of intratumoral CD3$^+$ T cells per 20× field. Bars represent the mean±SEM. See also FIG. 34.

In contrast, a robust increase in T cell numbers was observed, which included a marginal increase in CD4+ T cells and substantial increase in CD8+ T cells following 10-day T/P treatment that was not achieved with T or P treatment alone (FIGS. 23(A)-23(B)). KPC GEMM PDAC tumors phenocopy the T cell exclusion phenotype found in the human setting (Blando et al., *Proc Natl Acad Sci* 116, 1692-1697 (2019)), where T cells are trapped in the stroma outside of the tumor bed; however, 2-week T/P treatment led to robust T cell expansion and penetration into the tumor (FIG. 23(C)).

CD8+ T cells in T/P-treated transplanted PDAC tumors also expressed higher levels of the activation markers CD44 and CD69, whereas CD4+ T cells did not appear to be activated (FIGS. 23(D)-23(E), 34(D), and 34(E)). These phenotypes were SASP-dependent, as T cell expansion, activation, and tumor penetration were attenuated in p65-deficient tumors (FIGS. 23(F)-23(J)). Moreover, this SASP-dependent effect appeared to act directly on CD8+ T cells, as no changes were observed in other T cell suppressive immune subtypes, including GR-1$^{hi}$CD11b+ myeloid-derived suppressor cells (MDSCs), F4/80+ macrophages, and FOXP3+ regulatory T cells ($T_{regs}$) whose attenuation may indirectly lead to CD8+ T cell activation (FIGS. 34(F)-(I)). Therefore, SASP induction makes T cell "cold" PDAC tumors "hot".

Accordingly, the combination therapy methods disclosed herein are useful for preventing or treating pancreatic cancer in a subject in need thereof.

Figure 24A:
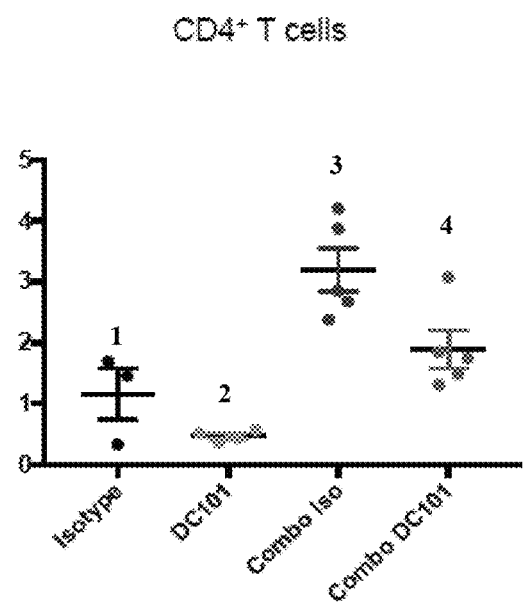
FIGS. 24(A)-24(B): Flow cytometry analysis of KPC$^{mut}$ cell line transplant PDAC tumors following 10-day treatment with vehicle, trametinib (1 mg/kg body weight), palbociclib (100 mg/kg body weight), or both in combination (n≥3 mice per group).
Figure 24B:
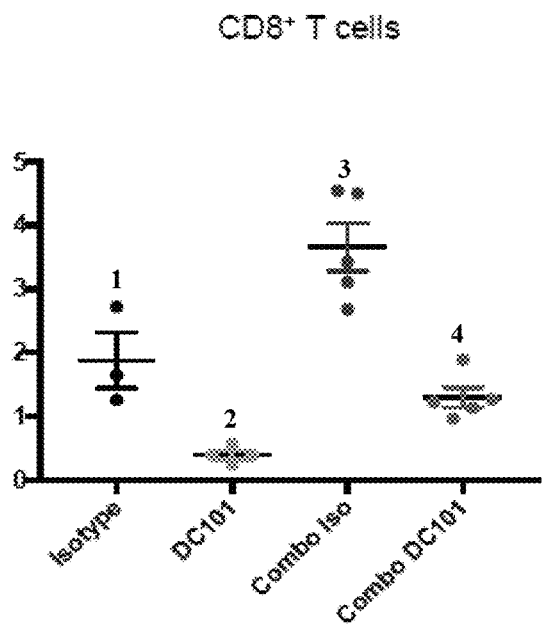
Figure 24C:
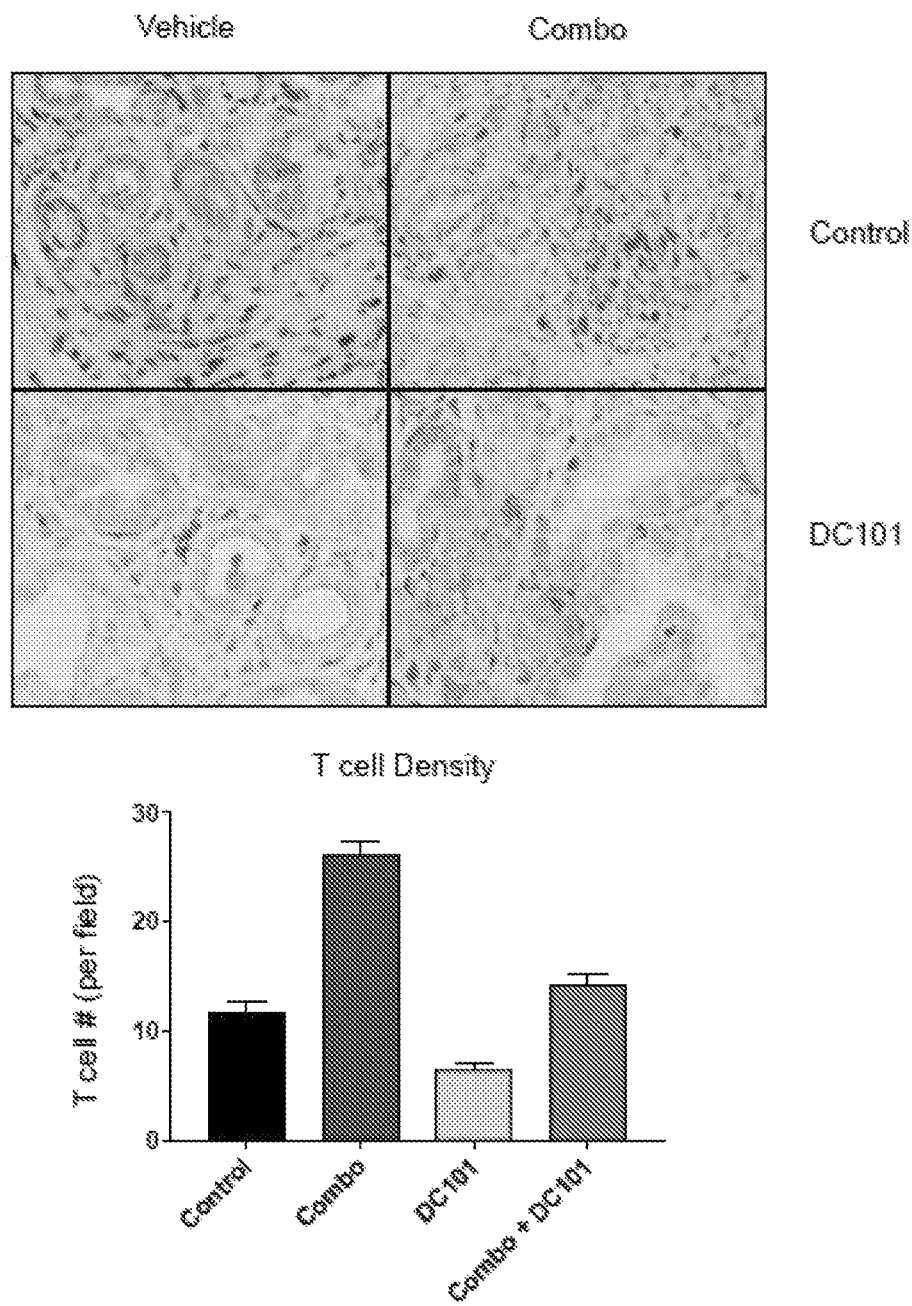
FIG. 24(C): CD3 immunohistochemical staining of KPC PDAC GEMM tumors treated with vehicle, trametinib (1 mg/kg body weight), palbociclib (100 mg/kg body weight), and/or a VEGFR2 blocking antibody (DC101; 800 μg per mouse) for two weeks (scale bar, μm). Dashed red line outlines tumor region. Bottom, quantification of intratumoral CD3$^+$ T cells per 20× field. Bars represent the mean±SEM.
Figure 24D:
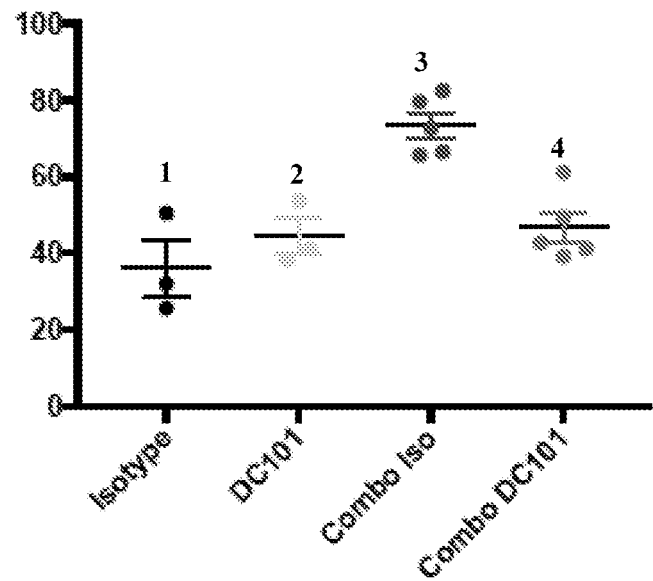
FIGS. 24(D)-24(E): Flow cytometry analysis of KPC$^{mut}$ cell line transplant PDAC tumors following 10-day treatment with vehicle, trametinib (1 mg/kg body weight), palbociclib (100 mg/kg body weight), or both in combination (n≥3 mice per group). (D) Percentage of CD69$^+$ CD8$^+$ T cells.
Figure 24E:
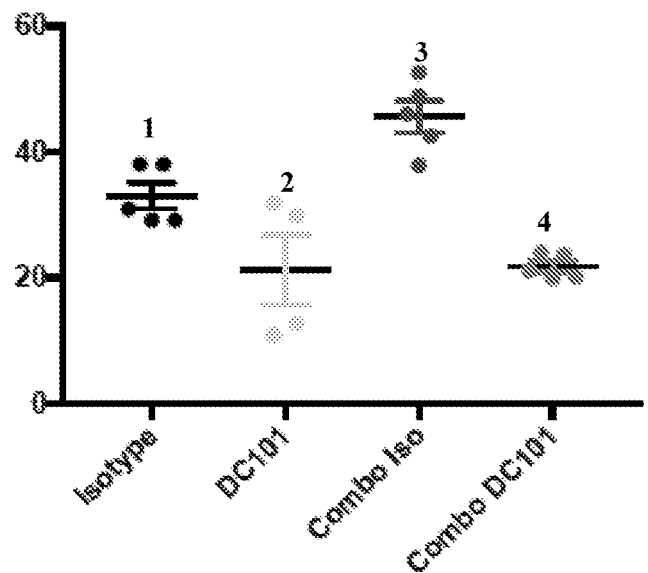
Figure 24F:
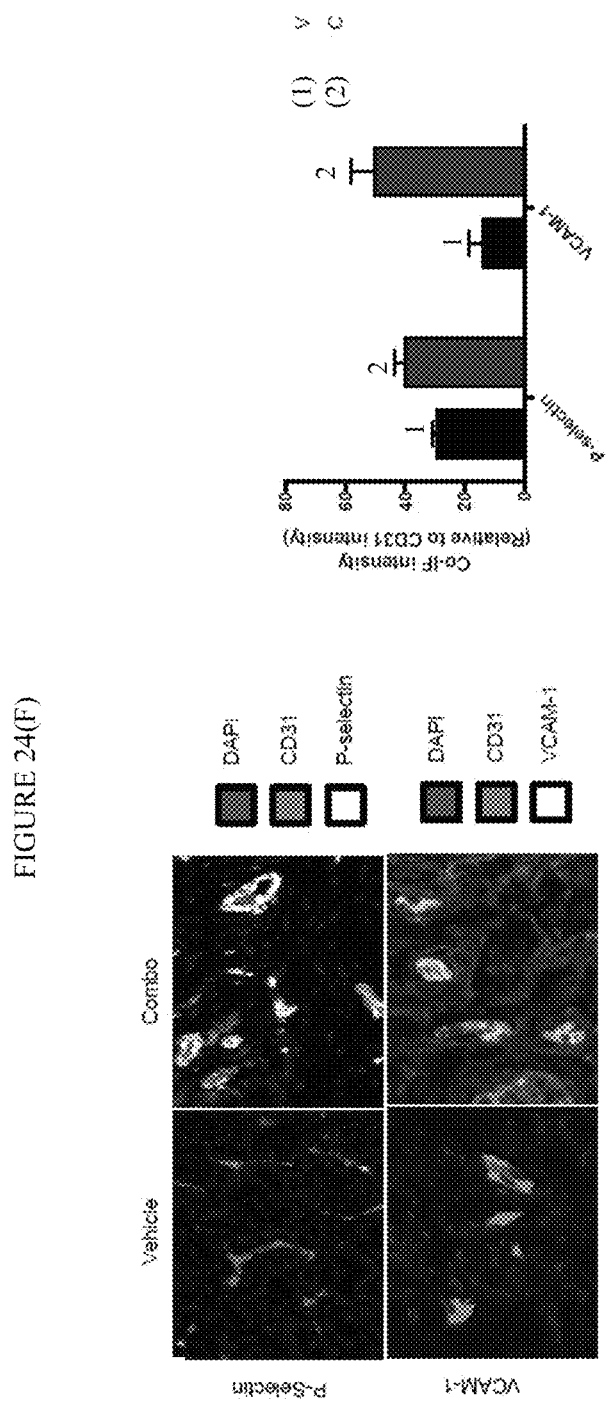
FIG. 24(F): Immunofluorescent images of P-selectin (top, white) or VCAM-1 (bottom, white) co-localization with CD31$^+$ blood vessels (pink) in KPC GEMM PDAC tumors treated with vehicle or combined trametinib (1 mg/kg body weight) and palbociclib (100 mg/kg body weight) for 2 weeks (scale bar, μm) (left). Right, quantification of P-selectin/CD31 and VCAM-1/CD31 co-immunofluorescence. Bars represent the mean±SEM.
Figure 24G:
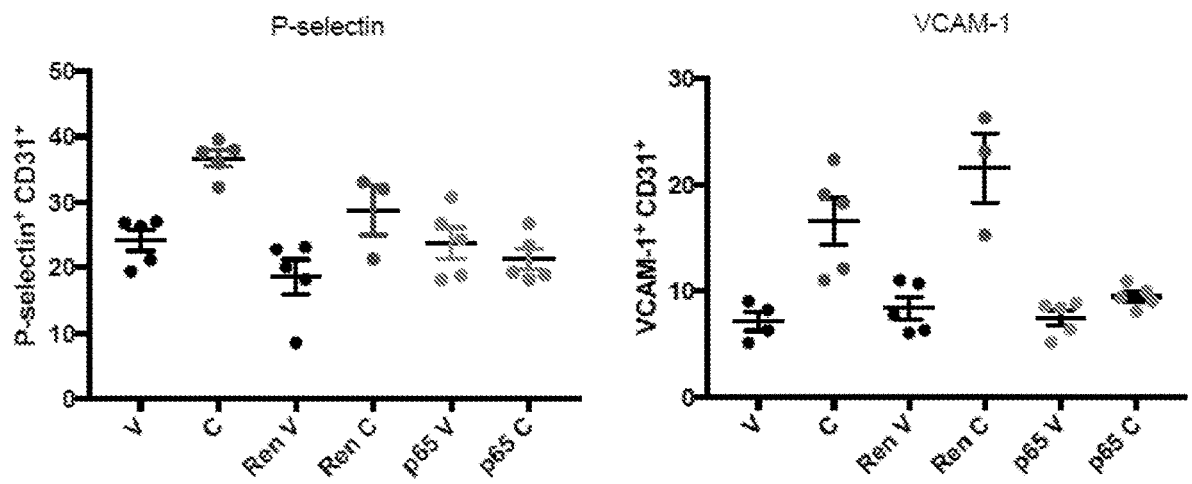
FIG. 24(G): Percentage of P-selectin- (left) or VCAM-1-positive CD31$^+$ blood vessels as assessed by flow cytometry analysis of indicated KPC$^{mut}$ cell line transplant PDAC tumors following 10-day treatment as in FIG. 24(A) (n≥3 mice per group). Data represent the mean±SEM.

Example 9: T Cell Infiltration is Dependent on SASP-Mediated Vascular Remodeling and Activation of VCAM-1 on Endothelial Cells Since the SASP contains both pro-inflammatory and pro-angiogenic factors, the contribution of vascular remodeling to increased T cell infiltration and activity following treatment was evaluated. Thus, VEGFR2 blockade to inhibit SASP-mediated neo-vascularization was used. 10-day treatment with the T/P combination and DC101 significantly inhibited the accumulation of T cells into KPC$^{mut}$ cell line transplant and GEMM PDAC tumors, including both CD8+ (and to a lesser extent) CD4+ T cells (FIGS. 24(A)-24(C)). Moreover, inhibition of SASP-induced neo-vascularization with DC101 significantly decreased the expression of the activation markers CD69 and CD44 on tumor-isolated CD8+ T cells (FIGS. 24(D) and 24(E)). Therefore, neo-vascularization mediated by the SASP is necessary for both increased CD8+ T cell infiltration and activation following T/P treatment.

In addition to better access and proximity to tumor cells, vasculature normalization can also promote increased immune cell homing into solid tumors through induction of integrins, such as P-selectin, and cell adhesion molecules like ICAM-1 and VCAM-1 that bind ligands on lymphocytes and promote their rolling, adhesion, and extravasation through blood vessels. Whereas these receptors are not commonly expressed on tumor-associated blood vessels, their expression can be induced in inflammatory contexts by SASP factors such as VEGF and TNF-α. Indeed, a SASP-dependent increase in the expression of P-selectin, ICAM-1, and VCAM-1 on the surface of ECs following combination treatment was observed (FIGS. 24(F)-24(G), and 35(A)-35(D)).

Figure 24H:
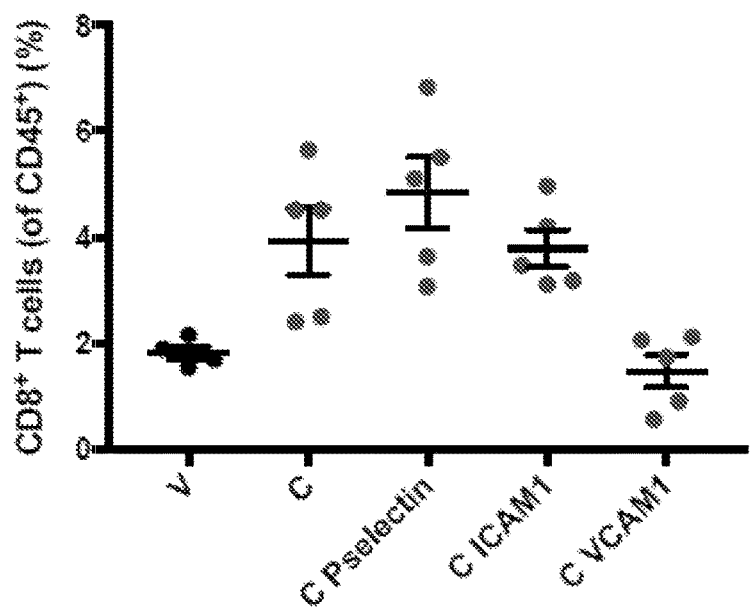
FIG. 24(H): Flow cytometry analysis of CD8$^+$ T cells within the CD45$^+$ population in KPC$^{mut}$ cell line transplant PDAC tumors following 10-day treatment with vehicle or combined trametinib (1 mg/kg body weight) and palbociclib (100 mg/kg body weight) and neutralizing mAbs targeting PSGL-1 (4RA10; 50 μg per mouse), ICAM-1 (YN1/1.7.4; 200 μg per mouse), or VCAM-1 (M/K-2.7; 200 μg per mouse) (n≥4 mice per group). Data represent the mean±SEM. See also FIG. 35.

Next, neutralizing antibodies that block the expression of these immunomodulatory cell surface molecules were used to examine the impact on T cell infiltration following T/P treatment in the KPC cell line transplant model. Blockade of VCAM-1, but neither P-selectin nor ICAM-1, significantly inhibited CD8+ (and to a lesser extent CD4+) T cell infiltration in PDAC tumors following T/P treatment to levels similar to those found in the control vehicle setting (FIGS. 24(H), 35(E), and 35(F)). VLA-4, the ligand on lymphocytes that binds VCAM-1 on the endothelium, was also highly induced on T cells found in PDAC tumors in a SASP-dependent manner following T/P treatment (FIGS. 35(G) and 35(H)), demonstrating a pathway through which SASP-orchestrated and VLA-4/VCAM-1-mediated T cell/EC interactions contribute to making "cold" PDAC tumors "hot".

While the contribution of the inflammatory SASP to the T cell accumulation observed following treatment cannot be completely ruled out, antibody-mediated depletion of individual pro-inflammatory SASP factors implicated in T cell chemotaxis (CCL5, CXCL9) and activation of VCAM-1 expression on ECs (TNF-α) did not inhibit T cell accumulation or activation following treatment (FIG. 35(I)). Taken together, these data demonstrate that the SASP not only leads to increased neo-vascularization and vascular perfusion but also increased expression of immunomodulatory receptors such as VCAM-1 on ECs that, collectively, promote increased T cell extravasation into PDAC tumors.

Accordingly, the combination therapy methods disclosed herein are useful for preventing or treating pancreatic cancer in a subject in need thereof.

Example 10: Therapy-Induced Senescence Dually Enhances Antigen Presentation and PD-1/PD-L1 Expression Cytotoxic T cells recognize their targets through TCR-MHC Class I (MHC-I) interactions and, by doing so, can eliminate transformed cells. Accordingly, tumor cells can evade checkpoint blockade immunotherapy through low antigen presentation or loss of the antigen presentation machinery (McGranahan et al., *Cell* 171, 1259-1271 (2017); Sharma et al., *Cell* 168, 707-723 (2017); Zaretsky et al., *N Engl J Med* 375, 819-829 (2016). Despite mouse models of PDAC having poor immunogenicity, KPC GEMM PDAC tumors express a similar range of mutational burden to what is found in human PDAC, including a number of mutations that are predicted to generate neo-epitopes (Jones et al., *Science* 321, 1801-1806 (2008); Waddell et al., *Nature* 518, 495-501 (2015)).

Figure 25A:
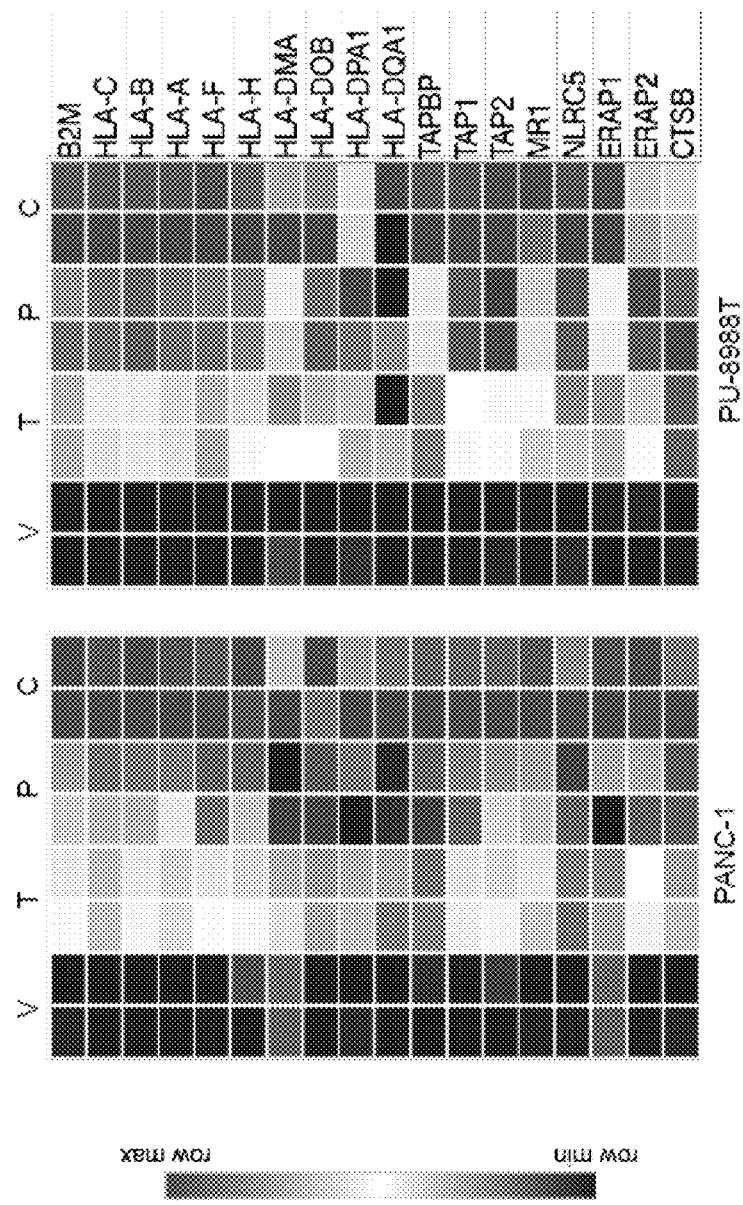
FIG. 25(A): Heat map of expression of genes related to antigen processing and presentation in human KRAS-mutant PDAC cell lines (PANC-1, PU-8988T) following 8 day treatment with trametinib (25 nM) and/or palbociclb (500 nM) as assessed from RNA-seq analysis data. Two biological replicates per cell line are shown.
Figure 25B:
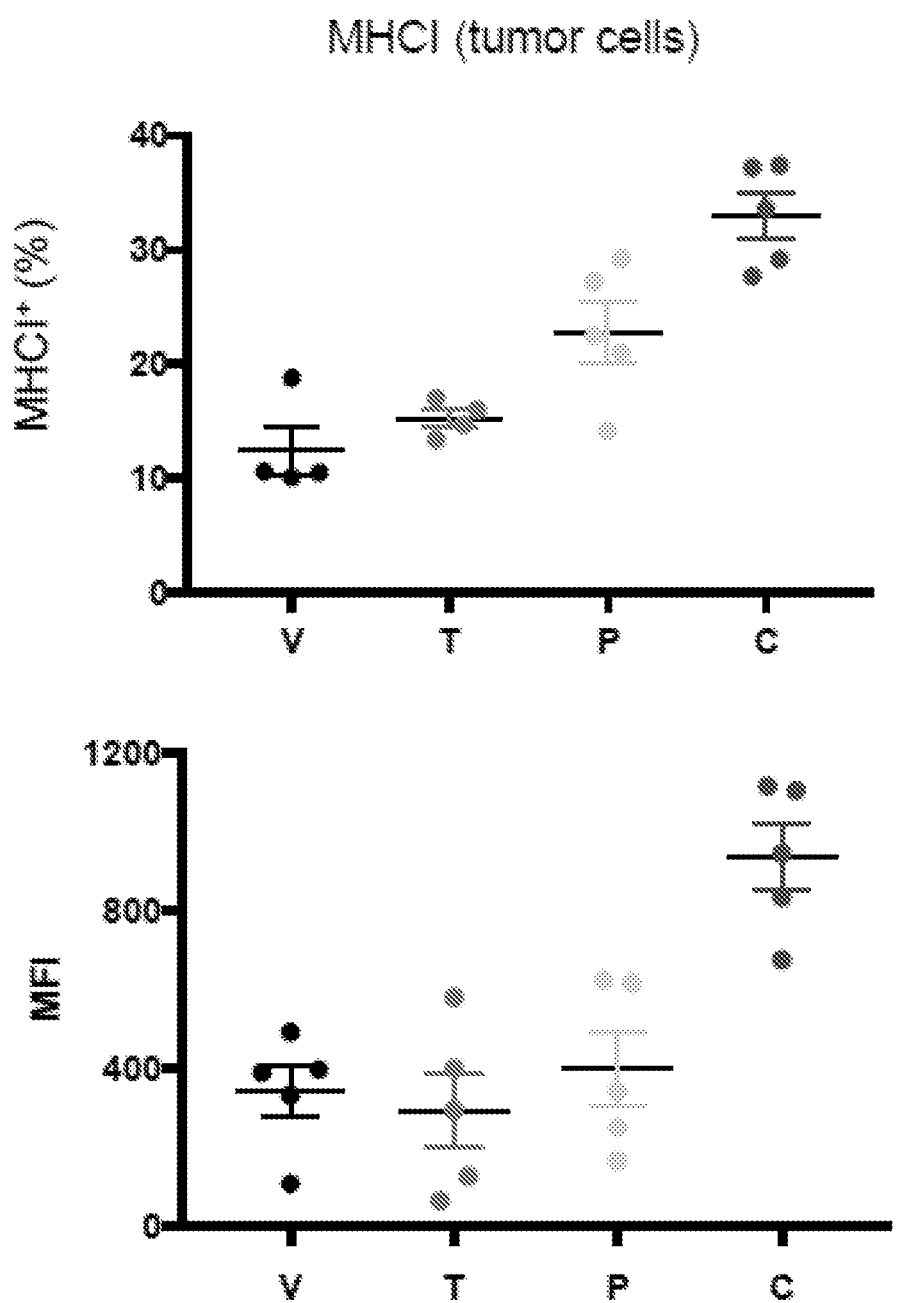
FIG. 25(B): Percentage of MHC Class I (H-2k$^b$)$^+$ tumor cells following flow cytometry analysis of KPC$^{mut}$ cell line transplant PDAC tumors treated for 10 days with vehicle, trametinib (1 mg/kg body weight), palbociclib (100 mg/kg body weight), or both in combination (n≥4 mice per group). Bottom, quantification of mean fluorescent intensity (MFI) of MHC Class I (H-2k$^b$)$^+$ on tumor cells.

As MEK or CDK4/6 inhibitors as single agents have been reported to increase expression of MHC-I and other members of the antigen processing/presentation machinery in various tumor contexts (Brea et al., *Cancer Immunol Res* 4, 936-947 (2016); Ebert et al., *Immunity* 44, 609-621 (2016); Goel et al., *Nature* 548, 471-475 (2017)), the ability of the combination of both drugs to enhance antigen presentation in PDAC was investigated. Indeed, HLA molecules, B2M, TAP1/2, and other members of antigen processing/presentation machinery were significantly upregulated in human PDAC cell lines following T/P combination treatment as compared to single agent T or P administration (FIG. 25(A)). In KPC PDAC cell line transplant tumors, 10-day combination (but not single agent) treatment increased both the percentage of MHC-I+ PDAC tumor cells as well as the surface level expression of MHC-I (FIG. 25(B)).

Figure 25C:
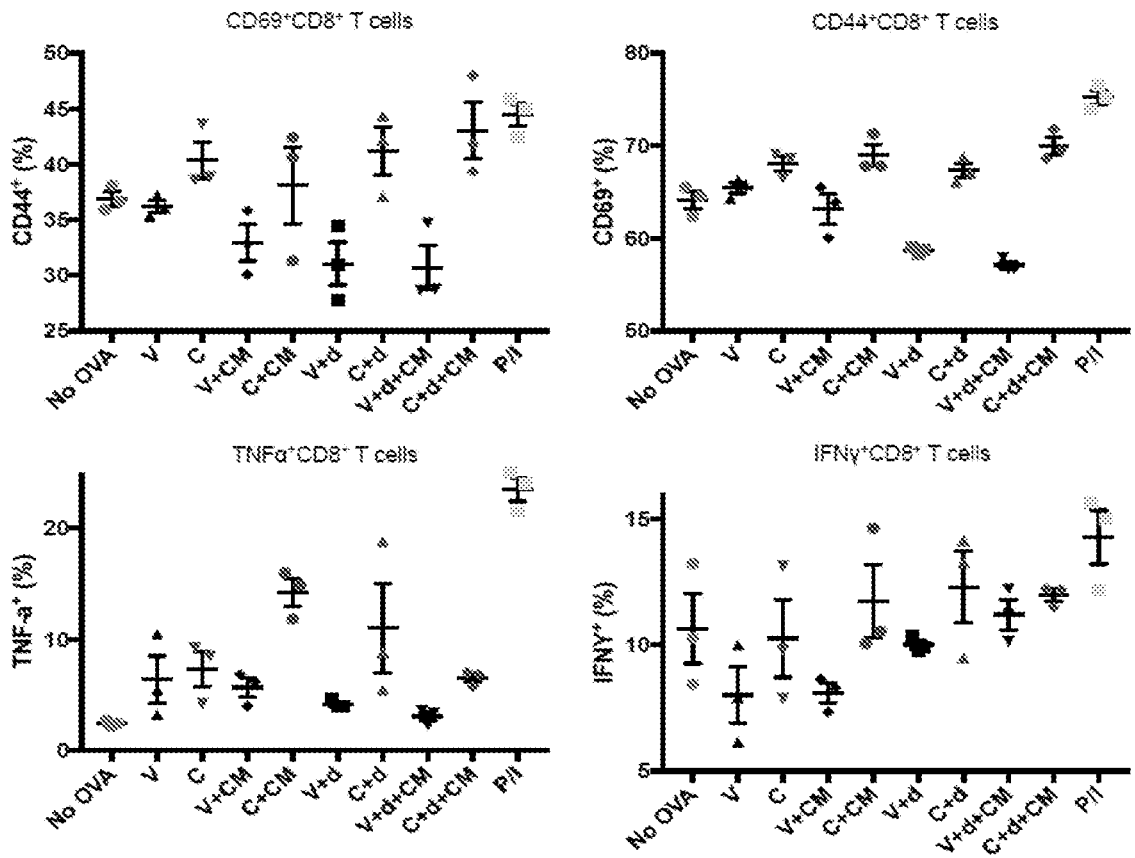
FIG. 25(C): Flow cytometry analysis of T cell activation markers in OTI$^+$ CD8$^+$ T cells co-cultured with control or OVA-expressing KPC PDAC tumors in the presence or absence of drugs and/or conditioned media for 6 hours following 7 day tumor cell pretreatment with vehicle or combined trametinib (25 nM) and palbociclb (500 nM). PMA/ionomycin (P/I) stimulation served a positive control for T cell activation.

To determine the direct functional consequences of increased antigen presentation following T/P treatment on T cell activity, MHC-I/TCR interactions were modeled using the OT-I/ovalbumin (OVA) system. Splenocytes derived from OT-I TCR transgenic mice were co-cultured with OVA$_{257-264}$-presenting KPC PDAC tumors cells and superior CD8$^+$ T cell activation was observed upon culture with T/P pretreated tumor cells, as evaluated by expression of the T cell activation markers CD44$^+$ and CD69$^+$ T cells and by secretion of the T cell effector cytokines TNF-α and IFN-γ (FIG. 25(C)). This effect appeared to be independent of the presence of the T/P drug combination or SASP conditioned media, and suggests that T/P-mediated upregulation of MHC-I is sufficient to enhance tumor cell reactivity and CD8$^+$ T cell activity.

In addition to increased MHC-I expression on tumor cells, there was also a significant increase in the expression of MHC Class II (MHC-II) on conventional antigen presenting cells (dendritic cells (DCs)), as well as ECs and PDAC tumor cells themselves in vivo, suggesting that treatment may also lead to enhanced antigen cross-presentation and priming of T cell responses through MHC-II (FIGS. 36(A)-36(D)). Thus, senescence induction following combination treatment leads to increased MHC Class I and II expression and presentation/cross-presentation of antigens in PDAC tumor cells that may contribute to enhanced CD8$^+$ T cell recognition and anti-tumor activity.

Figure 25D:
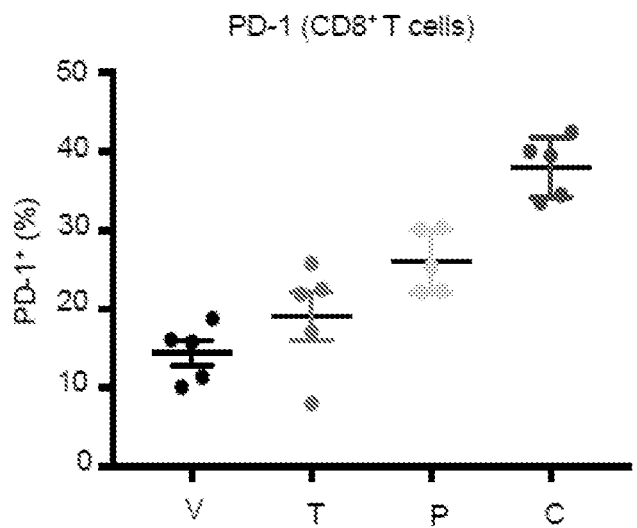
FIGS. 25(D)-25(F): Flow cytometry analysis of KPC$^{mut}$ cell line transplant PDAC tumors following 10-day treatment with vehicle, trametinib (1 mg/kg body weight), palbociclib (100 mg/kg body weight), or both in combination (n≥4 mice per group).
Figure 25E:
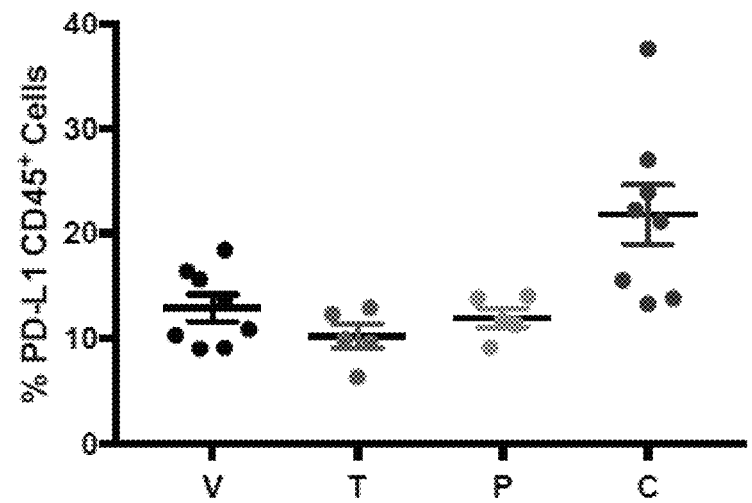
Figure 25F:
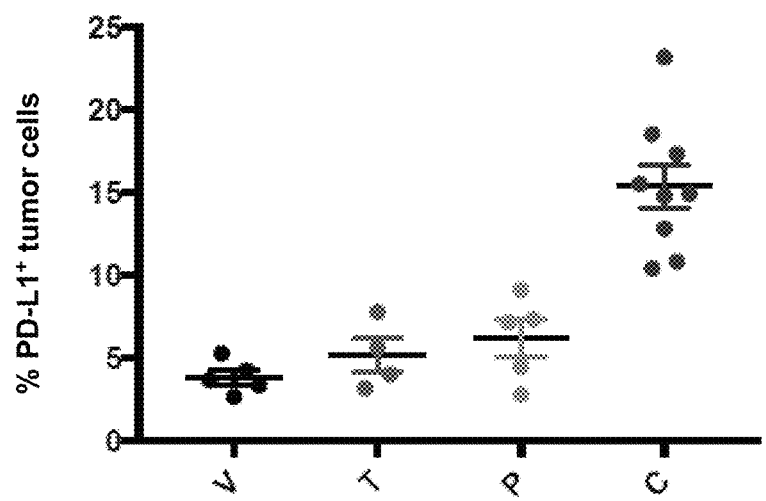

Despite increased CD8$^+$ T cell infiltration and activation, as well as enhanced antigen presentation to T cells following TIS, CD8$^+$ T cell depletion in conjunction with T/P treatment did not affect the survival of PDAC tumor-bearing animals (FIG. 36(E)). Thus, these T cells may not be playing a functional role in anti-tumor surveillance. Indeed, while T/P treatment led to increased CD44 and CD69 expression on CD8$^+$ T cells (FIGS. 23(C) and 23(D)), it did not induce expression of CD107a (FIGS. 36(F) and 36(G)), a marker of T cell degranulation critical for T cell-mediated cytotoxicity. Upon closer inspection, CD8$^+$ (but not CD4$^+$) T cells in the T/P treatment cohorts exhibited increased expression of PD-1, a marker of prior T cell activation that can ultimately contribute to exhaustion and dysfunction, compared to T or P single agent treatment (FIGS. 25(D) and 36(H)). In concert, CD45$^+$ immune and CD31$^+$ endothelial cells, as well as the tumor cells themselves, upregulated cell surface expression of PD-L1, a ligand for PD-1, only after combined T/P treatment (FIGS. 25(E), 25(F), and 36(I)). Of note, T/P treatment induced PD-L1 surface expression on human and murine PDAC tumor cell lines in vitro as well, demonstrating a direct effect of the drugs in inducing these ligands in tumor cells (FIGS. 36(J) and 36(K)). Therefore, despite initial influx and activation following TIS, CD8$^+$ T cells are unable to exert antitumoral activity in the PDAC TME, potentially through PD-1/PD-L1-mediated suppression.

Accordingly, the combination therapy methods disclosed herein are useful for increasing the efficacy of immunotherapeutic agents in patients with pancreatic cancer.

Example 11: Senescence Induction Potentiates PD-1 Checkpoint Blockade Immunotherapy in PDAC Induction of the PD-1/PD-L1 inhibitory axis following T/P treatment provides a clear rationale for combining senescence-inducing agents with PD-1 checkpoint blockade. Consistent with its lack of efficacy in human PDAC patients and further validating the mouse models of PDAC, PD-1 blockade alone had no impact on tumor growth or the survival of KPC$^{mut}$ PDAC organoid transplant or KPC GEMM mice (FIGS. 26(A)-26(D) and 37(A)). However, T/P treatment in combination with PD-1 blockade led to potent PDAC tumor regressions and culminated in extended long-term survival in both models (FIGS. 26(A)-26(D) and 37(A)). Following just two weeks of treatment, the triple T/P/PD-1 therapy led to large areas of necrosis that marked areas of tumor destruction (FIG. 26(E)), a phenomenon that was not observed with the T/P/G chemotherapy regimen.

Consistent with the impact of SASP-mediated vascular remodeling on T cell numbers and activity in the PDAC TME, p65-deficient PDAC tumors, as well as those treated with the VEGFR2 blocking antibody DC101, had no signs of tumor destruction and failed to regress following T/P/PD-1 treatment (FIGS. 26(A), 26(B), 37(B), and 37(C)). As such, suppression of neo-vascularization reduced the survival benefit of triple T/P/PD-1 therapy (FIGS. 26(A) and 26(B)). Mechanistically, two-week T/P treatment, followed by a single dose of PD-1 blocking antibody, led to significant increases in granzyme B-positive cells and tumor cell apoptosis in KPC$^{mut}$ organoid transplant tumors compared to PD-1 treatment alone (FIGS. 26(F) and 26(G)). In all, these findings demonstrate that senescence-inducing drugs can potentiate PD-1 checkpoint blockade and produce robust PDAC tumor responses through vascular remodeling-mediated CD8$^+$ T cell mobilization and activation.

Accordingly, the combination therapy methods disclosed herein are useful for increasing the efficacy of immunotherapeutic agents in patients with pancreatic cancer.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for increasing the responsiveness of a pancreatic cancer patient to at least one chemotherapeutic agent or at least one immunotherapeutic agent comprising administering to the patient an effective amount of a MEK inhibitor and an effective amount of a CDK4/6 inhibitor.

2. The method of claim 1, wherein the at least one chemotherapeutic agent is selected from the group consisting of abraxane, capecitabine, erlotinib, fluorouracil (5-FU), gemcitabine, irinotecan, leucovorin, nab-paclitaxel, cisplatin, irinotecan, docetaxel, oxaliplatin, tipifarnib, everolimus, sunitinib, dovitinib, ruxolitinib, pegylated-hyaluronidase, pemetrexed, folinic acid, paclitaxel, MK2206, GDC-0449, IPI-926, gamma secretase/RO4929097, M402, and LY293111.

3. The method of claim 1, wherein the at least one immunotherapeutic agent is selected from the group consisting of immune checkpoint inhibitors, ipilimumab, 90Y-Clivatuzumab tetraxetan, pembrolizumab, nivolumab, trastuzumab, cixutumumab, ganitumab, demcizumab, cetuximab, nimotuzumab, dalotuzumab, sipuleucel-T, CRS-207, and GVAX.

4. The method of claim 1, wherein the MEK inhibitor is selected from the group consisting of trametinib, cobimetinib, binimetinib, selumetinib, PD-325901, TAK-733, CI-1040 (PD184352), PD0325901, MEK162, AZD8330, GDC-0623, refametinib, pimasertib, RO4987655, RO5126766, WX-554, HL-085, CInQ-03, G-573, PD184161, PD318088, PD98059, RO5068760, U0126, and SL327.

5. The method of claim 1, wherein the CDK4/6 inhibitor is selected from the group consisting of palbociclib, ribociclib, and abemaciclib.

6. The method of claim 1, wherein the pancreatic cancer comprises a KRAS mutation, optionally wherein the KRAS mutation is G12D, G12V, G12C, G12R, G12A, G13D, Q61L or Q61H.

7. The method of claim 1, wherein the MEK inhibitor and the CDK4/6 inhibitor are administered sequentially, simultaneously, or separately.

8. The method of claim 1, wherein the MEK inhibitor and/or the CDK4/6 inhibitor is administered orally or intravenously.

9. A kit comprising a MEK inhibitor, a CDK4/CDK6 inhibitor, and instructions for treating pancreatic cancer.

10. The method of claim 1, further comprising administering to the patient an effective amount of at least one immunotherapeutic agent selected from the group consisting of immune checkpoint inhibitors, ipilimumab, 90Y-Clivatuzumab tetraxetan, pembrolizumab, nivolumab, trastuzumab, cixutumumab, ganitumab, demcizumab, cetuximab, nimotuzumab, dalotuzumab, sipuleucel-T, CRS-207, and GVAX.

11. The method of claim 1, further comprising administering to the patient an effective amount of at least one chemotherapeutic agent is selected from the group consisting of abraxane, capecitabine, erlotinib, fluorouracil (5-FU), gemcitabine, irinotecan, leucovorin, nab-paclitaxel, cisplatin, irinotecan, docetaxel, oxaliplatin, tipifarnib, everolimus, sunitinib, dovitinib, ruxolitinib, pegylated-hyaluronidase, pemetrexed, folinic acid, paclitaxel, MK2206, GDC-0449, IPI-926, gamma secretase/RO4929097, M402, and LY293111.

* * * * *